(12) United States Patent
Hansen et al.

(10) Patent No.: US 8,889,845 B2
(45) Date of Patent: Nov. 18, 2014

(54) SURROGATE MARKERS FOR VIRAL INFECTIONS AND OTHER INFLAMMATORY RESPONSES

(75) Inventors: Thomas R. Hansen, Fort Collins, CO (US); Kathleen J. Austin, Laramie, WY (US); Alberto van Olphen, Tampa, FL (US); Lea A. Rempel, Edgerton, KS (US)

(73) Assignee: University of Wyoming, Laramie, WY (US)

( * ) Notice: Subject to any disclaimer, the term of this patent is extended or adjusted under 35 U.S.C. 154(b) by 580 days.

(21) Appl. No.: 12/793,092

(22) Filed: Jun. 3, 2010

(65) Prior Publication Data

US 2010/0240027 A1 Sep. 23, 2010

Related U.S. Application Data

(62) Division of application No. 11/622,124, filed on Jan. 11, 2007, now abandoned.

(60) Provisional application No. 60/757,965, filed on Jan. 11, 2006.

(51) Int. Cl.
*C12Q 1/68* (2006.01)
*A61K 39/12* (2006.01)

(52) U.S. Cl.
CPC ........ *C12Q 1/6883* (2013.01); *C12Q 2600/158* (2013.01)
USPC ............................ 536/23.5; 424/218.1; 435/5

(58) Field of Classification Search
None
See application file for complete search history.

(56) References Cited

U.S. PATENT DOCUMENTS

2007/0196823 A1    8/2007    Hansen et al.

FOREIGN PATENT DOCUMENTS

WO    WO 03/028582 A2 *    4/2003
WO    2004/028467    4/2004

OTHER PUBLICATIONS

Austin et al., Biology of Reproduction, 1996, 54:600-606.*
Shoemaker et al., Journal of Interferon & Cytokine Research, 2009, 29(1):23-35.*
Avalos-Ramirez, R., et al., "Evidence for the presence of two novel pestivirus species," Virology, 286:456-465 (2001).
Vassilev, V.B., et al., "Authentic and chimeric full-length genomic cDNA clones of bovine viral diarrhea virus that yield infectious transcripts," J. Virol., 71(1):471-478, (Jan. 1997).
Behrens, S-E., et al., "Characterization of an autonomous subgenomic pestivirus RNA replicon," J. Virol., 72 (3):2364-2372, (Mar. 1998).
Meyer, C., et al., "Recovery of virulent and RNase-negative attenuated type 2 bovine viral diarrhea viruses from infectious cDNA clones," J. Virol., 76(16):8494-8503, (Aug. 2002).
Jones, L.R., et al., "Quasispecies in the 5' untranslated genomic region of bovine viral diarrhoea virus from a single individual," J. Gen. Virol., 83:2161-2168, (2002).
Aoki, H., et al., "Method for detection of extraneous active bovine viral diarrhoea virus and classical swine fever virus in animal viral vaccines by RT-PCR, which amplify negative-strand viral RNA in infected cells," Biologicals, 30:27-35, (2002).
Sandvik, T., et al., "Detection and identification of ruminant and procine pestiviruses by nested amplification of 5' untranslated cDNA regions," J. Virol. Methods 64:43-56, (1997).
Werling, D., et al. "Ability to differentiate between cp and ncp BVDV by microarrays: Towards an application in clinical veterinary medicine?" Veterinary Immunology and Immunopathy, 108:1-2, 157-164 (Oct. 18, 2005).

* cited by examiner

*Primary Examiner* — Stacy B Chen
(74) *Attorney, Agent, or Firm* — Kathleen D. Rigaut; Robert C. Netter, Jr.; Dann, Dorfman, Herrell & Skillman

(57) ABSTRACT

Compositions and methods for the detection, diagnosis and treatment of BVDV and other viruses are provided.

3 Claims, 4 Drawing Sheets

SURROGATE MARKERS FOR VIRAL INFECTIONS AND OTHER INFLAMMATORY RESPONSES

The present application is divisional application of U.S. patent application Ser. No. 11/622,124 filed 11 Jan. 2007, now abandoned which claims priority to U.S. Provisional 60/757,965, filed 11 Jan. 2006, the entire disclosure of each being incorporated by reference herein.

Pursuant to 35 U.S.C. Section 202(c), it is acknowledged that the United States Government has certain rights in the invention described herein, which was made in part with funds from the USDA/CSREES, grant numbers 2004-35204-14916 and 2004-35204-17005.

FIELD OF THE INVENTION

This invention relates to the field of molecular biology and virology. More specifically, the present invention provides materials and methods for the diagnosis and staging of bovine viral diarrhea virus (BVDV).

BACKGROUND OF THE INVENTION

Several publications and patent documents are cited throughout this application in order to more fully describe the state of the art to which this invention pertains. The disclosure of each of these citations is incorporated by reference herein.

Bovine viral diarrhea virus (BVDV) costs the United States cattle industry more than 400 million dollars per year. The pathogenesis of BVDV infection has features that are unique to this virus and vary with the time of infection, virulence of the viral strain, and age of the animals at the time of infection.

When the infection occurs after 150 days of gestation (post-development of the immune system) or after birth, including adult animals, the infection is referred to as acute infection. The clinical manifestation of acute infections with BVDV range from sub-clinical or unapparent infections to embryonic death, abortions, stillborn, malformed or slow growing calves.

Certain strains of BVDV can cause a hemorrhagic syndrome with high morbidity and moderate mortality in adult animals. Acutely infected animals usually recover and eliminate the virus within 10 to 14 days post infection.

Animals vaccinated with modified live vaccines against BVDV have an immune response similar to the one induced by natural, acute infection. In contrast, infection of the fetus during the first 150 days of gestation, when the immune system has not yet developed, can lead to the generation of persistently infected (PI) calves. Some of these PI calves die soon after birth, but others live for relatively long periods of time without showing any clinical signs. PI animals cannot eliminate the infecting BVDV from their system, and continuously release high amounts of virus in their bodily secretions and excretions, making them a continuous source of infection within the herd and potentially to other herds as well. Furthermore, nursing PI calves can acutely infect their mothers and other normal nursing calves, which in turn infect their own mothers while they are pregnant, producing a new cycle of infection and eventually more PI calves.

Mucosal disease, an uncommon but fatal complication observed in PI calves, occurs when the virus mutates or the animal is superinfected with an antigenically related BVDV virus. Current vaccines are relatively inefficient in preventing fetal infections, therefore the identification and elimination of PI animals is essential to any successful program for control or eradication of BVDV.

Currently available tests for the detection of PI animals are based on the identification of the viral antigen in a blood or tissue sample (most commonly a skin biopsy) using detection methods that depend on the specific binding of anti-BVDV antibodies. Although these tests are widely used for the detection of PI animals they frequently fail to identify all infected animals (false negatives) resulting in the failure to remove all PI animals from the infected herd. Moreover, serological tests cannot differentiate between PIs and uninfected animals, or between acutely infected and vaccinated animals.

Identification and elimination of PI animals from an affected herd is the most cost effective measure to control and eradicate BVDV, underscoring the criticality of an inexpensive and convenient diagnostic test. It is an object of the invention to provide such a test and kit for performing the same.

SUMMARY OF THE INVENTION

In accordance with the present invention, methods and compositions for diagnosis of Bovine Viral Diarrhea Virus (BVDV) are disclosed. Specifically, a simple, convenient test for accurately diagnosing BVDV is provided. The instant method provides the means to differentiate cattle persistently infected with BVDV (PI) from control non-infected steers. Other markers are provided which enable the skilled person to identify 1) heifers carrying persistently infected fetuses; 2) heifers carrying transiently virally infected fetuses and 3) heifers carrying control, uninfected fetuses. Such differentiation may be accomplished by detecting altered expression levels of one or more markers shown in Tables 1-9, or the proteins or peptide fragments encoded thereby. Most preferably, the test can be easily conducted in the field by veterinarians or cattle producers.

In one aspect of the invention, BVDV surrogate markers are provided. A BVDV surrogate marker may be a nucleic acid or polypeptide or fragments thereof. Such markers are provided herein at Tables 1-9. Also provided in accordance with the invention are oligonucleotides, including probes and primers, that specifically hybridize with the nucleic acid sequences set forth in Tables 1-9. Antibodies immunologically specific for the BVDV marker polypeptides described herein are also within the scope of the invention.

In a further aspect of the invention, recombinant DNA molecules comprising the nucleic acid molecules set forth above, operably linked to a vector are provided. The invention also encompasses host cells comprising a vector encoding a BVDV specific marker of the invention.

In another aspect of the invention, methods for detecting a differentially expressed BVDV specific marker molecules in a biological sample are provided.

Such molecules can be BVDV specific marker nucleic acids, such as mRNA, DNA, cDNA, or BVDV specific marker polypeptides or fragments thereof. Preferably the BVDV surrogate marker exhibits expression levels which differ at least 2 fold from normal, uninfected cattle. The BVDV markers of the invention may be up or down regulated relative to the levels observed in non-infected control cattle. Exemplary methods comprise detection of isolated biological molecules which hybridize to BVDV specific markers which are affixed to a solid support, or mRNA analysis, for example by RT-PCR. Immunological methods include for example contacting a sample with a detectably labeled antibody immunologically specific for a BVDV specific marker polypeptide and determining the presence of the polypeptide as a function of the amount of detectably labeled antibody bound by the sample relative to control cells. In a preferred embodiment, these assays may be used to detect differentially expressed proteins encoded by the nucleic acids set forth in Tables 1-9.

In a further aspect of the invention, kits for detection of BVDV infection or lack thereof are provided. An exemplary kit comprises a BVDV specific marker protein, polynucleotide or a gene chip comprising a plurality of such polynucleotides, or antibody, which are optionally linked to a detectable label. The kits may also include solid supports, pharmaceutically acceptable carriers and/or excipients, a suitable container, and instructions for use.

In yet another aspect of the invention, the differentially regulated BVDV markers described herein may be used in screening methods to identify new therapeutic agents for the treatment of viral infections, including BVDV infection. Agents which affect the differential expression of nucleic acids or proteins associated with BVDV infection may prove efficacious for the treatment of BVDV.

BRIEF DESCRIPTION OF THE FIGURE

FIG. 1 is a schematic diagram showing some of the features of persistent and acute or transient BVDV infection.

DETAILED DESCRIPTION OF THE INVENTION

Figure 2:
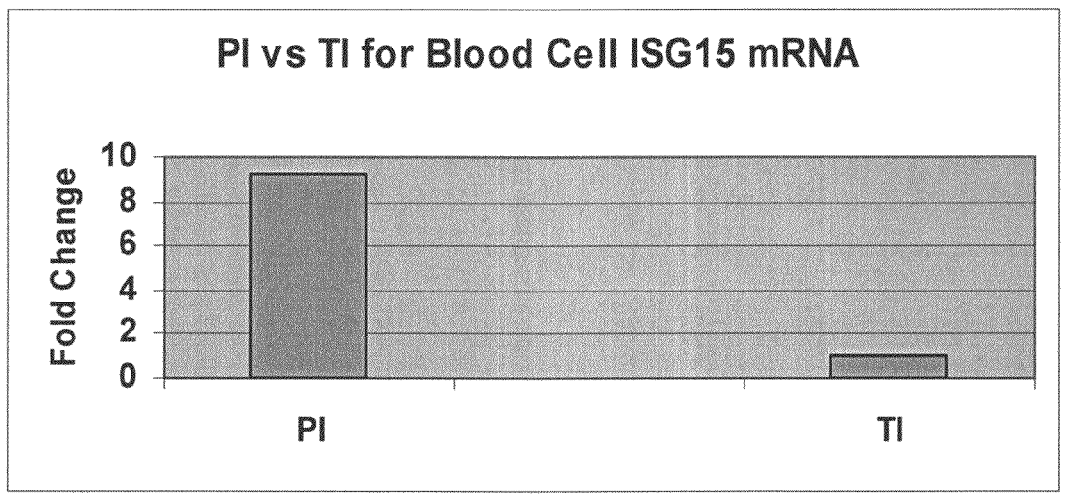
FIG. 2 is a graph showing upregulation of interferon stimulated gene 15 (ISG15) in blood from persistently infected calves. ISG15 mRNA levels were determined using semi-quantitative (adjusted for GAPDH) Sybr green Real Time PCR. Blood from three persistently infected (PI) and three calves that had been vaccinated against BVDV (TI) are represented in the analysis. ISG15 means differ between PI and TI ($P<0.05$).

Bovine viral diarrhea virus (BVDV) provides a challenge to cattle producers, because BVDV is a contagious and potentially lethal disease that is currently difficult and expensive to differentially diagnose. Current tests are performed on samples collected from young calves after birth. Thus, many of these infected calves have already shed virus and have infected other pregnant cows. Therefore reinfection of pregnant cows helps maintain the infectious cycle.

The complex host-viral interactions resulting from persistent infection are minimally understood, particularly in the bovine host. Thus, one purpose of the present research was to identify those genes and associated biological pathways which are activated or down-regulated in response to viral infection to facilitate a better understanding of the mechanism of virus action. Another objective of the research was to identify peripheral blood markers that will help distinguish pregnant cattle that are carrying persistently infected from those carrying transiently virally infected fetuses. Depending on the time of infection during gestation, noncytopathic (ncp) bovine viral diarrhea virus (BVDV) causes persistent infection (PI, <150 d) or transient infection (TI, >150 d.) in fetuses. TI fetuses develop immunity to the viral strain and clear the virus. PI fetuses do not recognize the virus as a foreign agent and once born continually shed the virus and infect other cattle. Detection and removal of pregnant cows or heifers carrying PI fetuses would greatly benefit the successful implementation of control programs. Provided herein is a simple and effective test for diagnosing BVDV, and identifying persistently infected (PI) animals.

Experimental evidence is provided which indicates that the pattern of gene expression in vaccinated or acutely infected and PI animals is different, and therefore the differential expression of genes can be used as a diagnostic marker for these types of BVDV infection. Genes that are differentially expressed in the cells of the blood or the skin of persistently infected animals (surrogate markers) are identified using gene chip analysis of mRNA of PI when compared to vaccinated or acutely infected animals. Antibodies produced against such surrogate markers can be used to develop a diagnostic test to detect PI animals, by analyzing the presence of the surrogate marker in an animal's blood or skin.

Thus, in accordance with the present invention, gene chip analysis has been performed on nucleic acids obtained from blood cells collected from bovines that are persistently infected with BVDV when compared to vaccinated control bovines.

In yet another aspect, the differentially regulated BVDV markers described herein may be used in screening methods to identify new therapeutic agents for the treatment of viral infections, particularly BVDV infections. For example, agents which down regulate the expression of genes which are upregulated in response to infection may have efficacy as antiviral agents.

I. Definitions

The following definitions are provided to facilitate an understanding of the present invention: The term "surrogate marker" or infection marker is a marker which is differentially expressed in animals infected with a pathological condition, such as a virus.

Specifically, a surrogate marker may be any gene expression product which is differentially expressed in persistently infected animals when compared to vaccinated or acutely infected animals, transiently infected and non-infected or non-vaccinated (normal) animals. A surrogate marker can be a polynucleotide, a protein, a peptide, or any gene expression product, but is preferably an mRNA or protein expression product. The surrogate markers described herein may also be useful for diagnosing invention with other RNA viruses which include for example, Influenza, HIV, Ebola virus, FeLv, FIP virus, Bluetongue virus, West Nile Virus, hepatitis C Virus and Epizootic Hemorrhagic Disease Virus. Thus, the term "surrogate marker" as used herein refers to those biological molecules which are differentially expressed in response to infection with any RNA virus.

A persistently infected calf is one that is infected in utero prior to 150 days of gestation, does not clear the virus and if it survives will continue to shed virus. A transiently infected calf is one that is infected in utero after 150 days of gestation, recovers and clears the virus. An acutely infected animal is one that is infected postnatally and recovers, clearing the virus. A control animal is one that was never infected with virus.

A "BVDV surrogate marker" refers to a marker which is differentially expressed in animals infected with BVDV. Specifically, a BVDV surrogate marker may be any gene expression product which is differentially expressed in any or all of acutely infected BVDV animals, persistently infected BVDV animals, vaccinated BVDV animals, and normal animals. A surrogate marker can be a polynucleotide, a protein or peptide, or any gene expression product, but is preferably an mRNA or protein expression product.

A "BVDV surrogate marker profile" is an expression pattern of surrogate BVDV markers which correlates specifically to acute BVDV infection, persistent BVDV infection, BVDV vaccinated cattle, or non-BVDV infected cattle.

A "sample" or "patient sample" or "biological sample" generally refers to a sample which may be tested for a particular molecule, preferably a surrogate BVDV marker, including one or more surrogate BVDV polynucleotide, polypeptide, or antibody. Samples may include but are not limited to blood or skin, serum, plasma, urine, saliva, and the like. Most preferably, the sample is a skin sample or a blood sample from cattle.

"Blood" includes but is not limited to whole blood, blood treated or mixed with anticoagulants, and any component of whole blood, including but not limited to serum, plasma, buffy coat, and purified peripheral blood mononuclear cells.

A "ruminant" is an even-toed, herbivorous, ungulate mammal (Order Artiodactyla) that chews cud (ruminate) and has a complex, usually four-chambered stomach containing microorganisms that break down cellulose. Ruminants include but are not limited to cattle, sheep, antelope, deer, giraffes, elk, moose, caribou, yak and camelids (e.g., camel, llama, alpaca, vicuna and guanaco).

The term "cattle" as used herein includes any of numerous types of domestic quadrupeds held as property or raised for use, such as livestock, cows, bulls, bovine, steer, oxen, bison, and the like. The term "cattle" generally refers to multiple animals, but may also describe a single animal.

The term "ruminant nucleic acid" or "ruminant protein" refers to a nucleic acid or protein whose sequence is of ruminant origin. Preferably, a ruminant nucleic acid or ruminant protein is of bovine origin.

A "BVDV surrogate marker detector molecule" is a molecule which facilitates detecting or quantitating a BVDV surrogate marker. A BVDV surrogate marker detector molecule can be any molecule which facilitates detection of BVDV surrogate marker, including but not limited to a probe or primer which specifically hybridizes with a BVDV surrogate marker nucleic acid, or an antibody or fragment thereof which specifically binds to a BVDV surrogate marker polypeptide or peptide fragment.

The term "differential diagnosis" refers to a diagnosis which is able to differentiate between two or more different types of BVDV infection (for example, acute infection, persistent infection, or not infected.) This test also identifies previously vaccinated animals.

The phrase "consisting essentially of" when referring to a particular nucleotide or amino acid means a sequence having the properties of a given SEQ ID NO:.

For example, when used in reference to an amino acid sequence, the phrase includes the sequence per se and molecular modifications that would not affect the functional and unique characteristics of the sequence.

The term "nucleic acid molecule" describes a polymer of deoxyribonucleotides (DNA) or ribonucleotides (RNA). The nucleic acid molecule may be isolated from a natural source by cDNA cloning or subtractive hybridization or synthesized manually. The nucleic acid molecule may be synthesized manually by the triester synthetic method or by using an automated DNA synthesizer.

With regard to nucleic acids used in the invention, the term "isolated nucleic acid" is sometimes employed. This term, when applied to DNA, refers to a DNA molecule that is separated from sequences with which it is immediately contiguous (in the 5' and 3' directions) in the naturally occurring genome of the organism or virus from which it was derived. For example, the "isolated nucleic acid" may comprise a DNA molecule inserted into a vector, such as a plasmid or virus vector, or integrated into the genomic DNA of a prokaryote or eukaryote cells.

An "isolated nucleic acid molecule" may also comprise a cDNA molecule. An isolated nucleic acid molecule inserted into a vector is also sometimes referred to herein as a recombinant nucleic acid molecule.

The term "complementary" describes two nucleotides that can form multiple favorable interactions with one another. For example, adenine is complementary to thymine as they can form two hydrogen bonds. Similarly, guanine and cytosine are complementary since they can form three hydrogen bonds. Thus if a nucleic acid sequence contains the following sequence of bases, thymine, adenine, guanine and cytosine, a "complement" of this nucleic acid molecule would be a molecule containing adenine in the place of thymine, thymine in the place of adenine, cytosine in the place of guanine, and guanine in the place of cytosine. Because the complement can contain a nucleic acid sequence that forms optimal interactions with the parent nucleic acid molecule, such a complement can bind with high affinity to its parent molecule.

With respect to single stranded nucleic acids, particularly oligonucleotides, the term "specifically hybridizing" refers to the association between two single-stranded nucleotide molecules of sufficiently complementary sequence to permit such hybridization under pre-determined conditions generally used in the art (sometimes termed "substantially complementary"). In particular, the term refers to hybridization of an oligonucleotide with a substantially complementary sequence contained within a single-stranded DNA or RNA molecule of the invention, to the substantial exclusion of hybridization of the oligonucleotide with single-stranded nucleic acids of non-complementary sequence. Appropriate conditions enabling specific hybridization of single stranded nucleic acid molecules of varying complementarity are well known in the art.

For instance, one common formula for calculating the stringency conditions required to achieve hybridization between nucleic acid molecules of a specified sequence homology is set forth below (Sambrook et al., Molecular Cloning, Cold Spring Harbor Laboratory (1989):

$$Tm=81.5° C.+16.6 \text{ Log } [Na+]+0.41(\% G+C)-0.63(\% \text{ formamide})-600/\#bp \text{ in duplex.}$$

As an illustration of the above formula, using [Na+]=[0.368] and 50% formamide, with GC content of 42% and an average probe size of 200 bases, the Tm is 57° C. The Tm of a DNA duplex decreases by 1-1.5° C. with every 1% decrease in homology. Thus, targets with greater than about 75% sequence identity would be observed using a hybridization temperature of 42° C.

The stringency of the hybridization and wash depend primarily on the salt concentration and temperature of the solutions. In general, to maximize the rate of annealing of the probe with its target, the hybridization is usually carried out at salt and temperature conditions that are 20-25° C. below the calculated Tm of the hybrid.

Wash conditions should be as stringent as possible for the degree of identity of the probe for the target. In general, wash conditions are selected to be approximately 12-20° C. below the Tm of the hybrid. In regards to the nucleic acids of the current invention, a moderate stringency hybridization is defined as hybridization in 6×SSC, 5×Denhardt's solution, 0.5% SDS and 100 pg/ml denatured salmon sperm DNA at 42° C., and washed in 2×SSC and 0.5% SDS at 55° C. for 15 minutes. A high stringency hybridization is defined as hybridization in 6×SSC, 5×Denhardt's solution, 0.5% SDS and 100 pg/ml denatured salmon sperm DNA at 42° C., and washed in 1×SSC and 0.5% SDS at 65° C. for 15 minutes. A very high stringency hybridization is defined as hybridization in 6×SSC, 5×Denhardt's solution, 0.5% SDS and 100 pg/ml denatured salmon sperm DNA at 42° C., and washed in 0.1× SSC and 0.5% SDS at 65° C. for 15 minutes.

The term "oligonucleotide" as used herein refers to primers and probes of the present invention, and is defined as a nucleic acid molecule comprised of two or more ribo- or deoxyribo-nucleotides, preferably more than three. The exact size of the oligonucleotide will depend on various factors and on the particular application and use of the oligonucleotide. Oligonucleotides, which include probes and primers, can be any length from 3 nucleotides to the full length of the nucleic acid molecule, and explicitly include every possible number of contiguous nucleic acids from 3 through the full length of the polynucleotide. Preferably, oligonucleotides, which include probes and/or primers are at least about 10 nucleotides in length, more preferably at least 15 nucleotides in length, more preferably at least about 20 nucleotides in length.

The term "probe" as used herein refers to an oligonucleotide, polynucleotide or nucleic acid, either RNA or DNA, whether occurring naturally as in a purified restriction enzyme digest or produced synthetically, which is capable of annealing with or specifically hybridizing to a nucleic acid with sequences complementary to the probe. A probe may be either single-stranded or double-stranded. The exact length of the probe will depend upon many factors, including temperature, source of probe and use of the method. For example, for diagnostic applications, depending on the complexity of the target sequence, the oligonucleotide probe typically contains 15-25 or more nucleotides, although it may contain fewer nucleotides. The probes herein are selected to be complementary to different strands of a particular target nucleic acid sequence.

This means that the probes must be sufficiently complementary so as to be able to "specifically hybridize" or anneal with their respective target strands under a set of pre-determined conditions. Therefore, the probe sequence need not reflect the exact complementary sequence of the target. For example, a non-complementary nucleotide fragment may be attached to the 5' or 3'end of the probe, with the remainder of the probe sequence being complementary to the target strand. Alternatively, non-complementary bases or longer sequences can be interspersed into the probe, provided that the probe sequence has sufficient complementarity with the sequence of the target nucleic acid to anneal therewith specifically.

The term "primer" as used herein refers to an oligonucleotide, either RNA or DNA, either single-stranded or double-stranded, either derived from a biological system, generated by restriction enzyme digestion, or produced synthetically which, when placed in the proper environment, is able to functionally act as an initiator of template-dependent nucleic acid synthesis. When presented with an appropriate nucleic acid template, suitable nucleoside triphosphate precursors of nucleic acids, a polymerase enzyme, suitable cofactors and conditions such as a suitable temperature and pH, the primer may be extended at its 3 terminus by the addition of nucleotides by the action of a polymerase or similar activity to yield a primer extension product. The primer may vary in length depending on the particular conditions and requirement of the application. For example, in diagnostic applications, the oligonucleotide primer is typically 15-25 or more nucleotides in length. The primer must be of sufficient complementarity to the desired template to prime the synthesis of the desired extension product, that is, to be able anneal with the desired template strand in a manner sufficient to provide the 3'hydroxyl moiety of the primer in appropriate juxtaposition for use in the initiation of synthesis by a polymerase or similar enzyme. It is not required that the primer sequence represent an exact complement of the desired template.

For example, a non-complementary nucleotide sequence may be attached to the 5'end of an otherwise complementary primer. Alternatively, non-complementary bases may be interspersed within the oligonucleotide primer sequence, provided that the primer sequence has sufficient complementarity with the sequence of the desired template strand to functionally provide a template-primer complex for the synthesis of the extension product. Polymerase chain reaction (PCR) has been described in U.S. Pat. Nos. 4,683,195, 4,800,195, and 4,965,188, the entire disclosures of which are incorporated by reference herein.

The term "vector" relates to a single or double stranded circular nucleic acid molecule that can be transfected or transformed into cells and replicate independently or within the host cell genome. A circular double stranded nucleic acid molecule can be cut and thereby linearized upon treatment with restriction enzymes. An assortment of vectors, restriction enzymes, and the knowledge of the nucleotide sequences that are targeted by restriction enzymes are readily available to those skilled in the art. A vector of the invention includes any replicon, such as a plasmid, cosmid, bacmid, phage or virus, to which another genetic sequence or element (either DNA or RNA) may be attached so as to bring about the replication of the attached sequence or element. A nucleic acid molecule of the invention can be inserted into a vector by cutting the vector with restriction enzymes and ligating the two pieces together.

Many techniques are available to those skilled in the art to facilitate transformation, transfection, or transduction of the expression construct into a prokaryotic or eukaryotic organism. The terms "transformation", "transfection", and "transduction" refer to methods of inserting a nucleic acid and/or expression construct into a cell or host organism. These methods involve a variety of techniques, such as treating the cells with high concentrations of salt, an electric field, or detergent, to render the host cell outer membrane or wall permeable to nucleic acid molecules of interest, microinjection, PEG-fusion, and the like.

The term "promoter element" describes a nucleotide sequence that is incorporated into a vector that, once inside an appropriate cell, can facilitate transcription factor and/or polymerase binding and subsequent transcription of portions of the vector DNA into mRNA. In one embodiment, the promoter element of the present invention precedes the 5'end of the BVDV surrogate marker nucleic acid molecule such that the latter is transcribed into mRNA. Host cell machinery then translates mRNA into a polypeptide.

Those skilled in the art will recognize that a nucleic acid vector can contain nucleic acid elements other than the promoter element and the BVDV surrogate marker gene nucleic acid molecule. These other nucleic acid elements include, but are not limited to, origins of replication, ribosomal binding sites, nucleic acid sequences encoding drug resistance enzymes or amino acid metabolic enzymes, and nucleic acid sequences encoding secretion signals, periplasm or peroxisome localization signals, or signals useful for polypeptide purification.

An "expression operon" refers to a nucleic acid segment that may possess transcriptional and translational control sequences, such as promoters, enhancers, translational start signals (e.g., ATG or AUG codons), polyadenylation signals, terminators, and the like, and which facilitate the expression of a polypeptide coding sequence in a host cell or organism.

As used herein, the terms "reporter", "reporter system", "reporter gene", or "reporter gene product" shall mean an operative genetic system in which a nucleic acid comprises a gene that encodes a product that when expressed produces a reporter signal that is a readily measurable, e.g., by biological assay, immunoassay, radio immunoassay, or by colorimetric, fluorogenic, chemiluminescent or other methods. The nucleic acid may be either RNA or DNA, linear or circular, single or double stranded, antisense or sense polarity, and is operatively linked to the necessary control elements for the expression of the reporter gene product. The required control elements will vary according to the nature of the reporter system and whether the reporter gene is in the form of DNA or RNA, but may include, but not be limited to, such elements as promoters, enhancers, translational control sequences, polyA addition signals, transcriptional termination signals and the like.

The introduced nucleic acid may or may not be integrated (covalently linked) into nucleic acid of the recipient cell or organism. In bacterial, yeast, plant and mammalian cells, for example, the introduced nucleic acid may be maintained as an episomal element or independent replicon such as a plasmid. Alternatively, the introduced nucleic acid may become integrated into the nucleic acid of the recipient cell or organism and be stably maintained in that cell or organism and further passed on or inherited to progeny cells or organisms of the recipient cell or organism. Finally, the introduced nucleic acid may exist in the recipient cell or host organism only transiently.

The term "selectable marker gene" refers to a gene that when expressed confers a selectable phenotype, such as antibiotic resistance, on a transformed cell.

The term "operably linked" means that the regulatory sequences necessary for expression of the coding sequence are placed in the DNA molecule in the appropriate positions relative to the coding sequence so as to effect expression of the coding sequence. This same definition is sometimes applied to the arrangement of transcription units and other transcription control elements (e.g., enhancers) in an expression vector.

The term "tag", "tag sequence", or "protein tag" refers to a chemical moiety, either a nucleotide, oligonucleotide, polynucleotide or an amino acid, peptide or protein or other chemical, that when added to another sequence, provides additional utility or confers useful properties, particularly in the detection or isolation, of that sequence. Thus, for example, a homopolymer nucleic acid sequence or a nucleic acid sequence complementary to a capture oligonucleotide may be added to a primer or probe sequence to facilitate the subsequent isolation of an extension product or hybridized product. In the case of protein tags, histidine residues (e.g., 4 to 8 consecutive histidine residues) may be added to either the amino- or carboxy-terminus of a protein to facilitate protein isolation by chelating metal chromatography. Alternatively, amino acid sequences, peptides, proteins or fusion partners representing epitopes or binding determinants reactive with specific antibody molecules or other molecules (e.g., flag epitope, c-myc epitope, transmembrane epitope of the influenza A virus hemaglutinin protein, protein A, cellulose binding domain, calmodulin binding protein, maltose binding protein, chitin binding domain, glutathione S-transferase, and the like) may be added to proteins to facilitate protein isolation by procedures such as affinity or immunoaffinity chromatography.

Chemical tag moieties include such molecules as biotin, which may be added to either nucleic acids or proteins and facilitates isolation or detection by interaction with avidin reagents, and the like. Numerous other tag moieties are known to, and can be envisioned by the trained artisan, and are contemplated to be within the scope of this definition.

A "specific binding pair" comprises a specific binding member (sbm) and a binding partner (bp) which have a particular specificity for each other and which in normal conditions bind to each other in preference to other molecules. Examples of specific binding pairs are antigens and antibodies, ligands and receptors and complementary nucleotide sequences. The skilled person is aware of many other examples. Further, the term "specific binding pair" is also applicable where either or both of the specific binding member and the binding partner comprise a part of a large molecule. In embodiments in which the specific binding pair comprises nucleic acid sequences, they will be of a length to hybridize to each other under conditions of the assay, preferably greater than 10 nucleotides long, more preferably greater than 15 or 20 nucleotides long.

An "antibody" or "antibody molecule" is any immunoglobulin, including antibodies and fragments thereof, that binds to a specific antigen. The term includes polyclonal, monoclonal, chimeric, and bispecific antibodies. Exemplary antibody fragments, capable of binding an antigen or other binding partner, are Fab fragment consisting of the VL, VH, C1 and CH1 domains; the Fd fragment consisting of the VH and CH1 domains; the Fv fragment consisting of the VL and VH domains of a single arm of an antibody; the dAb fragment which consists of a VH domain; isolated CDR regions and F (ab') 2 fragments, a bivalent fragment including two Fab fragments linked by a disulphide bridge at the hinge region. Single chain Fv fragments are also included.

With respect to antibodies, the term "immunologically specific" refers to antibodies that bind to one or more epitopes of a protein or compound of interest, but which do not substantially recognize and bind other molecules in a sample containing a mixed population of antigenic biological molecules. Exemplary antibodies bind to a protein or peptide fragment encoded by a nucleotide sequence set forth in Tables 1-9.

A "detection reagent" or a "marker detection reagent" is any substance which has binding affinity for a BVDV specific molecule, and includes but is not limited to nucleic acid molecules with sufficient affinity to hybridize to the BVDV specific marker, probes, primers, antibodies, fragments thereof, and the like. The "detection reagent" or "marker detection reagent" may optionally be detectably labeled.

The term "detectable label" is used herein to refer to any substance whose detection or measurement, either directly or indirectly, by physical or chemical means, is indicative of the presence of a target bioentity in a test sample. Representative examples of useful detectable labels, include, but are not limited to the following: molecules or ions directly or indirectly detectable based on light absorbance, fluorescence, reflectance, light scatter, phosphorescence, or luminescence properties; molecules or ions detectable by their radioactive properties; molecules or ions detectable by their nuclear magnetic resonance or paramagnetic properties. Included among the group of molecules indirectly detectable based on light absorbance or fluorescence, for example, are various enzymes which cause appropriate substrates to convert, e.g., from non-light absorbing to light absorbing molecules, or from non-fluorescent to fluorescent molecules.

II. Surrogate BVDV Nucleic Acid Molecules, Probes, and Primers and Methods of Preparing the Same Encompassed by the invention are surrogate BVDV nucleic acid molecules, nucleic acid molecules which encode isolated, enriched, or purified surrogate BVDV proteins or peptides, including allelic variations, analogues, fragments, derivatives, mutants, and modifications of the same.

Surrogate BVDV nucleic acid molecules, and nucleic acid sequences encoding surrogate BVDV proteins may be isolated from appropriate biological sources using methods known in the art. In a preferred embodiment, a cDNA clone is isolated from a cDNA expression library of bovine origin. Preferably, the sample is isolated from a bovine which has been vaccinated for, or has acute, or persistent BVDV infection.

Surrogate BVDV marker polynucleotides can be any one of, or any combination of the markers shown in Tables 1-9, and further may include variants which are at least about 75%, or 80% or 85% or 90% or 95%, and often, more than 90%, or more than 95% homologous to the markers shown in Tables 1-9, over the full length sequence. Surrogate BVDV marker polynucleotides also may be 60% or 65% or 70% or 75% or 80% or 85% or 90% or 95% or 97% or 98% or 99% or greater than 99% homologous to the markers shown in Tables 1-9, over the full length sequence. All homology may be computed by algorithms known in the art, such as BLAST, described in Altschul et al. (1990), J. Mol. Biol. 215: 403-10, or the Smith-Waterman homology search algorithm as implemented in MPSRCH program (Oxford Molecular). Someone of ordinary skill in the art would readily be able to determine the ideal gap open penalty and gap extension penalty for a particular nucleic acid sequence.

Exemplary search parameters for use with the MPSRCH program in order to identify sequences of a desired sequence identity are as follows: gap open penalty: −16; and gap extension penalty: −4.

Degenerate variants are also encompassed by the instant invention. The degeneracy of the genetic code permits substitution of certain codons by other codons, which specify the same amino acid and hence would give rise to the same protein. The nucleic acid sequence can vary substantially since, with the exception of methionine and tryptophan, the known amino acids can be coded for by more than one codon. Thus, portions or all of the markers could be synthesized to give a nucleic acid sequence significantly different from that shown in Tables 1-9. The encoded amino acid sequence thereof would, however, be preserved.

In addition, the nucleic acid sequence may comprise a nucleotide sequence which results from the addition, deletion or substitution of at least one nucleotide to the 5'-end and/or the 3'-end of one or more of the markers shown in Tables 1-9, or a derivative thereof. Any nucleotide or polynucleotide may be used in this regard, provided that its addition, deletion or substitution does not alter the amino acid sequence which is encoded by the nucleotide sequence, or it still shares a region of homology with one or more of the markers shown in Tables 1-9. For example, the present invention is intended to include any nucleic acid sequence resulting from the addition of ATG as an initiation codon at the 5'-end of the surrogate BVDV marker nucleic acid sequence or its functional derivative, or from the addition of TTA, TAG or TGA as a termination codon at the 3'-end of the inventive nucleotide sequence or its derivative. Moreover, the nucleic acid molecule of the present invention may, as necessary, have restriction endonuclease recognition sites added to its 5'-end and/or 3'-end.

Such functional alterations of a given nucleic acid sequence afford an opportunity to promote secretion and/or processing of heterologous proteins encoded by foreign nucleic acid sequences fused thereto. All variations of the nucleotide sequence of the markers shown in Tables 1-9 and fragments thereof permitted by the genetic code are, therefore, included in this invention.

In an alternative embodiment, utilizing the sequence information provided by the cDNA sequence, genomic clones encoding a surrogate BVDV marker gene may be isolated.

Alternatively, cDNA or genomic clones having homology with the markers shown in Tables 1-9 may be isolated from other species, such as mouse or human, using oligonucleotide probes corresponding to predetermined sequences within surrogate BVDV marker gene.

III. Surrogate BVDV Proteins (Antigens) and Methods of Making the Same

Encompassed by the invention are isolated, purified, or enriched surrogate BVDV polypeptides, including allelic variations, analogues, fragments, derivatives, mutants, and modifications of the same which are differentially expressed in BVDV animals. Preferably, surrogate BVDV marker polypeptides include polypeptides encoded by one or more of the sequences shown in Tables 1-9. Surrogate BVDV marker function is defined above, and includes increased or decreased expression in response to BVDV infection, cross-reactivity with an antibody reactive with the polypeptides encoded by one or more of the sequences shown in Tables 1-9 or sharing an epitope with the same (as determined for example by immunological cross-reactivity between the two polypeptides). Surrogate BVDV marker polypeptides or proteins can be encoded by one or more of the sequences shown in Tables 1-9, and further may include variants which are at least about 75%, or 80% or 85% or 90% or 95%, and often, more than 90%, or more than 95% homologous to the same over the full length sequence.

Surrogate BVDV marker polypeptides also may be 60% or 65% or 70% or 75% or 80% or 85% or 90% or 95% or 97% or 98% or 99% or greater than 99% homologous to polypeptides encoded by one or more of the sequences shown in Tables 1-9 over the full length sequence. All homology may be computed by algorithms known in the art, such as BLAST, described in Altschul et al. (1990), J. Mol. Biol. 215: 403-10, or the Smith-Waterman homology search algorithm as implemented in MPSRCH program (Oxford Molecular). Someone of ordinary skill in the art would readily be able to determine the ideal gap open penalty and gap extension penalty for a particular protein sequence. Exemplary search parameters for use with the MPSRCH program in order to identify sequences of a desired sequence identity are as follows: gap open penalty: —12; and gap extension penalty: —2.

A full-length or truncated surrogate BVDV protein of the present invention may be prepared in a variety of ways, according to known methods. The protein may be purified from appropriate sources, e.g., transformed bacterial or animal cultured cells or tissues, by immunoaffinity purification. Additionally, the surrogate BVDV protein may be produced using in vitro expression methods known in the art. For example, a cDNA or gene may be cloned into an appropriate in vitro transcription vector, such as pSP64 or pSP65 for in vitro transcription, followed by cell-free translation in a suitable cell-free translation system, such as wheat germ or rabbit reticulocyte lysates. In vitro transcription and translation systems are commercially available, e.g., from Promega Corp., Madison, Wis. or Invitrogen Corp., Carlsbad, Calif.

The surrogate BVDV proteins produced by gene expression in a recombinant prokaryotic or eukaryotic system may be purified according to methods known in the art. In a preferred embodiment, a commercially available expression/secretion system can be used, whereby the recombinant protein is expressed and thereafter secreted from the host cell, to be easily purified from the surrounding medium. If expression/secretion vectors are not used, an alternative approach involves purifying the recombinant protein by affinity separation, such as by immunological interaction with antibodies that bind specifically to the recombinant protein or nickel columns for isolation of recombinant proteins tagged with 6-8 histidine residues at their N-terminus or C-terminus.

Alternative tags may comprise the FLAG epitope or the hemagglutinin epitope. Such methods are commonly used by skilled practitioners.

IV. Anti-Surrogate BVDV Protein Antibodies and Methods of Making the Same

The present invention also provides methods of making and using antibodies capable of immunospecifically binding to surrogate BVDV proteins. Polyclonal antibodies directed toward surrogate BVDV proteins may be prepared according to standard methods. In a preferred embodiment, monoclonal antibodies are prepared, which react immunospecifically with the various epitopes on the surface of the surrogate BVDV protein. Monoclonal antibodies may be prepared according to general methods of Kohler and Milstein, following standard protocols.

Purified BVDV antigens, or fragments thereof, may be used to produce polyclonal or monoclonal antibodies which also may serve as sensitive detection reagents for the various types of BVDV infection (acute, PI, vaccination reaction, and not infected). Recombinant techniques enable expression of fusion proteins containing part or all of BVDV. The surrogate BVDV protein itself, or surface proteins or antigens from the surrogate BVDV protein may be used to advantage to generate an array of monoclonal antibodies specific for various epitopes of the surrogate BVDV protein, thereby providing even greater sensitivity for detection of the surrogate BVDV protein (and thus BVDV infection) in samples.

Polyclonal or monoclonal antibodies that immunospecifically interact with BVDV antigens can be utilized for identifying and diagnosing BVDV. For example, antibodies may be utilized for affinity separation of proteins with which they immunospecifically interact. Antibodies may also be used to immunoprecipitate proteins from a sample containing a mixture of proteins and other biological molecules.

Other uses of anti-surrogate BVDV protein antibodies are described below.

V. Methods of Using Surrogate BVDV Polynucleotides, Polypeptides, and Antibodies for Screening and Diagnostic Assays Surrogate BVDV nucleic acids may be used for a variety of purposes in accordance with the present invention. Surrogate BVDV nucleic acids (DNA, RNA, fragments thereof, etc.), or protein-encoding DNA, RNA, or fragments thereof may be used as probes to detect the presence of surrogate BVDV nucleic acids or protein in a sample. Methods in which surrogate BVDV nucleic acids and protein-encoding nucleic acids may be utilized as probes for such assays include, but are not limited to: (1) in situ hybridization; (2) Southern hybridization (3) northern hybridization; (4) gene chip analysis and (5) assorted amplification reactions such as polymerase chain reactions (PCR).

Exemplary surrogate BVDV nucleic acids and nucleic acids encoding exemplary surrogate BVDV proteins or peptides are described in Tables 1-9.

The surrogate BVDV nucleic acids of the invention may also be utilized as probes to identify related surrogate BVDV variants. As is well known in the art, hybridization stringencies may be adjusted to allow hybridization of nucleic acid probes with complementary sequences of varying degrees of homology. Thus, BVDV surrogate marker nucleic acids may be used to advantage to identify and characterize other genes of varying degrees of relation to BVDV surrogate markers, thereby enabling further characterization of BVDV surrogate markers. Additionally, they may be used to identify genes encoding proteins that interact with BVDV surrogate markers (e.g., by the "interaction trap" technique—see for example Current Protocols in Molecular Biology, ed. Ausubel, F. M., et al., John Wiley & Sons, NY, 1997), which should further accelerate identification of the molecular components involved in BVDV. Finally, they may be used in assay methods to detect BVDV.

Polyclonal or monoclonal antibodies immunologically specific for proteins encoded by BVDV surrogate markers or peptide fragments thereof may be used in a variety of assays designed to detect and quantitate the protein, as well as to detect ruminant BVDV by detecting upregulation of BVDV surrogate markers. Such assays include, but are not limited to: (1) flow cytometric analysis; (2) immunochemical localization of BVDV specific markers in a body cell, tissue, or fluid; and (3) immunoblot analysis (e.g., dot blot, Western blot) (4) ELISA; (5) radioimmunoassay of extracts from various cells.

Additionally, as described above, anti-surrogate BVDV marker protein can be used for purification of surrogate BVDV markers (e.g., affinity column purification, immunoprecipitation).

Further, assays for detecting and quantitating surrogate BVDV markers, or to detect ruminant BVDV by detecting upregulation of BVDV specific markers may be conducted on any type of biological sample where upregulation of these molecules is observed, including but not limited to body fluids (including blood, serum, plasma, milk, or saliva), any type of cell (such as skin cells, or blood cells, or endothelial cells), or body tissue.

From the foregoing discussion, it can be seen that surrogate BVDV marker nucleic acids, surrogate BVDV marker expressing vectors, surrogate BVDV marker proteins and anti-surrogate BVDV marker antibodies of the invention can be used to detect surrogate BVDV marker expression in body tissue, cells, or fluid, and alter BVDV specific marker protein expression for purposes of assessing the genetic and protein interactions involved in BVDV and infection.

In most embodiments for screening for surrogate BVDV mRNA, surrogate BVDV nucleic acid in the sample will initially be amplified, e.g. using PCR, to increase the amount of the template as compared to other sequences present in the sample. This allows the target sequences to be detected with a high degree of sensitivity if they are present in the sample.

Thus any of the aforementioned techniques may be used as a diagnostic tool for detecting surrogate BVDV markers.

Further, these techniques could be used to diagnose infectious diseases in humans, by detection of a surrogate marker (rather than a viral antigen). For example, differential gene expression could be measured in HIV, Ebola, Hepatitis, and Herpes viral infections, etc. These tests are advantageous in that they are directed to detection of a theoretically harmless surrogate marker, rather than the infectious agent itself.

Such techniques could also be used to diagnose infectious diseases in companion animals by detection of a surrogate marker (rather than a viral antigen). An example of a potential application would be the diagnosis of feline infectious peritonitis of cats and latent viral infections caused by herpes viruses for which current diagnostic tests (based on isolation and characterization of the virus) have a marginal reliability. In addition, this technology could also be used for the diagnosis of cancer through the identification of surrogate cancer markers.

The instant inventive method improves upon the accuracy of current BVDV tests. A combination test, which measures both BVDV itself, and also one or more BVDV surrogate marker, to differentially diagnose BVDV infection provides superior diagnostic results in the field.

VI. Assays for Differentially Diagnosing BVDV Using Specific Surrogate Markers

In accordance with the present invention, it has been discovered that Bovine Viral Diarrhea Virus (BVDV) is correlated with increased expression levels of certain markers, including but not limited to mRNAs and proteins.

Thus, these molecules may be utilized in conventional assays to differentially diagnose BVDV. The detection of one or more of these differentially expressed BVDV surrogate molecules in a sample is indicative of BVDV. Similarly, specific patterns of expression allow detection of acute versus persistent infection. Alternatively, the absence of these molecules in a sample indicates that a ruminant is not infected with BVDV.

In an exemplary method, a blood sample is obtained from a bovine suspected of having an acute or persistent BVDV infection. Optionally, the blood may be centrifuged through a Hypaque gradient to obtain the buffy coat. The blood or buffy coat preparation is diluted and subjected to polymerase chain reaction conditions suitable for amplification of the BVDV surrogate marker encoding mRNA.

In certain applications, it may be necessary to include an agent, which lyses cells prior to performing the PCR.

Such agents are well known to the skilled artisan. The reaction products are then analyzed, e.g., via gel electrophoresis. An increase in BVDV surrogate marker mRNA levels relative to levels obtained from a non-infected bovine is indicative of BVDV in the animal being tested. Alternatively, an increase in BVDV surrogate markers in AI animals relative to PI animals, or in PI animals, relative to AI animals, can differentially diagnose acute infection, or persistent infection.

In an alternative method, a skin tissue sample is obtained from the bovine suspected of having acute or persistent BVDV infection. The cells are then lysed and PCR performed. As above, an increase in BVDV surrogate marker mRNA expression levels relative to those observed in a non-BVDV infected animal being indicative of BVDV in the test animal.

It is also possible to detect BVDV using immunoassays. In an exemplary method, blood is obtained from a bovine suspected of being infected with BVDV. As above, the blood may optionally be centrifuged through a Hypaque gradient to obtain a buffy coat. The blood or buffy coat sample is diluted and at least one antibody immunologically specific for BVDV surrogate markers is added to the sample. In a preferred embodiment, the antibody is operably linked to a detectable label. Also as described above, the cells may optionally be lysed prior to contacting the sample with the antibodies immunologically specific for BVDV surrogate markers.

Increased production of BVDV surrogate markers is assessed as a function of an increase in the detectable label relative to that obtained in parallel assays using blood from non-BVDV infected cow. In yet another embodiment, the blood or buffy coat preparation is serially diluted and aliquots added to a solid support.

Suitable solid supports include multi-well culture dishes, blots, filter paper, and cartridges. The solid support is then contacted with the detectably labeled antibody and the amount of BVDV surrogate marker protein (e.g., a protein or peptide encoded by a nucleic acid of Tables 1-9) in the animal suspected of being infected with BVDV is compared with the amount obtained from a non-AI or PI animal as a function of detectably labeled antibody binding. An alteration in the BVDV surrogate marker protein level in the test animal relative to the non-AI or PI infected control animal is indicative of acute or persistent BVDV.

In another embodiment, a first antibody which binds to a first epitope on a target protein is placed in the well of a cartridge. Whole blood, blood collected in the presence of anticoagulants (e.g., sodium citrate, heparin), plasma, or serum is placed into the well of the cartridge. The target protein, if present in the sample, is bound by the first antibody, and then migrates laterally by a wicking action, through a filter which has been sprayed with second antibody. The second antibody has affinity for a second epitope on the target protein, or alternatively for the first antibody. The second antibody is optionally labeled with a detectable label (e.g. radiolabel, gold, biotin, enzyme, etc.) The second antibody localizes the antigen, and results in the appearance of a line on the filter. The first and second antibodies may be generated against the full length target protein, or against the N-terminal or C-terminal halves of the target protein, so that they recognize different epitopes of the target protein.

The foregoing immunoassay methods may also be applied to any type of sample, including a urine sample.

VII. Kits and Articles of Manufacture

Any of the aforementioned products or methods can be incorporated into a kit which may contain a BVDV specific polynucleotide, an oligonucleotide, a polypeptide, a peptide, a solid support (e.g., filters, cartridges, gene chips) an antibody, a label, marker, or reporter, a pharmaceutically acceptable carrier, a physiologically acceptable carrier, instructions for use, negative and positive control samples, a container, a vessel for administration, an assay substrate, or any combination thereof.

The following materials and methods are provided to facilitate the practice of the invention. The Examples illustrate certain embodiments of the invention. They are not intended to limit its scope in any way.

Example 1

Bovine viral diarrhea virus (BVDV) infections are responsible for important economic losses due to reproductive wastage, and respiratory and digestive disease in cattle. Infection of the early developing fetus frequently results in persistent infection (PI). PI animals are the main source of new infection in herd mates. The complex host-viral interactions resulting from persistent infection are minimally understood, particularly in the bovine host. We hypothesized that gene expression would differ in bloods collected from PI when compared to non-infected steers. In preliminary studies, bloods were collected from three PI or three control steers and were processed to yield total cellular RNA. Labeled RNA was used to screen six independent bovine Affymetrix DNA chips, and analyzed for fold-changes at the University of Colorado Health Sciences Center Microarray Facility. The top 100 up-regulated genes belonged to MHC class I (45-fold), antiviral (32-100 fold), transcription factor (8-12 fold), interferon stimulated genes (5-28 fold), bone remodeling (4-9 fold), and chemokine (2-4) families. The top 100 down-regulated genes belonged to adhesion (5-10 fold), T-cell receptor (5-10 fold), extracellular matrix (3-5 fold), growth factor (2-3 fold), and transcription factor (2-3 fold) families. We conclude from these findings that persistent infection with BVDV results in antiviral responses in blood cells which includes induction of type 1 interferon-induced genes, chemokine-mediated immune responses and bone remodeling with a concomitant suppression of extracellular remodeling, adhesion and T-cell-mediated responses. Thus, in accordance with the present invention, single and/or multiplexing diagnostics for identifying cattle that are persistently infected with BVDV are provided.

BVDV is divided into two biotypes: cytopathic (cp) and non-cytopathic (ncp). There are at least two recognized genotypes based on the sequence of the 5' untranslated region, type I and type II, and additional sub-genotypes. Within each genotype, there are several strains that cause different degrees of clinical signs. The pathogenesis of BVDV infection has features that are unique to this virus and that vary with the virulence of the viral strain and age of the animal at the time of infection.

Figure 1:
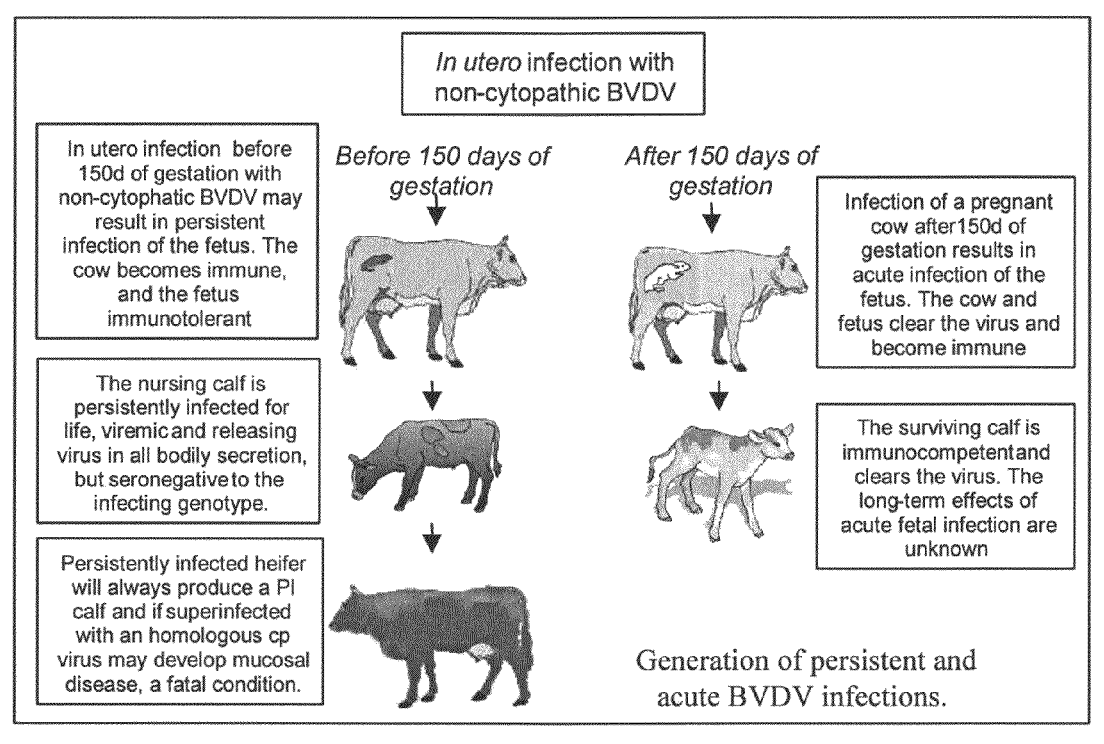

Particularly interesting are the outcomes of infection of the fetus. Infection of the fetus during the first 150 days of gestation, when the immune system has not yet developed, can lead to the generation of PI calves (FIG. 1). Some of these PI calves die soon after birth, but others live for relatively long periods of time without showing any clinical signs. PI animals cannot eliminate the infecting BVDV from their system and continuously release high amounts of virus in their bodily secretions. This makes them a continuous source of infection within the herd and potentially to other herds. When the infection occurs after 150 days of gestation (post-development of the immune system) or after birth, the infection is referred to as acute and these animals, which clear the virus, are frequently called transiently infected (TI). The clinical manifestations of acute infections with BVDV range from sub-clinical, or unapparent infections, to embryonic death, abortions, stillbirths, and malformed or slow-growing calves. Although recent studies indicate that transient infection of the fetus may cause long-term detrimental effects in the development of the calf, the basis for these effects is not clearly understood.

Acute infection with the ncp biotype results in inhibition of double-stranded RNA-induced apoptosis and type 1 interferon, both indicated as plausible contributors to the establishment of persistent infection. However, in vitro and in vivo infections with the cp biotype induce apoptosis and are associated with increased type I interferon production.

The role of PI animals in the perpetuation of BVDV infections cannot be overemphasized. The presence of a single PI calf in a herd can cause severe losses within that herd and any herd with which the PI calf makes contact. The large percentage of seropositive cattle due to vaccination in the USA diminishes the value of serology as a monitoring test. In addition, PI animals have absent, extremely low or fluctuating titers against the strain that causes the persistent infection, potentially leading to misdiagnosis, particularly when serology is used as the only test. Current diagnostic tests based on the detection of viral antigen or viral RNA are effective tools for the identification of postnatal detection of PI animals. However, since PI animals shed high amounts of virus, early elimination of PI fetuses should greatly contribute to disrupting the infectious viral cycle.

In other preliminary studies, we demonstrated that calves persistently infected with BVDV present a differential pattern of gene expression in the blood when compared to vaccinated or acutely infected age-matched herd mates. We investigated the gene expression profiles in the whole blood of one year old PI and non-infected calves that were naturally infected with BVDV using DNA microarray approaches.

Blood samples were collected from three BVDV PI and three vaccinated, non-infected control calves in sodium citrate tubes and placed on ice. RNA was isolated using the QIAamp RNA Blood Mini Kit following the manufacturer's instructions (Qiagen). Red blood cells were selectively lysed, and white cells were collected by centrifugation. White cells were then lysed using highly denaturing conditions, which immediately inactivate RNases. After homogenization using the QIAshredder spin column, the sample was applied to the QIAamp spin column. Total RNA binds to the QIAamp membrane and contaminants were washed away, leaving pure RNA which was eluted in 30-100 μl RNase-free water.

The total RNA was isolated and used for transcriptional profiling by screening the Affymetrix bovine DNA chip. Biotinylated cRNA (15 μg), generated from each RNA sample (n=6 total), was hybridized to the bovine Affymetrix GeneChip (features of which are shown below) Array (n=6 total). Data were analyzed using Affymetrix Microarray Suite Software version 5.0 for absolute and pair-wise comparison analyses. Normalized expression values for the mean and standard deviation of three replicate average difference scores were calculated for each gene. Comparisons were performed using the Student's t test (P<0.05 was considered significant). The raw data were interpreted using GeneSpring (version 5.0, Silicon Genetics, Redwood, Calif.) and GeneSifter software (vizX Labs, LLC, Seattle, Wash.)

| Critical Specifications | |
| --- | --- |
| *Bos taurus* (Bovine) probe sets | 24,072 |
| *Bos taurus* (Bovine) transcripts | approximately 23,000 |
| UniGene clusters | approximately 19,000 |
| Unique probe sets to single species: | |
| Number of arrays in set | one |
| Array format | 100 |
| Feature size | 11 μm |
| Oligonucleotide probe length | 25-mer |
| Probe pairs/sequence | 11 |
| Hybridization controls: | bioB, bioC, bioD, from *E. coli* and cre from P1 *B. subtilis* |
| Poly-A controls: | dap, lys, phe, thr, trp from *B. subtilis* |
| Housekeeping/Control genes: | actin, GAPDH, efIα, 5.8S rRNA, 12S rRNA, 18S rRNA, cyclophilin B, glutathione S-transferase, lactophorin, translation initiation factor eIF-4E |
| Detection sensitivity | 1:100,000[1] |

[1]As measured by detection in comparative analysis between a complex target containing spiked control transcriptions and a complex target with no spikes
©

Results

Two hundred genes were up-regulated in blood from PI when compared to vaccinated control calves. Known attributes of the top 100 up-regulated genes and fold changes are listed below.

| | |
| --- | --- |
| 45 fold | MHC Class I Molecules |
| 10-32 fold | Antiviral genes |
| 8-12 fold | Signal Transduction Molecules |
| 5-28 fold | Type 1 Interferon-Induced Genes (FIG. 2) |

TABLE 1-continued

Preferred blood cell gene markers that are up-regulated in bloods from steers
that are persistently infected with BVDV when compared to non-infected steers.

| No. | Ratio | p-value | Identifier | Gene Name |
|---|---|---|---|---|
| 14 | ▲ 4.90 | 0.04225 | CB461321 | Transcribed locus, weakly similar to XP_513247.1 interferon, alpha-inducible pro |
| 15 | ▲ 4.59 | 0.00458 | CK950701 | Transcribed locus, strongly similar to XP_342643.1 similar to cDNA sequence BC02 |
| 16 | ▲ 4.54 | 0.02465 | CB443498 | Transcribed locus, moderately similar to XP_514164.1 similar to Putative lymphoc |
| 17 | ▲ 4.47 | 0.01648 | CK848208 | Transcribed locus, weakly similar to XP_524747.1 similar to histocompatibility 2 |
| 18 | ▲ 4.40 | 0.02120 | BM031140 | Transcribed sequence |
| 19 | ▲ 4.23 | 0.02478 | CK940917 | Transcribed locus, moderately similar to XP_036729.2 ubiquitin specific protease |
| 20 | ▲ 4.19 | 0.03751 | CK771386 | Transcribed locus, weakly similar to NP_071430.1 28 kD interferon responsive prot |
| 21 | ▲ 4.17 | 0.04972 | CB419688 | Transcribed locus |
| 22 | ▲ 4.10 | 0.01674 | BI680405 | Transcribed locus, weakly similar to NP_071430.1 28kD interferon responsive prot |
| 23 | ▲ 3.98 | 0.02600 | CK774949 | Transcribed locus, moderately similar to NP_001538.3 interferon-induced protein |
| 24 | ▲ 3.92 | 0.00922 | CK971030 | Transcribed locus, weakly similar to XP_223172.2 similar to hypothetical protein |
| 25 | ▲ 3.86 | 0.03593 | CK726556 | MRNA for signal transducer and activator of transcription 3 (stat3 gene), clone |
| 26 | ▲ 3.70 | 0.03241 | NM_176674 | cytochrome c oxidase subunit VIIa polypeptide 1 (muscle) |
| 27 | ▲ 3.60 | 0.02815 | CB433212 | Transcribed locus, moderately similar to XP_036729.2 ubiquitin specific protease |
| 28 | ▲ 3.56 | 0.01118 | BM362372 | Transcribed locus, weakly similar to NP_071430.1 28kD interferon responsive prot |
| 29 | ▲ 3.54 | 0.04033 | CK776938 | Transcribed locus, moderately similar to NP_004109.1 forkhead-like 18 (Drosophil |
| 30 | ▲ 3.43 | 0.01886 | CB450623 | Transcribed locus, strongly similar to XP_514712.1 LOC458321 [*Pan troglodytes*] |
| 31 | ▲ 3.38 | 0.04495 | NM_174437 | protein C receptor, endothelial (EPCR) |
| 32 | ▲ 3.36 | 0.03686 | CB432365 | Transcribed locus, moderately similar to XP_520524.1 similar to DEAD/H (asp-Glu- |
| 33 | ▲ 3.17 | 0.03882 | BE756263 | Transcribed locus, strongly similar to XP_516406.1 exosome component 7 [Pan trog |
| 34 | ▲ 2.99 | 0.02763 | CK945008 | Transcribed locus, strongly similar to NP_766063.2 FERM domain containing 4A [Mu |
| 35 | ▲ 2.92 | 0.03043 | CK846935 | Transcribed locus, moderately similar to NP_077024.1 likely ortholog of mouse D1 |
| 36 | ▲ 2.91 | 0.01736 | BM433504 | Transcribed locus, strongly similar to NP_032583.1 FXYD domain-containing ion tr |
| 37 | ▲ 2.90 | 0.02889 | AV665367 | Transcribed locus |
| 38 | ▲ 2.85 | 0.04763 | BF440165 | Transcribed locus, moderately similar to XP_036729.2 ubiquitin specific protease |
| 39 | ▲ 2.81 | 0.03809 | CB453859 | Transcribed locus, moderately similar to NP_071451.2 interferon inducedwith hel |
| 40 | ▲ 2.77 | 0.00656 | NM_174609 | solute carrier family 6 (neurotransmitter transporter, serotonin), member 4 |
| 41 | ▲ 2.74 | 0.02272 | NM_178109 | protein kinase, interferon-inducible double stranded RNA dependent |
| 42 | ▲ 2.71 | 0.01431 | NM_174180 | gb: NM_174180.2/DB_XREF = gi: 31342651/GEN = SDR1/TID = Bt.5530.1/CNT = 32/FEA = FLmRNA |
| 43 | ▲ 2.68 | 0.04209 | BM251565 | Transcribed locus, moderately similar to XP_290768.4 chromosome 17 open reading |
| 44 | ▲ 2.59 | 0.00995 | NM_174183 | selectin P |
| 45 | ▲ 2.59 | 0.01398 | CK774054 | Transcribed locus, weakly similar to XP_359137.2 similar to reverse transcriptas |
| 46 | ▲ 2.56 | 0.01791 | CD831204 | Transcribed locus, strongly similar to NP_006858.1 RNA binding protein with mult |
| 47 | ▲ 2.51 | 0.03471 | CK947001 | Transcribed locus |
| 48 | ▲ 2.51 | 0.04073 | CK980170 | Transcribed locus, moderately similar to XP_290768.4 chromosome 17 open reading |
| 49 | ▲ 2.50 | 0.02076 | NM_174007 | chemokine (C-C motif) ligand 8 |
| 50 | ▲ 2.50 | 0.02784 | CB466484 | Transcribed sequence with weak similarity to protein pir: JL0118 (*H. sapiens*) JL01 |

TABLE 2

Preferred blood cell genes that are down-regulated genes in bloods from
steers that are persistently infected with BVDV when compared to non-infected
steers. In this illustration, CK848330, BP102272, AU278490, and BE723387 are
preferred down-regulated markers in persistently infected steers.

Pairwise Analysis: BVDV Steers Con vs PI[Reports: Ontology|KEGG|Scatter Plot]   [Results: Export | Save]

| | Group 1 | Group 2 |
|---|---|---|
| Conditions: | Control | PI |
| Experiments: | 46038, 46039, 46040 | 46041, 46042 |
| Significance: | 1.5, t-test | |
| Normalization: | None | |
| Quality Cutoff: | None (Calls) | |
| Data Transformation: | Log Transformed | |

Show: 20 Sort By: Ratio p Cutoff: 0.05 Search (116 results found) [1-20] [21-40]

| No. | Ratio | p-value | Identifier | Gene Name |
|---|---|---|---|---|
| 1 | ▼ 112.22 | 0.00018 | CK848330 | Transcribed sequences |
| 2 | ▼ 69.02 | 0.00027 | BP102272 | Transcribed sequences |
| 3 | ▼ 54.58 | 0.00006 | AU278490 | Transcribed sequences |
| 4 | ▼ 9.38 | 0.00639 | BE723387 | Transcribed locus, strongly similar to NP_653311.1 septin 10 [*Homo sapiens*] |
| 5 | ▼ 8.72 | 0.02468 | NM_174296 | similar to granzyme B (granzyme 2, cytotoxic T-lymphocyte-associated serine este |
| 6 | ▼ 8.09 | 0.00259 | U73186 | T cell receptor gamma chain variable region BVG3.1 |
| 7 | ▼ 5.22 | 0.04616 | AW315720 | Transcribed locus |
| 8 | ▼ 4.37 | 0.01686 | CK977019 | MAD2 mitoitic arrest deficinet-like 1 (yeast) |
| 9 | ▼ 3.93 | 0.00579 | BF043343 | Transcribed locus, strongly similar to NP_254277.1 GATA binding protein 2 [Rattu |
| 10 | ▼ 3.49 | 0.01155 | CK777919 | Transcribed locus |

TABLE 2-continued Preferred blood cell genes that are down-regulated genes in bloods from steers that are persistently infected with BVDV when compared to non-infected steers. In this illustration, CK848330, BP102272, AU278490, and BE723387 are preferred down-regulated markers in persistently infected steers.

| No. | | Ratio | p-value | Identifier | Gene Name |
|---|---|---|---|---|---|
| 11 | ▼ | 3.40 | 0.01676 | D13661 | T cell receptor delta chain |
| 12 | ▼ | 3.10 | 0.00948 | CK773758 | Transcribed locus, weakly similar to NP_149038.1 mucin 13, eptithelial transmembr |
| 13 | ▼ | 3.09 | 0.02798 | CB535048 | Transcribed sequence with weak similarity to protein ref: NP_508658.1 (*C. elegans*) |
| 14 | ▼ | 3.07 | 0.04211 | BP110719 | Transcribed locus, moderately similar to NP_037306.1 transforming growth factor |
| 15 | ▼ | 2.79 | 0.02192 | CB451804 | Transcribed locus |
| 16 | ▼ | 2.68 | 0.04161 | CK75615 | Transcribed locus, moderately similar to NP_659401.1 RNA (guanine-9-) methyltran |
| 17 | ▼ | 2.65 | 0.02821 | C13656 | T cell receptor delta chain V, D and J regions |
| 18 | ▼ | 2.61 | 0.03624 | CK769833 | Transcribed locus |
| 19 | ▼ | 2.52 | 0.03126 | CK776879 | cadherin 2 [N-cadherin] [N-cadherin 1] |
| 20 | ▼ | 2.46 | 0.03230 | AW481170 | Transcribed locus |

Figure 3:
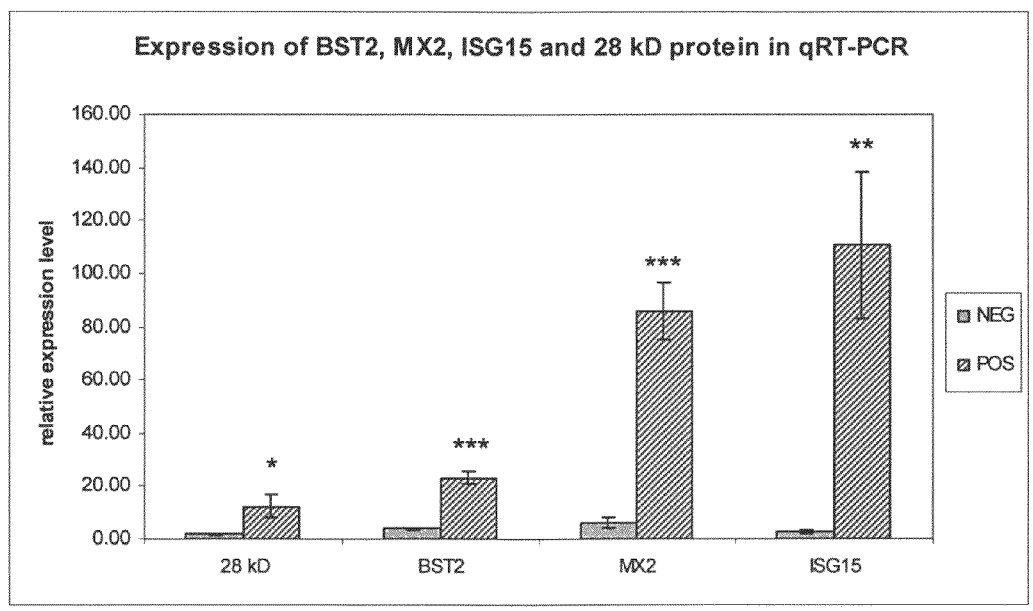
FIG. 3 is a graph showing select blood cell markers that are upregulated in bloods from persistently infected, when compared to non-infected steers using semi-quantitative Real Time PCR (GAPDH used as a control). The 28 kD (interferon induced 28 kD protein; CK771386), BST2 (bone marrow stromal cell surface antigen 2; CK846889), MX2 (myxovirus resistance 2; NM_173941) and ISG15 (Interferon stimulated 15 kDa; NM_174366) markers were all useful blood cell mRNA markers for distinguishing persistent viral infection (positive) when compared to control non-infected steers (negative). In this illustration, ISG15 and MX2 are preferred markers.

As can be seen by the data presented herein, persistent infection with BVDV causes up-regulation and down-regulation of genes in blood cells. Persistent infection with BVDV results in antiviral responses in blood cells. The results show induction of interferon-induced genes, chemokine-mediated immune responses and bone remodeling genes. Suppression of extracellular remodeling, adhesion and T-cell-mediated responses is also observed. One gene, called interferon stimulated gene 15 or ISG15 was confirmed to be up-regulated in bloods from PI when compared to control vaccinated steers using blood cell mRNA and Real Time PCR approaches (FIGS. 2 and 3).

Example 2

We hypothesized that gene expression in white blood cells would differ in pregnant heifers carrying PI, TI or uninfected (control) fetuses. Non-vaccinated heifers were purchased, confirmed to be seronegative for BVDV and were placed on growing rations until they were old enough to be artificially inseminated and confirmed to be pregnant. Heifers were infected with noncytopathic BVDV2 on day 75 to generate PI fetuses, on day 175 to generate TI fetuses, or were not infected (n=6 heifers per treatment). Bloods were collected on days 0, 37, 75, 78, 82, 90, 120, 160, 175, 178, 182 and 190 of gestation for RNA, serology and virology. Fetuses were delivered on d.190 by C-section and necropsied. Maternal blood mRNA on day 190 of gestation was screened using the bovine Affymetrix gene chips.

BVDV infection in heifers and fetuses was confirmed using ELISA and qRT-PCR. Infected pregnant heifers were seropositive for BVDV by days 15-45 post infection. PI fetuses weighed less and were smaller with maldeveloped bone and muscle tissue (P<0.05) when compared to TI or UI fetuses. Screening of 24,000 transcripts on the bovine Affymetrix DNA chip using mRNA from blood cells of heifers on day 190 of pregnancy revealed 67 differentially expressed genes (1.5 fold or greater; P<0.05) based on infection status of the fetus: 32 genes in PI vs. TI, 26 genes in PI vs. control and 47 genes in TI vs. control. These genes were classified based on ontology analysis in primary categories of immune response, antigen presentation, inflammatory response, chemotaxis, protein folding and modification, transport, and defense response to bacteria. Specific genes that are differentially expressed are described in Tables 3-9.

TABLE 3

Preferred upregulated blood cell markers in heifers carrying persistently virally infected, when compared to non-infected fetuses (Control vs. PI: upregulated in PI).

| | Group 1 | Group 2 |
|---|---|---|
| Conditions: | Control | Persistently Infected |
| Experiments: | 44009, 44010, 44011 | 44012, 44013, 44014 |
| Significance: | 1.5, t-test | |
| Normalization: | None | |
| Quality Cutoff: | None (Calls) | |
| Data Transformation: | Log Transformed | |

Show: 20   Sort By: Ratio   p Cutoff: 0.05   Search   (35 results found)   [1-20] [21-35]

| No. | | Ratio | p-value | Identifier | Gene Name |
|---|---|---|---|---|---|
| 1 | ▲ | 2.42 | 0.04287 | CK977019 | MAD2 mitotic arrest deficient-like 1 (yeast) |
| 2 | ▲ | 2.16 | 0.01372 | CA923353 | Transcribed locus |
| 3 | ▲ | 1.96 | 0.01319 | CB461169 | Transcribed sequences |
| 4 | ▲ | 1.94 | 0.01118 | CB445920 | Transcribed sequences |
| 5 | ▲ | 1.86 | 0.00314 | NM_174324 | adenylate cyclase-inhibiting G alpha protein |
| 6 | ▲ | 1.85 | 0.02151 | CK778261 | Transcribed locus, strongly similar to XP_519864.1 similar to cyclin E2 isoform |
| 7 | ▲ | 1.75 | 0.04560 | BF042221 | Transcribed locus |
| 8 | ▲ | 1.72 | 0.00155 | CB463330 | Transcribed locus, strongly similar to XP_214478.2 similar to Succinate semialde |
| 9 | ▲ | 1.70 | 0.04465 | CK979795 | Transcribed locus, strongly similar to NP_055551.1 KIAA0101 [*Homo sapiens*] |
| 10 | ▲ | 1.69 | 0.02380 | CK960396 | Transcribed locus, strongly similar to XP_523625.1similar to CDC6 homolog; CDC1 |

TABLE 3-continued

Preferred upregulated blood cell markers in heifers carrying persistently virally infected, when compared to non-infected fetuses (Control vs. PI: upregulated in PI).

| No. | Ratio | p-value | Identifier | Gene Name |
|---|---|---|---|---|
| 11 | ▲ 1.68 | 0.02461 | CK957227 | Transcribed locus, strongly similar to XP_526535.1 similar to chromosome condens |
| 12 | ▲ 1.68 | 0.03122 | CK846626 | Transcribed sequences |
| 13 | ▲ 1.67 | 0.03347 | CB443446 | Transcribed locus, strongly similar to XP_346407.1 toposomerase (DNA) 2 alpha [ |
| 14 | ▲ 1.66 | 0.00532 | CK837929 | Transcribed locus, moderately similar to NP_006579.2 sulfotransferase family cy |
| 15 | ▲ 1.64 | 0.03202 | CB447702 | Transcribed locus |
| 16 | ▲ 1.61 | 0.02709 | CK874647 | Transcribed locus, strongly similar to NP_004144.2 origin recognition complex, s |
| 17 | ▲ 1.61 | 0.03926 | CK774460 | Transcribed locus, strongly similar to NP_006452.2 sperm associated antigen 5 [H |
| 18 | ▲ 1.59 | 0.03385 | BI682736 | Transcribed locus |
| 19 | ▲ 1.59 | 0.04521 | CK972892 | Transcribed locus, weakly similar to NP_689775.2 cell division cycle associated |
| 20 | ▲ 1.58 | 0.03836 | CB535138 | Transcribed locus |

TABLE 4

Preferred downregulated blood cell markers in heifers carrying persistently virally infected, when compared to non-infected fetuses (Control vs. PI: downregulated in PI).

|  | Group 1 | Group 2 |
|---|---|---|
| Conditions: | Control | Persistently Infected |
| Experiments: | 44009, 44010, 44011 | 44012, 44013, 44014 |
| Significance: | 1.5, t-test | |
| Normalization: | None | |
| Quality Cutoff: | None (Calls) | |
| Data Transformation: | Log Transformed | |

Show: 20 ▼ Sort By: Ratio ▼ p Cutoff: 0.05 ▼ Search (15 results found) [1-15]

| No. | Ratio | p-value | Identifier | Gene Name |
|---|---|---|---|---|
| 1 | ▼ 2.82 | 0.01126 | NM_175827 | chemokine (C-C motif) ligand 5 |
| 2 | ▼ 2.69 | 0.03202 | CB425639 | Transcribed locus, weakly similar to NP_631937.1 placenta-specific 8 [*Mus muscul* |
| 3 | ▼ 2.24 | 0.04464 | NM_174511 | Chemokine (C-C motif) ligand 3-like 1 |
| 4 | ▼ 2.22 | 0.00573 | CB534503 | Transcribed locus, weakly similar to XP_519213.1 paraoxonase 2 [*Pan troglodytes*] |
| 5 | ▼ 2.07 | 0.02014 | CK945488 | Transcribed locus, moderately similar to NP_001326.2 cathepsin W (lymphopain) [H |
| 6 | ▼ 2.03 | 0.02292 | CB461397 | Transcribed sequence |
| 7 | ▼ 2.01 | 0.02229 | BM251259 | Transcribed locus, moderately similar to NP_001326.2 cathespin W (lymphopain) [H |
| 8 | ▼ 1.96 | 0.04149 | CK775256 | Transcribed locus, moderately similar to NP_077215.2 natural killer cell group 7 |
| 9 | ▼ 1.91 | 0.04699 | CB463807 | Transcribed sequence with moderate similarity to protein sp: P10159 (*H. sapiens*) I |
| 10 | ▼ 1.77 | 0.03397 | CK771825 | Perforin 1 (pore forming protein) |
| 11 | ▼ 1.73 | 0.02399 | CF930613 | Transcribed locus |
| 12 | ▼ 1.71 | 0.04130 | CB171451 | Transcribed locus, moderately similar to NP_001938.1 dual specificity phosphates |
| 13 | ▼ 1.70 | 0.02006 | CF763999 | Transcribed sequences |
| 14 | ▼ 1.59 | 0.03949 | CK962640 | Transcribed locus, moderately similar to NP_002155.1 indoleamine-pyrrole 2,3 dio |
| 15 | ▼ 1.57 | 0.02055 | BE723387 | Transcribed locus, strongly similar to NP_653311.1 septin 10 [*Homo sapiens*] |

TABLE 5

Preferred upregulated blood cell markers in heifers carrying transiently virally infected, when compared to non-infected fetuses (Control vs. TI: upregulated in TI).

|  | Group 1 | Group 2 |
|---|---|---|
| Conditions: | Control | Transiently Infected |
| Experiments: | 44009, 44010, 44011 | 44008, 44015, 44016 |
| Significance: | 1.5, t-test | |
| Normalization: | None | |
| Quality Cutoff: | None (Calls) | |
| Data Transformation: | Log Transformed | |

Show: 50   Sort By: Ratio   p Cutoff: 0.05   Search   (48 results found)   [1-48]

| No. | Ratio | p-value | Identifier | Gene Name |
|---|---|---|---|---|
| 1 | ▲ 7.55 | 0.00024 | CK960499 | 2'-5'-oligoadenylate synthetase 1 (OAS1) |
| 2 | ▲ 5.03 | 0.00015 | CB464371 | Transcribed locus, strongly similar to NP_849200.1 tubulin tyrosine ligase-like |
| 3 | ▲ 3.57 | 0.00411 | NM_174366 | Interferon-stimulated protein, 15 kDa |
| 4 | ▲ 2.91 | 0.00075 | CB433489 | Transcribed sequence with weak similarity to protein pir: S48218 (*H. sapiens*) S482 |
| 5 | ▲ 2.89 | 0.00318 | CK955157 | Transcribed locus, moderately similar to XP_513514.1 similar to Interferon-induc |
| 6 | ▲ 2.88 | 0.00351 | CB460780 | Transcribed locus, moderately similar to XP_513514.1 similar to Interferon-induc |
| 7 | ▲ 2.86 | 0.03887 | CB530781 | Transcribed locus |
| 8 | ▲ 2.63 | 0.01280 | NM_173941 | myxovirus (influenza virus) resistance 2 (mouse) |
| 9 | ▲ 2.61 | 0.00228 | CK777675 | Transcribed locus, moderately similar to XP_513514.1 similar to Interferon-induc |
| 10 | ▲ 2.15 | 0.01295 | CB432365 | Transcribed locus, moderately similar to XP_520524.1 similar to DEAD/H (Asp-Glu- |
| 11 | ▲ 2.07 | 0.00093 | CB445920 | Transcribed sequences |
| 12 | ▲ 2.03 | 0.03937 | CK980927 | Transcribed locus, moderately similar to XP_228897.2 similar to Gene trap ROSA 2 |
| 13 | ▲ 2.00 | 0.04814 | CB536841 | Transcribed locus, strongly similar to NP_742051.1 thioredoxin domain containing |
| 14 | ▲ 1.96 | 0.03946 | AF016394 | neutrophil beta-defensin-9 like peptide |
| 15 | ▲ 1.95 | 0.00706 | CK848208 | Transcribed locus, weakly similar to XP_524747.1 similar to histocompatibility 2 |
| 16 | ▲ 1.94 | 0.00547 | CK848475 | Transcribed locus, strongly similar to XP_521554.1 interferon-induced protein wi |
| 17 | ▲ 1.92 | 0.01884 | BE666861 | Transcribed locus |
| 18 | ▲ 1.87 | 0.01922 | CB430886 | Transcribed locus |
| 19 | ▲ 1.87 | 0.01703 | BM031140 | Transcribed sequence |
| 20 | ▲ 1.82 | 0.00650 | CK971030 | Transcribed locus, weakly similar to XP_223172.2 similar to hypothetical protein |
| 21 | ▲ 1.80 | 0.00386 | CK776302 | Transcribed locus |
| 22 | ▲ 1.79 | 0.02243 | CK848830 | Transcribed locus, weakly similar to NP_002263.1 keratin 4 [*Homo sapiens*] |
| 23 | ▲ 1.78 | 0.02470 | CK777062 | Transcribed locus, strongly similar to NP_002420.1 maxtrix metalloproteinase 19 [ |
| 24 | ▲ 1.74 | 0.03253 | BI680405 | Transcribed locus, weakly similar to NP_071430.1 28kD responsive prot |
| 25 | ▲ 1.71 | 0.04939 | CB536836 | Transcribed sequences |
| 26 | ▲ 1.69 | 0.03453 | BE668756 | Transcribed locus, moderately similar to NP_060520.2 MANSC domain containing 1 [ |
| 27 | ▲ 1.68 | 0.00238 | NM_174601 | solute carrier family 1 (neutral amino acid transporter), member 5 |
| 28 | ▲ 1.66 | 0.00635 | CB535112 | Transcribed sequence |
| 29 | ▲ 1.65 | 0.01121 | CK774420 | Transcribed locus, strongly similar to XP_356099.1 ribonuclease H2, large subuni |
| 30 | ▲ 1.65 | 0.04721 | BE753440 | Transcribed sequence with moderate similarity to protein sp: Q9275 (*H. sapiens*) T |
| 31 | ▲ 1.64 | 0.00825 | CB465021 | Transcribed locus |
| 32 | ▲ 1.61 | 0.02079 | CK776907 | Transcribed locus |
| 33 | ▲ 1.61 | 0.02346 | CB422521 | Transcribed locus, weakly similar to NP_004326.1 bone marrow stromal cell antige |
| 34 | ▲ 1.60 | 0.04267 | CK846935 | Transcribed locus, moderately similar to NP_077024.1 likely ortholog of mouse D1 |
| 35 | ▲ 1.60 | 0.04557 | BM087443 | Transcribed locus, moderately similar to XP_519171.1 similar to putative homeodo |
| 36 | ▲ 1.60 | 0.03689 | CK774101 | Transcribed locus, moderately similar to XP_520399.1 similar to centrosomal prot |
| 37 | ▲ 1.60 | 0.01013 | CK968996 | Transcribed locus, strongly similar to NP_003095.1 sorbitol dehydrogenase [Homo |
| 38 | ▲ 1.60 | 0.00120 | CB463330 | Transcribed locus, strongly similar to XP_ 214478.2 similar to Succinate semialde |
| 39 | ▲ 1.58 | 0.01549 | NM_174081 | molybdenum cofactor sulfurase |
| 40 | ▲ 1.57 | 0.04647 | AW426236 | Transcribed locus |
| 41 | ▲ 1.57 | 0.02922 | CB172358 | Transcribed locus, strongly similar to NP_004808.2 tight junction protein 2 (zon |
| 42 | ▲ 1.56 | 0.00399 | CB168658 | Transcribed locus |
| 43 | ▲ 1.56 | 0.02344 | CB441353 | Transcribed locus, weakly similar to NP_004891.3 apolipoprotein B mRNA editing e |
| 44 | ▲ 1.55 | 0.03157 | CK769183 | Transcribed locus |
| 45 | ▲ 1.54 | 0.01408 | CK966858 | Transcribed locus |
| 46 | ▲ 1.53 | 0.01227 | CK770915 | Transcribed locus, moderately similar to XP_218427.2 similar to poliovirus recep |
| 47 | ▲ 1.52 | 0.03676 | CB464450 | Transcribed locus |
| 48 | ▲ 1.51 | 0.01286 | CK969631 | Transcribed locus, weakly similar to XP_496435.1 similar to FLJ46489 protein [Ho |

TABLE 6

Preferred downregulated blood cell markers in heifers carrying transiently virally infected, when compared to non-infected fetuses (Control vs. TI: downregulated in TI).

|  | Group 1 | Group 2 |
|---|---|---|
| Conditions: | Control | Transiently Infected |
| Experiments: | 44009, 44010, 44011 | 44008, 44015, 44016 |
| Significance: | 1.5, t-test |  |
| Normalization: | None |  |
| Quality Cutoff: | None (Calls) |  |
| Data Transformation: | Log Transformed |  |

Show: 50    Sort By: Ratio    p Cutoff: 0.05    Search    (41 results found)    [1-41]

| No. | Ratio | p-value | Identifier | Gene Name |
|---|---|---|---|---|
| 1 | ▼ 487.07 | 0.00000 | CB444277 | MHC class II DQA1 |
| 2 | ▼ 11.06 | 0.00371 | AB008573 | MHC class I heavy chain, partial cds, clone P5647.6 m |
| 3 | ▼ 3.89 | 0.00475 | CB433789 | Transcribed locus |
| 4 | ▼ 2.36 | 0.04120 | AV609250 | Transcribed sequence with strong similarity to protein pir: A40261 (*H. sapiens*) A4 |
| 5 | ▼ 2.34 | 0.03538 | CK776354 | Transcribed locus, strongly similar to NP_000023.1 aminolevulinate, delta-, synt |
| 6 | ▼ 2.17 | 0.00884 | BE752683 | Transcribed sequence |
| 7 | ▼ 2.13 | 0.01796 | CK972404 | Transcribed locus |
| 8 | ▼ 2.04 | 0.02469 | CB423642 | Heat shock 70 kD protein 2 |
| 9 | ▼ 2.00 | 0.01152 | CB430069 | Transcribed locus |
| 10 | ▼ 1.98 | 0.04868 | BE487674 | Transcribed locus, strongly similar to NP_780325.1 purinergic receptor (family A |
| 11 | ▼ 1.93 | 0.00865 | CB534503 | Transcribed locus, weakly similar to XP_519213.1 paraoxonase 2 [*Pan troglodytes*] |
| 12 | ▼ 1.92 | 0.00788 | CK775223 | Transcribed locus, strongly similar to NP_110396.1 N-acetylneuraminate pyruvate |
| 13 | ▼ 1.90 | 0.03876 | CK847570 | Transcribed locus |
| 14 | ▼ 1.88 | 0.01828 | M37974 | osteoglycin (osteoinductive factor, mimecan) |
| 15 | ▼ 1.88 | 0.00863 | CB456756 | Transcribed locus, moderately similar to NP_663424.1 RIKEN cDNA 1810023F06 gene |
| 16 | ▼ 1.87 | 0.04989 | NM_175827 | chemokine (C-C motif) ligand 5 |
| 17 | ▼ 1.86 | 0.03720 | BP107527 | Embroynic ectoderm development protein |
| 18 | ▼ 1.81 | 0.01772 | CK945488 | Transcribed locus, moderately similar to NP_001326.2 cathepsin W (lymphopain) [H |
| 19 | ▼ 1.79 | 0.01237 | CB467996 | Transcribed locus, strongly similar to NP_001059.2 topoisomerase (DNA) II beta 1 |
| 20 | ▼ 1.72 | 0.02167 | CB461397 | Transcribed sequence |
| 21 | ▼ 1.71 | 0.00526 | CB534327 | Component 3 |
| 22 | ▼ 1.71 | 0.02438 | CK773609 | Transcribed locus, strongly similar to XP_232315.2 similar to CG4853 gene produc |
| 23 | ▼ 1.69 | 0.04044 | CK846542 | Transcribed locus, strongly similar to XP_048070.4 zinc finger protein 292 [Homo |
| 24 | ▼ 1.66 | 0.03462 | CB417623 | Transcribed locus, strongly similar to NP_005793.2 topoisomerase I binding, argl |
| 25 | ▼ 1.65 | 0.01097 | CK953227 | Transcribed locus, moderately similar to XP_518477.1 similar to beta-tubulin cof |
| 26 | ▼ 1.65 | 0.01448 | CK845887 | Transcribed locus, strongly similar to NP_065683.1 ATPase, H+ transporting, lyso |
| 27 | ▼ 1.64 | 0.04173 | D90419 | T-cell receptor delta chain |
| 28 | ▼ 1.62 | 0.04086 | CB431455 | Transcribed locus |
| 29 | ▼ 1.61 | 0.04302 | CB419791 | Transcribed locus, strongly similar to NP_076281.1 pantothenate kinase 1 [Mus mu |
| 30 | ▼ 1.60 | 0.00548 | CK846165 | Transcribed locus |
| 31 | ▼ 1.60 | 0.03304 | CK838029 | Transcribed locus, strongly similar to NP_000687.2 aldehyde dehydrogenase 9 fami |
| 32 | ▼ 1.59 | 0.03900 | CB435377 | Transcribed locus, strongly similar to NP_067067.1 Ras-related GTP binding D [Ho |
| 33 | ▼ 1.58 | 0.04870 | CB428714 | Transcribed locus, moderately similar to NP_002332.1 lymphotoxin beta (TNF super |
| 34 | ▼ 1.58 | 0.03882 | CK966877 | Transcribed locus, strongly similar to XP_510092.1 similar to glutathione transf |
| 35 | ▼ 1.58 | 0.00735 | CB531127 | Transcribed locus, weakly similar to XP_235485.2 similar to CEM15; cDNA sequence |
| 36 | ▼ 1.57 | 0.00519 | CB460964 | ATP-binding cassette transporter subfamily B, member 1 (ABCB1) |
| 37 | ▼ 1.56 | 0.04297 | CB434065 | Transcribed locus, strongly similar to XP_516173.1 LOC460038 [*Pan troglodytes*] |
| 38 | ▼ 1.54 | 0.03573 | CK849477 | Transcribed locus, moderately similar to NP_037407.3 ankyrin repeat domain 11 [H |
| 39 | ▼ 1.54 | 0.00116 | BP106941 | Transcribed locus, weakly similar to XP_521146.1 similar to ATRX [*Pan troglodyte* |
| 40 | ▼ 1.53 | 0.02401 | NM_175716 | chemokine (C motif) ligand 1 |
| 41 | ▼ 1.52 | 0.1837 | AW478035 | Transcribed locus |

TABLE 7

Preferred upregulated blood cell markers in heifers carrying persistently virally infected when compared to transiently virally infected fetuses (TI vs. PI: upregulated in PI).

|  | Group 1 | Group 2 |
|---|---|---|
| Conditions: | Transiently Infected | Persistently Infected |
| Experiments: | 44008, 44015, 44016 | 44012, 44013, 44014 |
| Significance: | 1.5, t-test | |
| Normalization: | None | |
| Quality Cutoff: | None (Calls) | |
| Data Transformation: | Log Transformed | |

Show: 50   Sort By: Ratio   p Cutoff: 0.05   Search   (35 results found)   [1-35]

| No. | Ratio | p-value | Identifier | Gene Name |
|---|---|---|---|---|
| 1 | ▲ 9.95 | 0.00366 | AB008573 | MHC class I heavy chain, partial cds, clone P5647.6 m |
| 2 | ▲ 3.82 | 0.02074 | CB433789 | Transcribed locus |
| 3 | ▲ 2.25 | 0.01319 | CB530181 | Transcribed locus |
| 4 | ▲ 2.13 | 0.01153 | M37974 | osteoglycin (osteoinductive factor, mimecan) |
| 5 | ▲ 2.05 | 0.02681 | CB420023 | Transcribed sequence |
| 6 | ▲ 2.05 | 0.00024 | CB461169 | Transcribed sequences |
| 7 | ▲ 1.93 | 0.01489 | CB460964 | ATP-binding cassette transporter subfamily B, member 1 (ABCB1) |
| 8 | ▲ 2.89 | 0.00831 | CB534327 | Component 3 |
| 9 | ▲ 1.82 | 0.01041 | CK945043 | Transcribed locus |
| 10 | ▲ 1.77 | 0.03692 | CB423642 | Heat shock 70 kD protein 2 |
| 11 | ▲ 1.77 | 0.03010 | CB443498 | Transcribed locus, moderately similar to XP_514164.1 similar to Putative lymphoc |
| 12 | ▲ 1.77 | 0.04638 | CB458416 | Transcribed sequences |
| 13 | ▲ 1.76 | 0.03425 | NM_174373 | potassium inwardly-rectifying channel subfamily J, member 2 |
| 14 | ▲ 1.76 | 0.01755 | CB435377 | Transcribed locus, strongly similar to NP_067067.1 Ras-related GTP binding D [Ho |
| 15 | ▲ 1.75 | 0.04017 | BE758040 | Transcribed locus, weakly similar to NP_000486.1 collagen, type IV, alpha 5 (Alp |
| 16 | ▲ 1.69 | 0.04108 | AY298812 | SMC4 structural maintenance of chromosomes 4-like 1 (yeast) |
| 17 | ▲ 1.67 | 0.00189 | CK953227 | Transcribed locus, moderately similar to XP_518477.1 similar to beta-tubulin cof |
| 18 | ▲ 1.66 | 0.03204 | BM285504 | Transcribed locus, strongly similar to NP_005618.2 serum/glucocotricoid regulate |
| 19 | ▲ 1.66 | 0.01417 | CB439678 | Transcribed locus, strongly similar to NP_938022.1 hypothetical protein LOC28551 |
| 20 | ▲ 1.65 | 0.02078 | AJ235267 | T-cell receptor beta chain variable segment, clone IC100 |
| 21 | ▲ 1.64 | 0.01508 | AV615989 | Transcribed locus |
| 22 | ▲ 1.62 | 0.04868 | D90132 | T cell receptor, beta cluster |
| 23 | ▲ 1.60 | 0.04572 | CK771797 | Transcribed locus, moderately similar to NP_612441.1 serine dehydratase-like [Ho |
| 24 | ▲ 1.60 | 0.04743 | CB424072 | Transcribed sequence |
| 25 | ▲ 1.60 | 0.01012 | CB420282 | Transcribed sequence with weak similarity to protein ref: NP_054886.1 (*H. sapiens*) |
| 26 | ▲ 1.59 | 0.04919 | CK946910 | Transcribed locus, strongly similar to NP_005233.3 coagulation factor II (thromb |
| 27 | ▲ 1.57 | 0.04409 | BE237119 | Transcribed locus, moderately similar to NP_001600.1 acyl-Coenzyme A dehydrogena |
| 28 | ▲ 1.56 | 0.04897 | D90013 | T cell receptor, alpha |
| 29 | ▲ 1.55 | 0.04232 | AV604293 | Transcribed locus, strongly similar to NP_0053572.1 nuclear factor, interleukin 3 |
| 30 | ▲ 1.54 | 0.03887 | CK727097 | Transcribed locus |
| 31 | ▲ 1.53 | 0.01790 | BE723538 | Transcribed locus, moderately similar to NP_060924.4 nucleolar and spindle assoc |
| 32 | ▲ 1.53 | 0.01296 | CK778261 | Transcribed locus, strongly similar to XP_519864.1 similar to cyclin E2 isoform |
| 33 | ▲ 1.52 | 0.02640 | AJ006574 | T-cell receptor beta chain variable segment, clone C55 |
| 34 | ▲ 1.52 | 0.01496 | CK847994 | Transcribed locus, strongly similar to NP_061198.1 myosin VC [*Homo sapiens*] |
| 35 | ▲ 1.52 | 0.03625 | BM253121 | Transcribed locus, strongly similar to NP_061974.2 apolipoprotein M [*Homo sapien* |

TABLE 8

Preferred downregulated blood cell markers in heifers carrying persistently virally infected when compared to transiently virally infected fetuses (TI vs. PI: downregulated in PI).

|  | Group 1 | Group 2 |
|---|---|---|
| Conditions: | Transiently Infected | Persistently Infected |
| Experiments: | 44008, 44015, 44016 | 44012, 44013, 44014 |
| Significance: | 1.5, t-test | |
| Normalization: | None | |
| Quality Cutoff: | None (Calls) | |
| Data Transformation: | Log Transformed | |

Show: 20   Sort By: Ratio   p Cutoff: 0.05   Search   (16 results found)   [1-16]

| No. | Ratio | p-value | Identifier | Gene Name |
|---|---|---|---|---|
| 1 | ▼ 3.87 | 0.04453 | CK960499 | 2'-5'-oligoadenylate synthetase 1 (OAS1) |
| 2 | ▼ 2.36 | 0.01971 | AW658483 | Transcribed locus |
| 3 | ▼ 2.33 | 0.01380 | NM_174366 | Interferon-stimulated protein, 15 kDa |
| 4 | ▼ 2.29 | 0.00929 | CK771750 | Transcribed locus |
| 5 | ▼ 2.24 | 0.02029 | CK955157 | Transcribed locus, moderately similar to XP_513514.1 similar to Interferon-Induc |
| 6 | ▼ 2.17 | 0.01340 | CB460780 | Transcribed locus, moderately similar to XP_513514.1 similar to Interferon-Induc |
| 7 | ▼ 2.13 | 0.01958 | CK777675 | Transcribed locus, moderately similar to XP_513514.1 similar to Interferon-Induc |
| 8 | ▼ 1.94 | 0.01880 | CB433489 | Transcribed sequence with weak similarity to protein pir: S48218 (*H. sapiens*) S482 |
| 9 | ▼ 1.73 | 0.03188 | CK848208 | Transcribed locus, weakly similar to XP_524747.1 similar to histocompatibility 2 |
| 10 | ▼ 1.67 | 0.04677 | CB432365 | Transcribed locus, moderately similar to XP_520524.1 similar toDEAD/H (Asp-Glu- |
| 11 | ▼ 1.63 | 0.04720 | CK972160 | Transcribed locus, strongly similar to XP_485628.1 similar to hypothetical prote |
| 12 | ▼ 1.57 | 0.03785 | AB008649 | MHC class I heavy chain///MHC class I heavy chain, partial cds, MP-1.6 m |
| 13 | ▼ 1.56 | 0.04230 | CB459838 | Transcribed locus, moderately similar to NP_004122.1 granzyme B (granzyme 2, cyt |
| 14 | ▼ 1.56 | 0.04946 | BF230904 | Transcribed locus, weakly similar to XP_346800.1 ectonucleotide pyrophosphatase/ |
| 15 | ▼ 1.54 | 0.04682 | BF041863 | Transcribed locus |
| 16 | ▼ 1.53 | 0.02518 | CB422521 | Transcribed locus, weakly similar to NP_004326.1 bone marrow stromal cell antige |

TABLE 9

Figure 4:
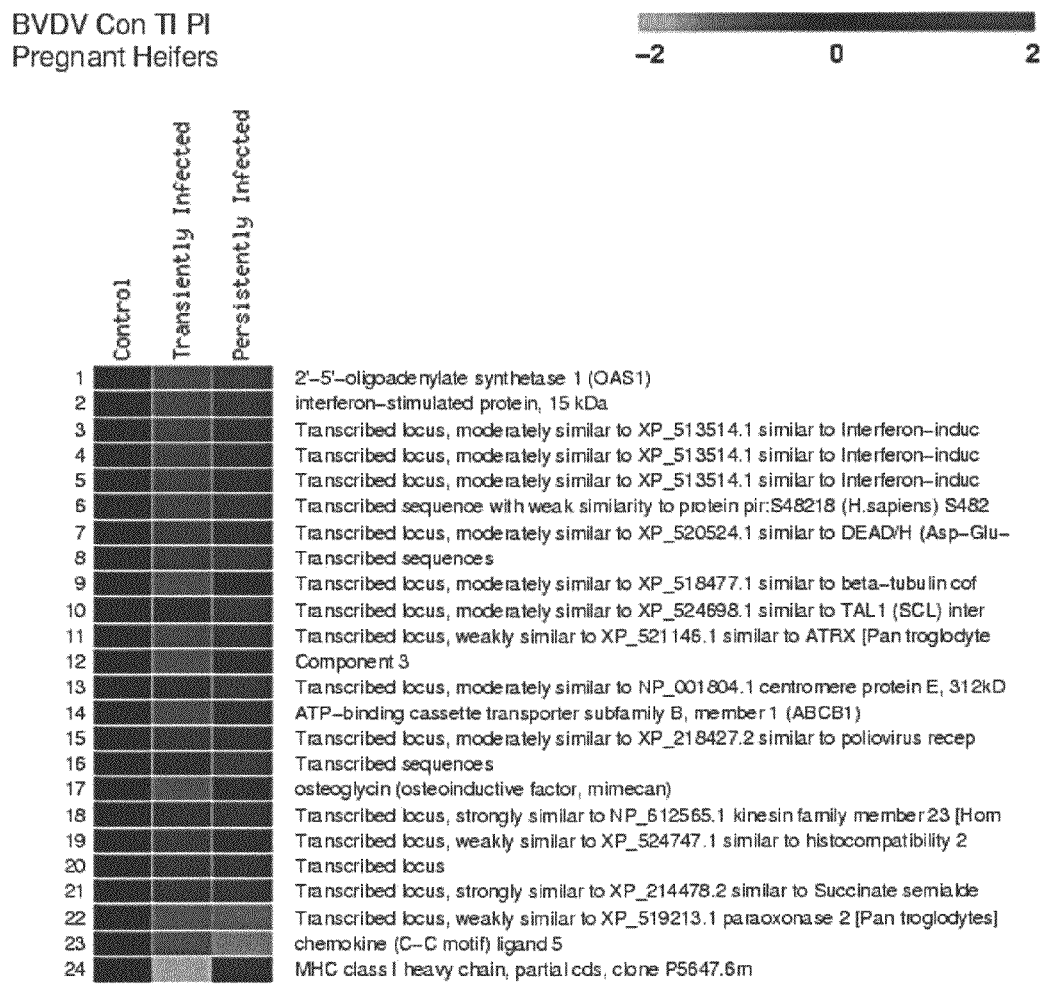
FIG. 4 is a heat plot illustrating three-Way ANOVA analysis of blood cell gene expression from mothers carrying control vs. TI vs. PI virally infected fetuses described in Table 9. This analysis represents a fold change of 1.5 fold or greater with $P<0.01$. Table 9 provides the actual P values for each comparison and a more complete description of each gene.

Analysis of blood gene expression using a three-way ANOVA in heifers carrying control vs. TI vs. PI fetuses. Analysis represents the top 24 genes that were differentially expressed in at least one of the treatment groups. The value in the ANOVA column represents the P value when determining if one of the three means differs. Please refer to the heat plot in FIG. 4 for an illustration of these data.

| ANOVA | Control Mean | TI Mean | PI Mean | Control SEM 1 | PI SEM 2 | TI SEM 3 | Gene Identifier | Gene Title |
|---|---|---|---|---|---|---|---|---|
| 0.006032 | 8.00309 | 10.9193 | 8.96783 | 0.188264 | 0.138741 | 0.660686 | CK960499 | 2'-5'-oligoadenylate synthetase 1 (OAS1) |
| 0.003154 | 10.115 | 11.9521 | 10.7336 | 0.256113 | 0.176554 | 0.231053 | NM_174366 | interferon-stimulated protein, 15 kDa |
| 0.003028 | 6.90223 | 8.43096 | 7.26529 | 0.101244 | 0.219103 | 0.222812 | CK955157 | XP_513514.1 similar to interferon-induced protein 44 (Antigen p44) |
| 0.003101 | 8.16371 | 9.68817 | 8.57334 | 0.191589 | 0.15614 | 0.212549 | CB460780 | XP_513514.1 similar to interferon-induced protein 44 (Antigen p44) |
| 0.003419 | 6.74951 | 8.13573 | 7.04487 | 0.104431 | 0.170809 | 0.23341 | CK777675 | XP_513514.1 similar to interferon-induced protein 44 (Antigen p44) |
| 0.001684 | 7.22418 | 8.76654 | 7.80757 | 0.137263 | 0.093874 | 0.232921 | CB433489 | pir: S48218 (*H. sapiens*) S48218 microtubular aggregate protein - hu |
| 0.008299 | 8.21365 | 9.31672 | 8.57504 | 0.110353 | 0.233574 | 0.116391 | CB432365 | XP_520524.1 similar to DEAD/H (Asp-Glu-Ala-Asp/His) box polype |
| 0.00315 | 8.16901 | 9.22019 | 9.12652 | 0.048718 | 0.109524 | 0.209197 | CB445920 | Transcribed sequences |
| 0.002321 | 9.87333 | 9.15127 | 9.88773 | 0.12978 | 0.095443 | 0.033274 | CK953227 | XP_518477.1 similar to beta-tubulin cofactor C [*Pan troglodytes*] |
| 0.009597 | 5.57083 | 5.66441 | 6.21629 | 0.161879 | 0.077099 | 0.026107 | CK971667 | XP_524698.1 similar to TAL1 (SCL) interrupting locus; SCL interrup |
| 0.000202 | 8.26679 | 7.64432 | 8.09498 | 0.036558 | 0.065628 | 0.028333 | BP103941 | XP_521146.1 similar to ATRX [*Pan troglodytes*] |
| 0.005323 | 6.91205 | 6.14205 | 7.06362 | 0.125015 | 0.061868 | 0.179441 | CB534327 | Component 3 |
| 0.003199 | 5.25886 | 5.54151 | 5.89927 | 0.099747 | 0.072327 | 0.051183 | CB443429 | NP_001804.1 centromere protein E, 312 kDa [*Homo sapiens*] |
| 0.00661 | 7.76552 | 7.11499 | 8.06201 | 0.028002 | 0.114012 | 0.201076 | CB460964 | ATP-binding cassette transporter subfamily B, member 1 (ABCB1) |
| 0.006969 | 5.88815 | 6.50156 | 6.25403 | 0.108627 | 0.090517 | 0.04993 | CK770915 | XP_218427.2 similar to poliovirus receptor homolog [*Rattus norvegi* |
| 0.002739 | 4.50737 | 4.44439 | 5.47889 | 0.218718 | 0.048776 | 0.067073 | CB461169 | Transcribed sequences |
| 0.003618 | 7.02454 | 6.11085 | 7.19863 | 0.035911 | 0.234515 | 0.075039 | M37974 | osteoglycin (osteoinductive factor, mimecan) |
| 0.007258 | 7.29919 | 7.80462 | 7.90756 | 0.145198 | 0.007311 | 0.065739 | CK950633 | similar to NP_612565.1 kinesin family member 23 [*Homo sapiens*] |

TABLE 9-continued

Analysis of blood gene expression using a three-way ANOVA in heifers
carrying control vs. TI vs. PI fetuses. Analysis represents the top 24 genes that were
differentially expressed in at least one of the treatment groups. The value in the
ANOVA column represents the P value when determining if one of the three means
differs. Please refer to the heat plot in FIG. 4 for an illustration of these data.

| ANOVA | Control Mean | TI Mean | PI Mean | Control SEM 1 | PI SEM 2 | TI SEM 3 | Gene Identifier | Gene Title |
|---|---|---|---|---|---|---|---|---|
| 0.006348 | 9.11153 | 10.0777 | 9.28636 | 0.01768 | 0.189202 | 0.15531 | CK848208 | similar to XP_524747.1 similar to histocompatibility 28 [*Pan troglod*] |
| 0.000656 | 4.52089 | 5.16352 | 5.09881 | 0.106526 | 0.017049 | 0.016545 | CB168658 | Transcribed locus |
| 0.0004 | 5.60571 | 6.28826 | 6.3913 | 0.053773 | 0.063446 | 0.087055 | CB463330 | Succinate semialdehyde dehydrogenase (NAD(+)-dependent succir |
| 0.002006 | 4.94446 | 3.99497 | 3.79603 | 0.173649 | 0.094759 | 0.123417 | CB534503 | Transcribed locus, weakly similar to XP_519213.1 paraoxonase 2 |
| 0.009713 | 10.8281 | 9.92825 | 9.33185 | 0.253205 | 0.201907 | 0.221374 | NM_175827 | chemokine (C-C motif) ligand 5 |
| 0.00064 | 11.0449 | 7.57803 | 10.8921 | 0.258042 | 0.509224 | 0.189688 | AB008573 | MHC class I heavy chain, partial cds, clone P5647.6m |

Early detection of persistently infected calves is the best method of controlling and eradicating BVDV from infected herds. Current diagnostic tests for BVDV include skin biopsies and serology which do not distinguish acutely infected animals from persistently animals. These PI animals go undetected and continue to propagate virus within the herd.

Current methods of detection also have a high rate of false negatives due to the fact that they are based on mutating viral antigens. Most importantly, current tests cannot detect a pregnant cow/heifer which is carrying a persistently infected calf. The present invention describes a method whereby BVDV can be detected in acutely infected calves, persistently infected calves as well as cows or heifers carrying an infected fetus through the identification of differentially expressed surrogate markers described in Tables 1-9. Surrogate markers can exist as mRNA or protein antigens and allow differentiation of type of BVDV infection. By the methods listed previously persistently infected (PI) calves can be differentiated from acutely infected calves and acutely infected calves can be distinguished from non-infected calves. Heifers and cows carrying PI fetuses can also be distinguished from heifers/cows carrying transiently infected fetuses and cows/heifers carrying PI or TI fetuses can be distinguished from cows/heifers carrying non-infected (normal) calves. The same markers can be used to create therapeutics for treating secondary effects of viral disease and monitoring the anti-viral response in infected cattle. The global approach presented herein will aid the prevention, diagnosis, control and treatment of cattle infected with BVDV as well as other RNA viruses.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A gene chip for diagnosing BVDV in a ruminant test animal comprising a plurality of isolated BVDV surrogate markers selected from the group consisting of SEQ ID NOs: 3, 8, 54, 72, 90 and 137, wherein the markers are attached to the gene chip.

2. A kit for differentially diagnosing BVDV infection between day 0 and day 190 follow pregnancy, comprising at least one BVDV surrogate marker detector molecule, and reagents for detection of the same, said kit comprising a gene chip comprising a plurality of BVDV surrogate markers selected from the group consisting of SEQ ID NOs: 3, 8, 54, 72, 90 and 137, or a solid support comprising a plurality of BVDV surrogate polypeptide markers selected from the group consisting of polypeptides encoded by SEQ ID NOs: 3, 8, 54, 72, 90 and 137, wherein the markers are attached to the gene chip or solid support.

3. The kit of claim 2, wherein said BVDV surrogate marker detector molecule is selected from the group consisting of a probe or primer which specifically hybridizes with a BVDV surrogate marker nucleic acid, and an antibody which specifically binds to a BVDV surrogate marker polypeptide.

* * * * *

SEQUENCE LISTING

```
<160> NUMBER OF SEQ ID NOS: 206

<210> SEQ ID NO 1
<211> LENGTH: 661
<212> TYPE: DNA
<213> ORGANISM: Bos Taurus

<400> SEQUENCE: 1
aatggggttg acaattttaa tcacatcgtg caaaatgttg ttacattcag gtgacatttt      60
tcatctagcc agcatttctc taaggataac acagtgcgta gactcacatt cagaagtgag     120
ctctttgacc tgaatagtga atcgagaaag ccattcagtc atggcagcca ctccatccat     180
gcacatacca acacagatgc ccaattcagg ggtcctgatg tgtaatcatt caaagacttg     240
aatagttctg tggttgtggt gttggttggc aacaaaactg cacataacat atctgcatgc     300
acatcctctc atcctctgaa aaatagattc ctcaaaaaca agactgttgc tttgttgtca     360
acattcatag acttgtcagc ctggattgca taccactgtg actcattaac ctctaacaat     420
tgtgcctcaa tgccctctgc tatttcaaaa attcatctag tttcagtgct agccaaaaga     480
ggaacacgtg ccatcttctg aactgcagcc tctcctaaaa gttcctgaca aatgtccttg     540
gcagttggca ggatcaactc ttcaccaact cttcttagct caagcgtgtg gttagccact     600
aagaatgatg ctttcagtgc agacacgttt gatgaagtgg tagccttcaa taactgcttc     660
```

| | |
|---|---|
| t | 661 |

<210> SEQ ID NO 2
<211> LENGTH: 846
<212> TYPE: DNA
<213> ORGANISM: Bos taurus

<400> SEQUENCE: 2

| | | | | | |
|---|---|---|---|---|---|
| aaagtgataa | aggaagttta | tttggatttg | cggctctgaa | aagttcagtc | tctgctcccc | 60 |
| aacctcctcc | caccacggct | catggaggag | ctctggctgc | tgttcctgct | gctgtggtcc | 120 |
| cttttcttc | cgctgctttg | agaactgtgc | cttccccggc | ttctagaccc | atgttttga | 180 |
| gatttctcgc | cctcatgact | actcctcctc | ttcctgtcag | cctcgtcttt | cctcttgtag | 240 |
| gagtgggccc | acacagggct | cctcctcctc | ctttgcaggt | tatagtagtc | gtcatggtgg | 300 |
| tccagcctca | ccctcctcac | tgagctcttc | ccaaaggtgg | agccagtcca | aattggaggt | 360 |
| aagtagatgt | cttcatttcc | ttcgcaaaat | tcattgtttg | gatttctgaa | cacgtgaaga | 420 |
| aagttgcagt | atttccctct | gggacactgc | tgtatttcaa | ataaaccaca | aattgccata | 480 |
| ttccattggg | tcactgggca | gaattcacac | tgaagctgtc | gtcctgcata | ccatcgtcca | 540 |
| ttaaacagag | aaagggctgc | ctggcattct | tcttcccta | aactggatca | ctttccccac | 600 |
| gttcttaaac | tcagggagca | cgtcatcata | aaagtccagg | aactgctggt | agatttcttc | 660 |
| ttcactgtac | tctaagtttg | cgtcagggtc | gtagtcatcc | cttccacact | gctccatccc | 720 |
| aaacgttgta | aacatgcttt | taataagcag | tgtgggactt | gatgttggga | aattgtgttt | 780 |
| acgtgaacac | ctatctccaa | atctgcaagc | tcctgtttta | ctgtagaatg | gacaattagc | 840 |
| tcgatc | | | | | | 846 |

<210> SEQ ID NO 3
<211> LENGTH: 2966
<212> TYPE: DNA
<213> ORGANISM: Bos taurus

<400> SEQUENCE: 3

| | | | | | |
|---|---|---|---|---|---|
| ccctcctaca | agtgcacagg | tgacaacgcg | gagcccagca | gaagtgacag | cagaaccttc | 60 |
| agactctccc | gtggaagcgt | agagtccact | tgtctccagg | cccaccaacg | tcccttttgt | 120 |
| gttctgtgcc | cgtttgctgc | catcagcccc | gtctgcagac | aggcctgagc | tgggctgctg | 180 |
| gtctcccctg | agtcggtgag | cagcagagct | tgccgagagg | accagaggca | ctgagccccg | 240 |
| aagaccgcac | accccagctc | tccgagcaga | cagtcatgtc | gatgtccttc | aggcctttga | 300 |
| agtacaagag | gcacactcag | acttccactc | agcaccaccc | aaagcaagac | atttacttcc | 360 |
| atcagcagcc | accagggcca | ccattggggc | agacaatgag | tccccacaa | tggcaggtgg | 420 |
| aagagagcaa | cccggacttc | cttcccaaca | acttcaatca | gctgaatttg | gaccctcagc | 480 |
| agccagaagc | aaaaggggc | caacagatgt | caaaggggcc | ggaaaacaac | ctgtacagaa | 540 |
| agtatgagga | gaaggtgcgg | ccctgcattg | acctcatcga | ctccctacgg | gccctgggcg | 600 |
| tggagcagga | cctggcctg | cccgccattg | ccgttatcgg | ggaccagagc | tccggcaaga | 660 |
| gttccgtgct | ggaggctctg | tcgggggttg | ccctccccag | gggcagcgga | atcatcaccc | 720 |
| ggtgtccgct | ggtgctgaaa | ctgacaaagc | gggagtgtga | atggaccggg | aaaatcacct | 780 |
| accgcaacat | tacgcagcag | ctgcaaaatc | cctccgaagt | ggagtgggag | attcggagag | 840 |
| cccagaacat | catagctggg | aatggacttg | gcatcagcca | tgagctcatt | aatctggaga | 900 |

```
tcacctcccc tgaggtccca gatctgaccc tcattgacct tcctggcatc accagggtgg      960
ctgtggaaaa ccagccacaa gacattggac tgcagatcaa ggcactcatc aaaaagtaca     1020
tccagaggca ggagaccatc aacttggtgg tagtcccctg caacgtggac atcgccacca     1080
cagaggcgct gagcatggcc caggaggtgg accccgatgg agacaggacc atcgggatcc     1140
tgaccaaacc agacctggtg gacaagggca ccgagaaagg tgtcctgaag gtcatgcaga     1200
acctcaccta tcatctcaag aagggctata tgatcgtgaa gtgccgggc cagcaggata      1260 tcaccaacaa gctgagcttg gcagaggcaa ccaggaaaga aacgatgttc tttgagacgc     1320
atccgtattt cagaattctt ctggatgaag gaaaggccac agtgcctctt ctggcagaaa     1380
gacttaccac cgagctcatc tggcacatca ataaatcgct ccccttgtta gaaaaccaaa     1440
taaaggagaa gcaccagagg gcgacagagg agctacagca atacggggac gacattccca     1500
gcgatgaagg ggataaaatg ttcttcctca ttgagaaaat taaggtattt aatgaggaca     1560
ttggaaagtt aatagaagga gaagaaattg taatggagac agagtctcgc ttatgtaaca     1620
aaatcagaga ggagtttaca agctggatac tcatacttac caccaatatc gaaaaagtta     1680
aaagtatcct taacgaagaa gtctcaaaat atgaaagaa gtatcgaggc aaagaacttc      1740
ttggatttgt caattacaag acatttgaga ctgtcgtgaa gcattacctg gggcagctga     1800
tagacccagc actcaagatg ctccagaagg ccatggaaat tgtctggcaa actttcaagg     1860
acacagccaa aaagcatttt gctgaatttt gcaatctgca tcaaacagtc cagaacaaga     1920
tcgaagacat aaaaacaaaa caaatggcag aagcagcaaa tctgatccaa cttcagttca     1980
ggatggagaa gctggttttt tgtcaagacc agatttacgg cgtggttctg aacaaagtcc     2040
gagaagatat ttttaattcc atgggaaagg cttcagagac gcctcagtcg aagcagccct     2100
ttttaaatga tcaatcttcg atttcctcca tcgttgagat tggggtccac ctgaacgcat     2160
atttcatgga aaccagcaaa cgtctcgcca atcagatccc gttcatcatt cagtatttta     2220
tgctccaaga gaatggcgat aaggtccaga agccatgat gcagctacta caggacacac       2280
agcactattc ctggctgctt caagaacaga gtgatacagc taccaagagg aaattcctga     2340
aggagaagat ttttcggctg actcaggcac agcaagctct ctacgaattc ccccatttca     2400
aggggtaaat gccaaaggaa cagcagtact tctgggtttt gcttatgtgc atgatcatta     2460
agggaggtgg tccaggaatt ggcctcttgt gtggggccag acctctctgc tgctgtctgc     2520
atctatctct gctgtactgc actcagaaca agagtttata tctgaagtcc tgagccgctc     2580
agagctgtca cctcctccag gaggtcttcc cggtcctctg tgaagagggg tctctccagt     2640
ccttgggccc catagctccc agttacaata ttcttaaata ctaccaccat tctttgttca     2700
cttgtcaccc ctccccatta gattaggaga cctcagagag gtaaggtcag ttcttattct     2760
tttgtatttc cagaatcttg cgtggcctct ggcgcatagt agttcactta ataaatatct     2820
cattgaacaa atgaatgatg gggattacct gaggctgtgg cttaaatcca gtttggttgt     2880
ttggaatggt gtcccttggc tggtcctttt cttataaatt cagtcgtacc acctgcttcc     2940
catcatttgc tgtgatgatg tttccc                                          2966
```

<210> SEQ ID NO 4
<211> LENGTH: 637
<212> TYPE: DNA
<213> ORGANISM: Bos taurus

<400> SEQUENCE: 4

```
gctactattt ttgttattat tgacaataaa ttggaccatc acctttcccc tcaggttcac       60
```

```
agaaaaaagt caaggctggg attccactct tttgcctgag tctctcctgg tggctcaaaa    120
aggctattgt caggctccaa tggggagcat tgtctatgaa agaaaagaca gcacaaaata    180
acaggaaggc tgggggtcag gaaacctgga ttctggtccc aggtctgaca tcaattcaca    240
gctgtctttg gatccaagcc ccctagccct aaaagtgaaa agggctggcc caaacggctc    300
tggagacctt gcctccaaga tactctggcg ttcaaaggat ggtacatgtc cagttctctt    360
ccacctgggg agaggctcct ccgtggaact ggattcctgg agagggtcta tagtgctgtc    420
taaaatcata ggcctggaac atcaggtcac tgtgttcttg gggcgacaca tcccaggagc    480
ccacgggaga cccatcccat tcttaaagc acgggtaatc cagccagacc aaagccgctc    540
gtgcaagccg ctcccagcta tgcgtcttt accagcaac atttcctgta gggtccgccg    600
ggtccagaat cacaggcctg ggttttgcaa gttgctt                             637
```

<210> SEQ ID NO 5
<211> LENGTH: 707
<212> TYPE: DNA
<213> ORGANISM: Bos taurus

<400> SEQUENCE: 5

```
tttttcattt ttttaatttt attgttttta tctttatata catattttt tcattttct       60 aagtgcaatg tttactttta tattatttct ctttggggaa agagaaatgt agtttccctc    120
aggttgagag aaattcactt catatttcat ttgaatcaca gtgacttaac atttgaagta    180
aggatatctt ttctgaggaa aaaaaaaatc acttaaaccg aactttaaa atctgcaagt    240 cttgaaaaaa agattctgaa gtagaatatc tacgtggagg cttaacagaa tcaggcaaca    300
tttagatgcc atcagtggc caaaacggca gctggattat taattaaaga gttcttgag    360 caaaaaattg tctgtgattt tgctgtttta gagcaatgat aggaaactat tacttcccag    420
gcaatgggat agtgttacat gaataaaatt acacgaataa agttcaggtg gtatttccac    480
cagaagaggg ttttgttcct tgacccaatt caaatgacgt ttttcttcga gctcttctt    540 agcagtaaga gaaggctctg gaactttctc acgttgccct agattacatc cttatttcaa    600
gtggttcaga gttaaatggg aaagagtagc tttgtgccac agccttattc acagaaaagc    660
caggtccagt cgcagccccc tgctccgctg tcacctggtg cttttgc                   707
```

<210> SEQ ID NO 6
<211> LENGTH: 810
<212> TYPE: DNA
<213> ORGANISM: Bos taurus

<400> SEQUENCE: 6

```
catgttgaag ttactgtatt tggtcttttt agagcagcct agcttatatt ctagtcacta     60
tagggtgccg tgaccagctt gtaatgatat agaaagctct tcttctattc taatccatcc    120
cagaagtcca cggtgagctt ggaggaagaa gatgtgaaga ggtagtgctt tggaagataa    180
atagagagat gagatccaga aagagagaa agagaaatag acaacgtgat caattcattt    240
ctgttcagag ttgcccagag tcaacatcct tacgggtaga ttgaggttca ccaccacctc    300
tcaccaccca ttttcttgg gggttggagc caggtcatag aaagtcagat gccacagaga    360
tgttttcaga gggagtcagg acccaatgct gcattgttca cagggtccga gtcatcacag    420
attctggtga cttcctcctc ctgcatggtt tccttctgag aagccatctc cactgaattt    480
tcaccctctc tcagcttatg aaaattcctc cttctccagg tgtagtaggc ccccaggccc    540
```

-continued

```
agcagaaggg agagaaggcc agccagcagt cccaggaccc agaggagctg ctggaacagc      600
tgcaggcggt gcagggctct ggttccaaag taggtggcag cagaggcaga gcccagggaa      660
ttagaggcag agcacacata ttccccctgg tcactgggcc tcagctcctc tatgaccacc      720
ctcaaggcat tgggggtgac tgagacatgg atgtgtggct tggcaggagc aaccttggac      780
tggctagagg ccaccagccg actgccaagg                                        810
```

<210> SEQ ID NO 7
<211> LENGTH: 603
<212> TYPE: DNA
<213> ORGANISM: Bos taurus

<400> SEQUENCE: 7

```
ttttgctat tgttacttac ataactttta attttacata aaacattgtt aattatagct       60
gtacaacaaa ttaacctaca atttatccgt ttaaaacaac aaacacatta tctcacacaa      120
tttctgaggg ataggagtcc tggaactgct cagctgggtg gtcccggctc tcagtctctt      180
cggattgcta ctgagatgtc ggcagcagct ggggtcccag ctgaaggctg agaccagct       240 tataaacccc acactctgtt ggccgctcca tagcaaagga cagctggcct cctccaagtg      300
gaggatgtta gagacagaga gagacaggcc aggatgcccc tgcgacctca tcttctacag      360
gaccttactg ctgatgcagg tcaacctcag tacattcaga agtagagtac caggtcgggg      420
ctcttggggg ggctgcctcc tgggaggctg tcaaccccag ggcctgtttc cttgcccagt      480
ggtgcctccc aggataggta tggcccctag agcttcaagg ggcagagagc agccagacac      540
ggctccagaa ccctctgggc tcagcttctt tcttggggga aggggagca ggtcctggag       600 cct                                                                    603
```

<210> SEQ ID NO 8
<211> LENGTH: 591
<212> TYPE: DNA
<213> ORGANISM: Bos taurus

<400> SEQUENCE: 8

```
agagaggcag ccgcagccaa ccagtgtctg cagagagcct ggcaccagaa cccacggcca      60
tgggcgggga cctgacggtg aagatgctag ggggccagga gatcctggtg cctctgaggg      120
actccatgac ggtatccgag ctgaagcagt tcatcgccca gaagatcaat gtgcctgctt      180
tccagcagcg cctggcccac cttgacagca gggaggtgct gcaggaaggg gtgccccttg      240
tcctccaggg cctgagagct ggcagcaccg tcctgctggt ggtgcagaac tgcatctcca      300
tcctggtgag gaacgacaag ggtcgcagca gcccctatga ggtccagctg aagcagactg      360
tggctgagct caagcagcag gtgtgccaaa aggagcgtgt acaagcagac cagttctggc      420
tgtcttttga agggaggccc atggatgatg agcacccgct ggaggaatac ggcctcatga      480 agggggtgcac cgtgttcatg aatctacgtc ttcggggtgg gtagggaagg gccaggaggg      540
ccttagggag ggctccccat gcagcgcagt gaataaagtt gtagcaaagc c               591
```

<210> SEQ ID NO 9
<211> LENGTH: 578
<212> TYPE: DNA
<213> ORGANISM: Bos taurus
<220> FEATURE:
<221> NAME/KEY: misc_feature
<222> LOCATION: 436
<223> OTHER INFORMATION: n = A,T,C or G

<400> SEQUENCE: 9

```
tttttacccca ttgcattttt attaaaatac attgttttat cctttagatg tatactgact      60
tcaagatttc catcaacgtt tttatcaaac aacataggta gtttaaatgg gcctactttg     120
cattctgtaa ttgtagtctc ttgaaagaca aaaacagcga ttaaatagtt ccttcccca      180 tagtcctttt gcatatatgc cccaacaatc tgatcttcac tgtgaatcac tgttagagta    240
ggtccttgat tagagcatat ctgaagcaac ctatcagtag aaaatccatg gacactggcc    300
ttatagagaa ggctaaactg cttttctcca aagtaatttt gcagcttttt ttcttgcatc    360
catgtcaaac gagttgccac ttccatactt ctcaatctgt ttggaggatt tcttcaaggg    420
ctgaagctga gggtanctgc tctgtctgac agctaggcag gcacaaagtg agagcaaaaa    480
ctttcccagc aaccttgagg ctttggagaa gcagagaaca ggaaactgaa acttagtgag    540
gtccagccca gttggctgtg tgctcacttc ctctagta                            578

<210> SEQ ID NO 10
<211> LENGTH: 185
<212> TYPE: DNA
<213> ORGANISM: Bos taurus

<400> SEQUENCE: 10
gttctggagc cgtgtctggc tgctctctgc cccttgaagc tctagggggcc atacctatcc    60 tgggaggcac cactgggcaa ggaacaggcc gtgagggtgt gacagcctcc caggaggcag   120
cccccccaag agcccccgacc tggtactcta cctctgaatg tactgaggtg acctgcatca   180
gcagt                                                                185

<210> SEQ ID NO 11
<211> LENGTH: 573
<212> TYPE: DNA
<213> ORGANISM: Bos taurus

<400> SEQUENCE: 11
cccattttat gtgtttattg atcaccatag gccttgagca ttaacattca aatttctatt     60
taaacatgct aaaataggat atgttaataa taccttagtt tgcaaacata catgaataat   120
gtctgatata acgccaggaa taaaaatatt ctagcacaga actcagcatt tccaaatgct   180
gtcatatatt caacaccagg agaaaatcat cttccatttc aacaagcctt agttttatt    240 tgagtttcca aatttgacct tcaccacgtg gcgggctgcc gtctatgggg tcacacagga   300
ctgaagcgac ttagcagcag cagcagcagc agcagcatct tctccattta aagcattgac   360
cactgttttc tcaagaggaa aattctctaa aaagtcatct gcagcccgca gcatctcttt   420
cagtgcaaag aggatcagga catctatgac aggctccagt tcccactctg aggtataatt   480
actaaccaca aagatgtcaa aaagagggaa tccaagtttt ctgtgaactg cctctagctg   540
aagtttcaca ggcacacatt tgtatacgtc tat                                 573

<210> SEQ ID NO 12
<211> LENGTH: 674
<212> TYPE: DNA
<213> ORGANISM: Bos taurus

<400> SEQUENCE: 12
cccattttat gtgtttattg atcaccatag gccttgagca ttaacattca aatttctatt     60
taaacatgct aaaataggat atgttaataa taccttagtt tgcaaacata catgaataat   120
gtctgatata acgccaggaa taaaaatatt ctagcacaga actcagcatt tccaaatgct   180
```

```
gtcatatatt caacaccagg agaaaatcat cttccatttc aacaagcctt agttttatt      240 tgagtttcca aatttgacct tcaccacgtg gcgggctgcc gtctatgggg tcacacagga    300
ctgaagcgac ttagcagcag cagcagcagc agcagcatct tctccattta gagcattgac    360 cactagggg cagaaatgac ccaacattta gtttgtttcc gttgactgtt tcagattttg     420
aatccgagac gtcgtatgct cctaaagcta aggtgtacc ttctttaaac tgcatatcaa     480
acaaacaaac aaaagaaag aaaaaaaaaa ctgaattcaa ttttgtctct ttcattttt      540 atgagttacc aagtccaaat cttatgttta ttttcaacta caataaaatt aaatttacaa    600
tagagagatt gatagttgat tattggtttg ttgtaatatg agactagcaa tgtccttcag    660
tatctgggtt tatg                                                      674

<210> SEQ ID NO 13
<211> LENGTH: 674
<212> TYPE: DNA
<213> ORGANISM: Bos taurus

<400> SEQUENCE: 13
gcctggacat ggatgacata ccctatatct tagaaggcca ttttcctgac aaataccagt     60
ttaattcctt aaaactaagg ccaaaaggca ttggtaacca tacagtctgc ccattgctga    120
aggacagaat tcattgtgtg gcatttgtgt tcagtgccaa ctctgttgga cagctctccc    180
atgagatggt ggaaaagatc aaaagaattc gaagggagtt gattaagtct gatgtggtcc    240
atgtggtgtt gctcacgcat gtggatacct tggatctgat tacaaaaggt gacctcatag    300
acgtatacaa atgtgtgcct gtgaaacttc agctagaggc agttcacaga aaacttggat    360
tccctctttc tgacatcttt gtggttagta attataccctc agagtgggaa ctggagcctg   420
tcatagatgt cctgatcctc tctgcactga agagatgct gcgggctgca gatgacttct     480
tagagaattt tcctcttgag aaaacagtgg tcaatgctct aaatggagaa gatgctgctg    540
ctgctgctgc tgctgctaag tcgcttcagt cctgtgtgac cccatagacg gcagcccgtc    600
acgtggtgaa ggtcaaattt ggaaactcaa ataaaaacta aggcttgttg aaatggaaga    660
tgaccttcaa aaaa                                                      674

<210> SEQ ID NO 14
<211> LENGTH: 637
<212> TYPE: DNA
<213> ORGANISM: Bos taurus

<400> SEQUENCE: 14
tttttgcggg tgttttctga gagacgttta ttctgtgtgt gtgtgtgttt tttttttacc     60
tcggtcattg ccaagtgtga cagaggaagc tctggactgc agctggaaaa ggaagacaag    120
gaggaaggcg gggcttccag gcagctgccg gctacttctt ctccttgctc tctttctgtc    180
tgctttcgac ttgcttgtgg acagtatagc ccagaaaggc cccgatcttg gccatgaggg    240
cactgccacc gctagcgccc aggctctgca gcgtggccac cagcccccg gccggcactc     300 cgcctccgtt cgccacggcc gaccagctca tcagtgagga ggccaacgag ttggcggcga    360
tgccggtgct cgcgaagccc agcatgggca gtgccgcggc catgagtccg cctccaacgg    420
ccatgtaggt caccatgccc cagaagctcg agtcgctgtt ttcctctgag tatcttttt     480 cgtcttcctc ctcgcagcag ccgcaggtgt agagtagcag gtagcatagg aagagcgata    540
ccgccttctg ccgcatggtg gcgcagctca aggctttgtc accgtatctt ggaggagagc    600
agagaaagaa tcttcctgcc tggatggagc ctgctgc                             637
```

<210> SEQ ID NO 15
<211> LENGTH: 690
<212> TYPE: DNA
<213> ORGANISM: Bos taurus

<400> SEQUENCE: 15

| | | | | | |
|---|---|---|---|---|---|
| gatttgatag | aatgatttat | tttcccatta | caggaaagtc | atgagtgact | tgttctgagg | 60 |
| tatgtttctg | agctacgaag | gacatctatt | aggaagctct | gcacttgaag | gttcctcttt | 120 |
| aggtgacagc | attttatggc | tggacagtct | ctgcgggaac | cagattccct | gttgtgtcca | 180 |
| actgcataca | tttacacgtg | catgcagaca | cgggacactc | ggcgtgatcc | ctgaaccaac | 240 |
| taagcatgtg | tccggcatgt | ccaccgtgcc | tgcaattgtg | acaccatgta | aaccagttgt | 300 |
| taaactgagc | taatttttg | tccttgctca | agtctacttt | ttcatctgat | ttggatcctc | 360 |
| caggacaact | agaaacaggt | gttcccatat | taatgaggca | aagtgcacag | cgaggaaggg | 420 |
| gttttcgaca | gccagggcaa | cttgtgactt | tagatttcgt | tggtgagcca | ctgacaccat | 480 |
| actgactgaa | acctcggccc | tgatggggaa | cagtggaaca | gctgtaggag | atagactttc | 540 |
| cacaaaaatt | gcaactcaca | aacacctgtg | ctaaaggctt | agaactggga | tccaacttac | 600 |
| tcctgtgaat | atcaaattca | gctcgtttgt | gccaaaacct | ccaggcatct | aacaaatttc | 660 |
| tataattctc | aatccagtac | tgaactcttt | | | | 690 |

<210> SEQ ID NO 16
<211> LENGTH: 701
<212> TYPE: DNA
<213> ORGANISM: Bos taurus
<220> FEATURE:
<221> NAME/KEY: misc_feature
<222> LOCATION: 538
<223> OTHER INFORMATION: n = A,T,C or G

<400> SEQUENCE: 16

| | | | | | |
|---|---|---|---|---|---|
| tttttgcaac | aaaacgtttt | tttatttcaa | aacgcagtca | ctgtaataat | aataataaca | 60 |
| acaacaataa | tataaaaaag | cgtttctcct | cctttcaccc | tcgtgcaaaa | tgccagatgc | 120 |
| actcaggtgg | cttgaaggta | cctagctttg | gacgtggcgt | cttcctgcag | tgctgcacag | 180 |
| cagcgaactc | agtcccaagt | tccttttggt | ggatccgcgt | ggtagttcag | ttctagaagt | 240 |
| cggtggcttc | tcagaagcaa | gttcagacag | cacaggacgc | ccgctcgagc | ccgcccttcc | 300 |
| ggctctggct | cactcgcccc | tctcgggggt | ctcgcttccc | ttccctccgc | cggccctcga | 360 |
| gctcctaaga | ggcgtgcagc | cggttggaca | gggcccggca | gccctggact | gcctccagcg | 420 |
| gcttgccttg | ctcccgcggg | gccgactccc | ccgggcggc | ccgcagctcg | gccagggtcg | 480 |
| cctcgcgctc | ccgccggcgg | ccggcggccg | cgaaagggcc | gcacacggcc | tccatcangc | 540 |
| cgagcacggc | gccgaagagc | gccagcacgc | cgcccagcac | gtacattcgc | accagcttcg | 600 |
| cgctgggctt | ctgcgccatc | agctccttgg | ccagggaat | cagctcctgg | accgtctcca | 660 |
| tctgggctgc | ggggctctcg | gggtgggggg | tgacctgcgg | g | | 701 |

<210> SEQ ID NO 17
<211> LENGTH: 809
<212> TYPE: DNA
<213> ORGANISM: Bos taurus

<400> SEQUENCE: 17

| | | | | | |
|---|---|---|---|---|---|
| gattcttcat | ctttctttat | taatagttct | aacttcttca | gctatccagt | gaactttaaa | 60 |

-continued

| | |
|---|---|
| atcatttggg agtacttgta taaaagaacc ttataattga cttgcagtag tagacttccc | 120 |
| ttccactttt cactttcatg cattggagaa ggaaatggca acccacttca gtgttcttgc | 180 |
| ctggagaatc ccagggacgg gggagcctgg tgggctgccg tctatggggt cacacagagt | 240 |
| tggacacaac tgaagtgact tagcggcagc agcagcagca gtaaccttat ttgatcactc | 300 |
| tactttggaa atatggctag ggtggtttgg aattcaatca atgaaaatca ggcacgggat | 360 |
| cattagagga aaaatgcttt ttctcagaga atgaaatgt taatctcttg gaacacttg | 420 |
| tttcttttaa ttaacttaaa ttcatatttt catccagagc taagtgatac attctccttc | 480 |
| ctttatttat ctccagcatt tcattctctc acagtcttcc tttccataag gagaaaattt | 540 |
| taaatataca ttatcacact ggggagatcg ggagatatgc ttaagagcag gtatgcttgc | 600 |
| tcccttccag gcagtgtgcg aatttctgtg aatacaaaga taagcaaaat ccaaccctg | 660 |
| cttcttgaaa agctcactat ttagagaagc agatatctct aaccatttta tgctcagtgt | 720 |
| ggttagtact gacactgagt tttaaattaa gtattgaaac aattaagaca gtaagtaag | 780 |
| ggaatagtta acttttctga ggatatatt | 809 |

<210> SEQ ID NO 18
<211> LENGTH: 362
<212> TYPE: DNA
<213> ORGANISM: Bos taurus
<220> FEATURE:
<221> NAME/KEY: misc_feature
<222> LOCATION: 18
<223> OTHER INFORMATION: n = A,T,C or G

<400> SEQUENCE: 18

| | |
|---|---|
| tggcacccac agcatgtngg acagggaaga gaagctagga ggcagacact ggggtctgga | 60 |
| aactagactt ggtctggaca gtgctggcct gcaccctgtg gggcctcctc tggctgctga | 120 |
| gatgtctgcg agccatgctg agggggcat ctgggtgggc ccaagctgga tctccagccg | 180 |
| aggagggcag ggacagggcc tatcatgcct gaggacctgg ggtgggggtg ggctgggctg | 240 |
| ggctgggctg ggagcgcccc gtgacacact gtgcttttcc catgtgctct gtgtgtgtct | 300 |
| gggctgtgcc cggggtttca caaataaagt cgtgtggcag cagtggggga aaaaaaaaa | 360 |
| aa | 362 |

<210> SEQ ID NO 19
<211> LENGTH: 732
<212> TYPE: DNA
<213> ORGANISM: Bos taurus
<220> FEATURE:
<221> NAME/KEY: misc_feature
<222> LOCATION: 680
<223> OTHER INFORMATION: n = A,T,C or G

<400> SEQUENCE: 19

| | |
|---|---|
| ccgaggtgag tagggagggc gccgtagacg cggggaccga agtggacgga ccggcgtcg | 60 |
| cccctttgcgc cagccccgca gcctcctgga gggccccaca ctgtggctgt acttcctccg | 120 |
| cattcgactt ggcagcgcgg gtctgacgct tcgcggctct taagagggcc tcccaaggcc | 180 |
| agctcatgag cgctcttctg ggaagtgagg tctagctgtc ctgaagacgc ctgcagcagc | 240 |
| tgtcagtcca gggaccttgg agcaaccact gatgggcccg gtcggtttac acaacattgg | 300 |
| acagacatgc tgtcttaact ccctgatcca ggtgcttgtt agaaatgtgg gatttgccaa | 360 |
| gatactgaag aggataacgg tgccaggcgg agctgaggag cagaggagga gtgtcccctt | 420 |
| ccagctgctc ttgctgctgg agaagatgca ggacagccgg aagaaggcgg tgcagcccac | 480 |

```
ggagctggcc tactgtctgc agaagtacaa cattccgatg tttgtccagc atgatgctgc    540
ccagctctac ctcacagtct ggaacctgat caagaaccag atcacagacg tggacttggt    600
ggcaaggctg caagccctct acaccatccg gttgaaggag cctttgtct gtcttgaatg     660 tacctcggag atgagcagan acagcagcat gctggccctc ccctgtctg tctttgatat     720 gcactggaag cc                                                         732

<210> SEQ ID NO 20
<211> LENGTH: 793
<212> TYPE: DNA
<213> ORGANISM: Bos taurus

<400> SEQUENCE: 20
catcattcta ctcataagta tttagacacc agaaaggtaa acagagcaaa aatacagaca      60
tagccccacc tgaacagctg ctcctggtta tggaaatcgt ttgggggagg taatctgaaa    120
aagctgtctg aagcagaccc tctaggtgag cacctctcct ccctgcccca ggcagcttga    180
cttccacacg aaggtcttac atgtggccat gtgggctgtg cacttgaccc cagtagggga    240
cctgccctcc ttgtagcctc agtgtctgac cctactgtgg cctttgggat tgccttccat    300
gtaggctgtg agcttgaccc ctgtggtggg gggcctgcct tccctgtagc ctcagtgtct    360
gaccctgatg tggcctttgg gattgccttc catgtaggct gtgagcttga ccctgtggt     420 ggggggcctg ccttccctgt agcctcagtg tctgaccctg atgtggcctt gggattgcc     480 ttccgtgtag gctgtgagct tgaccccgtg gtgggggggc cgccttccc tgtagcctcg    540 gtgtctgacc ctgatgtggc ctttggattt gccttccgta taggctgtga gcttgacccc    600
tgcggtgggg ggcctgccct cccttttagcc tgactgtctg accttgatgt ggcccttggg    660
attgtccctc cggtgggctg tggttctgcc atctttgtgg tctgaagctg tgtcccttgt    720
gtggcttgtg cctcctgtgt ggactgctgg cctgacatcc ttataacctg agagtatgtc    780
atccgggggg cct                                                        793

<210> SEQ ID NO 21
<211> LENGTH: 667
<212> TYPE: DNA
<213> ORGANISM: Bos taurus

<400> SEQUENCE: 21
tttttaatat aaatatcatg aagtttattt aaatgatgat tgtgtcaagt tctatagctt      60
cttgttcctt tgtgtctttg gtgaaaatga acaagtaaat gaaattctag tgttttagct    120 cttagagta agaggcatgt atcatctggt gagtcattcc tcagaagatt ctggagttca     180
tcatgaagtt ttctgttctc agcttgcaat ttctccttga gcttttaac ctcttcctaa     240 agagtgatac ataaaatgaa agagctgagc aaaaagtggt gtccagatca ttgtttatag    300
aaagtcccag tcactgactt tcccttactt attttaaaca atcagtagta aaagatagtc    360
cctaattcct cctttccatt catatccatt ttacctctta ctcttggttt cctacttgtg    420
taattcttct tcccggtctg ttcctatagc tgcagaaaca tcatctctca atccctgaaa    480
tattggtatc ccaagaatta tatcctaagg ccccttctcc ctttgtcctg aagcaatctg    540
aatcacatct tgacttcagt tctcatgcac acacaaagga acatcagatc tagtattaca    600
aggagaggtt gaaattagta aaatgcacgt tttatccatt atgaatatca taactataac    660
tcaatac                                                               667
```

<210> SEQ ID NO 22
<211> LENGTH: 580
<212> TYPE: DNA
<213> ORGANISM: Bos taurus

<400> SEQUENCE: 22

```
tgaaagtact gtcaacatgg acgccaagcc tcagagcaag agaatagctt tggatatcag      60
ggaatgggag cagacatttc aagaactgat ctgtcaggag aagccccggg ccagatggac     120
cctgaagatg gatggaaacc ttcagccaga ctgtgtggcc ccggggtgga ggcaatacca     180
gcagaaagga tttggcaggt tccagtgttc ctcatgccgt cgaagctggg cttccgccca     240
agtgcagata ctatgtcaca tgtacctgga gaaccagaaa tccccgggca aggtgctcat     300
gaggatcttt ggacagaggt gcaagaagtg ctctcggtct cagtttgaga agcctgattt     360
ctccccagaa agcagcaaga ggattctgaa aaacctggtg cagcgtattc tggagaaatt     420
ctacagaaat ggtatcagga aggtttcaga gctacctgtg atcccggaag tacgtttgga     480
tgggtcccat gacaaggcca actgtgaagc atgtgttctg ggctactgtg accgaacctt     540
agaaaacggc atgacagggc agaaaaatc ctctctctcc                            580
```

<210> SEQ ID NO 23
<211> LENGTH: 830
<212> TYPE: DNA
<213> ORGANISM: Bos taurus

<400> SEQUENCE: 23

```
attctcctga tttaatccct ggtttatttt cacaccctgt atgaaatggt ggatggcctt      60
gtcttcacac ttcctctggt acagctgaaa gttgccatat cgcaggtgga gcacttgttt     120
ggctacggga ggaagctctt tgctgaattc tttttgaaag taatactctg cttcttcata     180
ctgaccgact tgtgcatgga ggcaggcgag ataggagccg atacggaaga aatttccatt     240
actctcatca gctctcttta aatgatctat agcatgtctt actaatttct gtaattcctc     300
tctctccccg cccatttct ctacttccag gactttggcc ctatagcagc acccaatatg      360
gcaatgcagg tagatgttgt tgggcatgca ttttagagcc tttctcagga gttctatagc     420
aaggtccaag tcacctttc ttcgatacag cttgctgcc cctcgaatca catctgtggc       480
caatggggct ttttccagag cttcttcaac taatctctct ccttcatctt ttttattcat     540
cttttgaagt ttcagggcca ggaggacttt gacatactgg ttgtcaggat tcagctgaat     600
ggcttgcctc aaagggttaa tggggttctg agatggtggc tggttatcca gccggtagct     660
cgcgatggcc agtccagagg cgaactctgg gttcttgggg ttcttctcca gagccttctc     720
aaaacacacc ttggcccttt cattttggtt tcttccacac tttaaccgtg tccacccttc     780
ttcacagtcc agctcaagac tctcaattct gtaggggctg gaaaacttct                830
```

<210> SEQ ID NO 24
<211> LENGTH: 667
<212> TYPE: DNA
<213> ORGANISM: Bos taurus

<400> SEQUENCE: 24

```
gcatctttat ttatttattt acttatgata catcttggag attttctcac attaccacaa      60
atacagcttc cttttactt tagtgatata gagcattcct gtgtaattgt gtctcagcat      120
ttacctcact agtatgtgat aggggactt taaagatgtt tccagtcttt tggaattata     180
acaatccttc aatgaatgta ccaccattca ttccatattc agcttgggta cataaatgtt     240
```

```
taaaataagt ccttaagtga gaacttgctg gatcagcagt gttttgcattt aaattttggt    300 atacatctgt atcaatctgc actcctccta gcaaatatca ggctgccaat ttcctgtaac    360
ccttgccagg ccagtgtcct gtcaaaacta tacttcttgg cccactgaga ggtgacacag    420
ttatctccta attatacttt gcataccttt tataatcagc aaaggtaaac attttaatta    480
tcttcttata tgtttaccca tttaaaaaat gtggttgttg ccctttcctt gctgatttat    540
gtggggttgt tagatcgagt ctaaagaaac tctctcccata tctatatcat aggtgactgt    600
cccttctctt tatgctttgc tgaaactttg ctatgaatca tcattatctt ttactcattt    660
tcatttc                                                              667
```

<210> SEQ ID NO 25
<211> LENGTH: 320
<212> TYPE: DNA
<213> ORGANISM: Bos taurus

<400> SEQUENCE: 25

```
catctctcac tttagctatc tctgagcaat ctgggcactt ttttaaaata gagaaatgaa     60
tgaatgtggg tgatatgctt taatctacat gcaaataaga atacacgctc cacaactgag    120
atcaggggaa tgtggaaggg gcggcgagag ggagaaagag gaaacatctt tttttgccct    180
cctcccccgc cccccggccc cctttctcag cagcttgttg tcgttgtgag tcaagtgcct    240
cctggtgcca gctgcatcct tctgcctatt ctgtaagctg atgccatggg cagcctctcg    300
cctcatcctc cccgcgtcga                                                320
```

<210> SEQ ID NO 26
<211> LENGTH: 418
<212> TYPE: DNA
<213> ORGANISM: Bos taurus

<400> SEQUENCE: 26

```
gaattcgggc agagagaggt agtgggggag agcccggccg aagacgagga cacaggatga     60
gggccctgcg ggtctcccaa gcgctggtcc gctccttag ctcaaccgcc cggaaccgct     120
tcgagaaccg agtagctgag aaacagaaac tcttccagga ggacaatggc ctcccggtgc    180
acttgaaggg cggtgcaaca gacaacatcc tgtatcgagt gacgatgact ctgtgtctgg    240
ggggcactct ctacagcctg tactgccttg gctgggcctc cttccctcac aagaagtgaa    300
accaagaagt ctgcaggacc cgaacaggca tcaataaatg tgctggtttc ctggggaaca    360
cagcccagct ccatgctccc taaaaaaaaa aaaaaaaaa aaaaaaaaaa aggaattc       418
```

<210> SEQ ID NO 27
<211> LENGTH: 645
<212> TYPE: DNA
<213> ORGANISM: Bos taurus
<220> FEATURE:
<221> NAME/KEY: misc_feature
<222> LOCATION: 509
<223> OTHER INFORMATION: n = A,T,C or G

<400> SEQUENCE: 27

```
agggagagcc ctgcagtgct gaggagcagt gtggagggca ctatgagctc tttgctgtga     60
tcgcccacgt ggggaacgct gactatggtc actactgtgc ctacatccgg agttctgaag    120
atggagaatg gttctgcttc aacgactcca atgtttcttg ggggtgctgg aagacgtcc     180 agtgtaccta tgggaatcac agctaccgct ggcgggagac tgcctatctc ctgttttacg    240
```

```
tgaagactga gtcctaatgg atgctcccta aaccttcaga gacctacaga gtgtcatctt      300
ccttttctgt tcctgtctct gcagattgta agagattctg caatgaggag aggcaccgtt      360
ttcaagctgt ttacatttta tttataataa gtggtgattc ttaaaatatt tagcagtgac      420
actacacagg tctggatcgg tcagaatggg agccactggt ggactcatgg tctggattgc      480
tcctgctgca caaggcagtg atctgttanc tgggagctgc agagtcaagg tgctcccagg      540
ggaggagaga ccaggccagt gctggtagca agaggcagtc gggtaacaaa gggctgtggt      600
caagaattat ttcaatattc tacagctaat gtgactatac tgata                     645

<210> SEQ ID NO 28
<211> LENGTH: 549
<212> TYPE: DNA
<213> ORGANISM: Bos taurus

<400> SEQUENCE: 28
gcacgagcct ctcctcacaa cggtgatgag ggtggccaaa accaatctag gagccactca       60
gcagcgggga gtgggtactc tggtgcccat ataggctcag ggcccagcca ggtcactgct      120
gggatccaag tgcctaggag aggccctcag tctaaacggg agatggccca gctgttcaca      180
gcaggggcag atcgacaggc tgcacgggca acaggccccc agcccatcca agtagcaaga      240
tcacttcccc cagggtggac tgatccacgg cccgttcaag cagtaggccc actacctgca      300
gggtgtgcat attcacagtc tacactgggg agaggaccac aggcccccg gatgacatac      360 tctcaggcta taaggatgtc aggccagcag tccacacagg aggcacaagc cacacaaggg      420
acacagcttc agaccacaaa gatggcagaa ccacagccca ccggagggac aatcccaagg      480
gccatatcaa ggtcagacag tcaggctaaa gggagggcag gccccccacc acaggggtca      540
agctcacag                                                             549

<210> SEQ ID NO 29
<211> LENGTH: 496
<212> TYPE: DNA
<213> ORGANISM: Bos taurus

<400> SEQUENCE: 29
atcatcacac tggctttatt ggccctgaga gccacagagt aaatccccag ggggccctgc       60 ttccccctcac ccccaagtct gtccagaggc cctagggctg gctgagtgtt caccgctgca     120
atcttggctt cctgtcccag ctgtcgtgag cttgccaggc ccgcatcctt tgagagctcc     180
ccagatccca gagtcaggct caacctggag ggcgtagttg gcaggggcta tgcagggacg     240
gcctgaggcc ggctggcctt cactcaaaga agaacattcc tggcgtccgg tacaggcagg     300
gggtcagccc cagtgggtag ctggagcttc cctggacagg gaagctgcct gcaacccagg     360
gttccttggg gtcagctggc aggggcagcg gggcccggag ggaggctgga ggggtggatg     420
gtgcagggga gggggctgct gaggccaaga ggtgctccag tcctgggtca gaccccatgc     480
agaaattcaa cgcctg                                                     496

<210> SEQ ID NO 30
<211> LENGTH: 415
<212> TYPE: DNA
<213> ORGANISM: Bos taurus

<400> SEQUENCE: 30
tttttgcaca agctctgcat ccttctgggt gaacttacat gttctctcaa ggatgttccg       60
gacagtgctg atctcttcag cgacgctgcc tctcaccttc ccctcggcca tcttgcagcg     120
```

-continued

| | |
|---|---|
| ggtcaagagg ttcaccaggt atctgagcct ctggatttca cttttggaggt catctaactc | 180 |
| ctggctgctg aagctcaaac gcttcttggc aagccattcg tgaacctggt ctaatcgagt | 240 |
| cctcactttc tcttgctcta agacatgcac ttttttcagg gaatcatata ggccagccag | 300 |
| gtggtcatag aagctgatat aattctcaac aaggcccagg tccttcactg acagattttt | 360 |
| ctgggccagc ttctcttcca acttcaagaa atcttccggg agctcctggc agatg | 415 |

<210> SEQ ID NO 31
<211> LENGTH: 1408
<212> TYPE: DNA
<213> ORGANISM: Bos taurus

<400> SEQUENCE: 31

| | |
|---|---|
| ccaccttcca gcctcctccg tccagccttc tccccttcca gacagtcctc atttcttctt | 60 |
| ctcctaggca gcagccggcc ggagccccca gtctgccaga gccaagagcc caggtggggt | 120 |
| tgagaacctc agcaaagaat gttgacaaca ctgctgcccc tgctgccact gctcctgccc | 180 |
| ggctgggccc tctgcagcca ggaagcctca gatggcccgt gggacctcca catgacccag | 240 |
| gtctcctact tccgcaaccc ctctcaagtg tggcaccggg gcaacgcgac gctggggggg | 300 |
| gtcctgacgc acgtgctgga aggcccaggc cgcaatgtct cgatccaaca gctgcagccc | 360 |
| ttgcaggagc ccgacagctg ggcactcacg aagatatacc tgaatcgcta cctgaggag | 420 |
| ttcgtgggct tggtgcaggt ggtgcaccag gagcggggcg tgacctttcc tctgatcatt | 480 |
| cgctgcttcc tgggctgcga gttgcctcct gagggctcgg aagcccgtgt cttcttcgaa | 540 |
| gtggctgtga atgggagctc cttttgtaaat tccagccaa aaacagcctc atgggtggcg | 600 |
| gaacctcatg caccatccag agtggtcacc tacacggttg accagctaaa caagtacaat | 660 |
| cgaactcggt acgaactgag ggaatttcta caggacacct gtgtgcaata catacagaaa | 720 |
| cacatcacca cgaacaactt gaaaggaagc caaacaggcc gttcctacac ttcactggtc | 780 |
| ctgggcgtcc tggtgggctg tttcatcgtc actggagtgg ctgtaggcat cttcctgtgc | 840 |
| acaggtggac ggcggcggtg ttgattctct ccagccctcg ctggaaaaag gctagactga | 900 |
| ttcagctcac tgcagaactg tgcacactct ccatctggga cattatattc cagaagattt | 960 |
| agagtggcag ctcatttctt ctctgagatc gtcccaccaa gagtttgggg gaaggaaggg | 1020 |
| gaggagccta ggtagacatg gtactcggct tgctaagaac caaagaactc ctatattttg | 1080 |
| ctgaattggt ctgggaagtg aatgcttatt tgtatttgta gaaaacagat gatggagttg | 1140 |
| gggcaacgga ggtggtctat ggcccttctt tcaaagacag aatctgaggc attcaaaaca | 1200 |
| cacaaccaag taaaacaagt catccgcaac ccaaataacc aacatctgtg ctttcaggga | 1260 |
| tgttagattt gggaagagac actggtgcaa tagaggtagt ggtaaccaga gaaatgatga | 1320 |
| aagtgtgaaa ttcaagtaat atgggagcaa ggagttatta agtaatcaat aataataact | 1380 |
| aataaaattc cttacttatg tatacagc | 1408 |

<210> SEQ ID NO 32
<211> LENGTH: 656
<212> TYPE: DNA
<213> ORGANISM: Bos taurus

<400> SEQUENCE: 32

| | |
|---|---|
| tttttcgcgc tgaattttaa taatagatgc cacatgttgc tacacagaga atacaagtaa | 60 |
| atgtgactct tacgcctatg gatatgtata tacattgaac ctttggaatt actaacgtgg | 120 |

```
gggatcagaa aaagaagcca atagaaaaga ctggggaaga gttagaagag caagtggcca    180
agacagagtt ccaagaaaga agtatctaac ggcaaaaaca gaaaaagatc agatggactc    240
ataagtgccc aatggatgtg acaaccagag tcactgatga ccttgacaaa ataatttca    300 atagatcgtt aagggcaaaa gtcggtttca gtgggtcagt cagttcagtc gctcagttgt    360
gtctgagttg tttcgacctc atggactgca acacgtacat aagcaagctt agcaaggacc    420
agacactaaa tatttcaaac ttgcaagcag gtcatggtca tgtggtctct gttgcactat    480
tccactgcca ttattttttg caaaaacagc cacagacaat acataaatga atggatgtgc    540
ctgtgttcca ataaaacttt atttataaaa tcaggcagtg atggattggg ccacagaagt    600
ggccaatagt ttgttaacca ctgacctaca gaaaccaaag ccttaattat catctt        656

<210> SEQ ID NO 33
<211> LENGTH: 449
<212> TYPE: DNA
<213> ORGANISM: Bos taurus
<220> FEATURE:
<221> NAME/KEY: misc_feature
<222> LOCATION: 380, 381, 382, 383, 384
<223> OTHER INFORMATION: n = A,T,C or G

<400> SEQUENCE: 33
tgatctggga agatcccaca tgctgtggag caactaagcc tgtgcaccac aactgctgat    60
cctatgctct agagcccagg agccacaagg acggagctca cttgccctag agcctgtgct    120
ccgaaacaga agccactgca atgagaaggc tgtgcaccag agctagatag taaccccctgc   180 tcgccgcaac aagaaaaagc tctagcagca acaaagaccc tgcacagcca aaaattaaaa    240
agaaaaaatt ttaaatgcgt atcaattaca tgaaactcaa gtgctttgta attgttattc    300
gtttatttga taaatatgta ttgatcacct actttgtgaa atggtatgcc agacagtaat    360
gaatacaatt ctttctctcn nnnnaaaaaa aaaaaaaaaa aaaaaaaaaa aaaaaaaaaa    420
aaaaaaaaaa aaaaaaaaaa aaaaaaaaa                                     449

<210> SEQ ID NO 34
<211> LENGTH: 610
<212> TYPE: DNA
<213> ORGANISM: Bos taurus

<400> SEQUENCE: 34
gcgaaaaaat aggatacact tttactggtt gttttaatga gagagaacca cttttggcaa    60
ccatcacctt acgcttccta cagatcccca gaggaaagca gctctgtgtc ttggactgaa    120
cccccatgca ggctggggcc gaacggactc tctgttgctc cccacggggc tgttctcctt    180
cgcgtccagg ctcgtggaga tccaagtcag caatgctagc tgggggctct ccgacttgcc    240
catcacattg ggtgagtttt caggctctcg gtggagaggg aggtgaatgt tcaggaaagg    300
gttatagagg gggacacgtc acagatggtc gacttccaca tgtgggatgt ggtagcagtt    360
gaggatttaa gaaatttcat tgcagaagga atgtcttcct cttgggccct cttaattttt    420
tgtgtgtgtt tttatttttt tttttaatct ttggcagcgt aaaactgatt gtgatcctcg    480
aatgcgtctc tgacgtgttc agcttcctgt ttccgttctc ccctccgcc aacagccact    540 cctcctagga aatatttcag ctgaatattc ccctgaggca gcctcttcac aacatgcttg    600
gatggcctac                                                          610

<210> SEQ ID NO 35
<211> LENGTH: 841
```

```
<212> TYPE: DNA
<213> ORGANISM: Bos taurus

<400> SEQUENCE: 35
acacacgttt tccacttctt tatttttaat ttatggagaa tctcaaaaaa tagaagtggc      60
cttggcaggg aaggaatgtt gaaggggaac cgtgatgatg cctagtcagg gtggccattc     120
tcctgcctca ggtctgccct acacccctca ccccagttcc atccagtgta tatgaaggtg     180
tgtatgtaca tatgagggga tctgggatga gctgtggctc tccggctgct tcctcagtgt     240
aggagtcaag ccagcctggg agcctggggt tcctctgtgg ctggttggtc agccagtagt     300
caggaactgg tgactcctgt gggaggggct ggacccaggc tttgcccagg agatggtggc     360
tgttgtggat tcttctgccc cctgcaggtt gtactgggca ttgcaggaca agtcagtcag     420
tccagagaga ggcccgccag gccctcagca tattgcacat agtcaaagtc aggcacagtg     480
aagggcacgc gggaccactt cttggcccgg actcgccctt gtggtgtctc cagcagcata     540
ctcccaactt tgagcactgg cagcttcact gacttgtaga ttatctgcag accccaggcc     600
tccccgcagt tccggcagct aatggcaccc ccgggcctcc agtccttgaa acttctgttg     660
atgtccacag gctgctttga gatgttgtag tagatcgaga agttggggtt cacattgacg     720
tggtgggtac cctccaccct ccgtaggtca ctcccgtaac ccacggacac catgcagttg     780
atgcagagga gctgcacctg ctccgccagg aacttgcgct gccgactctc tcgctgggct     840
g                                                                    841

<210> SEQ ID NO 36
<211> LENGTH: 331
<212> TYPE: DNA
<213> ORGANISM: Bos taurus

<400> SEQUENCE: 36
aggcatgggc atcattgtcc tcatgagtgg gaaatgcaaa tgcaagttcc gacagaagcc      60
cagccaccgt ttaggagatg ccccacctct catcacccca ggctccgccc aaaactgttg     120
agaatggatc agcagaaaga gctccaagga ctactctttc cccaagtcct ggctctgcaa     180
gggagcctga actccaggat ggaattctcc actccctcct cagactgcct ggccagggct     240
ccatctcacc tctccctaga ggggtctctg ttcaattttt actctaaaat gattttttgtc    300
tcatacccaa aaaaaaaaaa aaaaaaaaaa a                                    331

<210> SEQ ID NO 37
<211> LENGTH: 536
<212> TYPE: DNA
<213> ORGANISM: Bos taurus
<220> FEATURE:
<221> NAME/KEY: misc_feature
<222> LOCATION: 475, 477, 480, 486, 498, 511
<223> OTHER INFORMATION: n = A,T,C or G

<400> SEQUENCE: 37
ccacgcgtcc ggttaaaggc aaatgtttca atagggtttg atcccttgta gtcaaatcag      60
ttctcaagca taaaggagga aatgatgaac atggactgag gcaataagct agtatagtag     120
catctaagaa cgaagctgaa ggatggaaag gcagagagac acgggtgccg tgttgtgacc     180
cattggaagt tacagccaac gtgacttccg tgaaagaaac tctgtgagca aaagtgcacc     240
attcactgtc aactaagaga ttttacggag gcaaacatgc aaagcactct ctgtcggtct     300
tgctgggggg gcgggtgggc agggaggggc tggggcaggc tctctcctct ctctctgtgg     360
```

```
tcggccgcaa ggctctccct cccccctggat gggggccggg aggcttaccg gggtcagcgc    420
ttctggtctg gtaaatatat atgatgtatt gtttcgtttt gggttttttt ttttncntan    480
ctttgnggag ggaacagngg atcctcacag naaaacaggc cccttccaag ccctaa        536
```

```
<210> SEQ ID NO 38
<211> LENGTH: 587
<212> TYPE: DNA
<213> ORGANISM: Bos taurus
<220> FEATURE:
<221> NAME/KEY: misc_feature
<222> LOCATION: 550
<223> OTHER INFORMATION: n = A,T,C or G

<400> SEQUENCE: 38
cccctcgagt ttttttttt tttttttaat ttttggctgt gcagggtctt tgttgctgct     60 agagctttt tttgttgcgg cgagcagggg ttactatcta gctctggtgc acaggcttct    120
cattgcagtg gcttctgttt cggagcacag gctctagggc aagtgagctc cgtccttgtg   180
gctcctgggc tctagagcat aggatcagca gttgtggtgc acaggcttag ttgctccaca   240
gcatgtggga tcttcccaga tcagggatca aacccatgtt tcctgcattg gcaggtggat   300
tctttaccac tgagccacta gagaagccct gaaagttttt aaaattataa acagaaatga   360
tatacaatca gtacctatca gtatagtcac attagctgta gaatattgaa ataattcctg   420
accacagccc tttgttaccc gactgcctct tgctaccagc actggcctgg tctctcctcc   480
cctgggagca ccctgactct gcagctccca gctaacagat cactgccttg tgcagcagga   540
gcaatccagn ccatgagtcc accagtggct cccattctga ccgatcc                 587
```

```
<210> SEQ ID NO 39
<211> LENGTH: 671
<212> TYPE: DNA
<213> ORGANISM: Bos taurus

<400> SEQUENCE: 39
tttttgggcc tcattgtact tcctcagatg ttctgcacaa acacgatctt tgcgatttcc    60
ttcttttgca gcttttttt ccatttgaat gagccattgt tcgtagggtt gagttccaaa    120
atctgacatt ggattaattt ggcaaaatgt ttgaatcttt gtcattattt ctagcagctt   180
atctttaaat ggatctttt tggtatcatc tgcaattaca aacttttgc atggctcctt    240 tatttgctct ttaagtagat taatattttg tttcacggtt ttaatggtaa ctgcatcaag   300
attggcacat attttaaaa tgtgttcttc ggctttggct tgcttttgg ctcctccaac    360 acctggtgaa gctgttagtc ccactatctg aggtaaggga atcactggtt tgttttcttt    420
cttaagttta ttgtttttca acttctgttt caaataacgc ctcatgatgt tgttatagac    480
cgcttctttg ttggtgtgat ggcattcatc aataatgatg agagaaaagt ctgacaactc   540
tataccatca tcttcacctt cttctgagtt taaaagggag ttttcaagga tttgagctgt   600
actgataata acatcatgag acttgacaac ttctggaaaa tgtatttca attgggtatc    660 accacttaat c                                                         671
```

```
<210> SEQ ID NO 40
<211> LENGTH: 2595
<212> TYPE: DNA
<213> ORGANISM: Bos taurus

<400> SEQUENCE: 40
tcacctacta gccagcagga tggagaccac cccccttaaat tcccagaagg agctatcagc    60
```

```
gtataaggat ggagaagatt gtcaggaaaa tggggttcta cagaagggtg tccccgcccc        120
tggggataag gcagagtccg gccagatctc aacgggtac tcagcggttc cgaaccctgg         180
cgcaggagac gacactcagc actccatccc ggctgccacc accgccctag tggctgaggt        240
tcatccagca gagcgggaga cctgggccaa gaaggtggat ttcctcctct ctgtcattgg        300
ctatgctgtg gacctgggca acgtctggcg cttttcctac atttgttacc agaatggagg       360
gggggcgttc ctccttccct acactatcat ggccattttt gggggatcc cgctcttcta        420 catggagctc gcactggggc agtaccaccg aaatggatgc atttcgatat ggacaaaaat       480
ctgcccaatt ttcaaaggga taggttgcgc catctgcctc atcgccttct acatcgcctc       540
ctactacaac accatcatag cctgggccct ctactacctc atctcctcct tcacggagca       600
gctgccctgg accagctgcg agaactcctg gaacactggc aactgcacca actacttctc       660
cgaggataac atcacctgga cgctccactc aacgtccct gcagaagaat tttacacgcg         720
gcacgtcctg cagatccacc ggtcgaaggg gctccaggac ctgggggcc tcagttggca         780 gcttgtcctg tgcatcatgt tcatcttcac tgttatctac tttagcatct ggaaaggcgt       840
caaaacatct ggcaaggtgg tttgggtgac agccaccttc ccttacatca ttcttttgat      900
cctgctggtg aggggggcca ccctccctgg agcctggagg ggagttctct tctatttgaa      960
acccaactgg cagaaactcc tagagacggg ggtgtgggtg gatgcagccg cccagatctt      1020
cttctctctc ggccctggct ttggggtcct actggctttt gcgagctaca acaaattcca      1080
caacaactgt taccaagacg ccctggtgac cagtgcagtg aattgcatga cgagcttcgt      1140
ttcaggattt gtcatcttca cagtgctggg gtatatggct gagatgagga agaagatgt        1200 gtctgaggtg gccaaagatg caggccccag cctcctgttc atcacatacg cagaagccat      1260
agccaacatg ccagcatcca cattctttgc catcgtcttc ttcctgatgt taatcaccct      1320
gggcttggac agcacgtttg caggcttgga ggggtgatc acagctgtgc tagatgagtt       1380
tccacatgtc tgggccaagc gccgggagtg gtttgtgctt ggcgtggtca ttacctgctt      1440
ctttggatct ctggtcacct tgactttcgg cggggcctat gtggtgaagc tgttggagga      1500
gttcgccacg ggacctgcag tgctcaccgt ggccctgatt gaagcagttg ctgtgttttg      1560
gttctacggc atcaatcagt tctgcagtga tgtgaaggaa atgcttggtt tcagccctgg     1620
atggttctgg aagatctgct gggtagccat cagtcctctg tttctcctgt tcatcatctg      1680
cagttttttg atgagcccac cacagctacg acttttccag tatgattatc ctcggtggag      1740
catcatcctg ggttactgca taggaacctc atctttcatc tgcatcccca catatataac      1800
ctatcggctg attgtcactc cagggacact taaggagcgt attattaaag gtatcacgcc      1860
agaaacaccg acagcaattc cctgtgggga catccgcttg aatgctgtgt aaaacatcaa      1920
caaaaggaag atggcttccc aatacctctt cctccagtcc tgacaagtca cacatcgcct     1980
tctccctcta agtcaatgag tttccggcta agcctatcaa tggaagggcc ttcttcatag      2040
agacacagtc ccaaaagact acggtgccca gatttttcg gcctccagtc actttgtgtg      2100
aaatctccgg gacatgttac cacgttagac tctgtgatgc agctaaagtg gactgctttg     2160
aatgtgtgaa gctgtgtgtg aaaaccacca tgtcatcatt ggactagtt taggatcaag      2220 tctgtgaaag tctcctatgt cattccttct tatgatcatc agtatctaat attgtttgct     2280
tccaaagatt tcaactgctc atgactgcat aaaccatgta ggaaaaaaca gggatactgt      2340
cttgctagcc atatgttttc tgagtagcag agaatcctat agctggagtc tattagaacc     2400
```

| | | | | |
|---|---|---|---|---|
| ctgtaacctg | tgtgctgctg | tggaatcagg | agaggaagat | ttaagaagct taaattgaaa | 2460 |
| aaataatgtg | tatgtgtgag | catgtgtgtc | tgtgtgtaca | actgttccag tgtatcctta | 2520 |
| cccattacaa | actatatgaa | ttcctctagt | tttttttac | attaacaaat tccacctact | 2580 |
| aaaaaaaaaa | aaaaa | | | | 2595 |

<210> SEQ ID NO 41
<211> LENGTH: 1766
<212> TYPE: DNA
<213> ORGANISM: Bos taurus

<400> SEQUENCE: 41

| | | | | | |
|---|---|---|---|---|---|
| agcgcggtgg | gagctgacag | tcattttctt | cccgcgaaga | attttttaaac cagcaggtta | 60 |
| ctagaggaaa | aaaaatggcc | actggtcgtt | caccatgttt | ctacatagaa gaacttaata | 120 |
| aataccaaca | aaagaacggt | gtagaagtta | ggtattgtga | actggctaag acaggacctc | 180 |
| cacataattt | taggtttaca | tatcaagtta | taatagatga | taaagaatat ccaaaggctg | 240 |
| aaggtagatc | aaagaaggaa | gccaaaaacg | ctgcagccaa | attagctttg gaataattta | 300 |
| ataaagaccg | taagtcagtt | agttttttcat | ctcagctgac | aacaaatatt ccagaaggac | 360 |
| cacccattga | gaattacata | ggccgtctta | atacgatctc | ccagaagaaa aacctatgtg | 420 |
| taacttatga | agaatgtaaa | tcaaaggggtg | atgggcccga | aggatttcat tatatatgca | 480 |
| aaattggaca | agaagaatat | ggtagtggtg | tgggttccac | taaacaggag gcaaaacagt | 540 |
| tggctgccaa | actggcttat | gaaaagatag | aatcagaaac | aatgagagat ggtttcagtg | 600 |
| ctgcgtgtgg | tgatgtcgaa | agaaactctc | cagcagtgag | tacatctagt tctgaatcac | 660 |
| cgtctgaaaa | tggcttctca | acaaatgcat | cagaaagaag | tgataacaac agtggcacat | 720 |
| taaacagctc | ttccgtgtct | ccaggggacg | gttccagaaa | taattccagg aaggtgaaga | 780 |
| gaagtttggc | gcctacattt | gtctctcctg | tgaagacaga | aggaaacatt tatagtgtga | 840 |
| acgaaaggtt | attcaacgat | ttcacagaag | taacaccaat | tggctcaggt ggatttggcc | 900 |
| aagttttcaa | agccaaacac | agaattgata | agaagactta | tgttattaaa tgtgttaaat | 960 |
| ataatagtga | gaaggtggag | cgtgaagtga | agctttggc | aacacttaat catccaaata | 1020 |
| ttgttcatta | ccacaattgt | tgggatgggc | atgattatga | tcctgagcaa gcttaaaatt | 1080 |
| cttcaagatc | aaagactagg | tgccttttca | tccagatgga | atattgtgat aaaggtacgt | 1140 |
| tggaccaatg | gattgagaaa | agaagaggca | agaagccaga | caaacgtttg gctttggatt | 1200 |
| tctttcaaca | aataacaaca | ggagtgcatt | atatacattc | agaacagtta attcatagag | 1260 |
| acccttaagcc | aggtaacata | tttttagtag | ctatgaccca | aacaagatt ggagactttg | 1320 |
| gacttgttac | atacctgaaa | atgatgaaa | cgcggacaag | taaaaaggga actttacgat | 1380 |
| acatgagccc | agaacagctt | tcttctgtga | aagactatgg | aaatgaagtg acatctatg | 1440 |
| ctttggggct | gattcttgca | gaacttcttc | atatatgtct | cacttcttta gaaacacaga | 1500 |
| agttctttga | cgatctaagg | aatggcagat | tagatgtatt | tgacgacaaa gaaaaagatc | 1560 |
| ttctggagaa | attactctca | gtggaccca | agaaacgacc | taccgcatct gagatactga | 1620 |
| agactttgaa | ggagtggaat | aatgttacag | aaaaaaagag | acgaaacaca tgttagatac | 1680 |
| ttcaaaaagt | atcctgcttc | tgataattcc | attttcctgt | aactgtctaa agtctgcttg | 1740 |
| ggaatattga | tggtatttat | cttcta | | | 1766 |

<210> SEQ ID NO 42
<211> LENGTH: 1940

<212> TYPE: DNA
<213> ORGANISM: Bos taurus

<400> SEQUENCE: 42

```
ttctgagccg cggctgtccc gggagcgaac ggataaggcg gcgtagaccc aatcgtccga      60
tccactcgcg ctccgcaccc gggccctctc caagttggaa aggacaaaaa gaaggcaata     120
aatgctaaca agggagagag agggagccgg atcgagcggc aactcccagc ctccgctgga     180
agagagaggg agggagggag ccgaagagag cgggcgcgcg cgagggcgag ccatgcacgt     240
aaagaaactg acacccggac cccccacttc tcctgcacgt tgctggcaat cagatcgcgt     300
ttaagcaatt tcctgagccc aagaatagca atgagtctgg agactttcgc gggctgaaat     360
tgggagctcc aagcactttt cccccctact ttcttttttt ttttccctgg aaaagagggg     420
gggggcgct acaatttgga gacggttttt tttttaatc ttgcactttg aaaccgcggg      480
actgtagcag ggtgcgcgcg tgtgtcctgt tttgttcggt ccggggagtt tcgccccgc      540
cgcccggctc cgcggcgcgg aggatggtgt ggaaacggct gggcgcgctg gtggtgttcc     600
ctctgcagat gatctatctg gtggtgaagg ctgcggtcgg actggtgctg cccgccaagc     660
tgcgggacct gtcccgggag aacgtcctca tcaccggcgg cggagaggc atcgggcgcc      720
agctagctct cgagttcgca gagcgcggcg ccagaaagat cgttctgtgg ggccggactg     780
aaaaatgcct gaaggagacg acggaggaga ttcggcagat gggcactgag tgccactact     840
tcatctgtga tgtgggcaac cgggaggagg tgtaccagac agctaaagct gtgcgggaga     900
aggtgggtga catcaccatc ctggtgaaca acgccgccgt ggtccacggg aagagcctga     960
tggacagtga cgatgatgcc cttctcaagt cccagcacat caacaccctg gccagttct     1020
ggaccaccaa ggccttcttg ccgcggatgc tggagctaca gaacggccac atcgtgtgtc    1080
tgaactccgt gttggcactc tctgccatcc ctggcgccat cgactactgc acgtccaaag    1140
cctcagcctt cgccttcatg gagagcctga ccctggggct gctggactgt ccgggcgtca    1200
gcgccaccac cgtgctgccc ttccacacaa gcaccgagat gttccagggc atgagggtca    1260
ggttccccaa cctcttcccc ccactgaagc cggagacggt ggcccggaga acagtggaag    1320
ctgtgcagct taaccaggcc ctcctcctgt tgccgtggac aatgcatgcc ctcattatct    1380
tgaaaagcat actcccacag gctgccctcg aggagatcca caaattctca ggaacctaca    1440
cctgcatgaa cactttcaaa gggcggacat aaagacagga cggagaaaca ggctcaaaag    1500
ccacggaacc tgaggggca cgggcacctg ggcacacgcc tacatgcctg tccctcagca    1560
cacttctgct gggtgagcag gactgcttct atcctgggga agaatccggc tgcccccta    1620
gccagcccca ggacctttgc acaggactga tgggcataac tctgaccccc atggggaggc    1680
aagaaatcag ccagcagctg ccttgacact tttgtacatt tctgattctg tagagtttat    1740
tgttaaatcg cttctcaagt ctaaccagcc ttggcaatgt gcatagacta tttccgggat    1800
ggtctgtgcc cacatgctcc tccttcgcct ccaaaattca ctcatcctca gcttgtgcaa    1860
actggttgaa cggcaggaat atataaaata aagagagaaa gcttttgcga aaaaaaaaa    1920
aaaaaaaaaa aaaaaaaaaa                                                 1940
```

<210> SEQ ID NO 43
<211> LENGTH: 665
<212> TYPE: DNA
<213> ORGANISM: Bos taurus

<400> SEQUENCE: 43

-continued

```
ctttagcaag tttattgaaa caggtatgac aagtataaca aaatttacat ttgcctgtgc      60
tagaccagta tatttctgta caaacaacaa gatagtgtta gctaatgaca gttaacactt     120
tgaaagcata acatacaaaa aacgtatct tcatcacacc ccccctcccc ccaaaaaaaa      180
accccttcat aacagcgggg aaaaaattct cccctgcccc ccaaaggagg tcttcacagg     240
ctggccagct ccatcccaat tctgaggtgt caaaggagtt ccaagtgcaa actgaaatga     300
tgaacaagca actccccaac tcccacatcc attaaacaca caatctagga aacggatgtc     360
ctcgcggagt gcctttgcat agaattatta gataaacata ggttactata ttacaagtgg     420
atatggtacc agatcctagg tccctgtgct ccccttcctc aaccacaatg aagagaaacc     480
aaaataatga atcggagca caaattgttc tgcagctccc tccagtggcg ctgaagagcc      540
tacattgtcc ttggcaagca ttttctattt ttgtagctct caccattctg tgggcccaat    600
ttcaagttga ttgagtcatc atcttattca gaatgtgtgt gaaagacatt tacccggacg    660
cgtgg                                                                 665

<210> SEQ ID NO 44
<211> LENGTH: 2703
<212> TYPE: DNA
<213> ORGANISM: Bos taurus

<400> SEQUENCE: 44
cacaagagag atggccagct gcccaaaagc catctggaac tggagatttc agagagcggt      60
cttcagaact gtccaactcc tttgcttcag tgtcctgatc ttcgaggtaa taaaccagaa     120
agaagtatca gcatggacct accactacag caataaaaca tattcatgga attattcccg     180
ggcattctgt cagaagtact acacggattt agtggccatc cagaataaaa acgagattgc     240
ttatctcaac gagaccatac cttactacaa ctcttactac tggattggta ttcgaaagat     300
caacaataaa tggacctggg tgggaaccaa aaagactctc actgaggagg ctgagaactg    360
ggctgacaat gagcctaaca acaagaggaa caaccaggac tgtgtggaga tctacatcaa    420
gagtctgtca gcccctggca gtggaatga tgagccctgc tggaaaagaa agcgagcact     480
ctgctataga gcctcctgcc aggacatgtc ctgcagcaag caaggagagt gcattgagac    540
cattgggaac tacacctgct cctgttaccc tggattctat ggaccggagt gtgaatatgt    600
cagagagtgc ggcgagtttg atcttcctca acatgtgcac atgaactgca gccaccctct    660
tggaaacttc tcttttcaact cacactgcag cttccactgc gctgaaggct atgcgctgaa    720
cggacccagt gagctggagt gtttggcttc tggaatctgg acgaattcac ccccacagtg    780
tgtagctgtc cagtgcccgg ctctgaagtc tccggagcaa ggaagcatga gctgtgtcca    840
gtccgcggaa gcattccagc accagtccag ctgcagcttc agctgcgaag agggattcgc    900
attagttggg ccagaggtag tgcactgcac agccttgggg gtgtggacag ccccaactcc    960
ggtgtgtaaa gcattgcagt gccaggatct tccgacctca actaaggccc gggtgaactg   1020
ctcgcatccc tttggcgact ttaggtacca gtcgacctgt agcttcacct gcgatgaagg   1080
ttcattcctg gtgggagcaa gtgtgctgca atgcctggat acggggaact gggatgctcc   1140
tttttccagaa tgccaagctg ttacctgcgc agctctgcca aaccctcaga atggagaaaa   1200
gacttgtgtc caacctcttg gaggttccag ttatgagtcc acatgctggt tcacatgtca   1260
tgagggattc tctttatccg gaccagaaag actggactgt actccatctg gacactggac   1320
gggctcccca ccaacgtgtg aagaagtgga cacagtatca gctcctgctc caggggtgca   1380
atgcccaacc ctcatcgctc cgaagcaggg aacaatgtcc tgtcagcacc atgtgaggaa   1440
```

```
ctttggtttg aataccactt gccactttgg atgcaaagct ggattcacac tcctgggaga    1500
tagtgctctc cagtgcagac cttccagaca atggacggca gcagctccca cgtgcagagc    1560
tgtcaaatgc gccaagctac ctgttactga gccaatagtg atgaactgct ccaacccttg    1620
gggaaatttc agctatggat caacctgcag cttccattgc ccagagggtc aattacttaa    1680
tggctcagaa agaacagtat gccaagagaa tggtcagtgg tcaacgacca tgccaacctg    1740
tcaagcaggg ccactgacta tccaggaaac cctgacttat gttggtggag cagcagctgg    1800
tacaacaggc ttagtgacgg gttcaattct cctggctctg ctaagaaggc gttgcagaca    1860
aaaagatgat ggaaaagcc ccttgaaccc tcaaagccac ctaggaacat acggagtttt    1920
tacaaatgct gcgtttgacc caagcccta agagacctgt ccttgtcttg gtgacctcgt    1980
ccaatcccca caggatccta tttttgaaca tcagctttcc cgaaaagact tgattataac    2040
tgttgagtat ttgctgccat tttctgtaaa tacttgtgaa taaaggacat ggaatttcct    2100
ttagattagt tctgcaccag agcagacgga ctggaccaca agccccaatt ctccacccac    2160
caccccttcc tgctccattt cctcttcctc aacacaagc ctcagaagct gggactgagt    2220 cttctctgctg tgttctgtgg gctttggcct agctgtcact gcggtacta attagctaga    2280 gtccagagca tctgactcac cagaagacca gactggaaaa ataaaaatgc ctttattttg    2340
ggactggagg aggttctcct ctactttgtt ggaaggcagg aggtgtctct gacttgtggg    2400
aatttctata ggatttcctg gtcttcagt gcttgctgtt ggtgaagcct tctggacttc    2460
cttgaagctc caagagaggc ctctggatgg caccagaggc tgcagaggcc acagaagact    2520
ggtgctccag acaggaaggt acacgtcatg tagaccgtcc ctccgccgtc actctccccc    2580
agaggaccca gagaccaatc cttgaatgtc tagttaaaag gattccctaa atgccatgtt    2640
ctagtgtttg atattttgct gaataaagtc tgtatccatc aaaaaaaaaa aaaaaaaaaa    2700
aaa                                                                 2703
```

<210> SEQ ID NO 45
<211> LENGTH: 789
<212> TYPE: DNA
<213> ORGANISM: Bos taurus

<400> SEQUENCE: 45

```
gaaagaagac aaaaaatcac ttctttattc acagtagcca agatatggaa acaactcaaa     60
tgtccagcag cagatgaatg gataaagaaa atgctgtaaa gccatacagt agaatattat    120
tcagccttaa caaagaaatc cttccatttg tgacagtcat gatgtgaagt gaaataagcc    180
agtcaaaaaa ggacaaattc tgcatgattc cacttacatg aggtatccag aacactcaaa    240 ctcgggggt ggggagaggg acagactggg agtttggggg tagtagatac aaatgactac    300
ataataaaac agggaagcaa caaggtccta ccatatagca gagggaacta tatttaacat    360
cctataacaa accataatgg gaaatatgaa aagactacgt atacagatag gtgtaactga    420
atcactttgc tgtgcagcag aaactaacac aacactgtaa gtcaacatac tcttcaatgg    480
gaaataataa aaattaaaat agctcagagt catcgaagta gagaacagat gggatggggg    540 aggtgggga gagttgttta aggagcacac agttagagtt caaaaacctg ctgttcagcg    600
tgtgacaata gttgacagca ttgtattgtg cactgaggaa agtgtgaagt gggtagatct    660
cacgttgtgt tcttaacgcc catacacaca tatacacaca cacaaagacc ccatgttctg    720
tgatcccatt ttcacagaaa cgttccaaac aggcagatct ccagagagaa aaaggagccc    780
``` agtggtgac 789

<210> SEQ ID NO 46
<211> LENGTH: 716
<212> TYPE: DNA
<213> ORGANISM: Bos taurus

<400> SEQUENCE: 46

| | | | | | |
|---|---|---|---|---|---|
| tcccgggatt | gcggactcac | tcccgggacg | cgcgtcctcg | ccccatcctt | tcttccttcc | 60 |
| tgccttccct | cgcgcccgcc | cgccctctcc | aggtctccct | agcgggtcgc | gattgtctcc | 120 |
| gtcccctccg | cgctgcgccg | cgcgctcgcc | ctgccccgtc | tcccctcgc | acttcctgag | 180 |
| tcgccggccg | ccgctgcccc | gactccagcc | cgcggcgccc | ggggaaggga | gaagtgggcg | 240 |
| agcgcgccct | cgcccagccc | cgcgcccag | ccctgcccgg | cgagggagga | ccggaagat | 300 |
| gaacaacggc | agcaaagccg | agaaggagaa | caccccgaac | gaggccaacc | ttcaggagga | 360 |
| agaggtccgg | actctctttg | tcagcggtct | ccctctggac | atcaaacctc | gggagctata | 420 |
| tctgcttttc | agaccattta | agggctacga | aggttctctt | ataaagctca | catctaagca | 480 |
| gcccgtaggt | tttgtcagtt | ttgacagtcg | ctcagaagca | gaagctgcca | agaatgcttt | 540 |
| gaatggcatc | cgcttcgatc | ctgaaatccc | gcaaacacta | cgactagagt | ttgctaaggc | 600 |
| aaacacgaag | atggccaaga | acaaactagt | agggactcca | aaccccagta | ctcctctgcc | 660 |
| caacactgta | cctcagttca | tttccagaga | gccatatgag | ctcacagtgc | ctgcac | 716 |

<210> SEQ ID NO 47
<211> LENGTH: 669
<212> TYPE: DNA
<213> ORGANISM: Bos taurus

<400> SEQUENCE: 47

| | | | | | |
|---|---|---|---|---|---|
| ccggagagcc | taaaattatt | tattaaagtc | atcagctgta | taacagaaac | agatataatt | 60 |
| gctcaaatca | agcttcctag | gaatataata | catggctaaa | atagaacata | agctactgaa | 120 |
| agagagcagg | gagtggccag | ttttttccat | gaagggtcaa | atagtaaaca | ttttaggtta | 180 |
| ctgtggcaac | tactttatat | catttcagca | gccatagata | atatgtaggc | aaacaagagc | 240 |
| gtctgtattc | caacaaattg | catttataaa | aacaggcggt | gggtctgttt | ctggcctgtg | 300 |
| ggctacaggt | agccaactcc | tgaggtagag | gattgtccca | ttgccaagga | ggagatctct | 360 |
| gtggagtcta | aaaaactaaa | aagaacaagc | ccataatcag | agagattcca | tataaaatgc | 420 |
| ctactgaatt | ggataaaaac | aaattttatt | ctaaaaaagt | tcaaaaaggt | aaaaagagga | 480 |
| cactcaggtt | ttagctgcca | gaaaactact | gtgggccaaa | cagcatgatg | tgacttctta | 540 |
| gaaaatctaa | tgtgctccag | cccccattca | ggaaagcaga | gcgtccagaa | caaaacaagg | 600 |
| tgatcacccc | aggggacgg | ggctacgtct | ccccaagtca | caacagcaat | cttcacaccc | 660 |
| aggaagtgc | | | | | | 669 |

<210> SEQ ID NO 48
<211> LENGTH: 683
<212> TYPE: DNA
<213> ORGANISM: Bos taurus

<400> SEQUENCE: 48

| | | | | | |
|---|---|---|---|---|---|
| ttcccgggaa | agtcaggcca | ttctgcgagt | gccttgatgc | caaactagcc | agccctcacc | 60 |
| catgcccaca | aatgattcac | tgccaaattt | caagggtcag | agcccaagc | tttcattgtg | 120 |
| aagagcgctg | ggccaagagt | caaggacact | gttagtgact | tagtttccac | atctacaaaa | 180 |

```
tgaagggact ggattgaagg ccagatttcc tgccagttct agtattctag taaattctaa      240
gtgaaagttg atcagtgtga aattagatca aacgcatcgt tctggcattt ctggggaaag      300
tttttgcttc tgtaggattc tgataaataa taaagctctt agcatggtct tgattttccc      360
aagtgtatga ctacctggtc ctttctttgg gtctcagtca aggcacagaa acagactcag      420
aatatacaac caggcaagtt tctgataaag gaaaagaga atagtcaaca caccccaagc       480
ttgtgctgct attctcactg taagtgttgt gtcgtatttt caaaatccac ttggtgcttc      540
tgacctctct gggctaattc ctgttcctgg gtagctcggc acctgttagc cctgagacaa      600
aagttgttta caagtcagag gtaaatgtct ttcacacaca ttctgaataa gatgatgact      660
caatcaactt gaaattgggc cca                                              683

<210> SEQ ID NO 49
<211> LENGTH: 839
<212> TYPE: DNA
<213> ORGANISM: Bos taurus

<400> SEQUENCE: 49
cagatttcca cagactgaga ccaactcagc aatcgccaac tctcaggctg aagcccccgt       60
gctcaccctc aacatgaagg tctccgctg ggattctgtg tctgctgctc gtggcagcca      120
ccttcggcac ccaggtgctc gctcagccag attcagtttc tacccaatc acctgctgct      180 ttagtgtgat caatgggaag atccccttca agaagctgga cagctacacg agaatcacca      240
acagccagtg tccccaggaa gctgtgatct tcaagaccaa gcggacagg gatgtctgtg      300 ctgaccccaa gcagaagtgg gtccagactt ccataaggct cctggaccaa aagtcccgaa      360
caccgaagcc ttgaaccttc ataccctagac tgagagacag agtcttggaa atcttatttt     420
atttcttccc aaccttcccc aggtgtatta ttgtattata atggcaaaaa agagttttt      480 tttttaaata atttaaacac ttagtttctt aaacaatatt taattatgtt taagttattg      540
ttattttact ttatctgcca taaatcctaa tgaatataag atacaacatc tggtgatgag      600
tttcctgtga gcttgattaa gttcacagca agatggtgct atttcccatc ttactgcatg      660
taggatggtg aggtccttcc actgattatc agagtgaaac acttttggaa tcttaggaaa      720
tcagtgctcc tgtaagtgga tgtgtgctat gtagtattgt gatggaaagt aatgttatta      780
catgactatg gaattttcaa ataaaaaat acatataatt tcaaaaaaaa aaaaaaaaa       839

<210> SEQ ID NO 50
<211> LENGTH: 523
<212> TYPE: DNA
<213> ORGANISM: Bos taurus

<400> SEQUENCE: 50
tttttgactt aaacatcaaa atttatttga tcatagttgc ccatagaagc ccaagatcaa       60
ggagctggca aacttggctt ctgctgaaat ctgtcttcct gccacctctg ctttatagta      120
tgcctgcctt cttgtttgtc tccacatggc ctttcctctg tgcatgaaga aagacagaga      180
gggctctgtt gtctcctctt cttccttgcaa agacacctgt ccacttcagt taggggccac      240
ccttaaaatc tcatttaact gtaattacct cctaaaaggt cctatctcca agaatggtca      300
gcttgtcaaa tgaaaaatcc acatgtacgg ggtcactgag agaagatctt gggtcttgc      360 atttgtaata tccagtcttg tgtatttgga tctcttcaga cttttattc aacaaattct      420 cattataata ccaatatatg tctccttgag ctggagaaag ggaatccctg cacgtgagag      480
```

```
tcacttcatc tttgtggaag tttgtggacc atggagggtt gag                    523
```

<210> SEQ ID NO 51
<211> LENGTH: 796
<212> TYPE: DNA
<213> ORGANISM: Bos taurus

<400> SEQUENCE: 51

```
aactgcatct ccaagacaat ttctttttta ccagatctat ttcatttagc atcaccttct    60
tcaatgcttg tatgaataac tgaaaagctt ttttattcct tctctacaaa acatgccaaa   120
gagaaagtga tctgtttaat cattccatct cagtatctta atatcacagc tactttagtt   180
tttccaacta atgaaagaat tgcaatctcc tattaaattt gttcttgtgt gtcctccatg   240
tactagtgaa attaaagtat attttggtct aggtcttgta aatctcttca ttctcctcag   300
cacttaagaa cagtacttca ttcaagtgaa taatttacaa aatatgggaaa atctaggaag   360
aatcttttt attgtcttcc tgattccatg ccataataat cttgattgtc atcttaccca    420
tttaactata ataaaaacag aatattaatg aattaaagga caaactctga ggcctttat    480
taatcttctg gcttcaatct aggtcaatga gcacatgaca ttgatacttt ctagagccaa   540
gaaatatatc ttcactttac attgaaagaa ccatattgtt tttctatttt ttaaatttcc   600
aaggcaagtc aataggtttt ctggaccaga cttcaccaag aaaataggaa caagaattca   660
aggaacagga ataggatcta gggaacggga actcaaatat ttacttaaaa ctcaaagatg   720
ttttggatc ttcagttata atctttgatc tatctaaagc cctttagact aggcccattt    780
catatctctt atgctc                                                  796
```

<210> SEQ ID NO 52
<211> LENGTH: 661
<212> TYPE: DNA
<213> ORGANISM: Bos taurus
<220> FEATURE:
<221> NAME/KEY: misc_feature
<222> LOCATION: 655
<223> OTHER INFORMATION: n = A,T,C or G

<400> SEQUENCE: 52

```
aaaaacagta cattttttatt tgacattaaa caacaaactc cccaattgtc tcagttgtga    60
catatagaca gctttaggtt gcttttttgg tggttatccg aactgaacaa gacttttcag   120
tcttcacaac aaccaaggct cagatattat gtgtttcaca tcagttcaca agtccatgtg   180
tgtcttccat tcatcagagc atttggcata gatcctttta aggtaaaagg gtagatgtaa   240
agctgtttct ttttcttaag aaaaaaaaaa ttgttcacaa cttcatttat gccacaaaaa   300
tcagatgaca gaatgttcta ttattcttgt ttatcagtag tgtggccttg ggatgccaga   360
aactgtgaaa tgaagactgt tactttctcc tttccaataa tgcatctctc atccctacct   420
ggagaaaggg gagttactga gtccagctaa tagtacatat taaacaccaa acattattaa    480
tatcagatac accttacact taaactaaaa atataacaaa gcaaaaactt acaaacaatt   540
aacccaaaaa tcccattcaa aacttccggc tcccctacca ggcaaattat cttcctgcca   600
tctttctttt cccttcttat tttaccgatg ggtctcgttt cttggccagt aaacnttcag   660
t                                                                  661
```

<210> SEQ ID NO 53
<211> LENGTH: 357
<212> TYPE: DNA
<213> ORGANISM: Bos taurus

```
<400> SEQUENCE: 53
actgatctaa agatacgttt tttttttttt ttaaggtaac atcaaaaagg acatctcaaa      60
agaagtagat ataaatggag acatgagaag aagggagaa ctgaaaatgt ccaagagtag      120
ggaaaagagc aatagaaaca gctggggttt aagagtctca tcttggaatt cctttggtc      180 ctggggcttc tttctttcct ggtatctctg tcacgaacct ccagtttccc atctaattta     240
gtcttgaaat atctgtctct cttgggcctt ctgtcttata tagataggtt tgagtcctgg     300
gtctttgtgt gtgctagggc acttccatct tttgggtcac aggtcttcaa gacaagg        357

<210> SEQ ID NO 54
<211> LENGTH: 542
<212> TYPE: DNA
<213> ORGANISM: Bos taurus

<400> SEQUENCE: 54
tctgaatatt aaagataaaa atttaggtaa ttcatattgt aaagcatatt tgaattcagt      60
gccttagcat ttgcagaaca atttaatggt ttctaacttt ttcttaacat tcattaagtt     120 ttcactttt gtacctgaat attctaaatg aaactgatat ttactcttga caataaaat       180 gtatctacat atttactaaa ctgtgtttaa atcaccttaa cttttctttt tgcatattga     240
tcttaaacac tttatcagaa ctagttaatt atatgtttga gttattttaa acaggggtg     300 gatgatcagt acttctcaga caacagagtg ttttacatgg cacatgtcag attctgagca    360
gtgtattttt cacgaatttc tgtttaagtc gcaaaagaaa ccttttcctt tgtagcacag    420
cttatccgga ccaacacttt aaataccatt ttttaatcta aagttcacaa atgtctctta    480 gcccttaga  actttagtaa cataagttat aagtatcaca gaaaaagctc tgcacttttt    540
tc                                                                    542

<210> SEQ ID NO 55
<211> LENGTH: 876
<212> TYPE: DNA
<213> ORGANISM: Bos taurus

<400> SEQUENCE: 55
tctgggcagt cttcctggag agatggtcct gctcctgctc ctggtggccc ttctgtcccc      60
tactggggag gcagggaaaa tcatcggggg tcacgaggcc aagccacact cccgtcccta     120
catggcgttt cttctgttca agacttcagg gaaatctcac atatgtgggg gtttccttgt     180
gcgtgaggac ttcgtgctga cagcagctca ctgcctggga agctcaatca atgtcaccct     240
gggggcccat aacatcatgg aacgagagag acccagcag gtcatcccag tgagaagacc      300 catccccac ccagactata atgatgagac tttggccaac gacatcatgt tactgaagct      360
gactaggaag gctgacatta cggataaagt gagccccatc aatctgccca ggagcttggc     420
ggaggtgaag ccaggatga tgtgcagtgt ggccggctgg gggcgactgg gggtaaatat      480
gccctctaca gacaatctac aggaggtaga tcttgaagtc caaagtgagg agaaatgtat    540
cgctcgcttc aaaaactaca tccccttcac acagatatgt gctggagatc aagcaagag     600 gaagaattct ttctcggtg actctggggg cccgcttgtg tgtaatggtg tggcccaggg     660
cattgtgtcc tatggaagaa atgatgggac aactccagat gtctacacca gaatctccag    720
ctttctgtcc tggatccatt caacaatgag acggtacaaa cgccagggat cagtgtgatg    780
tgtgctcagg gtggaccct ccatgttccc tgggattgga agcattgatc aaagtgtgtg     840
```
aaggaaggtt gcctggaact taataaacat tcatct                            876

<210> SEQ ID NO 56
<211> LENGTH: 357
<212> TYPE: DNA
<213> ORGANISM: Bos taurus

<400> SEQUENCE: 56
atgtcaccat tggaagcatt cacattttc tccttctgga cttttggaca tgggttatca    60
aaagtggagc aggcccagat ctcccttcc acagaagcaa agaaagtat tgacatacat    120 tgcaagatag agagcacaaa ttttgaatca gacactgttc actggtaccg gcagaaattg   180
aatcaggttt tggagcatct ggcttatgtg acctcaatca caactgcagc tcgaaaacaa   240
gtagatggga agaacaaaat tgaggcaaga aaagatgctc gaatgttcac ttcgaccttg   300
acggtaaatt tcatagaaaa agaagatgtg ggcatttact actgtgctgg ctgggga      357

<210> SEQ ID NO 57
<211> LENGTH: 224
<212> TYPE: DNA
<213> ORGANISM: Bos taurus

<400> SEQUENCE: 57 gaatttaat ctagaagatt taattaacat gctgtctctg tatttcagag gcaaacaaga    60
aatgaggaaa attgcattgt agatcagttt tatgtgcagt gtactatttg ctgggctaga   120
aatgagataa agagtattta ttttgttca tatcttgtac tacttttcta ttaaaatcat    180
tttatgaaaa aaaaaaaaa aaaaaaaaa aaaaaaaaa aaaa                       224

<210> SEQ ID NO 58
<211> LENGTH: 694
<212> TYPE: DNA
<213> ORGANISM: Bos taurus

<400> SEQUENCE: 58
aaaacataca catttaactt tatttcatca ttgccattta aagcttgatt ttataaaaca    60
taaaagacat tcttaagagt tctatatcac aacaatttga aaagtgggaa tatccacagc   120
tttataggct caagttacat acattaaact caaataattg gacatttttt caatacagaa   180
actatacaaa tgaaataaat gacaagagga tgcaatagga gaaatatgtc actacttatg   240
gactatcatt agttactttc aggatgtaaa tgaagattct gaatattcat atttcttttg   300
ttctatttca tatttaaata ttctctaca ttctgagtca agttacttga ccaaaagtct    360
gatttagaaa ggtatttagc aaaagttttt ccacctatgg ttactacctc caaaggaagt   420
aacactgcag tactgatgca atctgtgcag taacttatgt caaccctatg gaaagtcaga   480
taggtaccaa aaacggaaca attttgcaca gattcagtta agtatcatgt taagttttcc   540
tcatctaaaa attaaccaat gaaataaaac ataccaacta cagttgatct ggtaggaaaa   600 ccacattga gagttacaag tacgttattg tccatatctc atcctcagtc attgacagga    660
attttgtagg ctaccatgct atttactta tgaa                                694

<210> SEQ ID NO 59
<211> LENGTH: 306
<212> TYPE: DNA
<213> ORGANISM: Bos taurus

<400> SEQUENCE: 59 ttttttttt ttttttttc acaaaagta tttattatt cttaacagta ttcactttga      60

```
aggagtagga agagagcata cagttttttac agacaatata taaatgttgt acataattaa    120
caataactta gttcactaat ccaaaataaa acgagccaaa taaaacataa aaccagaaaa    180
tactgccgat tcttcttctt atgcggatac tagtacaaaa taagttactt ccggctgtgg    240 tgcccctat tgcacttggc ctacatcagc acagtcctct tcctgggccg gcccccgcca     300
gccgcc                                                                306

<210> SEQ ID NO 60
<211> LENGTH: 855
<212> TYPE: DNA
<213> ORGANISM: Bos taurus

<400> SEQUENCE: 60
aatgtttcta tactttta ataatgatta ccttctcaag ggaagaataa caaagaagga       60
tcagaaaagg tgtggtaaat aatttcaatt taataaggaa tgtgttaata gagaaatcaa    120
gtcactaaat gaaacagtac cacccaaata cagcacaaca tggtctacag gcaacaaaat    180
gctataacac taaatcagaa gtgattcctt attataatca tgttatttta ataaccaaac    240
atttttggac aaggtccacg atgaattata ttccatagaa aactgcatat aaaaagcctc    300
tatccttttt acaataacat ttttcaacac agcctctcaa tagctaatac ccacctaata    360
aggaagtgaa ggaattcttt tctatttctc ctaatcatct cattcaaatc ctatcaccat    420
gaatttcctg ggtacttggc tttaaaatat tgtattacta taaactttca attcaagccc    480
tggataggtc tacattcact tcagcaggag catcttgaaa tgctgaatta tcatcttcaa    540
tttccttcag tcatttattg tagctgccaa actgaaatgg cacaccttaa aggcaacact    600
aaactgaaag taaataataa aaagagtctc ttaaatgttt catttatgaa agcttatttt    660
tcctgccatc aaattttgtg tactatctga aatatatcac tttacaaaac tgacatctta    720
cctgcaatta ttctgccatg acacatttgc cagacttcaa ggtttatcag gggtggggag    780
tcggggagag gactggcatc ttttctcaac ctttttataac agatgagtaa taagagcta    840 ggctggtttt gcttt                                                     855

<210> SEQ ID NO 61
<211> LENGTH: 438
<212> TYPE: DNA
<213> ORGANISM: Bos taurus

<400> SEQUENCE: 61
atgccgctct ccagtctgct ctgggtgttc ctggccatca ccttctctgg atctggtgtg      60
gcccagaaag ttattcaaga ccagccatac ataaccagtc aaatagagca atctgtcatt    120
ctgaaatgtc ggtatgaatt aagtcagagt gggtacacgc actactttt ttggtacaag     180 cagcttccca gtggagagat gactttcctt attcgtcagg aatcacttgg cccaaatgca    240
aggaatggcc gctactctgt aaaccttcag aaagcacaga actccatcag cctcaccatt    300
tcagccttac agctgggaga ctctgcaaag tactttgtg cagtccgggt tacagcggga    360
ccttggggta cacactacaa cgtacgaagt gggtatccac taatatttgg caaaggaacc    420
tatctgaacg tggaacca                                                  438

<210> SEQ ID NO 62
<211> LENGTH: 853
<212> TYPE: DNA
<213> ORGANISM: Bos taurus
```

<400> SEQUENCE: 62

```
attaaagaca ttttatttgt tatcttttat atttcacagt caagaaaaaa aataattaaa      60
aataacttgc acggagacag acattagac acaagcaagg atactgttaa cattaaagaa     120
agactgtgct cgaggtgact gcccccattc ttggctgtgt gtatgttggt ggccgctgct     180
gagcctctga gggaaggctg atgctttggt gaagtacctc tggaatctgt atcacaaggc     240
tcgagggaca tttccagtcc aggccttcta gttgacatta agaaggtcct gcattgccag     300
taactgctcc tcaaaaacta agacatatgt ctcttttttct gtccctggg tgtgaggcca      360
ggtcacaaac tcccagcagg gaaatgaaat ccctatattt gaggaacaga agtagcatct     420
ctgttttaac ttgctagagg atgaacctga gcaccttgaa ggatggtatc tcctcccatt     480
gccgggacct ccatagctgg tgtgtaagag tcttccaaaa ttaggccact tatctgcagt     540
gtatcaactc caagcaacat tcttctagac tcttccagga gtgaataatc ccagggagct     600
tccttctaga taggaaattg ttattgttgc cccaccagga agaaaaacta accactgtcc     660
tgactggagc aaatcaacta tcttgcaaat gctcacagta tctatatgca tttaatttca     720
taggtacttg gttggcaaac aagctgtatt cattgtaaat agtcacaact tccattcgga     780
gaggctagat gttggatgga agagaagtac caaaggccag atcttcaagg ctgctcccett     840
ctccatcagt ctt                                                        853
```

<210> SEQ ID NO 63
<211> LENGTH: 471
<212> TYPE: DNA
<213> ORGANISM: Bos taurus

<400> SEQUENCE: 63

```
tttttgggcc aagggacaaa tgggattctg tacattaact gaaaatggtg acttggatag      60
ccagcactca agatcaggaa tgctagaggt agacagcgta tcccagtcta atggatgagc     120
aatgacaac ttattttttt cactgaatta acaaaaattg cactggcttt aagcagaaac      180
aggactgagt ctgggctggg gctgggctgg ggctggggct ggggctgggg ctggggctgg     240
ggctggggca gggcaggga ctgggctgg gattggggca ggggctggga tcctaggtaa       300
cataaaggac tgcaagcagc acttaagcac attagcagtc ccttgtatcc ccttcggtaa     360
tgtagaggga attaaagggg gagagggaat cttagactaa agcacgggac tgtaactgcc     420
tttatgtaca ataacagtcc cttgtacact ttggggtaat gcaaatggag t              471
```

<210> SEQ ID NO 64
<211> LENGTH: 487
<212> TYPE: DNA
<213> ORGANISM: Bos taurus

<400> SEQUENCE: 64

```
ggcacgagga aaacacaaga gagccttgct tcatcagtgt taaaaaaaaa aattgaaaaa      60
agcggtacta gttcaaacac ttcggaagtt tgtgttctgt ttgttaaaac tggcatctga     120
aacgaaaaaa aagttgaagg ctttatattt tacctactct gtaagtgaga gagacaagaa     180
gcaaaacctt tttttttctta agaaaaaaat aaacactgga agtatttgtt agtgttaatt    240
atgtgaaaga aaaaaaaaca aacaggaaaa tcccgttcag tggagttgct gtacatatgt     300
tcttatccca tgcctcactt gattttttctg tattgctatg caataggtat ctttcccatt    360
cttactctta gagttaacag tgagttattt attgtgtgtt actatataat gaacatttca     420
ttgcccttgg aaaataaaac aggtgtaaaa aaagtggaga ccaaatactt tgccagaaac     480
```

```
ccatgga                                                              487
```

<210> SEQ ID NO 65
<211> LENGTH: 680
<212> TYPE: DNA
<213> ORGANISM: Bos taurus

<400> SEQUENCE: 65

```
tttttcacat gtacaccgtt tattgttttt aaaaaagaac cagattaaaa tattaataac    60
cattaaaaac agggaaatcc acacaatgat aaacttagct gattcaaaat ttccatttgg   120
attaaattta cctttcgagt tatgatgaag ttgcacttaa ttgtaaaatg attccattca   180
cacagcatgg gttgttcata aattctgacc tcttatccaa caaaacacag ccttttggta   240
acatttatgt aaccatggaa acctgtagta cacatttta ttactgattt ctacaggcat    300
caatacaaaa agttactaaa cttgaatgag agtttacagt tgggtggagc ccctgtggtg   360
gggagaggcc ggcactgttg agccttctct gctcatcccc agaagcagaa gcatcatggt   420
catttctaaa tataccagct cagctatttta ccaaaacacc aaaactataa ctggttttat  480
agctctgctt acaacaagca ccaattttaa attgagccta aatgtgtagt aaggcaaaga   540
aacagttaac tgtcaagaaa acaaacatcc agaaagaaat ctgaaagaag gcttggacta   600
aaaaagtgca tacacacatg cagaatggtc ccctgactgc tccgtgtcat ttctgattta   660
cacaagttaa aacggtcatc                                               680
```

<210> SEQ ID NO 66
<211> LENGTH: 633
<212> TYPE: DNA
<213> ORGANISM: Bos taurus

<400> SEQUENCE: 66

```
agaataattc ttacttgatt atttaagcta ctcttaggag tagctatttc acaaatagat    60
gtacagaaga tgaattaaca catccaaagc catgtagtct tagggctaat tcattgttat   120
gtaaactttc tagttagtca acatgtatct gggcacttcc tgtgagacag gcactatggg   180
agatacaaaa gagcataaaa tgtggtccct cttcatccca gtgaacagcc aagatgtcaa   240
gtaaaggcca atgagtacta ccaccatctt ctgctctgct cttggtcaa gacaactcca    300
gcaacttcac ctcctgcagc tgcctcctta ggctctctat cattccactg agttccgaag   360
aacatagcct tttctggaag aaactccttt cttcaatgct tcaggccagt tttgagtctc   420
aaagtaagta gacaggatat caaacacttg attgatggtc agtatctctg aatgatagtt   480
cttcccattc tggcatttga ccatatattc ctggattggt aagcgggcag tcttaacaga   540
gtgttcttgg gccttctgaa atgtcacctt cttctgaatg ctttcatcca caagtccacc   600
aaggatgtaa actttgttta gatcaacatt ttc                                633
```

<210> SEQ ID NO 67
<211> LENGTH: 459
<212> TYPE: DNA
<213> ORGANISM: Bos taurus

<400> SEQUENCE: 67

```
atgccgcttt ccagtctgct ctgggtgttc ctggccttca ccttctctgg atctggtgtg    60
gcccagaaag tcactcaaga ccagtcagat gtatccagcc atgtggggca gtcagtcacc   120
ctgaactgtc ggtatgaaac aagttggacc gcttactacc tttactggta caagcaactt   180
```

```
cccagtggac agatgactta cgttattcgt cagggttcag aagtgacaaa tgcaaggaaa    240
gaccgctact ctgtaaactt aagaaagca gataaatcca tcagcctcac catttcagcc    300
ttaaaactgg aagactctgc aaagtacttc tgtgctctca gtggcctcac acagcgttgg   360
actgggattt acgggggtat aggggtggt aggggtaccc tagcgtacgg gattgacaag    420
ctcatctttg gaaagggac ccgcctcatc gtggaacca                           459
```

<210> SEQ ID NO 68
<211> LENGTH: 873
<212> TYPE: DNA
<213> ORGANISM: Bos taurus

<400> SEQUENCE: 68

```
acaggtctat tgttgtctt ttattgtatt tctagaaagg caatatcaac ttaccctgtt     60
aaaatcacct tgtgaaaata aattttctgg aaatgcattc tttataaatg gaaagcatgc   120
aataatgtgt aaatttacag aagcacttta aactggttag ctcaggtaat agtttgcaaa   180
gtaggttttg ttttggagc aattacagat atccttaaac ttcgtaagtc ttaattctga    240
ttaaggctgt aagaacagag agttctctta atgattaatt acataattga aatgacttgt   300
aagaagtgac tgattgaagt tttgaatcat ccaaaagtta aaaagcaggg ccaatatttt   360
aaaagatgac acttttcaca attccaaatt ttttggaagt cattttttatg ccatatcagc   420 attaactttt agtggactat ttttgcctta ctttatggca ggcactttga agtgattaag   480
gaagcactgt cttcttactt gattagtcct tgttatttt tggttttgaa ggaaatgttt    540
gtaaatgagt aaaagacccc agataaatgt atctgggcct atgtattact tcttaaatgt   600
gaatactcat gtattaatga aaataaaaca caccataagc aaatgaaact gtgtttgaat   660
ttccacaagt tacgtttaga tttgttaatg ccttgcattt catgtttagg aatcagacca   720
ttctaatgcc ttcttaagct tatacttgtt atcagcattg gcagtttggc tttcattaac   780
aaataatcct tcacaataaa agaatccaga tctaatttca ttcctttact agttgtttct   840
gcagacacct ggcttcgtgg cgtacaccgt gct                                873
```

<210> SEQ ID NO 69
<211> LENGTH: 827
<212> TYPE: DNA
<213> ORGANISM: Bos taurus

<400> SEQUENCE: 69

```
caccagatcc aaaattagca ttttattcag aacgctgggg tcagaggtgt atcatttata     60
ttctggtaca caatacagag gcaaagctgt tgtcagaagt ctctccagtt taaaagcttt   120
tttttttttc attttttttt aaaaacacac actgcagtag taccaccagt gtcaggtcac   180
ccctttcatt tcttgtcttt ccttttttt tgttttttt tggtacaaat tatgtaaaac     240
atttgtgcta aaaacttttc tccctcccca aacaaaaga gaaataaaa aataaaaaaa     300 attaaaaaat taaaaattga gtattctaac tacagctcaa caattgaatc aaatgtcact   360
ttgttttgta aatactttat ccataacgaa agatataaac atgcaaaaaa cctgaatcca   420
tagtccaaat aatacataca catgttctga agtttctgca cttctccata gactatgcca   480
ataaaacatt atgtacacat accattttta cagtgaagtg gaaaaaatac agtaaataaa   540
aaagtgtaca tggattaaga ccaaaatgtg tctaacattc tagttatga aaaaattcaa    600 ttttgctaca aattggtgat atgaaaactc ccttttatttg caaccagctg cgtaagtttt   660 aagatttttag tggaaaaaaa aaacaaaaca agaaactaaa gtctaaaact agaaataatg   720
```

```
tacattttcc aatctcatgg tctcagcccc caaggtaata aaattgctcc atgagtggtt    780
ggtttgtctg tttaattcca tattttaat aaaagcaaat gcgatgt                  827

<210> SEQ ID NO 70
<211> LENGTH: 316
<212> TYPE: DNA
<213> ORGANISM: Bos taurus
<220> FEATURE:
<221> NAME/KEY: misc_feature
<222> LOCATION: 262, 263, 266, 268, 280
<223> OTHER INFORMATION: n = A,T,C or G

<400> SEQUENCE: 70
gctttgcata tctgtccagg tatttctgta ggagtgattc ctaaagtgga acagagtcaa     60
agggcatgtt catttccaat tttggtatat gccttttata aatgatgtta ttgatactca    120
caaatgactg acttttaaac aagccttagt ggtataagag ctcctctgga agtctcacat    180
caatgactgg ctgatattaa tagactgtaa agatatcatt tagcattgta tatatattga    240
ataaaagtat tttcaaaatt cnnaananaa aaaaaaaan aaagaaaaaa aaaaaaaaaa     300
aaaaaaaaaa aaaaaa                                                   316

<210> SEQ ID NO 71
<211> LENGTH: 477
<212> TYPE: DNA
<213> ORGANISM: Bos taurus

<400> SEQUENCE: 71
gacctataag atatttaata acacacttta atcttaacca cataagaatt atgttatgtg     60
tgaaagactt ccaaagagca gatggtcctt cagtttgcag tattggcagg aagatgggag    120
gcctgtgctg gttagtgaac ttgctattta agttttaaac tggtggggag aaaggaaagg    180
aaacgtctgg agaaggtggg atgacagtaa accagttggg gtggggagga gcctgcaaga    240
cgcgcttgga cccagcgagg tggttctctg ctggagttag gaggggggttt ggcagcatga    300 aatccacctg gcaggcggtt tggaaggtaa gtcacctatg tcataaggta agtcacccat    360
gtagctgcct ttgaatcgat ggctaaaaat gcttgggatg taccttgtag gcagcaaaca    420
ttcagaatca tcgaaagatt ctgagctaaa gagaaatgta atgagtcttg ttgtggg       477

<210> SEQ ID NO 72
<211> LENGTH: 651
<212> TYPE: DNA
<213> ORGANISM: Bos taurus

<400> SEQUENCE: 72
tttttgcgag cgaaattttt atttacatgt tgtatctaga agcagataca taaattcttt     60
atacgattaa tctccaaaaa tgtgcaagaa attactatag tttgtttaca aaccaaaaca    120
cgtattaaaa tcaatggact ttggataatt cattctgtgg tgttctcagt acaaatggaa    180
cacacctgat tcgaaacata cagaaaaagt gtaaactaca gcaatctgga ttgcaggtat    240
taattccatg gcactctgac gactataaaa tttctttaac ccaacacgta tacttagtac    300
aaaattctat aagaattttt catcatctct ggaagtagag cttggatcac ttttcagaaa    360
cagcaactac acatttgcca tgttatgatg attaataaaa aggatgttta taaaaaatct    420
ttacaggatt aaaaaagtat taaaccgaat ttgtgatcac tagcgtacca atctttgttt    480 tagaattta aagttactta tggaactggc aagtgttcct tattagagtt ttcaacgtaa     540
```

```
ctgtctattg ctggtagtgt gatttcaaat taagacttca cattggatga aaagccatga        600
agatttaaaa cggattattt tgaatcattc ataaagcaaa tctctctcat a                 651

<210> SEQ ID NO 73
<211> LENGTH: 195
<212> TYPE: DNA
<213> ORGANISM: Bos taurus

<400> SEQUENCE: 73
gggcgatctc tccccccttt ttaaatagta acatcatcat ctgttgaaga ataactatgt         60
cagtatcgtc ctaagtactt gacgtttaac tgcccaacag ccctcagtca gtcctgttat        120
tctccagtga gctcctcacc tgtaataact tttaattttt taataaatta aaaactttat        180
taataattgc aaaaa                                                         195

<210> SEQ ID NO 74
<211> LENGTH: 3099
<212> TYPE: DNA
<213> ORGANISM: Bos taurus

<400> SEQUENCE: 74
tggccggcgt caggaggaat tcgaacgcct gcatccagaa agaaagaatt cacctgtgtt         60
tcgaggcagc gcgccggact tcgagggagc ggcagccagc tttcgctcct ggcacaatgg        120
gctgtacgct gagcgccgag acaaggcgg cggtggagcg gagtaagatg atcgaccgga        180
acctccgcga ggatggcgag aaggcggcgc gcgaggtcaa gctgctgctg ctcggtgctg        240
gtgaatctgg gaaaagtaca attgtgaagc aaatgaaaat tatccatgaa gctggttatt        300
cagaagagga atgtaagcag tacaaagctg tggtctacag taacaccatc cagtcaatta        360
tcgctatcat tagggccatg gggagattga agattgactt cggtgactca gcccgggcgg        420
atgatgcccg ccaactcttt gtgcttgctg gcgctgcaga ggaaggtttt atgactgcag        480
aacttgctgg agttataaag agactttgga agacagtgg tgtacaagcc tgcttcaaca        540
gatcccgaga gtaccagctt aatgattctg cagcatacta tttgaatgat tggacagaa        600 ttgcacaacc aaattatatt ccaactcaac aagatgttct cagaactcga gtgaaaacca        660
caggaattgt tgagacccat tttactttca agatcttca ttttaaaatg tttgatgtgg        720
gaggacagag atctgagcgg aagaaatgga ttcattgctt cgaaggagtg accgccatca        780
tcttctgtgt ggcgctgagt gactatgacc tggttctagc tgaagatgaa gaaatgaacc        840
gaatgcatga aagcatgaag ttattcgaca gcatatgtaa caacaaatgg tttacagata        900
catctattat acttttctg aacaagaagg atctctttga agaaaaatc aagaagagcc        960 ctctcactat atgctatcca gaatatgcag gctcaaacac atatgaagag gcagctgcgt       1020
acattcagtg tcagtttgaa gacctcaata agagaaagga cacaaaggaa atatacaccc       1080
acttcacgtg cgccacggac accaagaacg tgcagttcgt cttgatgcc gtaacagacg       1140 tcatcataaa aaataaccta aaagactgtg gtctcttctg agtgttggcg gcaaatggta       1200
aaatgcattt tcaaaccaaa tgagtactta catgtggatc tctctagact agagtcttgc       1260
agcaacacag aatgtagtat atggcgagtg catctgggac ctgaccaaag ctgttctatt       1320
tgtttttttt ttaactgaaa gtaatggaag gacctttcgt aagtgtgaga ggtggtcctg       1380
cagtgtgaaa ctaagggcag tgttaaagct gggctctagt gtacggatga cttctacata       1440
catgtaaata tgcaaatgta tgtatacatg tatttatgac tttagttttc cacattactt       1500
ttagacattc agtaagcggc aacttataat tttagcgtgg tggctttgga aataacagaa       1560
```

```
atattaagta ctttgtactg aatgacagac tattgtcatg tttgccagtt ctaaacagct    1620
ttatttatgt ttctgtcctg taaattttta agtacaatga ttaatattgg gacacattgc    1680
agctcttgtc ttgattatat gtagtatact tgtaatcata aatgttattt gtacaaacat    1740
tgcacagact atttttaataa catgatttgt tctttaaatt tatgtgtttt attgaaatgt    1800
tcttgaagaa gatgactata cctgcctttg gatcagttaa acactgtatg catttcagtt    1860
tttcttttaa gggtgcatgc taatctgatt ctacattaga tttggtttaa aaactgtaaa    1920
atgcaggttt ctgaggatat acatatagac ttataaacac ttaattttta ttcagttggt    1980
ttgttttcac tttgaatttt aatatttgga tggtattcat gcattgcctt aaaggtgatg    2040
ccaagttaat ttttatacac ttcaaataac tacattttta tttataagta agtttaggtg    2100
ggtgcaagag catttttgtg ggtaaaaaat aagttagcat aatgaatttt gagacattca    2160
tttgtgtatt tcctttggga aatcccttgt acgtaccata catgacagct ctttgttcgg    2220
aaggtaacag gaaagacctc gaagattctg ctaccgataa aatgcagcct ttaaattcac    2280
atatgtaagt aactagtttc aaatttaatt atcacactat attaaaatta cttttttccc    2340
tgagattatt caaatttcct ccacttgctt gagtttgtat tatttcttta aactgtgcta    2400
ttatctctga gaatgaaatg ggcaattaca cttaggaaaa tgagtaatcg tatttaatta    2460
agttagcaat tgtatgtatt ctcaagtaag tattacattt ttgctagata ttaaaatttt    2520
gatagtcact tttgttttaa ttattcacag tatctctcta tgaccttgtt ttcagcaaag    2580
tgaacagcat tccataccctt acttctcttt ttttactcat cttaaaaaca ttatgtagtg    2640
tttcaataaa ctttgtgggt aagtagtttc taaatttagt tgtgtgttat cattttgttg    2700
aggtctattt gttgcagtgt gtgtgtgttt gtgtgtgtgt atgtaaccag aaactacatt    2760
tacatctgtt tcatttgggg gattttttcct ttttgtaatg taaagaagtt caaagttatc    2820
agaattcttt aaataaatgt gttagtttag attcttatg tgcctttcat gaaagaaatg    2880
ttttcattaa ttttatggat agaagacctg ttgtattcat cttatgaagc tatgtatgaa    2940
attcaactgt cctgtgaatc gatttgaatc atgagaaata acagcttaaa aagccacaaa    3000
gaagcacata ttggtgacca ccattgatga attcctgaac tttactctgt gtaattgtgt    3060
tactaataaa atctaataaa ttcggatttt taaaatttt                          3099
```

<210> SEQ ID NO 75
<211> LENGTH: 832
<212> TYPE: DNA
<213> ORGANISM: Bos taurus

<400> SEQUENCE: 75

```
acaattttta acttttattt tttaaatgat gggctaaaaa taaacagtat taaaagatta      60
agtttatata atacatatgt acatatttag tggcgttttc ttttcagaca gaatactgaa     120 acatatattagt ttaaaaagga aaactataca gaagacttca taccataaca atagcttaaa    180 tttataatttt cttccaagga aaaagagtca catgttcaat aacaataaac tagtaaatct    240
aggataattt tctaatctac ttttgaggct gacatttcat tttaaaaaa actagaatat    300 ttaagagtag ctatatacag taagttctat gtcaaggttt tgttgctttt ttaaataaat    360
agatttctag gagtcagtat acatttactg ctttttctgcc ttaagaaaat agaagtttag    420
gtcaagtgtt aagctttatc actttgacac tgtccttaac tcataatgta agaatttgaa    480
aaggacctta gcagttttgc aaatataaat aaagccttag tcacactaaa ttaagataac    540
```

```
cctaaagatt ttttttagag taataaagtg acttttcata taaatagttt gaaagggtac      600
ttaagttttt cgccccaatt gtgatgtaca aagagttatt ataaagcaaa ctttatgtca      660
aagccccaag taggagccac agcatttatc ttgtttataa cttctttggt attcccactg      720
ttcagagtac agtttaaaca ccatgttcat ctaagcttta ctggttaaaa atgttacata      780
tagcaaggca aataaaaata gtcaaacaga ttaaagttca cccatttttta aa              832
```

<210> SEQ ID NO 76
<211> LENGTH: 441
<212> TYPE: DNA
<213> ORGANISM: Bos taurus

<400> SEQUENCE: 76

```
tgacgtttat aggccttttt ttttttttt ttggctacat tgataataaa aactcatgtg       60
gaggaactcc aggaatgttt agaagaccaa aagtccccaa tgacaacaaa aagcaactaa     120
gtttgaactt tgtttctctc ctcattcctg ttttcgttga tttcccacat gtagtccttt     180
ttgctcagga agtctttggg ggaaattaag gcttttttgaa agctctgaac tgggtgatca     240
ggttagcagt gtctgtccac tgtcttgaga ggttggaaaa tgaactaccc gaaatagtca     300
ccgaaataca aaacaaagct tgattttctc ttcatatttg aattaagttc ttctgtttga     360
ctggaagggg ttttgtata actaaaacct cagtgcataa aggagattta aaaggggcat     420
ataactgagt gggtgaaagt a                                                441
```

<210> SEQ ID NO 77
<211> LENGTH: 645
<212> TYPE: DNA
<213> ORGANISM: Bos taurus
<220> FEATURE:
<221> NAME/KEY: misc_feature
<222> LOCATION: 380, 423
<223> OTHER INFORMATION: n = A,T,C or G

<400> SEQUENCE: 77

```
ggctggaggt cggcatggtt ggcgttaacg aaggactgat ctcctccgtg gagtgccctt       60 tcggggggcgt gaagcagtct ggccttgggc gagagggctc caagtacggc attgacgagt     120
atcttgagct caagtatgtg tgcttcggag gcttatagga ttcttcaaaa aataaaaagg     180
gaggcttacc tatgtatggg gacatgccat ccattatttt aaataaaccc atcgggtagc     240
tgaactagga attttaaaaa accaatcatc caatccttat aagcagatac aaatcctacc     300
cctcctccta gctgacctgg gaccaataca tgccacaagc ctgtggccac agatccctga     360
gaaccagcag tgggttatan gaatgaggcc ccgtaaacca agccccccaac caaccccccaa     420 ccncctggcc acccaaccca tgacctcatc cgccctcaaag caaggtgcaa caagctggtc     480
ctgaagcccc ctcaccacag tgggaccaca gcctgggcaa tgacatagcc agcacccacg     540
tggctccaga gctaagaccc agagggctgc gggggacatc tcttgagtgt gactgacagt     600
ctgggcagga tgccactgca tgcctggtga ccgccaactg ggcat                     645
```

<210> SEQ ID NO 78
<211> LENGTH: 621
<212> TYPE: DNA
<213> ORGANISM: Bos taurus

<400> SEQUENCE: 78

```
agttttatga aaatagtatt catttattaa aaacaaactt cagaaaagta tgtctgttaa       60
acatggctaa ctttgataac aggaagtcag tgagcaaaaa gcttgatgag gaagaaaaat     120
```

```
atcagttact aagtactact atatccactt cgattatacc cctggttatc ttgaaaagca        180
tgatagtagc tctaaggact ttagacagtt ctgggtgtat ggcacgatct gtctttcatg        240
ttttattgat ttccaacttt aaaagcatag gcccaaaggg taatatttta tgacactaaa        300
ccaaaggtat attctaggga aattcctctc ttttaaagta gtctatgtaa ttttcctgtc        360
tgattccact atggaattcc actattccaa tataaaaaaa aattttatat ttttgctgtt        420
gttttcagaa gctttattaa ttctttaaac cttaggacca aactgcctgt aaattttcct        480
aaggagaaag tagacagcca tccagatttt tgcaacattg cctctttggc ccctttctt         540 aaaaagggta taggttcagt ttaattaaca ttacttttta aatgtgcaaa aatctacctc        600 tgcttttta aagcaaataa a                                                  621
```

<210> SEQ ID NO 79
<211> LENGTH: 649
<212> TYPE: DNA
<213> ORGANISM: Bos taurus

<400> SEQUENCE: 79

```
gttgcaactt gaaataaat atattcacaa tctgtagtca cattctcctg accaccccca         60
caaccttggg agtgcccagg aaattcaacg agtctttaaa atgtcgcagt gcggaagtct        120
ctgcaacata acacgaacac agcacactcc aaaaaaaaga tatcctttga tcaaagtgtc        180
ctccaatctc cacgtcagct ggcttatttg tctggagtct cctttttcgt tctgcttcct        240
ctgatccaaa cgttcttgaa aatataccaa tgtttgagga gactaaaaaa tcaatatatg        300
aactttctgc agcacccatc tgtatacctg taagcatgtt ggttaggggc acactcaggg        360
tagaggcgat gagtgtaatt aaaaaggggt tccttggtag tttgtaattc ataaatataa        420
taaaactcaa agatataatt ctgtgctaat agtcacgaat ctatagatta ttttttatca        480
ggtttaagta aaaaaaaggt cacttgcttt cagacctgag tgtataaagt actaaaatga        540
agactccatc ggtctctaaa tgccagctgg atactttcgg gtggggtatt agtagaaaag        600
aatttaaggc aatccagtag ctaagatatt tccaactaaa gctttgtct                   649
```

<210> SEQ ID NO 80
<211> LENGTH: 402
<212> TYPE: DNA
<213> ORGANISM: Bos taurus

<400> SEQUENCE: 80

```
ctgcaaaaat caaactttaa ttttcataca agggtaactt tattaaagca aaaaactgaa         60
cataatttta aaggccattt ttcaaaggac tccacctcca tcatttcttc tcctaacttg        120
tatcttcatt gaaaaattgt gcaaggttaa gtttactttt ttctagtgct gctgttttgg        180
ctcgtcttgg taatctcatc ttcatttctg attctggttc tggaacttca tgatcacttt        240
caaagttagc ctcagcttca atagtctgac gtcttctgtt cgttctagct gaagctacca        300
cttttctccg tcctctgttg gtcttttgct gaggggattt cattcgagtt gcttttactt        360
ccttgacagg agttatgtat acatctttat tcttttcatc tt                          402
```

<210> SEQ ID NO 81
<211> LENGTH: 840
<212> TYPE: DNA
<213> ORGANISM: Bos taurus

<400> SEQUENCE: 81

```
agtttaaaaa tgtaaatata tttgagaaat ataataaggga aacaaaaatt atcatgatta    60
ggatttgact aaagagtaga tgaagttttt tcacatttgt ctatcttaca gataatactg   120
attatgcagt tatcaatgga catgcctatt tttgtgtata agaaagtgtt tggcttcaga   180
aaacaatact taaagttca ttaccattac caaaacttga caaatctgtg ttttgggtgt    240
gatattgttt gaagctatta ttaaatgaaa gagactgaga atcttgttgt aaagcatcct   300
tcagaaagat gttttatctc tatgtatttc tatatacatc tctttactat atcacaaaca   360
caaaaacagt attaatatat ttacatatat gtatcagacc aaaaattaat ttttccctac   420
aaaattatat ttattaggaa aatactagta gacactatat aaaagaacac aaggtgttta   480
agagaagatg gcaaccactc caatagctga gtgctactgc tttctcttaa taacatctct   540
ggaatggaga aaaaaggagg atgaatggtt tgtagataga cctgactacc ctggaaatat   600
ttggtaggca gaaggcagaa acctaaaaat cacagccta gatatgggaa aatggctaat    660 attttttgtct gtggtgaccc ctcctcttat acttaaaagt taattcttaa agggtttgta   720
ctaaagcaga gagcataact ttagtgggag aaatttccat cagaagaaac tttactaggc   780
ttctatgacc taaagatgaa tattaaacag taattgaaac gctggaagta ttattattaa   840
```

<210> SEQ ID NO 82
<211> LENGTH: 718
<212> TYPE: DNA
<213> ORGANISM: Bos taurus

<400> SEQUENCE: 82

```
tttttatgca atgtttacaa catttttatta aagtacaaaa tagttggaat taagctaaat    60
agaaaaacat agtaaatatt tacaaaaaca ttaacatcac tcaagtcaca cacatgtaat   120
gaatgcagga aggtcttgaa aagtttataa atggaaaatt atggagattt cccaaaatgg   180
atataaaaac tcactgctga gtatagtatc aatattcttt gagaatattg ttcctgactc   240 cttttgcaatc tgagggggaca agtcaagtgt tgagataatc acaacttaag atctaatttt   300
cttcatttta ttgacggttt ctgctgttat tcaaaggat atgaagaata tgaacaattt   360
ttcactgctt aaaaattcag catataaaag gctgagtgag tatttggaac tggaactaca   420
tagagttcta tctgatggaa aattacttat aaaactaaga taaaacagag aactaatcat   480
gctctatctc atatttactg aaagtaggca gagtagaaac tttatgtcaa agggctccaa   540
ttttagctta atgaactgtc aaactacatt atgctaaagt taccacacaa ctatcccgag   600
aggccaggag aacctaaaat catactttaa aagacaagaa aacagactaa acatatacaa   660
agcagagaag aaaacaaaac actgtccacg agatggtcac agtattatac agtattac     718
```

<210> SEQ ID NO 83
<211> LENGTH: 731
<212> TYPE: DNA
<213> ORGANISM: Bos taurus

<400> SEQUENCE: 83

```
tttgagagtt ttcaggctgg gaaagtgtgc tggggctcct ggtacgacca cgtgaagggc    60
tggtggcagg ccaaggacca gcaccgcatc ctctatctct tctatgagga catgaaggag   120
aacccaaagc atgaaattca gaagctggca gaatttattg gaaagagctt agatgataaa   180
cttctggata taattcttta ccacacttca tttagcatca tgaagcagaa cccgatggca   240
aactacacgt cggttgcgaa tgaacacatg aaccagtcga tttctccatt cattagaaaa   300
ggggtcatcg gggattggaa gaactacttc accgtggccc agaacgagag atttgatgat   360
```

```
gattacagga agaacatggc tgacaccact ctaactctcc actttcgatt ctcgtaagga    420
agaaaaagca ccagatttaa ttggtataaa gttgattacc ctgacccat gatattgaat     480 tcaggtggag ggaccagtgc ttcttgtgtc tgcttttgtt caccctaaaa aaagatggag    540
ctaacagagg ttggggccag gtggaaggcg gagacttaca accctggcat ccttgctaat    600
gatcatgatg cgtcagtttt ctgcagacca cacgcgtgtg aacacgttaa atatgctctg    660
atcatcacat aagaatatac tcaagttttc agattcagtg ttggtttaag caaatttata    720
aaaatagcac t                                                        731

<210> SEQ ID NO 84
<211> LENGTH: 641
<212> TYPE: DNA
<213> ORGANISM: Bos taurus

<400> SEQUENCE: 84
tttttggttt tggaggcaca ttttatttga ccgtactaga gattaacatc tagtaacagc     60
ataatacaaa aatgcaaccc caatctactt aaaactctta taatgggaac atgtctttca    120
agaaacgtgg aaaaaaaagt tggagatttc gagacacgtt gataaaaatg ttaacaaaaa    180
tcaaagctca ttccatcatc atcattcact ttacagtctc atgaaaagat tgtcattttg    240
ttttctccac aatatgtcaa aaatatatat acttatgcat aatattcaca ttctggaagg    300
caagagaaat cttcgaattt aattccctaa atttaaacat tacatatatt tcaattaaaa    360
taacctaaac attaaaaata gcagcaacac cagtctttaa attacagtag attattcaca    420
taatgtagac atatttgggt ggctctttca ttattatctg ataatttta caaactccaa     480 ggtaatggtc tcatcatcaa ataacataga atctagtgtc aataaatact atgcaaagaa    540
ttattataaa acacagattg ccaaacattc tccagactag agagaaccat actaaaacat    600 ttcagggag aatcaagttt gaaagatgtt tgaaagcatg c                         641

<210> SEQ ID NO 85
<211> LENGTH: 785
<212> TYPE: DNA
<213> ORGANISM: Bos taurus

<400> SEQUENCE: 85
cccggaaaaa gtaaatgatt taatggaaaa tcccaaaata catgacagcc atttccacac     60
tttgctacaa tgattccatg tgcttaaaaa aaggaaatag ggcttcttaa aaacagatca    120
cagtccttcc ttgtgaagcc cttcactcct ctttcaaagc atacagcaca tcatcctggc    180
tgacgttgag ccgcacccga cggagcacgt cattcctgct aggctccacg aggaggaaac    240
ggcaggcgcc caggcgagag cacaccgcca ttgtctccga catggtgggg tacgggaggc    300
cctccatcct gcacagcgcc acgtgctgaa tgtatacctg ttgaaatgtt gcttcctcca    360
gtcctgatcg acggaactct gcaaggatgg ctctcaggaa gctctgttcc aaaaacgagg    420
aatttttgat ggcagtgata tatgatgatg aaaacatctc atctatggct tctagtaaat    480
gggctgtagt aaccaggcca ggggagtcgg gcttctggca ggaaaactca cagatctctg    540
tcgcacgtct acaatgtcc aggcagcgtc gtgcatctcc agagagggct gcgaccttcc     600
tggctaccag ctggatggca tcatcctcaa aagcctttac gtgtctgagt cgggacaata    660
ggatctgccg cagctggctg tgagtataag gctggaagca catcctggtt agacccagtc    720
ggctggacac ccggttcatc atgatgcgct ctggcagatc catggtgtta gcaatggtca    780
```

```
ggacc                                                          785

<210> SEQ ID NO 86
<211> LENGTH: 843
<212> TYPE: DNA
<213> ORGANISM: Bos taurus

<400> SEQUENCE: 86
acattaaata tactttattt tataaacaga gctggctcta agccaattgg tcctgatgtt    60
ggggtaaggg agtgttgcag gtaaaaaggg gtgcaacaga ctccagcttt cagtttctta   120
gctcaaaaat tgcagcaatc cctgtagctc cttgcagccg ttcacgacat ctgggatgga   180
cagcagagtc tcgtaaatat gctgaacagt gtcatctaat ttcttaact cctcatcaga    240 gcgtcgcaaa ttctcttcca ggatgttct gtggctctgg aacttgacca tgagttttgc    300
cttctcattt ttcatctcca ggaacatcac tctcagttta tccacctctt gggagagcca   360
cactttctcc tggatccagt tcgtgtccat gggctgacag tcggggttct gctggcctgc   420
cagggtctct tggagcacct tagtctctgt ctctgcacgc cgaagggagc gggtgagctg   480
ggtcacctcc tccctaagcc ttatgagctc gccgctcttg tctatctgct ccaggatctt   540
ctcgttttgc tgctgtatca cttcctggag ttccttttca ttcttgtagc gcaagcacaa   600
ggtctggttc agcttctcta tgtccgcttc ctttgccttc tgggcttcct gatgctgttc   660
ttcctgggcc tgcagctgag cctgcagatc gcatatcttt tgctgcagaa tcctgacagc   720
ctcttcttta gactcctgca gcaaggaaca caggctctga agttccagag tcttagtacc   780
catttctgcc aggctcttct caatgcctgg ggtttctgta ggctcaaggg aaactgttga   840
tgc                                                          843

<210> SEQ ID NO 87
<211> LENGTH: 288
<212> TYPE: DNA
<213> ORGANISM: Bos taurus

<400> SEQUENCE: 87
acgagcgccc cataccatcc agtcacctgt gtggaggcct tcccatctgc ctgccctgcc    60
tggtggaggc gacgctggag gccgggaggg tcactgtgcc caagcgcgcg agctgtcacc   120
cctgcctaca tcgactcttg tgtcccccg ggtctggcat ggagcgaggt ccacatcaca    180
ataaatgcct ttgaacaaaa aaaaaaaaaa aaaggggggg gcccttaaa atttcccttg    240 ggggggccaa ctttacccct ccccttttt ttttgaaaaa gggggccc              288

<210> SEQ ID NO 88
<211> LENGTH: 649
<212> TYPE: DNA
<213> ORGANISM: Bos taurus

<400> SEQUENCE: 88
gtaggttcaa ctcaaatgat tttattggaa acttttaaaa cattgaggtt gaacaaagat    60
gggaactgga tgaaagaatc tttcaggcat gaatggtggg ttaccttctc tcttgcctaa   120
ctgctctgct ggcagtgtca gtgactgctt tagttctctg ataggtctga ttctctcgag   180
gtctcttgga gcgtgttctc tctcttctgg ccgaaaaagg atcttctttt gcagcctctt   240
gactgggtgg tacttttagg attggcaagt gtagaggtac agaagcttct cctcctcctc   300
ttcccaggta aactgcatc aggagcagcg gtaaagccct caccgttctc ctcacttgat    360
gtggagggca gcgtgcaagg atcctgcctg gaggacacag gctcgaagcc tctgctgtca   420
```

```
agagtaccta ctgttctcct cttggttctc tgtgaagtgc aagaagcagg aggcggtgga    480
agtgaaaccc acacgagccc tccttctctt tccaaacttt tctgcagcct caagctgcgt    540
cttactttgg tttcgctctt tgttctctga aggctttgct caatggaatc agataaatct    600
ttacacagtt cggaattttc taaactaatt tctaccaagc tgctcatgc                649

<210> SEQ ID NO 89
<211> LENGTH: 680
<212> TYPE: DNA
<213> ORGANISM: Bos taurus

<400> SEQUENCE: 89 ttttagcgt ccaaaataac ttttattact atataaaaac aagaaaaaat agatgcatat      60
tttttctaca aaattacaaa atattcaagc tatttaacat ttttgcataa atgtattgag    120
attaaaaagg tagattttaa acagaggaat ctttcccact taaagttttc aggtactttg    180
tagaggataa agaagttttc attcttctat actttcctat gtgtagctcg aagacatagc    240
agtaacagtt ttctgtcaga gttatctaaa aaaggacat acaaagataa aaattccatc    300
ttgctgcaat aaaattagca aaaagcttta cttcaagctt tcaaatttgg cagttgcggt    360
ctatcagttt tgcactggaa tttccaactc agcagggaaa gagcctaatt aaaagcaaga    420
catcctcttt attttgtcct ttagaaacaa aaatcacttg tcagtattcc tgaaaaagtg    480
cgattatctc ctttgtcatt tgatcataaa gtctgagata ctgtttctaa cccgcacagc    540
ttaaatgaaa ccaggagaag aaagggagga aggtactttg gagggtggat tcagtttgac    600
acaatgagca caggaatttg tacagttttg ataacattaa tttaaaaagt ataatcatct    660
gagtttctca ataaacccctt                                               680

<210> SEQ ID NO 90
<211> LENGTH: 736
<212> TYPE: DNA
<213> ORGANISM: Bos taurus

<400> SEQUENCE: 90
cggagctgca gaggatcagc acgcggatcg ccccagcctc tgcccacagc taccatgaag     60
gtctctgcca ctgccttcgc tgtcctcctg atggcggccg ccctctgcgc tcctgcttct    120
gcctccccat atgcctcgga caccacgccc tgctgctttg cctatatctc ccgcccgctg    180
ccccgcaccc acgtccagga gtatttctac accagcagca agtgctccat ggcagcagtt    240
gtctttatca ccaggaagaa gcgccaggtg tgcgccaacc cagagaagaa gtgggtgcga    300
gagtacatca acgctttgga gttgagctag ggtggaggac gccttgaacc tgaacttgcg    360
ccaactttgc ttctcgctct tgtcctaagc agcttgggag gctcccccgc aatgccctcc    420
tcccaccctc tcctgggaag gcacagattc caccccgcgc agcagcagct gctgtgaaag    480
accctcagtg ctcctggggc tctgcccttg tgcacaggag gtctctaagc tccgagctcc    540
tgagcccctg cccaccccacc gctctgcagt cagaaaggat gccggcgtct ctggagggga    600
aggagggcag gagactgggc tcctctggtc atgcccgtg accagagccc ccatctcggt    660
ccctcactgg ggagggctgc actggcaaat aagaagaaat cagctgttca ttaaaattct    720
ccaagcgatt gcaaaa                                                    736

<210> SEQ ID NO 91
<211> LENGTH: 651
<212> TYPE: DNA
```

<213> ORGANISM: Bos taurus

<400> SEQUENCE: 91

| | |
|---|---|
| tttttgagga agacactaat ttttaatggc agtcatctta gagaggagca ctagaaatgt | 60 |
| atttctttca aagcaaatca aaaattaaaa atgttttgaa gccatatgat tagctgaatt | 120 |
| agtttctaag gtttaaggtg agatagcact gaacagatgc agtatttcat tgcagcattt | 180 |
| tctttcacta ccatgtgaac ttgaccaagc attttttata aagcattcat tgcttttctc | 240 |
| ttttcaatat ctcgcttgag ttgacaaagg gcacagagcg gtaaaaatgt cagacacagg | 300 |
| caatccttgc aaatggatcc cgggatgccg tatcgggtcc gatacattgt cctcatggcg | 360 |
| acacttgatc cccataggca gcattcgttc atgtcagagg caatctgaca tgaaaggcac | 420 |
| aggggaaaga gagccccaca gagacagatc cctatgtcat caaagcagtc aaagatgcca | 480 |
| gtctgccagt cactggacgc cgagaccgcc gagctgtaac ctggctgtga aacaactggg | 540 |
| ttcatttttca agactgagtt caaaaaggta ctgccacaca caggctgact gcagaggaca | 600 |
| gcagctcaaa tcagcaggaa aaacctctgg aacaccgcac ttttgttctg t | 651 |

<210> SEQ ID NO 92
<211> LENGTH: 361
<212> TYPE: DNA
<213> ORGANISM: Bos taurus

<400> SEQUENCE: 92

| | |
|---|---|
| gcagcagcaa gcaccgagtc ccacctcggc tgcactgacg ctcaagccca cactccgtct | 60 |
| cgcagcatca tgaaggtcgc cgtggctgct ctcgccgttc tcctctgcgc catggccctc | 120 |
| tgcagccagg tcttctcggc accatttggc gctgacaccc caacggcctg ctgcttctcc | 180 |
| tatgtcgccc ggcagctttc tcgcaaaatc gtagctgact attttgagac cagcagccag | 240 |
| tgctccaagc ctggtgtcat cttccagacc aaaaaaggcc ggcaggtctg tgccaacccc | 300 |
| actgaggact gggtccagga atacatcacc gacctggagc tgaatgcctg agaggtccga | 360 |
| a | 361 |

<210> SEQ ID NO 93
<211> LENGTH: 668
<212> TYPE: DNA
<213> ORGANISM: Bos taurus

<400> SEQUENCE: 93

| | |
|---|---|
| tttttgtgat gattttagca attttatta aaggattttt attggtaagt gaagttttca | 60 |
| gatattccaa gactgatttg atattatatg cccaaaaaag ccatatgcga agtatctgtt | 120 |
| cccagctaaa cagatctcca tctcctgtga tgtccaagtt tcgggtcagc gttcactgtt | 180 |
| gagatgagat cactgtggcc cccacagatg tggcaagcag ttgtagtgaa gagctcccac | 240 |
| ttgtcagggt aggggtacgg atcagccagt cagaactcac agtaaagagc tttctggaac | 300 |
| acagttccaa ccagcatttt ccccttgtac acagaagcaa ccgtacttcc atgcaacact | 360 |
| ttaccatctt ctgcataaac caccgtaact ttgggttctt ctgctaaaat attctggatt | 420 |
| tggagcacct ctgatccagg aggattctct gggtcatagg agaagatttt catgccattg | 480 |
| gggtggcagc caacccacag gtcccctgtc acaggatcca cagatatgtt atccacgagt | 540 |
| gtgtcacagt ccagagactt caatggagtt aaagtccaat tagcatgctt ttcatacaca | 600 |
| tgaatcttat gagccagaaa ttcagctata tagacatact tgcagtcagg tgacatgctg | 660 |
| attccatt | 668 |

```
<210> SEQ ID NO 94
<211> LENGTH: 642
<212> TYPE: DNA
<213> ORGANISM: Bos taurus

<400> SEQUENCE: 94
atcagagccc cagacctgtg actggcggaa agttggcacc atctcacccg tcagggacca      60
gcgaaactgc aactgttgct gggccatggc ggcagcgggc aacatcgagg ccctatgggc     120
catcaagttc agacacttcg tggaggtctc cgtgcagcgt atggctgggg caggggctg      180 gggtgaggac caaaggaggt gggggtgcct gaggcctggg catacacatt gtcccttctg     240
gcaccagagc tgcttgactg tgaccgctgt gggaacggct gcaggggtgg cttcgtctgg     300
gatgcgttcc tcactgtcct caacaacagt gagtgcctgg ctgctccagg cagtcgtggt     360
gggggaagga tggggcgggt actgttcccg agctgaactg agcctcctcc tgggccttgc     420
ttatctccag gcggcctggc cagtgagaag gactatccat tcaatgggag tggcaaaacc     480
cacaggtgcc tggctaagaa gtacaagaag gtggcctgga tccaggatttt cataatactg     540 caggcctgcg agcagagtgc gggcacaatg gggacacggg tgggcacagg ggggagacgg     600
acagggacag acggaccagg acagacgggg ctatagacag ag                         642

<210> SEQ ID NO 95
<211> LENGTH: 576
<212> TYPE: DNA
<213> ORGANISM: Bos taurus

<400> SEQUENCE: 95
tttttggtat ctgcaacatt tatttcagaa aaaaatgtgt atgccaacca tccatatgac      60
acatgtttgt cacacatgca catatatgca aagataaagc acatagatac agtaatatt     120 gaatctagat ggaaagtata ttcttgcaaa tttcagtagg tttgaaattt tgcagattga     180
agatggaaga gaaaaaaaac atcagcttgg gcactggacc ttggacctgg tgggtctaaa     240
tgttcattgt acctcctcct atccaccccc ctctttttttt tttttttgct ttggggcctt     300
gggcaagtta tttccatctc ctgccaaggg ttttcccta ctataaacag ggttagtaat      360
actacctgtc ccaaagggtt atgaggagga aggatggtgg atgtaagggg ctggcagtgc     420
ctggtggaga gtgagcactc agttaacgcc tgctctaatt atgaagatat attttgctaa     480
gacaggttca cgggaaggaa cacatcaatg ggaaagttgg aatcctccca cctgcaaagc     540
gctggtaccc ttgcagaaaa ccacaaaata cccccct                              576

<210> SEQ ID NO 96
<211> LENGTH: 658
<212> TYPE: DNA
<213> ORGANISM: Bos taurus
<220> FEATURE:
<221> NAME/KEY: misc_feature
<222> LOCATION: 650
<223> OTHER INFORMATION: n = A,T,C or G

<400> SEQUENCE: 96
tacgggtctt gtcttgcttt attcaatccc cagcgagaat actggggaac taggcaaaag      60
ccttggggcg ggtggcaggg gaagataaca ggcacagcag gagagagcca aagggcagcc     120
aggcagcctc agggagggca agagacttgg tgctgcttct taggcttgtc cactctggcg     180
gtgaccggga acttggtgat gccgcaggtg ttactccctc gatgcagccg gaaatagccc     240
```

```
tcctcacccc actgaggccc ccaggagttc ttcaggatcc agtatgccat ggagcggcga    300
gggcgtgcgt gggatccgaa cgaggccgcc ttccctgcc tccctccac caacttggtt     360 ttaccaaaac ccaccagcag acagaatga tccacttgtg tggggtcaca ggtggtaggt    420
gtggccttga tcacacccctt ctggtattgc tgcagtagcg tcatattgat ggtcacggtg  480
atggggccct cggtggccaa gtgcctggcc atgctctgct cgcaggcctg cagtattatg   540
aaatcctgga tccaggccac cttcttgtac ttcttagcca ggcacctgtg ggttttgcca   600
ctcccattga atggatagtc cttctcactg gccaggccgc tgttgttgan acagtga      658
```

```
<210> SEQ ID NO 97
<211> LENGTH: 839
<212> TYPE: DNA
<213> ORGANISM: Bos taurus

<400> SEQUENCE: 97
gccagctgaa ggagtgaatt tattaatgaa atgaacaagg actaaggatg aacggcaggg     60
tgactaaatc agagagggaa ccgaaagaaa agaactaaaa agaggaagat acaggaaaga   120
cttccctgtt ggcccagggg ttaagactct gtgcttccac tccaggggga gcaggttcaa   180
tccctggtcc aggaagtttg catgccatgc agccaaaaag aaaaaaaaaa gacacaggga   240
agaaaagaga tggaaggaca aagaagagag acagcaaggg ccctgggccc atgcccgagc   300
ctagactggt ccccacactg gtaggagct cctggagggc agggcaggtg gcaggactga    360 ctccctctg ggtgcccggc gtcacccacc atggagctgg catgtcatcg gtttatgtcg    420
cagctgcatg accctttgaa taaccagatc ctggcaaatt tttgttgaat gaatgaagcc   480 acaaggaag aagcctgtgc aggctggag tcagggcagg ctggctggaa ggagagccag     540
ctgttgctta acagagctct aaggccatcc ttcggttcac acggcctcgt agtcgggccg   600
gtgggtcgtg cagtgagcgc ccagactcag gccacctgta cagagaaaga ggagagttga   660
aacccagccc aggtagaagg accatgagaa gaagctctgg acctggggt ttgcaggctg     720 gttccaccgc tcaatggtgt agaccgtcat ggccactatc aaggacaggg ctccagcaaa   780
gcccatgaag gtggagacaa tggggccgcg tccaggggca gacagtgaag ggatgcaag    839
```

```
<210> SEQ ID NO 98
<211> LENGTH: 661
<212> TYPE: DNA
<213> ORGANISM: Bos taurus

<400> SEQUENCE: 98 ttttacgtt taaaaaaac cattttatta caaaaacact tgaaatcagt tgcattatcc      60
atgtattcac agtagcagag ggacagtgat ggcagacaat ccccatgggg gacatgggtc   120
ctctggtaaa acaaacataa ataatgggga acaataccaa atacagtaat agcacagcaa   180
agaataaaaa aattaaatta agagaaggaa caggatctgc tgaggggagt cgtgagcatg   240
gagagggtgc atctcgctga gaagcgtcgg gttcaggtga tctttcctgc agaacacctg   300
ccccggagct cggagcagct cagttcaatt caaggtcatc cacgtactcc tggacccagg   360
gctcactggg gttggcgcag acctgcctgc cctttttggt ctggaatacc acagctggct   420
gggagcagag gctgctggtc tcgaagtagt cattcacaaa gttgcgagga atcttccgca   480
gagtgtaaga gaagcagcag gccgtgggag ggtctgagcc cattggtgct gagagcgctg   540
gagaacagaa ggcagccatg agcacgagga gggacaggac agtcacgcag agcttcatga   600
tcttggcaga ggagagattc acccggagct tggactgcag cacccaggag cttcagaacc   660
```

```
c                                                                           661

<210> SEQ ID NO 99
<211> LENGTH: 691
<212> TYPE: DNA
<213> ORGANISM: Bos taurus

<400> SEQUENCE: 99
caccatcaca tcacatttat tggtcagact gtgtacacaa tgagacaagt caagacagtc      60
ctggattttg gctgagaggc aaagcttggt gggccaagaa acagagtaa ccggagcagc     120 tggggccaaa gacgttaggt ctaatatgat gaaaaattca ccacgctaga agcggggctg     180
cgagggaatg gtgtaagtga caccaggcag cctggcgggc acagcgtccg ggctttctgc     240
cctgtccctg acctgtaggg cagtgaagca ctggctgcag ggcctgaccc agctccacct     300
acgttcctgg gctcgagaat attgaagagc taaggcagtt tggacagggc tgagggctgg     360
cctgtaaatc cagccacctc attggaagaa aaaagaagt ctcagttttc tgtctgtcta     420
atggagatat ggagatatag gccctctggg ttcctgcact gggttccttt ccagtttggc     480
acagaggtcc tctcaggacc cacttctctc accacactgg cccactccgg tttcctggag     540
gattccccag aagcccttgg ggggcatact gcaggcacct ctccccgtc aggtgaggca     600 agcatttgac ctggtaggag aatttcagga accgtggtc catggggcat gacacctcat     660
gtgagccaga ctttggggtg cggtcacaag t                                    691

<210> SEQ ID NO 100
<211> LENGTH: 484
<212> TYPE: DNA
<213> ORGANISM: Bos taurus

<400> SEQUENCE: 100
gcacgagggc atctttgagt gggcatccat tcccgctcac tgcataattc agcagaaacg      60
agaggagctg ggcgtgtaac tgttggaact gaccctcttc tctctaccca ttagctaact     120
ggttagcagc caagcccttta ggcagcttag tgtaaagata cactgttaac ccttcactgt     180 tctgtgggt cagtgagaac ctcttggtta aacttattga agtttatctg aatgatgtga     240
tagtttgatt caggtataat taagttagca gggggctagt ccagctgtat taatcattag     300
ctggaaactg gaaactgttc atatcttctc atcagcatgt gaggtctaag gtgggaattc     360
aggatgaaaa gtgcaatttt aagcttcaca ggaaagcatt tgggtgtgta aggtgtgatt     420
tctgaccaga gccctaattc tgcaatatga ccaaaaccaa ggaacataaa taacaatcag     480
gctc                                                                  484

<210> SEQ ID NO 101
<211> LENGTH: 431
<212> TYPE: DNA
<213> ORGANISM: Bos taurus

<400> SEQUENCE: 101 ttttttgag acttctaaag tcattttatt ttcacttaat cgacagatcg acagatgcag      60
aaatcgacta gatgtcaatt acaaaactga aggcagatct gagctatctc tgcccgagta     120
cacagttgat ttttcccctc ccagagtata cagtatccct ttcaaaccat ggctatgtat     180
gtcataacta tatttagaag tacgcagaga ggaaaatact actgcaattc aaggctgtaa     240
atgaaaggga aacacatcag agcctcatgg aatggaaagc tgaaacgtca gttcgtgttc     300
```

```
ctcaatcaat atcaaacgtc agatgacact ggaaggtgtt aattatgacc aaaaaaaaa    360 aaaaaaattc ttgtaacaaa tttccacttg aagaaaaggg gtaggcttt ttcatacagg    420 gagggtaaaa a                                                        431

<210> SEQ ID NO 102
<211> LENGTH: 718
<212> TYPE: DNA
<213> ORGANISM: Bos taurus
<220> FEATURE:
<221> NAME/KEY: misc_feature
<222> LOCATION: 679, 682
<223> OTHER INFORMATION: n = A,T,C or G

<400> SEQUENCE: 102
gaaagtatag tcacctcaac aagagaattt tccatacgct gaaatcctac aaagaaaatt     60
tccaaatctt ctatcattcc atctaaaact ttaaatatc tacaggacga tacaaaaaat    120
actgccatgt ttataaatga ttgcctataa ggatttttat accaaccact attaatttgt    180
agcaagtcag caaattagca acccagttca gttgtcaaaa atctagcaaa ttaaattcac    240
attgctttga tgtcagatta ttcctctgtg catttaaaaa tatttaatac tcaagtattt    300
cacagaaaaa aaatgtatc tactttctca ttaggttact gaaatgtttt aatgcattta    360
tgatttttgt tattagtgtg aattttaatg tagaggagaa tgcagtgtac taagtgatat    420
gccagtgtct aattacattc attttagaa aaaataatc attcttgaaa attagaatgc    480
atgaaaacct attttgtaaa ataaactgct tatggggagg ggaaagttg cctttaaaaa    540 tgtttcacta ttaccataga atctatactt aaaaactgca ttcccaagac tctcatgtaa    600
gttttatacc taacttcctg actatcaaag gagtatacct ctagagagaa aactggtgag    660
atgcttactt cctgactgna anggagtagc ttggtgaatt gtgcgacagt gttgtctc     718

<210> SEQ ID NO 103
<211> LENGTH: 652
<212> TYPE: DNA
<213> ORGANISM: Bos taurus

<400> SEQUENCE: 103
ctgatcaaga acaaccaact acgtgtggaa gttgagaagt tagcaacact caacattgat     60
ggcctccgag gccacagggc acagcgcctg gcacacttgg ttctgggata catcacaatg    120
gcgtatgtgt ggggtcaagg cgatggagac atccgaaagg tcttgccaag caatatcgct    180
gttccttact gcaaactgtc tgagaagctg ggactgcctc ctattctact ttatgcagat    240
tgtgtcttgg caaactggaa gaaaaaggat cccaatgggc ccatgactta tgagaacatg    300
gacattctgt tctcatttcc tggtggggac tgcggcaaag gcttcttct ggtttctctg    360 ttggtggaaa tagcagctgc ctctgcaatc aaagtgatcc ccagtatatt tgatgcagta    420
caacgtaaag actcagatac tttgcagaaa gcgctgcttg aaatatcttc cagcctgcac    480
aaagccctgg aagtgttttc ccaaattcat aaatatgtgg acccaaacct attttcaat    540 gttcttcgaa tatacttgtc tggttggaaa ggcaacccct tgctgtcaga gggtctgctg    600
tatgaaggcg tctgggacac cccaaagaag tttgccggag gcagcgcagc cc            652

<210> SEQ ID NO 104
<211> LENGTH: 629
<212> TYPE: DNA
<213> ORGANISM: Bos taurus

<400> SEQUENCE: 104
```

```
tttttaacct tcaaagaag tgcctttatt tatttacagg gtttaggaaa ggggaaaaaa       60
aaggtctaga aaaggaaat tccaaaatag gtgtcctcgg caagggttgg gcgcagtgac      120
aggttttgac cgggtccggg ctgtaagtct tggtcttgcc ggtggtcact tccaggtggt     180
gaggacggtc ctcccggcat ctctcaatcg gctcccttttg ggcccagcg actggcctgg    240 ccgacttctc agctctcgtt cagccccgtc accctgcgcc agctcctcgt catacaggat    300
ttcataattg ccgaggactt cctttggggg tgacttgttc catttacagt ctggaatttc    360
accattaggg accgcgatgt tgagggtgtc attgatcaaa ttgtacttaa ggattcggtc    420
gttggcagtg ctggaggtga gggacggaga tgcgtttacc tcgatcagcc agggcttcag   480
cttgtcatcg atgatgatgt cgtagccgta gcactcgaag cagtgcttgt cgttgttcat    540
cacgggcgcc acagccttca gggactgcac gatgatccag tggatctcgt cgaacagctt   600
gctggtcacc tccttgcctc gggtgctct                                      629

<210> SEQ ID NO 105
<211> LENGTH: 621
<212> TYPE: DNA
<213> ORGANISM: Bos taurus

<400> SEQUENCE: 105
catatttaaa gaattttat ttttctttca gtacacagag gtgatgcttt tcaaaatcaa     60
acataaacct gtcaaaagta tttttgttgg cttttctaaa ggactagata actgatgaat   120
taaaaacttc acacaagtcc ttctgttatt tttctcagtc actctgctgt gccgtgctta   180
gttgctcagt catgtctgac tgaccccatc gactgtagcc cttccaaatt cctctgtcca   240
tggggattct ccaggttcca tgccctcctc caggggatct tcacgaccca ggaattgaac   300
caaaaactcc tgcattgcag gtggactctt taccagctga gctaccatat atgcttttct   360
agttgcaaaa agtccttccc aaaacagtgg aaaatgaaat aacctaaaaa ttaagtcttg   420
tgaaaccagt gcttccctgg gacagattaa atgtggagtt ttatgtggga ttctgtattc    480
agtttatttt ggagttctgg ctacattcag cttagatttt tcagtgccat attagttaca    540
taacagtgct attcataatt aacttttgat gtctcatcta gaataaaagg acagtgttta   600
tttcctttga agaaaagtt c                                               621

<210> SEQ ID NO 106
<211> LENGTH: 510
<212> TYPE: DNA
<213> ORGANISM: Bos taurus

<400> SEQUENCE: 106
tttttgccaa ataaataaac agttctttaa taattactta aatatattcc agaagtgaag   60
agtgtttcta attcatttac aagtgctatc tgttacacca gtaaatgtta cttgacctct   120
ttataaagta aatagtgctg cataagaatt agtcctggaa tagtgtgctg aatttctatt    180
ttcaatccag tagattaaaa acacaattgt gaatggtata aaaacgtaag aatcattgtg    240
ataaaaccaa tctcaaaaat agagaatcca gactctcctc agataatttt ggaactcaga   300
agttttcctc tactcaaaca caagctccac atataatatt aaaggtgttt tcaccacgat    360
gcctctgcat aaaactcgag aatgtggcca tcagcagatg aacacactga aatcaagagt    420
ttagaaaaca catctcaagtg tgaagtaagc agaaataaaa agacgattta caaagaatta   480
gaactaattt ctaatcatca tcagagtctg                                     510
```

<210> SEQ ID NO 107
<211> LENGTH: 320
<212> TYPE: DNA
<213> ORGANISM: Bos taurus

<400> SEQUENCE: 107

| | | | | | |
|---|---|---|---|---|---|
| ctcgcgctcc | tcttcctggt | cctgtctgct | gggtcaggat | ttactcaagg | agtaagaaat | 60 |
| tttgtaaccct | gccgtataaa | tagaggcttc | tgtgtgccga | tcaggtgccc | tggacacagg | 120 |
| agacagattg | gcacctgttt | agcgccccaa | ataaaatgct | gcaggtagtg | gtaaaagaag | 180 |
| gcgaagatgc | ggccgggacc | gatgcggaga | ctgaaactgc | gcccttcgac | agaacgtcta | 240 |
| aaatttaaac | cagaataaat | tttgttcaag | gttaaaaaaa | aaaaaaaaaa | aaaaaaaaaa | 300 |
| agaaaaaaaa | aaaaaaaaaa | | | | | 320 |

<210> SEQ ID NO 108
<211> LENGTH: 874
<212> TYPE: DNA
<213> ORGANISM: Bos taurus

<400> SEQUENCE: 108

| | | | | | |
|---|---|---|---|---|---|
| aagtaaaaca | acattaaaa | attttaattt | atgagataca | ctgaagtatt | taggtatgtt | 60 |
| tgaatatgca | tagaaaaaat | atctggaagg | atacatatca | gattattaac | agtttacctt | 120 |
| gggcatgtgg | aattggggta | gggtgaagac | agtgctctta | ttttttaaatt | cttacacttc | 180 |
| tgtattttgt | gaaattgtac | aatgagaatt | tattaatttt | ataataatga | aaaccataat | 240 |
| agaaatttaa | aaaataaaca | tagtaagaaa | aagtgaaaaa | cacacacata | tatacaatag | 300 |
| ttttaagagc | ttcattggag | gtacagagaa | ttaaatcata | tggcacatt | ccccactaat | 360 |
| actgtggtgg | taaatataac | tgcatacttt | tagcaacatc | tcaattttaa | aagtcctctg | 420 |
| ggataagagc | ccttaagcag | tgacccttca | aggtgaatat | taaaactgaa | acagggtttt | 480 |
| aactgtttct | agaggatcta | caggaaaaca | tgtcaatctg | aaaacttcag | acaaaaggaa | 540 |
| aagcttcaca | gaagtaactc | tggaattcta | aaacagctaa | ccaaaggcca | gaaatgaccc | 600 |
| agttcagacc | caaaactaaa | tcactgaagt | cttggtaatc | tagggaaaca | ggttaggggt | 660 |
| atctatttta | cccatttgtt | tattatttct | cccaaatttt | caattggtct | gcttttttaat | 720 |
| ctcaattttta | ccctaaaaat | actgcaattt | taatgggaag | gaattaaatt | aattccatct | 780 |
| aattagcttt | aggtttattc | ttccagttaa | aacaactaga | aaaaactgag | actaatgatt | 840 |
| ttcccatcct | tgttttttct | catcactatt | tcta | | | 874 |

<210> SEQ ID NO 109
<211> LENGTH: 325
<212> TYPE: DNA
<213> ORGANISM: Bos taurus
<220> FEATURE:
<221> NAME/KEY: misc_feature
<222> LOCATION: 255, 256
<223> OTHER INFORMATION: n = A,T,C or G

<400> SEQUENCE: 109

| | | | | | |
|---|---|---|---|---|---|
| gcgacttgcg | tcttcagcat | gttctcatcg | gatctagaaa | ggaatatgta | cactggaacc | 60 |
| gtagtggtag | cttttcagtat | tgtaaagaga | ttgttctata | cagacctttt | tgctgttcct | 120 |
| cctgtatgta | ataaagtcct | ttctagatcc | tatgtgaaaa | gaaacgtgaa | gcgacttgcg | 180 |
| tcttcagcat | gttctcatcg | gcggagcctt | cttgtgttat | gtaaactgtg | ccatgttatt | 240 |
| aaaaaatgtg | aaccnngaaa | aaaaaaaaaa | aaaaaaaaaa | aaaaaaaaaa | aaaaaaaaaa | 300 |

```
aaaaaaaaaa aaaaaggggg ggggg                                          325

<210> SEQ ID NO 110
<211> LENGTH: 684
<212> TYPE: DNA
<213> ORGANISM: Bos taurus
<220> FEATURE:
<221> NAME/KEY: misc_feature
<222> LOCATION: 561
<223> OTHER INFORMATION: n = A,T,C or G

<400> SEQUENCE: 110
tttttcgaat gaccactaca gagataaatg ttttaaaacg ctcaattgtg gatatgtgta    60
ttttcaggcc cctggtaatt ttcaacacca aacgaaatca tcagcacagt ttttacataa   120
aaagctttac tgaaatatat ttttcatata cacatttaac tcacttatac aattcagtag   180
tttttagtct ttccagatct gtgcaatcag caccaaataa agtttagaat accagacaca   240
cacacacaca caaatccct gattttttta gcagtcgctc cccaccaagc cccaggcaac    300
gcctactctg gaggaaacta gatttatacc ccatttctga aagctggagg atttcctctt   360
tggtaggtaa tctattggga aaatttcaat actccagcag gtgcaagtcc tgaaacccct   420
tgctcgctga atgggaggaa ggctgacgct ataggagcat cgcctcttta aaccaccttc   480
tagtgtcttt tgacatttga ccgggaacct cacaaatact tcagattctg aggacagtga   540
tggcctcatt caataactca ncaaggtcga gggaaaaggc tctaaaagtc ctttcctgcc   600
tggttccatg ataacgataa gcagtcgccc cagtgctccg tagaataaac ctggggaagc   660
ggtcccgcga agccacttcc gcta                                          684

<210> SEQ ID NO 111
<211> LENGTH: 837
<212> TYPE: DNA
<213> ORGANISM: Bos taurus

<400> SEQUENCE: 111
acctttaaaa atattttaat gtagactggg gaacagtcgt gtagacgagg gtctgttttt    60
ccatctgttt aaacaatgaa gtaaacggta taaacttacg acattttaaa aagtgaaaca   120
agtgatgtta taaagataaa gtagtatgat attctcaaaa atggctcttt ataaaatgaa   180
aatcaggaca atgtcttctg gcaggtgata atggggtcgc aaagagtcag acacaactca   240
gcgactgaac aataacaaca gcaacaatct ttagaacaag cacatggcat atacccctact  300 caggatgcca ggcactttaa gcacatggca tatacccctac tcaggatgcc aggcacttta   360
agcacatggc atatacccta ctcaggatgc caggcacttt aagcacatgg catataccct   420
actcaggatg ccaggcactt taatcaatcc tccacttctg aaaagctatt aacatgacta   480
ttttttaaag gctgggatat gtgaactaca atagcagcag tttaaaacag aagaatagga   540
aataaaggga aataatatta cattattaca aatgtgttta ttaacttcta tggcagattt   600
tacttttacg taaaaacaat gatggttact ttttcaatg aacgtttata tgcatgagtt    660
gaaattatat taaagtttc caaagtaact gaaattagct gtaaaaaata ctctgaagtg    720
tagacacacg agagaatgat tgcccttctg tgaaatatgt cacagagtgt tccagcgggt   780
aatacataat attagagcta aaactgcaaa ctcaaaataa acctaaaaga cttaaat      837

<210> SEQ ID NO 112
<211> LENGTH: 636
<212> TYPE: DNA
```

<213> ORGANISM: Bos taurus

<400> SEQUENCE: 112

```
cagctgctac actttgttta ttgtcaccgt caccctgggg agctccggtt tcttctttct      60
ttttgcgggg aggtaccttc ttgactctgc ctctgtctat gctctgcctc ttgcttctca     120
tcttgtcctt tctctggggc cggggtgct tcctccgtgg tgcccccaaa gtctcagtca      180
ggtggggata agtcctgggg ttggggtggg gcaagcaggc ctggatcccg ccccagggg      240
ctggctcttc ctcagtccta tttccattgc tgtgggtgtc cgtcctctgg cctcatctcc    300
agtcctgtct cagggccgtg cccctcgctt tttccgctcc gtgttctgaa gcttggtcac    360
cagcttcctc tcatgcccac cagggctgtg gcggttggtg ttgatggcgg cttctctctt    420
gctgcgacct ttccggcctc ccactcccgg gtaaaaatga gccaggctgt aaaggtcgta    480
ctcgtctagg acggcatctt catcctctgg gcctgggggc tgcctggacg ggctggctgc    540
tcttgggaag gtggccataa tgtctgtctg tctgtctctc cctctcccgt cttctaaagc    600
tttgtttgtg tttggtttgc tgacacctcc cagttc                              636
```

<210> SEQ ID NO 113
<211> LENGTH: 527
<212> TYPE: DNA
<213> ORGANISM: Bos taurus

<400> SEQUENCE: 113

```
tttttcaaaa taaatgcaaa atttaatgaa aaatgagta caaagtgaat ggaaaggaac      60
aaaaacagtc aatgaatgaa ggaataaatg aattaacaag tgaagcagtt ttagagaagc     120
atgttaacgt aacagactag caagccacac ttccctcggg cctcttatcc agtaacagga    180
gccccactta acagggaacc cacacaaaga catacacaac atatatggag ttggtctgca    240
caagcaaaga ccacctagac tcaggttccc cataattggg gtgaccatac ttcccagttt    300
gcctgagaca atcatggctt atgcttgtcg acttggcgtc attattaaca aaatctcctt     360
tcactctcaa aagtctcagc ttgggcaata aattatatgg tgattctacc ccaaaatcaa    420
cttggttcat gaaagacatg atagtaaatg ccagcgatcc cactgacagc cctaacaatg    480
ccaacagatg atacggagac agaaatgagg gggaagtcag atcctgc                   527
```

<210> SEQ ID NO 114
<211> LENGTH: 269
<212> TYPE: DNA
<213> ORGANISM: Bos taurus

<400> SEQUENCE: 114

```
aactttatct ggaaccagaa aaagttgact gtttatgata ttaattctaa tggatttact      60
ttccttttta taagaattcc aataaaactt attccagatg tagttccttc caattaaata    120
tttgaataaa tcttttggta ctcagaaaaa aaaaaaaaa aaaaaaaaa aaaaaaaaa       180
aaagggggg ggcccttta aaatttccct ggggggggcc aaatttaccc cccccctt       240
tttttggaaa aaggggggccc ttaaggggg                                      269
```

<210> SEQ ID NO 115
<211> LENGTH: 2892
<212> TYPE: DNA
<213> ORGANISM: Bos taurus

<400> SEQUENCE: 115

```
cgcgctcggg tggtttggtg taggctagca gctgtttact cctgaggtct cgggccgccg      60
```

```
ccttcggcac cccggggctt gaatctcccc tcttggaccc aagaacctgg ccccctctct    120
tcccggagct ccgtcttcta gcccccagac tcagactccc cagccctctg tttccaggac    180
cccgccaacc gccaggttcc cgcctcccgg atccaggcgt cccggatctg agccaccagg    240
acctagtctc ttgaagacct ccgccgcccg gacgtcttca acacttccgg agccgaggac    300
cccagggtcc catttcgaga acctcccgta ttcctaaccc ctacggtcaa gaacgccagc    360
gctcccacct cccagctttc agcgccggac acagacagag aacagaggaa ccccagcgcc    420
cagccaaggg actctcaaac atttcagctt ctaagagcca aggaacttga gcgctgtgaa    480
ctcacaactg caaagaattc ttgaaagttc tagcctccgg actctgttaa agttttaagg    540
aacgtcagcg tcctgagaag gaaccccaag cgctcccaac ttgcaggcgc taaaggaacc    600
ccagcggcgt tcatcatggt ggccgatccg cctaagggag accccaaagg gtacgcggcg    660
gcggaaccca ccgccaacgg tgtctcgatg ttggtcccca tagaggacgt aggctcgtta    720
aaaggcggcc gttgcggttc cggggatcag gtgcgtcgct gccttcgcgc caacttgctg    780
gtgctgctga cggtagtggc cgtggtggcc ggcgtggcgc tggggctggg ggtctcggga    840 gccgcggcc cgttcgccct gggccccgcg cgcctggaag ccttctcctt tccgggagag    900
ctgctgctgc gcctgttaaa gatgatcatc ttgccgctgg tggtgtgcag cttgatcggc    960
ggcgccgcca gcctggatcc gagcgcgctc gggcgccttg gcgcctgggc gctgctcttt   1020
ttccttgtca ccacactgct agcgtcggcg ctcggcgtgg gcttggcgct cgcgctgcag   1080
ccgggcgccg ccttcgccgc catcaacacc tcggtcgggg cccggtgga agaggccccc   1140 agcaaggagg tgctcgattc gttcctggat cttgtgagaa atattttccc ctccaacctg   1200
gtatctgcag ccttccgctc atacactacc tcctataagg agagattgtt caacggcact   1260
ctggtgaagg tgcccactgg gggcgaggtt gagggtatga acattctggg cctggtggtg   1320
tttgccatca tctttggtgt ggccctgcgg aagttgggc ccgagggaga gctgctcatt   1380
cgcttcttca actccttcaa tgatgccacc atggtgctgg tctcctggat catgtggtac   1440
gcccctgtgg gaatcttgtt cctggtggcc ggcaagattg tggagatgga gaacgtgggg   1500
ctgctctttg ctagtctcgg caaatacatc ctgtgctgcc tgctcggcca tgccatccat   1560
gggctcctga cactgcccct catctacttt ctcttcgccc gcaagaaccc ctaccgcttc   1620
ctgtggggca tcatgacgcc gctggccacc gccttcggga cctcctccag ctccgccacg   1680
ctgccgctga tgatgaagtg tgtggaggag aagaatggag tggccagaca catcagccgc   1740
ttcattctgc ccatcggtgc cacggtcaac atggacggtg ccgccctctt ccagtgtgtg   1800
gctgcagtgt tcattgcaca gctcaaccac cggtccttgg acttcgtgaa gattatcacc   1860
atcctggtca cggccacagc atccagtgtg ggtgcgcgg gcatcccatc tggagggggtg   1920 ctcactctgg ccatcatcct cgaggcggtc aacctgccgg ttcacgacat ctccttgatc   1980
ttggccgtga ctggctagt ggaccggtcc tgtaccgtcc tcaacgtgga aggtgatgcc   2040
tttggggcgg gactcctcca gagttacctg gatcgcacag agaactgcaa ctccgtgccg   2100
gagctgatcc aggtgaagag tgagatgccc ctggccgcgc tgccggtccc cggcgaggag   2160
gggaaccctc tcctcaaagg ctgccgggga cctgctgggg atgctgacac ctgtgagaag   2220
gaatcagtca tgtgaatccc tgcagagacg ttccctgccc catgggggtg ctctggacat   2280
tggaatcatg ggggatggat gaacggacaa acaaggcctc ttgagggggcc ctggccacac   2340 actcgggagc catgggcctc agcttccctc cctgtcgtca gattcgggaa gcctcgctgc   2400
```

| tggggtgtat gttgcttgtg tgtgaatgag tgtgtgtgtg tgtgtgtgtg tgtgtgtgtg | 2460 |
| tgtgtgtgac tgtttccaaa tctgcccagt cctcaactcc tggcccccac ccaaggctag | 2520 |
| gaaaccatat aagacggaga agtagcatgg cctccacgcc ccatcctggc agcctgcctg | 2580 |
| gccttcctgt ctcagggcat agggaatcat gggaaattct gctctctgag agcaaggatg | 2640 |
| ttctgacagg ttgctggctc cttttctggt tattttagtg gctgtggctg tgtgtgtgtg | 2700 |
| tgcatgtgtg tgtgtgtgtg tgtgttctgt gactctccac ggtacatccc accctgtccc | 2760 |
| cgggccctct gtcccctcca caatacgaaa cactccttgg gaacactgaa gggagactca | 2820 |
| taacacgttg ttgttactct gaggatgttt ataacaataa aactgtcagt ttgtagtcta | 2880 |
| aaaaaaaaaa aa | 2892 |

<210> SEQ ID NO 116
<211> LENGTH: 639
<212> TYPE: DNA
<213> ORGANISM: Bos taurus

<400> SEQUENCE: 116

| tttttgcacg tttcatagtt ttattgagac ttttcggtt ttcattgtct atggtaggta | 60 |
| taattctaat gaccacgatt ataccaaagc tctgctgtta ttatcaacag cagatacaaa | 120 |
| gttggctgcc atgctgtgaa cacacacaca cacactccaa gttgtacact cctgcatgca | 180 |
| aacttatagg aaatgtacat tccttgtaaa acacaattat gcacaattag tctggaatct | 240 |
| gttaagctac cattgatata gataaacctg agaaagcaca aaatgtcaag taacactgtt | 300 |
| tccataccag tcattcaatg gcactattca tcacaaagaa atctagttca attacctata | 360 |
| ttaaaatcac agatattata aaaataaaca ttttgcaaa agcactaaca catactagag | 420 |
| ttcaaattca caatttttga tatgtaatat atattcccct tcatgttaat ttgtaatgat | 480 |
| gtgtataata taatgtacaa cagaattaaa aaaaaaaaa aactgtaaca ggattcagca | 540 |
| gccaaataat atatagatat tatttgtaaaa cttggaatta aagttatcaa atgaacagaa | 600 |
| aaaacattaa aattactagc aatgttgaac ctgctggta | 639 |

<210> SEQ ID NO 117
<211> LENGTH: 786
<212> TYPE: DNA
<213> ORGANISM: Bos taurus

<400> SEQUENCE: 117

| ccttcaagaa ttttaatcac gaactggggg ggggatggg tgttggggag caggtaaaca | 60 |
| gggtccaggc tggatcctag aggacagtgg ctgactccag gccccgctcc tggaagtacc | 120 |
| gatggggag gcggaggcag gtttggggc tttcactgaa gtaggacttg atcttcccag | 180 |
| gtcccttcgg atccccagtc tctgagtcct cccacttcac gtcttccgcc tcactctcca | 240 |
| ggatgctctg ggctgtgcgc cagctgaagc ggacaaactg ggggaagccg aacacagggt | 300 |
| ccacgtgctt cctcaaccag gctttcgtct tgggatcatt agggtagccc gagccataat | 360 |
| cagtgtccag gtcctgcagt ttctccacaa acttccagtt cttcacagcc tggtctcggg | 420 |
| ccaccttggc acagatactg gcagcactga ccacagggta gagggcatct gccttggcct | 480 |
| tgactgtcac ctcaatgcca gggaaacgct gctgcaatcg ttcctggtat gtctctggga | 540 |
| gccccacggt gtccacaaac acctgggcca cgttcacacc ctggtccaac gcaaactgca | 600 |
| ctagcccagt ggctgtatca tgagagaggg cgttcaggtt gtatttcacc cgcccaagca | 660 |
| tgctggtaga gatgaggttt ggagacagca cgtccagtgc ccagcccaca aagtcccgt | 720 |

```
cctcctccat tttcgcaaag agcctgtccc gctcgctctc cgacagggtc tttgagtctg    780
ccactt                                                               786
```

<210> SEQ ID NO 118
<211> LENGTH: 555
<212> TYPE: DNA
<213> ORGANISM: Bos taurus

<400> SEQUENCE: 118

```
cccactatac gaaaaggagc gtacaccttt gttccttggc ttctcagctt taaaagagga     60
agagccctag aagaaaaaga gaataaaatt ttggtcaaag agacaggcta cttctttatc    120
tacggtcagg ttttatacac cgataacacc tttgccatgg gacacctaat acagaggaaa    180
aaagtccatg tctttgggga cgaactgagt ctggtgactt tgtttcgatg tattcaaaac    240
atgcctgaaa cactacccaa taattcctgt tactcagctg gcatcgccaa gctggaggaa    300
ggagatgaac tccaactggc aatacccegg gaagatgcta agatatcccg agatggagat    360
ggcacgtttt tcggagccct gaagcttctg tgacctgctc acaccttgtg tgtggctctt    420 ttcttcccctt ctctgtgcct ctaaagagaa agcacttaac tggaaatacc aaaagggaaa    480
aacaaaatag ttaccatagc cttttctggg agctatttgt tttggtttgc tgcaactcga    540
ccaaaacagg aaatt                                                     555
```

<210> SEQ ID NO 119
<211> LENGTH: 574
<212> TYPE: DNA
<213> ORGANISM: Bos taurus

<400> SEQUENCE: 119

```
tttttcgttt taaaaaatta tctttattta ggttctgatt cagcacatgt atcaaaggct     60
aatcaacata aagaagtaaa taagacatta attggaagtc ttacatctct ctaaattctg    120
accaagaaat gtcaagattg ccactattag cagaactcca acctagtcaa gttgtagacg    180
agctattatg aacgacatac agtgtgcaca gatacgcaga ggccgaagac atgctagcac    240
ttggctctct cctcttcctc gctgatgtct ttcctcggga cggcccactt ttgctttcca    300
tgcctagttc ccaataaagt ccaagaagg ctcagggtca acctgatcca acactctgct    360
ggaggaatgc attcgcaaac tgttgtgcct gcaacttttgt ttttgccagg atgaagttca    420
gatcgagatg tacaatacaa tctagacgac agtgcagact aggtcaagaa ctaaagttga    480
gcagtaaccc cagttaaggc atgaatgcac acacacgc ttgcacacac acatcaccca    540
cactatcatg aacagaagat tccttccatt gcct                                574
```

<210> SEQ ID NO 120
<211> LENGTH: 834
<212> TYPE: DNA
<213> ORGANISM: Bos taurus

<400> SEQUENCE: 120

```
atgggtggat acattttatt tatttttta attaatttat ttattcgtgg ttgttgctac     60
gagtgggctt tttctagttg caagaagtgg gggctactca ctagttgcgg tgcacaggct    120
tctcactgtg gtggcttctc ttgttgcaga gctagggctc taggtgcaca ggtttcagca    180
gttgcagcac tcaggctcag cagttgtggc gcacaggctt agttgctcta tggcatgtgc    240
catcttccca gaccaggaat caaacctgcg tcccttgcat tggtaggatt cttatccact    300
```

| | |
|---|---|
| ggagcacgag ggaagtcctc cctacgccat tgcaatcacc tatttggctt tccagctccc | 360 |
| accctcagca accccagtc ccagtccta tctattttcc atccagtgtc cagaataatt | 420 |
| ctgtctaaac ataatgctgg tcaggttgct ctttcattca agagcctaca ttggatttcc | 480 |
| atttcactca cccacaatct gaggtcccca cgcatccttg cctggctgcc ccttgctcat | 540 |
| ctgctccagc tacactgtcc cctttgtgcg ctgaacatac agacagggtc taaccacact | 600 |
| gttccttctg cctgaaacac tctcccccca gatgtctgcc tcgctgcttc ctcttttcct | 660 |
| gaccaccaca taccataaat ggtgcccat cccatcaacc tccagtccct tcctttgctc | 720 |
| tgctgagtgt ctcttctacc aggacataag ctccaggagg aaagggactt tgtttagttc | 780 |
| atactgtatc cccagcaccg acaacagtgc ctggcacata gttcgttgtt gttc | 834 |

```
<210> SEQ ID NO 121
<211> LENGTH: 622
<212> TYPE: DNA
<213> ORGANISM: Bos taurus

<400> SEQUENCE: 121
```

| | |
|---|---|
| tccagcggcc gcggctcgag ctttgtcctg gctcccaatc ccttccggca gaaagtgcag | 60 |
| ggctgggact cacacttgga tgagcagact tgggacagat ctgtgtcacc ttgtcctgcc | 120 |
| acctccatcc cccaagctcc tattcatccc acagtaccca gctctgggag cccctcccca | 180 |
| gagacttctc tgcttctcaa aatgaagtcc tcgaagagtt ctctgatgac ttggtggtta | 240 |
| ggattccagg ctcccgtggc ctgggttcag tccctggtct aggaactaat atcccataag | 300 |
| ctgggagaca tgaccagtaa aaggaaaga acgctctccc tgtgtgtgcc ccctgctcct | 360 |
| aaaatggtgt ttgatggtgg cttttgttaa ctgagcccct ataagcgta tggtttctac | 420 |
| atgactacaa agaatgttcc cgaatgcttt actggaatga agcttgtgaa aaataacaaa | 480 |
| gagccaaagt ggaaactgtt tgagtgacaa aataaatatc atcacgtgta aaataaatat | 540 |
| ccatgaattc gcaggaatat aaatacatga ctgactaaaa caataaatga agagaggag | 600 |
| aaaaatctcc caggccgaaa aa | 622 |

```
<210> SEQ ID NO 122
<211> LENGTH: 547
<212> TYPE: DNA
<213> ORGANISM: Bos taurus
<220> FEATURE:
<221> NAME/KEY: misc_feature
<222> LOCATION: 24
<223> OTHER INFORMATION: n = A,T,C or G

<400> SEQUENCE: 122
```

| | |
|---|---|
| tattggtgtt ttcttagcgg gagnaccact tcagatgtt gactggctga cttcttggga | 60 |
| ctagcagacc tgcctcttgg tgtgatcccg ttttctgctt tcaagagatt tttcttatca | 120 |
| ccatgcccat gactgttagt gctttctttt tcaggcacag tgtccttaa ttcttctgcc | 180 |
| ttttcacata tctgaactct catcaatgat tcttcagtta ctggcacatg agactcttca | 240 |
| aatatggaag cagagtgcga aggtttcacg taggagcaca gaccggaagg agccaaacct | 300 |
| gaagaaggaa gagaaaaagc ctaggactgt gtaaaaaaat acatcacagc gcagttagca | 360 |
| aagatgtcac cggggacgta tgatttacaa gcagatgatg aaggtgata cagtcagaga | 420 |
| attacagcct ggaaggggac tacaggagat gatgtctgca ctcaacccac aagctctccg | 480 |
| gggaggaagg acgctggagg ggccgaggac cagtgggtgg tactgtacgc cagtgcgctc | 540 |
| agctgga | 547 |

<210> SEQ ID NO 123
<211> LENGTH: 736
<212> TYPE: DNA
<213> ORGANISM: Bos taurus

<400> SEQUENCE: 123

| | | | | | |
|---|---|---|---|---|---|
| cttgactaaa | acatctttat | tcataaatac | agtacattct | ggggttccac | ccgctcacaa | 60 |
| tggcagccgt | atctcatggc | tggcatagct | gatctttggt | ggtgacttaa | ggtcgtagtt | 120 |
| gaggacctct | tctcgagtgc | agggctgtgg | aagcctgtag | aaggctgcat | agcagggtgt | 180 |
| gctgctgagc | ttcctggctc | tccccttgct | gtccactggc | agtcttcaca | gtgtttgggg | 240 |
| agactttccc | aggcggcctc | ttcttttctg | tgttgtggga | cactaaagtc | caataggtaa | 300 |
| gatagttggg | attcctgggc | aggaaagtaa | tgaagagttt | actggagctg | ttctgctaaa | 360 |
| tttgttttta | gccagtattt | taaaattctc | atttgtaaat | tatagttatg | aaaagcaact | 420 |
| ccacataaaa | ccaagcctgt | ttattttaa | aatacaatga | agggacacta | tcattgtact | 480 |
| tactaagttt | gattttaccc | tttggtttct | agcaaaattg | aaggcataga | aaatctgcac | 540 |
| aatctacaaa | agctgaacct | tgcaggaaat | gaaattgagc | atattccagc | gtggttaggg | 600 |
| aagaagttaa | aatgtttgcg | agtcctcaat | ctgaaagcca | acaagatatc | atcagtaagt | 660 |
| tgttcaaagt | agcaagaata | tttacatttt | ttggacttgt | tgaggtaaaa | agattaaaat | 720 |
| ctaagtgttt | tttttt | | | | | 736 |

<210> SEQ ID NO 124
<211> LENGTH: 679
<212> TYPE: DNA
<213> ORGANISM: Bos taurus

<400> SEQUENCE: 124

| | | | | | |
|---|---|---|---|---|---|
| cttttttttt | tttttttttt | tttttttttt | tttgatttcc | atgagatcgt | gattttattt | 60 |
| gtttgattt | tatgtgtcct | agatccagga | aagtgagtcc | cttattctcc | ttttgtcata | 120 |
| aaaccaaaca | gccctagtgt | caagggagag | gcactgtgct | ctgaagtaaa | attgttcaca | 180 |
| accttttcacc | ctcaacccgg | agctgcagat | ttttgtgaaa | atcagcttct | gggccactta | 240 |
| agtcttgata | aagttgtaaa | tggtctcttc | ttacctgagc | taccatctcc | catctggcca | 300 |
| tagtcacaat | agaagcagga | attcaatagg | cagatttctt | tccttattca | acttccaggt | 360 |
| actccaggaa | gaaggggagt | tcccagcacc | tgcctgccaa | gctctgctct | acttgaactt | 420 |
| tgatcagcat | aaacaggtca | tcctgactac | aagttccccc | aaattctcct | tacttgggtt | 480 |
| tttttatttt | tatttttttt | aattttattt | tattttaaa | ctttataata | ttgtattggt | 540 |
| tctgccatat | cttacttgtg | tttttaaggc | acaactcccc | agcgtacggc | tctctgttta | 600 |
| caatgaatta | ttttaattat | tctaactact | caaaagaaac | ttccaccact | cccagtcaac | 660 |
| cactgaactc | cacatgctg | | | | | 679 |

<210> SEQ ID NO 125
<211> LENGTH: 2997
<212> TYPE: DNA
<213> ORGANISM: Bos taurus

<400> SEQUENCE: 125

| | | | | | |
|---|---|---|---|---|---|
| ccaggcagga | gtactggagt | ggggtgccat | cgcatctgcc | tagacttgat | taaccaaact | 60 |
| cttggatcct | cggtcttttt | cctctttcac | cttttgctca | gccgcatttt | cagagacacc | 120 |

-continued

```
gagcgcacgc cccactgggg agccgcaact ccggacaacg ccctggcaaa agccccgccc    180
cgaaccctgg agttcctccg gggagagtga gggtcccggg cgctgcgctg ggctcgggcc    240
agggagagtc gggccgggag gatctccagg ttccaggatt cccagcagca aaagcagttc    300
attgcatctt ccatccgcct gtccgtggga ccgcggatac acttgaactt tgcgttccca    360
gggtctgggg ggcatctcca tggactgcga tgcaaagcag acaaccacgg gcactgcttc    420
cccggtcccc aggaactgtc tatcttgacc atgcaggaac acattgttc ccccagagcc     480
agattacaag cttcatgaaa gatctcatgg aaaacgttta tggtaaccct cacagccaga    540
acatcagcag caagctcacc catgacacgg tggaacaggt gcgcttcagg atcctggcgc    600
acttccacac ctccccggag gactatacgg tgattttcac ctccgggagc acggctgctc    660
ttaagctggt ggcagaggct ttcccgtggg tgtccccagg cccggagggc agcggcagct    720
gcttctgtta cctcaccgac agccacacgt ccgtggtggg catgaggaag atcaccgcgg    780
ccatgaacgt ctcttccatc cccgtcaggc cagaggacat gtggtcggcc gagagacagg    840
acgcggctgc ggccggggac cccgccgccc agcctccgca tctcttctgc tacccggccc    900
agagtaactt ttccggaacc agatacccgc tgtcctggat aggcgaggtc aagtccgggc    960
ggaggcgccc tgcgagccgg cctgggaagt ggttcgtgct gctggacgcg gccgccttcg   1020
tgggcacctc gcctctggac ctgtcggttc accaggccga cttttgtcccc atctccttct  1080
ataagatctt tggcttcccc actggcctgg gcgctctgct ggtgaataac cgtttggctg   1140
ctctgctgag gaaaacctac ttcggaggag gcacggccgc tgcgtacctc gcgggagacg   1200
acttctacgt cccgagagag tcggtggctg agaggtttga agatggcacc atctcctttc   1260
ttgacgtgat agcactaaaa catggatttg atgccctaga gcgcctcaca ggtgggatgg   1320
agagcatccg gcagcacacg tttaccctgg ctcagtacac ctacactgcc ttgtcttccc   1380
tgcggtaccc caacggagcc cctgtggtgc agatttatag tgactctgac ttcagcagcc   1440
cagaggtgca gggtccggtc atcagcttca acgtgctcga tgaccatggg aacgtcgttg   1500
gttactccca ggtggataaa atggccagcc ttcacaacat ccatgtgcga accggctgct   1560
tctgtaacac tggggcctgc cagaggcacc tggggataag tgatgagatg gtgaagaagc   1620
atcttcaggc tggtcatgtc tgcggagacg atgtggacct catagacggg cagccgacgg   1680
gctctgtgag gatttctttt ggatacatgt ctacgcttga ggatgcccag gccttcctca   1740
ggttcatcat agcaacccga ctgcactcgt ctcatggcca gcctctccct ctggccaccc   1800
cgggggaggc tggagcccca ccagaagaca gcgaggctca gaacgccatg cctgccgccc   1860
gcgccagagg tagctcctca cctcaggaag acacttcccc acactccggg gtttggaaca   1920
actcacccac cgctgtggac gcagagggtc tgtgtccgcc cctgctggag gccactggaa   1980
cccagcagac cacttcagag aaagctgctg atgtcccaga tggggacctc aggtcacacg   2040
tcatcaccaa ccttttcctc tacccaatca gtcctgtgc agcatttgag gtgatcaggt    2100
ggcctctagg aagtcaaggg ctgctgtatg accgaagctg gatggttgtg aatcacaacg   2160
gcatttgcct gagtcagaaa caggagcccc ggctctgcct gatccagccc ttcattgacc   2220
tgcagcggag gatcatggtc atcaaagccc aagggatgga gcctatagag gtgcctcttg   2280
aggagaacag tgagcaggtt cagatttgcc aaagcaaagt ctgtgcggac agggtaaaca   2340
catatgattg tggagaaaaa atttccaact ggctgtcaaa gttttttggc cgtccctatc   2400
atttgatcaa acaaagttca gactttcaaa gaaatgcaaa gagaaacat ggcaaagatc     2460
agtctgctca cacgacagcc acccttttctc tggtgaatga ggcacagtat ctgctgataa   2520
```

```
acagatccag tatttggaa cttcagcagc aattaagcac aagctgtgag aatggcaaag    2580
aagaattatt cccaatgaac aatctcatct cacggttccg tgccaatatt attaccaatg    2640
gaacaagggc ttttgaagaa gagaaatggg atgaaatttc aattggttcc ttgcgtttcc    2700
aggttttggg accttgtcac agatgtcaga tgatttgcat cgatcagcaa actggacaac    2760
gaaaccaaga tgttttccaa aagctttctg agaggcgaga gagaaaggtg aagtttggag    2820
tgtacctgat gcatacgtct ttggatttat cttctccatg ttacctctcc gtaggatctc    2880
aggtgctccc tctgctgaaa gaaaacatgg aacaccacga tataccggct accgagtaat    2940
gtcaggatgc tagctcctga atttttttca gtatctatta aaatttctgt tttaccc       2997
```

<210> SEQ ID NO 126
<211> LENGTH: 255
<212> TYPE: DNA
<213> ORGANISM: Bos taurus
<220> FEATURE:
<221> NAME/KEY: misc_feature
<222> LOCATION: 227
<223> OTHER INFORMATION: n = A,T,C or G

<400> SEQUENCE: 126

```
ggtttaaaat aatggctcca ttatttttgt ccttaaacat agttttatg ggaaaattat       60 attttgtgat aatctttccc tcagtttaga gatcagacag aaggtgattg ttagtggtta      120
agggcataaa ggattgtgag acgaattttc aaattcgtag aacatgcat tgactgtaca      180 ctttgtagtg cccatcaaaa caataaaaga catttaaat gccgaanaaa aaaaaaaaa      240 aaaaaaaaaa aaaaa                                                      255
```

<210> SEQ ID NO 127
<211> LENGTH: 642
<212> TYPE: DNA
<213> ORGANISM: Bos taurus

<400> SEQUENCE: 127

```
tttttgcaa tgtcctcctt ttattaaatt ataaaactgg ctgtcaatgt acacattttg       60
gaaatgcatt tttctgcttt gtggagcaca tgattttaaa cagacaaaat atttctatat      120
taacttccca gtcttcgagc tatttgcacg ggtagccaaa ctaccaagta tagacattat      180
aatatacagt cagaatttat ggaaatatt acaaagacaa atgccttaaa aagatgatag      240
tgcagagaaa accatagctc tgaaacaggt ataaaattt agtcaaaata ttttagtcca      300
ttatggcttt gcataaagct tcaaggaag aaaattgaag acactactca tcaaaggcac      360
ttaaagaaat gtaataaaat acttctttga gtttagtttg agtccgacag tattttttat      420 ttatctttttt cacattctgt ctctcactga aacagtcctg gaaggcagct attaataagg     480
aaaaatagtt atcatttctt aatatacatg ttaaaaatac gcaaacagaa ttaatacaga     540
ttttggtcca tggaagcagg taacagtatc agactgtagt attttctctta attctgagcc     600 caaagccctc aattccccag acgcagtccc ctgggctccc ca                        642
```

<210> SEQ ID NO 128
<211> LENGTH: 732
<212> TYPE: DNA
<213> ORGANISM: Bos taurus

<400> SEQUENCE: 128

```
tttttttcgc ggttaattat gtatttatta aaatctacac attgttaatt ttatgtattt       60
```

```
taatacggca ataatactga aagaaatac acaaactgtt aatagagtta gcttggctaa      120
tggaaggaaa gtttcaattc aactcatttt aaacttttct gtagtaagca caaattctgt      180
gtacttttat ccacttaact ttcataacca gaaaaaaga aaagtttaaa atagttgaga      240
tatttgtgcc caaatttagt acttaccaaa cttctgtgct gtatttggtc tgaggcacct      300
gccctccgac ctccaagaca gagccttgaa catagttatg ccaccagttg tacatagcag      360
catgaaataa acatgagtta tttggtgtgt gtgtatatat acacacatat atatatgtgt      420
atatatgtat atatttctat tttcccagct ttaatatgag aggagttgct ccagtttacg      480
gagggaaatg cctacaccct agtggccctg attggagcag gactgtgagg tccaacacag      540
taactaacca accctcccag tctcaatccc gtgagtgctg ccagacagag ctggccagtg      600
tggcaatgga aagttagca gtcacattcc agggttcttc cctcaggaac tttgaaagga      660
aacatggcga gattggtttt gatgttttcc cttcacttga atcaaagtca ctgagtatac      720
agacaatgag at                                                         732

<210> SEQ ID NO 129
<211> LENGTH: 572
<212> TYPE: DNA
<213> ORGANISM: Bos taurus

<400> SEQUENCE: 129
tttttcctta atatttcatt ttattgcttt gcatttaaaa tctattaaaa tattcattta       60
tctaaaaatc ggaaactatt ctgatagtat tgattagaat cctactgacg tagatttgaa      120
acacaacata ggtttgaatg aaagtaaat ctactcagat ttttatttta aaaaaatcta      180
tttcttttga gccatttgtt ttttgctggt ctgtttgaat cagtctggag acagtagcaa      240
atgtcatgtt tacacttctt gaaagaaagt gttttgttct gctgttgaat agaggtctcc      300
tgccttcttt agagaggctg gcgtccatcc ttcagttttg ctgagtcttg agaatggcct      360
gcagttccgc acagagcgcc tgactctttta catttagccc ctcccagggc tgaaagggtt      420
ttcccttgtg gtccacgaag gtttcccagc agtgcttaaa gtcctcaaag gtcatgatgg      480
tgattcgggc cccagccgct tgcagttcgc acaggccact ctgatggcac ccaaaatggt      540
tgcgggtata gatgcgggag gcaaggatgt gc                                   572

<210> SEQ ID NO 130
<211> LENGTH: 523
<212> TYPE: DNA
<213> ORGANISM: Bos taurus

<400> SEQUENCE: 130
gataggaata taggttttaa tcattgtgct gctgctgtta accagagtgc aacgaatcca       60
cccttcatgg atgtggatgc cacagtgtaa atgagcaagt tcacacagc ccatcggtga      120 caaagggcca ggcctctgga ggggagggt gcccgcagga aaacggggt gaggaaaagg      180 gtagggagca gatcctgggc tggcagtctg cccttccac attgttacat tcccaccagg      240
accccaagca ggaccggtcc tttccggcca gggtggccaa cctgggccag ccccgtgaa      300 ccggacttcc ctcccaagcc agccgcctcc agccccaggg ccattcttgc tgagcagatg      360
aggtttgggg caggcccaca gccggccacc agcgggaag agatggagct caagggaggc      420
aagagggctt ggagacagcc cttgtctgtt cttcatccca ggagaccctc agcgggtgc      480 agagccaggg agaggacagc attgagcacc catcccctgg gtc                      523
```

<210> SEQ ID NO 131
<211> LENGTH: 575
<212> TYPE: DNA
<213> ORGANISM: Bos taurus

<400> SEQUENCE: 131

```
gaggttttt cagtacaatt tattcttctt acattttaat ttacatttat taaatacctt      60
agaaatatta cactcaaagt taatagactt ccagacagag accattaact aagaaggagc    120
agtctcacta agtcaacttc cctagttagt ttgctggcct cctcactatt cacatgctct    180
ctggtgctta ttactatgca actgtcttca agatgtggtt gaagcttgaa tctacatctg    240
gcatcaggcc aagtctgtta atccatgaat atcggccatc aactgcattt agggtacagc    300
ctgcagaagg ctctttcttg acagtcaatg atgatgaatg tggaaagact ggatattctc    360
ttgggagaag aaaatatacc ccaccttaag tgacagctac agtttcctaa cagaaaaaac    420
aattaggaaa gggaaaagat caatgataag aataaggaaa atactctgag aatagagtaa    480
gtacatatac ataatggagt aaataggctg ctcctgagtc catatgctta cttttatttt    540
taaaagtctg ataaaaattt actcaattac atttt                              575
```

<210> SEQ ID NO 132
<211> LENGTH: 782
<212> TYPE: DNA
<213> ORGANISM: Bos taurus

<400> SEQUENCE: 132

```
gctacggatt ccctggccgt ttaatggtta aaactccgtg cttccactgg aaaaggattg     60
ctcaatcact caaccatatt ttggactctg cgaccccatg gactgcagcc tgccaggctc    120
ctctgtccat gggattctct ggggaaaaat actggagtgg gctgccattt cctcctccag    180
ggaatcttcc tgactcaggg gtaaacaaat ctcctgcgtc tcctcgaacg aagaccacct    240
gctcggcttg gccggtgccc acggcattgg tgacggtgca aatgaaggtg gtgttgaaca    300
gccggtccac tgagtggacc atcagcttgg ggccctgggc cactgctgag gctgggaaaa    360
caccggaagt cgtgctccaa tcgtaacccg tgggctctgg tttgctgcgg acgttacagt    420
tcagggtggc ctcactacgg ccgatgtacc agttgtcatc ataaccggat atggaaacct    480
ggggggggta gcgcacaaag agaatcactg gcagcagttt gggctcctgg aaactctcat    540
gttccacttt gcaaatgacc ttgacaccgt ctgcttcgct caagggtgtc acaatgtaac    600
ggctagtgac ggtgaccgtg ccaagcaggg gccccgaccc ctgggtctct ttggcctccc    660
cgtccaaggg tgaaagccag gaaacccggg caggtggtcg gccacccgcg gagacacagc    720
gggccacggg tacaggatcc aaattgaatg tgacctcctg tttctcggca tggttctggg    780
gc                                                                  782
```

<210> SEQ ID NO 133
<211> LENGTH: 667
<212> TYPE: DNA
<213> ORGANISM: Bos taurus

<400> SEQUENCE: 133

```
tttttgcatt tttaatatta ttcctttact caaacagttt ttcaggtttc tcacatttgg     60
ccagggtttg taaatacaga ggatgctcat cacttggaag tcacactgaa actaacaaat    120
ttggatcgtc acagaggaat atagattctc aggttgtcag ctagcagtgg aaacaactct    180
ggttcccatc agcttttctg tgaggagggc ttctataaaa tattctataa aatagaaact    240
```

```
ctaataattt acagactttt acctctttac ccaagttctt cctggaaaca ttcatgatca      300
gtgattttga gtctgaaagc tgccacagtt tatttatttt ttaaaaataa cttttgatgg      360
ggtttgtgaa tatctttaag taatttttt tttttttta agtgtgagat gaagcaggat       420
ttgtggttta agtagtatc ttatttgggg caggatttca attttagttt tccagatttt      480
tcttaaaagt gagttttct ttttaaaaag gggcatcctt gaactctctt aagttctatg      540
cagaaatttt aagtttatgt gcatttttct ggggagaagg ttcaatttct tcaggacccg      600
tagcaattta aaatatactg ctttagacta cagagattat aaataagaat ctatcgatttt    660 acagtta                                                                667
```

<210> SEQ ID NO 134
<211> LENGTH: 651
<212> TYPE: DNA
<213> ORGANISM: Bos taurus

<400> SEQUENCE: 134

```
gaatgacatg tgtttatttg tgtgaatctg ccagtgatgg aattccaaac agtgaagaaa       60
cggcaagaaa acccaagtgc caaaaggctt tttaaaaact tcttttctat tataggttat      120
tacaagacgt tgaatatagt tccctgagct atatagaagt tccttattgt ttatctatta     180
atatttttca catagcagtg tctgctgtta atcccacatt cctaatttac cccttcccca     240
cgctttctct ttttgtaacc gtaaacttgt tttcttatgt ctgtgtctgt tttgtaaaca    300
agttccactt tatcatttcc tcctaggttc cacatacaag tgatatcaga tgatgtctgt    360 cttctccgc cagccttact ctactcacta tgctaatctc caggtccatc caggttgttg     420
caaacggcat tatttcattc ctttctacgg ctaagtaata ttccattgta tataggtacc    480
gcatcttctt tatccattcg tctgttggtg gacatttagc ttgcttccat gtcttggctg    540
ttgtaaacag tgctgctatt ggggtgcgtg tatcttttcg aattaaagct ttcatctttt    600
ctgggtatgt gcccgggagt gggactgctg gatcatatgg taactctatt t              651
```

<210> SEQ ID NO 135
<211> LENGTH: 702
<212> TYPE: DNA
<213> ORGANISM: Bos taurus

<400> SEQUENCE: 135

```
tttttcaata aagaaggat tattgcttct gtggtgacat ggaatcaggg tcactagaga       60
ttaagtaatt gggtggaata ccgtagcaat tccatggtat gcaactaatg agaagagaaa    120
gaaatatcac atagtcaggg caagaactct gaggtacatg tgaactctga ggtgatacag     180
catccgattt cccagagaag aggtgagcag aggagggcag aaggagaaaa ggtacatgat    240
gaacttggcc agaaaatagt tccaggtcat ctaatatgtc catttttctg ttcttgtaga    300
tggacagtgc accttcctac tggagtgtga ctcacaaggg ccttggtgt ctggaggctc     360 cacctgagcg cagacctcgg atgatgagga cagtgcccac cacgatgccc acgatgccca    420
cagtcaaccc cagggcacag accacagtct ctgtcagctc tgacataggg gctggaatct    480
caagctccca gtgtttcaga agtggctcat ccaggcccca gtgctccact ttgcagtcgt   540
aaacatcatc atcagaaggg aggaaggtaa gataaccaat cttgaggaag gaataatcac     600
ttttggggag gaagctggtc tcaaaaacac cctctgtgac tgcatgccca ttcctcaacc    660
atgtgatgtt gatcacaggg ggaaaatgt tgtccacgtg gc                         702
```

```
<210> SEQ ID NO 136
<211> LENGTH: 1343
<212> TYPE: DNA
<213> ORGANISM: Bos taurus

<400> SEQUENCE: 136
gaattcaata tgcgggtcgt ggggccgaga accctcctcc tgctgctgcc gggtgcgctg      60
atcctcactg agacccgggc ggggtcccac tccctgaggt atttctacac cgccgtgtcc     120
cggcccggcc tcggggagcc ccgcttcatc tccgtcggct acgtggacga cacgcagttc     180
gtgcggttcg acagcgacgc cccggatccg aggatagagc ctacagcgcg gtgggtggag     240
caggaggggc ccgagtactg gcatcaggag acgcagagaa ctaaggacac cgcacaattt     300
ttccgagtgt acctgaacac cctgcgcggc tactacaacc agagcgaggc cgggtctcac     360
acagtccaag agatgtacgg ctgcgacgtg gggccggacg ggcttctccg cgggtatgat     420
cagttcgcct acgacggcag agattacatc gccctgaacg aggacctgcg ttcctggacc     480
gcggcggaca cggcggctca agtcaccaag cacaatgctg aggcggcagg tgatgccgcg     540
cgtgtgagga tctacctgga gggcaagtgt gtggagtggc tccgcagata cctggtgacc     600
gggaaggaca cgctgctgcg cgcagaccct ccaaagacac atgtggccca tcaccccatc     660
tctgaccatg aggtcacctt gaggtgctgg gccctgggct ctatcccga tgagatctca     720 ctgacctggc agcgtgacgg ggaggaccag actcaggaca tggagcttgt ggagaccagg     780
ccttcagggg atggaacctt ccagaagtgg gcggccctgg tggtgccttc tggagaggag     840
cagagataca cgtgccatgt gcagcacgag gggcttcagg agcccctcac cctgagatgg     900
gaacctcctc agccctccat ccccatcatg gcatcattg ttggcctggt tctcctcatg     960
gtcactggag ctgtggtgac tggagctatg atttggagga agaagcactc aggtgaaaaa    1020
ggaaggggct acacccagac tgcaagcagt tacagtgacc agggctctga tgtgtctctc    1080
atggttccta agtgtgaga cagctgtctt ttggggactg agtgatgctt ggtcccactt    1140
tgtgacgtca gatctccaga cctgcagctg catctgaatg tgcctgtgct cctattagcg    1200
taacgtgaag aggtggggag actgcccacc gctcccccte cccaccctga cctgtgttct    1260
cttccctcat gcacactcct gttccagcag agacagagct ggaccctctc catcactgtc    1320
tttgcttcat atgcactgag taa                                            1343

<210> SEQ ID NO 137
<211> LENGTH: 637
<212> TYPE: DNA
<213> ORGANISM: Bos taurus

<400> SEQUENCE: 137
tttttataag aataaaatac aatttattaa agaatattgt acacatagat atggaacatc      60
tttttatcaa gaatttcaac accatagcaa tactaaattg tgttttaatt tcatgtataa     120
aagatgtgct gaaagatgca tgcctcaaca gttttatgt tattgaatat ggctgggggt     180
gacatccttc tatataaaaa caaactgcac agcatcacat aaagaataca acatcttaa     240 gttcattcat acagtcattt ctctaaactc cttaaggaga aatttaaatc tttgctcaac     300
tctaaaattc aacaaaatgc tcgagtttct caggaaataa aaaataacca atttgttttc     360
tgaccactaa ctacccattt cttaatatat atctctgacc caaattaagt cctttgctaa     420
aggaacaacc tacatcagct tcagtctaaa catagttttc tagagggttt tcaagtatct     480
taaaagattt accacttatg gtaaaaaaaa aaaaaaaaac tattatataa atagaacaca     540
```

```
tacattcgcc tcagtaattt ctagaatgtg tattgtccca gcattaagca atggtggaaa      600
taatatgcct ttaaaatcct acagattaaa aggcaaa                              637
```

<210> SEQ ID NO 138
<211> LENGTH: 671
<212> TYPE: DNA
<213> ORGANISM: Bos taurus
<220> FEATURE:
<221> NAME/KEY: misc_feature
<222> LOCATION: 223, 567, 634, 637, 645
<223> OTHER INFORMATION: n = A,T,C or G

<400> SEQUENCE: 138

```
cccatctgct ggaaggtgga caaagaggcc aggatggagc caccaatcca gacagagtac       60
ttgcgctcgg gaggggcgat gatcttgatc ttcatggtgc tgggggccag ggccgtgatc      120
tccttctgca tgcggtcagc aatgccgggg tacataggtg gtaccccgg agaggacgtt      180 gttagcatag aggtccttcc tgatatcaat atcacacttc atngatgctg ttgtacgtgg      240
tctcgtggat gccagcagac tccatcccga tgaacgaggg ctggaacagg gtctcagggc      300
agcggaaacg ctcattcccg atggtgatca cctgcccatc aggcagctca tagctcttct      360
cgagggagga ggaggatgcg gcagtggcca tctcattctc aaagtccagg gctacgtagc      420
acagtttctc cttgatgtcc cggacaatct cacgctcagc ggtggtcacg aaggaatagc      480
ctcgctcggt caggatcttc atgaggtagt cggtgagatc tcggccagcc aggtccagac      540
gcatgatggc gtggggcaag ggcgtanccc tcatagatgg gcacgttgtg ggtgacacca      600
tcttcagagt ccagcacaat gccagttgtg cctncanagg cgtanaggga cagcaccccc      660
tgaatagccc a                                                           671
```

<210> SEQ ID NO 139
<211> LENGTH: 772
<212> TYPE: DNA
<213> ORGANISM: Bos taurus

<400> SEQUENCE: 139

```
acactttgct ctttattttc agtctcaagt cagctaaagg cacacaaagc agaggacagg       60
aggcggccca gcttcaagtg aagtgcaggt ggagtgggga tccaaagcag ctggtttctt      120
aggcataagt ggtgacatac tggggcccca tgttcccaaa gtaggaacgt tcccactcac      180
tcatgagctc gaagtgtaca ggacggcggc agaaattgca ggcagctata gatatatcct      240 ggaggggggag tcccacctca gtccaggctt ctagcagctt ctccacaaag tcttccatca      300
tctgagggct gtggtggggg gagggtgcca agcgcagcag ctcctcaccc cggggggacag      360 ttgggtagtt gatggcctgc acatagatgc catacttgga gagcaggaga tcacagatcc      420
tggtgttcag cattgcatca cccacccgaa tggggatgat gtggctgggg catggaatga      480
caggaaggcc cctgtccatt agtagctgac gcatgtgctt gacattgcgt tggtgggccc      540
tcctcagggc ttggccctcc tctccttttga gcagtcgcac ggattccaga gccccagaga      600
gcaccatggg aggcagtgaa gtggtgaaga tgaagccagc agcataggaa cgtaccatgt      660
ccaccaagtc acgggtgctg gcaatgtagc cacccacaca gccaaaggct ttgccaagag      720
ttccagagat gatgtcaatc ttgtgcataa ttccatcacg ctccccaatc cc              772
```

<210> SEQ ID NO 140
<211> LENGTH: 517
<212> TYPE: DNA
<213> ORGANISM: Bos taurus

<400> SEQUENCE: 140

```
attgacattt gctgggagtt acagtgatag tttcatctca gcggttcaat ttcccccccc      60
agtcactgct agttttttctt tgactattac agttgccagg aagatccctg cttttcttat    120
tttaaaacca ggatttaagt ggcaagttgg atacagtggg atgggactag atttctcaaa    180
tctttacagt tgtaataaat tgaaggatta aaaaacctgt gttcatatag ccacatatat    240
agcacagttt tcaattctca aatcctagga gttggagcat gtgataccat cgaacatggc    300
ctattttgct taggttactg tatcagttgg agggaatatt tataaacaga tagtaaaaga    360
gaatagaaat agcctactag ttaactttaa ttataattat ttgtaaaaag cacacaatt     420
acaatgttca tggtcatttt aattgcttaa agcctttctc cttctgtact aaatggaaaa    480
gttctcaacc aaaaaaaaaa aaaaaaaaaa aaaaggg                              517
```

<210> SEQ ID NO 141
<211> LENGTH: 837
<212> TYPE: DNA
<213> ORGANISM: Bos taurus

<400> SEQUENCE: 141

```
cccaaacaaa atgaaacact tatttattca aatcagagaa taaaatgaca gtaaagttgc      60
aaccttggga tcaaataaaa cttatcccaa ctgtatgcac acggcagaca tgatttatca    120
aatctctaca ggatgataac ctgtttcaca caaataacac atagtataat taacatacac    180
aaaaacaaac tttgaatttg cttgaaaata atagatgtgc aggactgtga agaattcaac    240
aattactttg taataaactt ctgaacagta ttacctactg tttcaattta gtttgcattt    300
gaaattgact cttcaaatga atgggcttc cctgatggct caatgagtaa agaacccgcc    360
tgcaaggcag gagacacagg aaacgtgggt ttaatccctg gatcgggaag atccgctggt    420
ggaggaaatg gcaacccgct ccagtattct tgcctggaaa acatggacag aggagcctgg    480
caggctacag tccatggggt cacaaagagt tggacacgag tgagcatgca cattgacttc    540
agagggaata caatagcaga acacaccaac tttgtcagca atttaattgc ctaagcctga    600
gctaggagaa aggccccaat tccctccatc atggtggctt cttgagctag gagaaatcac    660
catggttttct gagcctatcc aactcttttta tgttattaaa gtctttggaa cttaaaacta    720
tatacttact taccattata gttcaacaat cgttatgca agggtcaaaa aatttttgat     780
ttactttttct agcttgttt ctatcatata cttttggtca aatttgtttg aatcatt       837
```

<210> SEQ ID NO 142
<211> LENGTH: 666
<212> TYPE: DNA
<213> ORGANISM: Bos taurus

<400> SEQUENCE: 142

```
tttttcatca ttttctttt atttcttaag tatacaaatg tttaattcta tgacttttgg      60
tgtgtttaca aagcaaaaca caggacacag ggtggcagtg ttgactcact tgaaacaaac    120
aaaaaaaaaa cccacggaaa gccatcctta ttaccaactt gcatgaaaat gcaaacattc    180
tggtgaacac actcactata acatacagaa ataacaaaaa cgagctagtt agagattaca    240
accttatcat agaacaaact gacacatcac aggagtaaat ataggggcaag accaaagtcc    300
ataggtctac tacagacaga caaaaagtaa ggccccctagt ccacctcctc aatggtgggg    360
ccagacccag agccccettt agggccctga gcccccaaagc cgccagcccc ggggccgccc    420
```

```
gcccctggt acagtctgct gatgatgggg ttacacacct gctccagctc cttcctcttg    480
tgctcaaact cgtccttctc agccaaggtg ttggcgtcca gccaagaaat cacctcctgg    540
cacttgtcca gcaccttctt cttgtccgcc tcgctgatct tgcccttcag ccctcatcc    600 tccacggcgc tcttcatgtt gaaggcgtac gactccagcg cgttcttggc agacaccctc    660
tcgcgc                                                                666
```

<210> SEQ ID NO 143
<211> LENGTH: 724
<212> TYPE: DNA
<213> ORGANISM: Bos taurus

<400> SEQUENCE: 143

```
tttttacgca ttaaaaaaat tttattgggg tatagttgat ttacaatgtg ttagtttcaa     60
gtatacagta aactgaatca gttatacata cactttggga tcctcttctc ttatagacta    120
ttacggagca ctgaatttcc tatgctatac aggtctttat tagttatcta ttttatactt    180
agtggtgtgt atgtatcaat tccaatcttc caatttatcc tgccccaaat ctttaccact    240
tctaggcata cagttcagtg gtaataacta tgttcataac actgagcaat tatcaccacc    300
atccatcccc atgagctctt tcaccttgta aaagtgaaac aatacccatt acatacttct    360
tcacttcctc attcccagct cctgacaacc accaggatta ttcttcttct aagaatatac    420
ccagacaacc tatgttttca ccaatttatc aaaaagaaaa ctcaataatt gtgttaatag    480
tataattaaa acctcaaata ttaaaaatat tatggtactc catctagaaa tcctcaacat    540
tggtgtcaat atatgacaaa cctaatttta gttttttgta atgtagctgg aaagaagtac    600
atacagctag atgtcaactg atgctcattc actttcacat ccctaaacct ttctgtaccc    660
tcttgttttt gctcaaaccc acctattttt atttgcttta aatattttta ttgcaatctt    720
tcta                                                                  724
```

<210> SEQ ID NO 144
<211> LENGTH: 499
<212> TYPE: DNA
<213> ORGANISM: Bos taurus

<400> SEQUENCE: 144

```
gctggcaact gaggaaaagg cctccaagtc agcaggagca aacacgctta ggaatttatt     60
tcggaacctt tgaaagactc ctctgcttac cccatctggg atccactgca ggaataccga    120
aaaggaaaac ttcatttaaa aggtgtaaga agtaagtgag attgaactgg gaatgtttaa    180
gtctcagaaa ctttgcactg aaaagcaaaa tgtgattgct aacttcagct taaacattct    240
gcagcataaa gaaactttca ttttggaata ttcatcttga ccacggaaac agaagtttac    300
aggatgagga gttttactct gtgtcagaac acagttttta tttaaacttt ataatccaat    360
ggattggctt cattgtgttt ttaatacgaa gccctgggat cacagatttt ctggaaactc    420
gaaaatgaac atttttcttt gttgaagaat caagtggaaa ctttatagca acaaacttca    480
tgtttctttt ggaagaaaa                                                  499
```

<210> SEQ ID NO 145
<211> LENGTH: 833
<212> TYPE: DNA
<213> ORGANISM: Bos taurus

<400> SEQUENCE: 145

```
agattacaaa tgaatatttta ttaaaatgaa agtatattgt agtagtttaa aattagaaaa     60
```

-continued

```
ctttaaaata gaattaagaa ccaggaatta agataatggg agctcctgaa ggcaaatgga    120
attaatcaag tacagttttc ctcttgattt gatctcatcc acatatgcaa aaatttctct    180
acaaaaattt tgtgaaatat tgaatgattt agggctatga ctccttttga agttttttgcc    240 cttttcacaaa taaaaacttt taaaagatca tagtaggtat ttaaatactt gttgactgct    300
gtaagatttc atttgctagg aaggttgagt tcaagctcat ctaaaaagtc tttgagaaat    360 aaaatgctgta ttcaaggtgc attatatttc aatgtacaca ccctgatttg atagacacta    420
gctacaagct tccatatttc catcctttaa atcagtgcaa gaaaggaaat ctaggctttt    480
cagtttagct tctgcattat cagtaaactc cctggaggct ttctgtagcg gaagacgggg    540
tgggcccatt ggaatcccgg agacaagggt catgatggct ttggtctgcg acactccaaa    600
acctagtttg accacaaagt tgataaatct ctgaatacaa aactgatggt tcagagctga    660
agagaagtcc tttcgttcaa aagcctccaa catctgcttt gtctttttc ccaggtagtt    720 ataggtactg cccaccgctc cagttgctcc catcaccaga gcacttaaca gttgctcatc    780
caccccaaaa aggaaagcaa actgtcgctg gcgattctga tccacacact gcc          833
```

<210> SEQ ID NO 146
<211> LENGTH: 817
<212> TYPE: DNA
<213> ORGANISM: Bos taurus

<400> SEQUENCE: 146

```
aatatgaacg tgtttatttt tccaactcgg atattgttct gaagtacact tgtaatctaa     60
ataccccttt ctctccttcc ctttacaaca taccatttca gtctgtttgt ttacagaacg    120
atggccttaa ggaaaaagcc ttattcacat tcccacaaaa gaaataaata aaatacttgt    180
ctctaggatc catttaacta aacttgactt aaatcctggt agaggctccc atctctataa    240
cagacacaaa agaggatgaa tgatctttca ctatcaaaac aaactcctaa atagagctaa    300
agtttattaa attattcaaa tacatttact atgctcctat aatgtgcaaa gtactgttcc    360
aaaatagaca cccttcctta gatgtacagt aggccactaa aataataatt tcaggagctt    420
aagacactgg tacagtcaaa atacccctaat gatatgaaat ggtctctgtt gctgctgctt    480
ccaaaagtgc ccggtttatt tctaaggaac agctcaggca tttggaagaa taattcaaac    540
ttaagcttta atacaagatg gagttaggca atgattgtac cttcaaacat aatataacag    600
tatgaagtac attctggtga tctaaaatgc tagcatctgt gcaaggtaac ctaagaaatt    660
tgacaccatt tttttttaa ggtaccaatt tcaaaataaa tcaaaataca aatcaattgc    720 catttagga aaaataaaaa tataggcacg ccaactcctc tcccagcact gaaattacac    780
ttcctcagac acactgccat cattggtaag catgggg                            817
```

<210> SEQ ID NO 147
<211> LENGTH: 2138
<212> TYPE: DNA
<213> ORGANISM: Bos taurus

<400> SEQUENCE: 147

```
gctaatgcaa gccatgacca tctattgagg aaaaccacaa aaaacttcaa aacagctaca     60
acggtattct aagaagactt caattgcgta cctttgttca aggtacctaa ttattaaaaa    120
actgaaatta tcaacattgc ttggattttt gatagaaaaa gaactaaaac cattttctga    180
aactattttt cagaatatca ctgatacata aaaacttta gcatctaatt aaagatcaca    240
```

```
aagggttaaa tactgttcgc tggccctgc tgcgtatacc ctgccaaaaa gtcctctaag      300
cttttaaata ttgcttcgat ggtctgcatt tttatttcca gggaaaaaga gagtattgtc      360
ccacagtcag caggccacta gcttattagt tttcagtcac cttaatttct attaaaatga      420
agactctgca atctacactt ctcctgttcc tgtttgtgcc tctgataaag ccagcaccac      480
catctcagca ggattcacgc attatctatg attatggaac agataatctt gaagaaacct      540
tttttagcca agattatgag gataaatacc tggatggaaa aagtactaag gaaaagaaa       600 ctatgataat agtacccgat gagaaaagtt ttcaattaca aaagatgag aatataacgc       660 cattaccccc caagaaagaa aatgatgaaa tgcccacatg cctgctatgt gtttgtttaa      720
gtggctctgt atactgtgaa gaagttgaca ttgatgctgt accacctttg ccaaaggaat      780
cagcctatct ttatgcacga ttcaacaaaa ttaaaaagct gaccgccaaa gattttgcag      840
acatacctaa cttaagacga cttgatttta cgggaaattt gattgaagac atagaagacg      900 gtacttttc aaaactttct ctgttagaag aacttacact agctgaaaat caactactga       960
agcttccagt tctccctccc aagcttactt tatttaatgc aaaatataac aaaatcaaga     1020
gtagaggaat caaagcaaat acattcaaaa aactgcataa cctctcttc ctctacttgg      1080 atcacaatgc tttggaatct gtgcctctta atttaccaga aagtctgcgt gtaattcatc     1140
ttcagtttaa caacataact tcaattacag atgatacatt ctgcaaggct aatgacacca     1200
gttatattcg ggaccgcatt gaagagatac gcttggaggg caaccccgtc atcctgggaa     1260
aacatcccaa cagttttatc tgcttaaaaa gattgcctat agggtcatac atttaaccac     1320
tatcaatgca gcatagctaa agtacacaca tacttataat ctgtctcaac aatgtctaaa     1380
ggagcataaa tatttaatat taattttgca tctgactatt gaaggaactt atgctttaag     1440
caagaatgtt aaaaaaaag tcttatatat aacaacaagt aaaagtaag attgaatctc       1500 taagttcaaa acagaaatgt gaaatatttt gaacagaatt acaaatccc tgtagttcgt      1560 aatagagtaa cacttaaaag gtacgttttt atataaatac ccaaaattaa gaagtgttac     1620
aaagttaaaa gataagtcca agaaactttc aactgtcttt cctggcttcc actggatccc     1680
taaagctttt aaggcatatg ttccaaagac tttgaaaagc tgaatatttc taaggatctc     1740 tcactttct ttcttttatg attttatacat tattcattat gaagtaggaa ctctgttttc    1800
tttcttttaa ggcagctact atatttttac ttagcctgag aaatagggta tagtcttata     1860
cctaagcaaa actttccaaa taaagcataa ttttactctc ttgacaaaga gctaatatag     1920
taatgttcaa ttattctgtt ttgtggttac acaattaaaa gctttagtga agtagtacga     1980
aaatttagtt taactcataa ataatcaaca ttctaagtcc accacaaaac attttaggaa     2040
gctaggcaca tcaaaatcag tatgcttatt aaaaaaactg aaagtccact ctgtttctca     2100
gaatatagcc ataaagttct ccactgtagg tatgtcat                            2138

<210> SEQ ID NO 148
<211> LENGTH: 639
<212> TYPE: DNA
<213> ORGANISM: Bos taurus

<400> SEQUENCE: 148
tttttggggc cacaactcgt ttttatttct cattttcctc tgggggtgca gcgtttggca       60
cttgtcaccc caggactggg tccctcactg catcaagctg gcgggcagga ccccacctgg      120
tcctcttctc tgccgaggga gcgacagggg actgttacag gccaaaaat ttggacacga       180 gggtggaccc agcgatgccc accaagagtt tggatgacag gcagagtccg cttgctccca      240
```

```
cggactggag cgtggccacc atgctgccgg cggcaactcc accccattg gcgatggcag      300 atattgacat catcttggcc gccaaggagg aggcagtgat tcctgcactg gtgaagccca      360
ccgcgctaag caccatgggc acagccgcca cggtggaagc tccgcccacc acagctgcag      420
cagccttggc tcctactggc aaagtgctca tggccgcagc gggggatccg agcaggaagg      480
agcctttcag cgtccccacc aaggatccca tggtagacgt ggcccccgcc agggcagtgc      540
tggatggcag agtgagcccc agcagagcag actttctgaa gacgtggacc agaaccagga      600
cctggacctg atctcgagct tggctgagtc tcgagccgc                             639

<210> SEQ ID NO 149
<211> LENGTH: 664
<212> TYPE: DNA
<213> ORGANISM: Bos taurus
<220> FEATURE:
<221> NAME/KEY: misc_feature
<222> LOCATION: 436, 609, 660
<223> OTHER INFORMATION: n = A,T,C or G

<400> SEQUENCE: 149
tttttataat ttgagtgtgt ttttgagttt tgaatatagc atttatagaa atataagcca       60
cagtgtttga aaatacagaa aggaaaactg caacatcttt aagggaaagg gggagctttt      120
ttatttgcaa agacttctct cattactgat gctgagaaat ggatgccaga aattccacca      180
aggcctcaca caaggagatc agtgatggca tggtgaggat gccatgagta tgtgggttga      240
ggcaacaatc ctggtgtcaa acctcaggct ctatagttac tctggtcgag aggaatgtgc      300
tcctcctgca ctctttcctt cctcacataa ttatgaactg cttccttcat gccaggaact      360
gtgctaaggt gctcaacgat aaagggaaga catgctgtca tggtgcttag agccaactgg      420
ataagactga actaanggtg tatagacgca tgttgttcag gtcaccaaag tcggtgttcc      480
aaactctttg gtgacccaaa tgggggcttt cagcatgcca gactttccct gtctttacct      540
gtggtttcag aggcttggct caaactacat tgccccattt aagttggtga tgccaccaaa      600
catctcatnt tctggacggt cccctttttcc tctggtctca acttccccag atctataagn      660
gaag                                                                   664

<210> SEQ ID NO 150
<211> LENGTH: 697
<212> TYPE: DNA
<213> ORGANISM: Bos taurus

<400> SEQUENCE: 150
tttttagaat aaaatatttt attctttgcc aggagactcc atggaaaaag gtaaacagta       60
tatgaacata gaaagcactg ttaaacgatc tcaatgtaca aacagccagt gagagcacat      120
cacagacctg ctaatatata aaaaaaaatc cactagtgcg taaatgagaa ctaagaagct      180
gacacttgta tctgttaacc atgccacccc acttcagagt gactgaacca ggcccgagga      240
tgcagcctct ctgcccatga ctttgggggg atcagcccct acctctcagg acacagagtt      300
gcctggtaca ggtggcagac cagcccatcg ccatcccatg aaacctccgt aatggctcgt      360
gaacaggtaa acaaaaacct attaacactg gacagtgctg ctgccttgga ggctatcatc      420
actgtaaaaa attgtgtagt tacgtcattg aacaagtact aaaccacttt taatttaaag      480
tgacatcaac aactgaacaa atgacgtctg taaccgagc tggcagttac actgatagag      540
aactctctcc tgctagtgca gtgaatctgt atacatttgc tgggcgacag gaaataaaag      600
```

```
acgcggtttg agagcatccg aagagcaagg acaagcgtct acactaaccg aattagagca    660
tctttagcct tatctcgtca cactacaata ctccgct                             697

<210> SEQ ID NO 151
<211> LENGTH: 541
<212> TYPE: DNA
<213> ORGANISM: Bos taurus

<400> SEQUENCE: 151
tttttgtgga acagaagtga agctttattg cgtggacagt gtgtatgaga gggtgtatgt     60
gtgtgggatc agttggggca gccaaagacg accatgttct ctgtgaagtt ggccaggtcc    120
tccgtcattt gggccaccgg agtcccctgc aggaggatct tggtctctga ctcggtgtct    180
gggacttgat cactaagatc tgcagctggg acttcctctc gctgcactcc cccttgaccc    240
agatgttctg gattcagtgt acgaacagcc acagttttgt tgactcttac gccttctggc    300
acgaccttca gggtcttctt gacaccatca ctgatgaagt ggttgtagac ggcagccttg    360
acctccacct cgtggaggcc gatcttcagg ggcacaatga cgtaaggcac cgccaccgag    420
gacctggctg ggattgttat agtctgctgg tggcgcttct tggcggtggc caggctacag    480
aaggctggat tgtagagcaa ttccaccctc accttgagat tttccgcctc ccggtagttg    540
t                                                                    541

<210> SEQ ID NO 152
<211> LENGTH: 781
<212> TYPE: DNA
<213> ORGANISM: Bos taurus

<400> SEQUENCE: 152
gtaagatgtt aataatcaaa agtagaaaat aaaaatctac atttcattaa aataagatgt     60
tatcatggac accatctccc atgatactct ttccccaccc ctccccaaag cagggccctg    120
ccctgttaaa gtaaacaaaa gaactttgtt aagtgccaaa ggttgatgca tgaaataatt    180
atttttttct tcataaaagt tatgtacaaa atggacccca accagtgagg cctcctcatc    240
tcaacccata tcaatcaaga ttaaaactca gtacataagt gtgcttcatc cagcatctgc    300
aggccgcatc cgtgccttca ggctctgtta aggagagtgg tcctgagggt cttccagctg    360
tccttttcca tgtggttttc tggacccttca cttttcaaagg aggcgatgaa gagagcttct    420
tcgctgtaga ttggagccgt cagcagataa ctctgaatct tcttgtcctt ctcaaaggga    480
cactccacct gtgtccatgt catgaactca tggatctgcc tggagatctc ccaaaatttc    540
ttgaagttaa tgtgtccatt gggcaggtgg ttggtgtgga ttttgtgcag gaagtagatg    600
tccttgacga aaaggttgaa cacggggatg acgatcttct cccggctgct gttggctgtc    660
tgggacctct gcgtggcccc ctgcagggct gtccggtagt tgcagaaatt gctggacggg    720
tccatgtggt gctccaagac gtcgaacttt gctgtcttaa ccttggacca cgttttcttc    780
a                                                                    781

<210> SEQ ID NO 153
<211> LENGTH: 578
<212> TYPE: DNA
<213> ORGANISM: Bos taurus

<400> SEQUENCE: 153
atgtctccta actttccgtc ctttggtttg cacatttgtg agaggatttg tattacattg     60
ttctgaagta attgcaatca cttgagaaga actttctgtt ttttcaggac ttttttttttt    120
```

```
tctagaagtt gtttttctgg gatcaccgct atattactga gggtattttc tttcattgct    180
cccaattcta aagcaggctg gaattccctt ttatttcct ctgtcagagc tagctgtctt    240
ttcacttgtg taattcgtgg ggctgatgaa ttttcactct gagactttct tccataaggt    300
ctttttattt ttaatttgac catttcttct gttgtaaaat gatgtaccaa ctgacagtgt    360
gcccgaagat tagaatttct tgtaaatgtc ttcgtacatg taggtactac acatttaaat    420
ggagcaaatt tcaactgatt ctttttaatt tcaagaatca tctctggagt gtactgatga    480
attttaccgt agtgcttaaa cagtgcatct tttgtcatag cactgtaatt acagccttgg    540
ttttgacaca caaagggttt attaactctg tcattaaa                            578

<210> SEQ ID NO 154
<211> LENGTH: 737
<212> TYPE: DNA
<213> ORGANISM: Bos taurus

<400> SEQUENCE: 154
tggtgggaaa cgaaaataca aaacacggca tttggagggt actaatgatg ttgctcaacc    60
atgtcatgaa tttgcttcta agtaaagga aggtcattat tcaaaatctt catcaaaatt    120
ggatggaggc tacaaaaatg agagtgatag cttttcagat agccggtcat cagacagaga    180
gacaaagcac aagaggagaa aaggaggac ccgcagcctg agtgtagaga tagtttatga    240
agggaaagct accgatacaa ccagacacca taaaagaaa aagaagaaac ataagaggaa    300
gcataagaga caccatggtg ataatgcttc acattcccca gttgtgatta ccattgacag    360
tgacagtgat aaagactgtg aagtaaagga ggatatagaa tgtgacccta gtggtcctca    420
aggccctctc caaagtgaag ttttggctcc atttgaatct aaagatgtag ttacaataga    480
agatgaattt ggtgtcctga gcaaggagtg tgatattacc atacttaata acaacttgaa    540
taatgccaat aaaactgtgg ataatatatc accccaggca gcttcaattg gacaaactct    600
tgatgtaaga gaagagagca ctctggcctc tgatttggag aaccaaccca gtactgtctc    660
ttttcagact gagccatcaa ggacatcatc attaatgtca gtgtctcttg gtagagacca    720
tgatgtgtct taaaact                                                   737

<210> SEQ ID NO 155
<211> LENGTH: 661
<212> TYPE: DNA
<213> ORGANISM: Bos taurus

<400> SEQUENCE: 155
gaaaatcata caacctttcc atttaatgaa gtcgtagtgt acagagcaga aagccaaatt    60
tgtaacagca gagaattaca gcaaaatgag ttgaaaaatt aagactcagc catgtttgcc    120
tcagttcttt tagtatatga gaatagatac ttagcactat tatgccaaaa gctatttgcc    180
cttcttaatt ttggaagctt tcttcccaac tcaattatca gtatccagta gtgattaagc    240
tggactccgg agccagagta cctggtttca aatccagccc accactccag ctgtgtagcc    300
tttgggcacc tttcttacct gtttccttac ttgaaaaatt gcgttaacag aacctaactc    360
aagattttga ggacttaata agtttacacc aggtaggtgc ttacaatggc gtcaataaca    420
ttttaagtgc gcaaaaactg gtagctataa ctactgtggc tttatgtgtg gttaagactc    480
atgaggctct tggagcccac tgccaaaact ggattcaagt cagtcaatga gtagctggat    540
gccaaaaacc caagccaaca tgtagctgaa gaccagatag gagtctttcc atcgatccac    600
```

```
taaaaaatac ttatggaagt taaacctgca agtcaaaaaa gctcttggtt aatggcagtt    660
t                                                                   661
```

<210> SEQ ID NO 156
<211> LENGTH: 853
<212> TYPE: DNA
<213> ORGANISM: Bos taurus

<400> SEQUENCE: 156

```
gaatgcccca aaagtttaat tacatgaaaa catgagtttg gcactcccac tcccctcatt     60
gcaatcattt tagtatttga caacaggctc caagttgaaa tgacttgccc gtgtagtttc    120
tctatgacat ggtgaagtca tatcaaatcc cagggcttac agataaataa tacagggctt    180
cctgcctcca gttagtgaga acaatcattt cattgatggc cttgcgcagg ctgactttaa    240
agacaagacg aaacttcttt cattggcaca gagactggaa caggaggtgg ccagacaggt    300
ggccacagcc tccagacgtg cagctactcc tcagctgtcc catccaggat ttgtttgaag    360
gagaatggag agaacttgta accagcccca gtgtagaact tgttttggaa ctccacccag    420
tgcagcctca gggcatgcag gaaagcagag aggccctcca tgatcagaag gatggctacc    480
gtcagaacag cgaacacggc aaaaatgatg aagaccccaa cgagtcctcc ccagcctcgc    540
gtgcgaaggc caatgtgcat caccattgtc cagagcactt cagacagttg tgcatgtgcc    600
agactgaggg cccaaagccg gaggtaggag gctgtgttgg aaatgcagcc caggcaatac    660
tcgatcgtgt gaatggcctg atgcacaaag atgtctccaa agttgaactc ttgatcgtgg    720
tcatcctgag ccccatgggc acctacgaaa gcaatgtgac cagagttgtc accctcggtg    780
ttctcggtgg tgtcttctgg gattctggag gcctgcagct gggatttccg atggttggct    840
ctaaggataa acg                                                      853
```

<210> SEQ ID NO 157
<211> LENGTH: 1600
<212> TYPE: DNA
<213> ORGANISM: Bos taurus

<400> SEQUENCE: 157

```
ggaattctta cagcccaaat gcaagggatg ccgctactc cataaatttt cagaaatcac     60
gtaaagccat cagcctcatt atctcagcct taaaactgga agactctgca aagtacttct    120
gtgctctctg gacccacagc gggtggggta gtagtgggat acatgagact gacaagctca    180
tctttggaaa agggacccgc tcatcgtgg aaccaaaaag tcaacctgct gccagcccat    240
ctgtttttgt catgaaaaat gggacaaacg tcgcttgttt ggtgaaggag ttctacccca    300
aagatgtaac tataagtctg caatcatcca agaaaataat agaatatgac ccggctattg    360
ccatctcacc tgggggaag tacagtgctg tcaagcttgg tcaatatgga gaccccgatt    420
cagtgacatg ttcggttgaa cacaacaagc aaacctggca ctctactgac tttgaaccaa    480
agaaaactat tccagaaaca actccaaaac cgatggcata tgaaaacagc acaaaagctg    540
aagctccagt gacctgccaa gagccccaag tggaacccgg aaggtgaac atgatgtccc    600
tctcggtgct ggggctccga atgctgtttt ccaagagtgt cgccgtcaat tttctcttga    660
ctgccaagtt attttttctt taaggctgac tggcatgaga aggctgcatt ccctgacaga    720
aaccaaaagc ctacagagaa gctatcgcct aggctttcaa cttttcgtg attcaagttg    780
acccgtccca gccttgctta aatggctgct ccccaaacag ttttcctta aaggcaacaa    840
acccagctta tccttcagcc tgatgaaaga cagaagtcct ggggagtggg ggcccaactg    900
```

```
ttttatatgc tgctttataa agggataaga gatatgaaga tatataggac tcattttttt    960
ccctatgact gacatacttt gaaagtggtg ttttgttcct ttgactttct ttgcctccag   1020
aactagaaag tgggatccat ccggttccca gctccatcct tcaagaggaa aaatagatcc   1080
tggggaaagg acaggggtgt ccttctacct aaatgtaaaa gcctctgctc aacccagcac   1140
tagatttgcc caaactagcg ttctcatcca caaaagcact ttctgctttc cctagtactt   1200
gagaaacaaa gcaacacttg actccctaat actctctgtg taggcaatgg ggtctcatct   1260
aaatactctc agagctatta gcagagatca gagtaaaatg cagaggagat gtgctttcct   1320
caacttaaca aacgtgaatt attgcaagtt ccaggcactg tgctgagagt gcaaaaataa   1380
gtaagacatg ggtcttgctt tcaagcaact cactgtgcaa gtatttttag agggagggat   1440
aggaatgagt tcccaatatt tccctataaa accagagtct ttctgaaccc ttgcctgccc   1500
atctgtatat ggggaatttg agggcattgg atctttggtg ttgatggttt tctgctattt   1560
ttctttgtct ctgttgcatt tattaaagtg cattttatgt                         1600

<210> SEQ ID NO 158
<211> LENGTH: 264
<212> TYPE: DNA
<213> ORGANISM: Bos taurus

<400> SEQUENCE: 158
ggtattttca ccactcagcc ttgaaaatgt actactattg tctctaaaca tgtgttgata     60
tttgtgtcat tcaagtacaa tttacttaaa tgaaagaaca tacatggatt ttcctttgta    120
gtcatttggt ggaggaggaa ggcatgtttt acttcatttc accagtagag taaactgacc    180
tgaactgtgt tagttggctt agaaaagtaa aaatcatttc tcattatggt aaaaataaat    240
cagtaaatgc aagacttgca aaaa                                           264

<210> SEQ ID NO 159
<211> LENGTH: 725
<212> TYPE: DNA
<213> ORGANISM: Bos taurus

<400> SEQUENCE: 159
tttttctgac acaattcggg attggtggga ttttcaaagt agtaacattc cggcttgccg     60
ttgaagccaa tggagtcgac gtaaagcagg ccctgaatca gacagtccag ttcgtccagt    120
ttgtggagct gcaggtcagc aatcgttctg aaatcctctt cgaacttgaa agccccgcct    180
cccgtggcac agagcgtggt gtgcaggctg agaagttct tctcgctgcc catctggatg     240
aacttgtgca ttgcacagct ggggaagcgg atgaagtgca ggttcccctt ccgcccacac    300
atggtcaagt ttttcagttc caggtggacg tctcggatcc cggttttccc ataagccgtg    360
ttagaagtca atacttcct gatgctcttt aggttctcca cctcctcctg ctcttcttca     420
gctgtaatat ccttcggctc aaagtagacc aatttaacca gcgtcccacc gatatccatg    480
ccgaaccacg ggaacgtttg ctttttgcca tttataagct tcattgggga gacccagaaa    540
gaggtaacaa gttgaaagaa gttcggctca gataagaaac agctgtatac ttgatctaca    600
aatttgcatc tcaaaacgtt cagtggggga gagactcttc tcaaactaac atatatacaa    660
gctttagatt gtgaaattac gcatttcagc tttcagcact gtatattact attggaaacc    720
tcaac                                                                725

<210> SEQ ID NO 160
```

```
<211> LENGTH: 846
<212> TYPE: DNA
<213> ORGANISM: Bos taurus

<400> SEQUENCE: 160
cagatcttac attgtatttt atttaatttc acaatctggt aacaatcact tattccacag      60
gacaaagaag atacatggac cataactgtc aaggctttgt caacttcata gctgagttag     120
ctggaaacag gccaggccct aagtgacttt ttcacacctt ctccttagag caaggctatt     180
ctgtattcca cttaacaacc acccacacat ctaacacagc tgcatttgaa gctgggccca     240
aaccaaattt acggttatgt aaacagctgt aaattcgaca ataaggcaac tttcttctgg     300
ttccaagcat ttatttgtca ctcttattta ggtagaaatc ctaataacta acaaggtggt     360
tgtgcctcct catctactag agcatctaaa tcttttctcc ccttgattat aagtattta      420 cttacaatta agtagaagta gaaaccttca ctactcctca ttcctttca gccaaacaac      480 taaaaatctc actttgaaat tactcttttt cattgaaatt actaatttta atcagctcaa     540
tgaactgggc aactaacagc cccatcgtca caagtcaaga gaatacttag aacttagtac     600
ataacaagtg aacacttaaa atttgtttta tacaggactt cattcccaga tatattttca     660
ctctcatact gaatgagaac ctttaaagtt gcatttaact attattttgt gtctctactg     720
ctagtagtcc atattaaatt atatttcact attctttaat cagatctttc tacctagagt     780
agaggacaca ttttaagttt aaataaatta gcacttcaca ggatattggg atttcagatt     840
ttaaaa                                                                846

<210> SEQ ID NO 161
<211> LENGTH: 741
<212> TYPE: DNA
<213> ORGANISM: Bos taurus

<400> SEQUENCE: 161 ctacccctt cagatcgcct gctggaagtc ggctccagct ctggcttgtg gtaacgccat       60 ggtcttttaaa ccttctccct tcacgcccgt gtccgtgttg ctgctggctg aaatctatac    120
tgaggctgga gtccctcctg ggctcttcaa cgtggtgcag ggaggggctg ccacaggcca    180
gttcctgtgt cagcatcgtg atgtggccaa agtctccttc actggaagcg tgcccaccgg    240
ctcaaagatc atggagatgt ctgctaaagg aatcaaacct gtcaccctgg aactcggagg    300
caagtctcca cttatcatct tctcagactg tgacatgaag aatgctgtga agggggcgct    360
gatggccaac ttccttactc aaggcgaggt ttgttgtaat ggtacaaggg tatttgtgca    420
aaaggaaatt cttgatcaat ttacagagga agtggtgaaa cagacgcaaa ggataaaaat    480
tggagatccc cttctggaag atacaaggat gggtcccctc atcaaccgac acatctgga    540 gcgagtcctt gggtttgtta agtggcaaa ggagcagggg gctaaagtgt tatgtggtgg    600
agacgtcttt gtacctgaag accccaaatt aaaggatggg tattacatga gaccttgtgt    660
gttaactaat tgccgagatg acatgacctg tgtaaaagaa gaaatctttg gaccagttat    720 gtccattta tcatttgaca c                                               741

<210> SEQ ID NO 162
<211> LENGTH: 655
<212> TYPE: DNA
<213> ORGANISM: Bos taurus

<400> SEQUENCE: 162
tttttgcggc aaagtgctta ctttatttaa aaaaagaaga ttaaaagaaa ggtggcagga     60
```

```
tttttttttt ttttacaaca aacgtatgtc atatgtccca atctcctcct cttcttgag      120 tttttacaa caaacgtatg tcttgtgtcc caatcttctt cctcctcttc ctttagtgca      180
acacgtagca gcagcttcaa tgaaacgtct gatttcaaaa gatgctcctg aaacctcacc    240
tacagcagca ccctaggcgt cccgttgggg gtggctcctt ttttcttctg cagccgattc    300
tgaacctttc gcgatttcac tactttcatt ctcacctcaa aaacttcatg gatggccttc    360
cggaagcaat gaaaattata gtcaatcagc ccttttcttt caaagctttc ctctctgaca    420
aagcacacaa gagccaggaa ctttgtcacc tcttttaaat aaagaactgt tgtattattc    480
agctttataa tggctgttga ttccttgtca taaggggttc ctgctccatc ttctttgagg    540
ccataaatac atgaaatatc aatgaccaca tcgatcatgt cacagcagag ctcgtacgtt    600
tgcatatcca caggggtact atctgttgca atataaatct tactgaccac atcaa        655

<210> SEQ ID NO 163
<211> LENGTH: 505
<212> TYPE: DNA
<213> ORGANISM: Bos taurus

<400> SEQUENCE: 163
tttttcgggt agagaggaat ttattagggt ctcttgaaga acttgggatc actggggtct      60
ggaatcactc atcagaggcc atccaaggag tgacagggtg ttcccttgtg acagtggtat    120
ttgccctggt aatacatgct gctgcccata gccaccgaga gaaagctgaa ggcatagaat    180
ccagcccgaa ggaggaggac tgtgccagcc gctagctgag gaggtccttc atccaccacc    240
agcagggtcc cattccctgt tccgacaccc atgcccagca cctccaccct gcacgcgtag    300
actccagtgt cacggcctcg ggtgtcccag atgtgcagct cagcctggtg gtcacagagg    360
aagcgggaag aggggagagg ggccaggcgg ccctggaact ctgcggtctc attcctcacc    420
tccatccctg gggccacttt gtcccggtac catgtgacag aaccaatggc caaactccct    480
tggctggcat tgaaggaaca gggca                                          505

<210> SEQ ID NO 164
<211> LENGTH: 622
<212> TYPE: DNA
<213> ORGANISM: Bos taurus

<400> SEQUENCE: 164
gcggccgctt tttttttttt ttttttgttt ttttttttt ttttttttt ttttgtcgcc       60 tgggctttat tttaatgatc aaattccagg ggggctgtc tcggaagtca tttaacagtc    120
gaggaaatga aaaacacac ccaaacttcc tcatggctcc ggtaaactgg ccaaacttt     180 caccctactt ttactgcatc ctcctgactg cctgggaccc ggacaccagg taacctcctg    240
ccttacccac tcccgcatcc tcccacccca ccctgcccac aggtgccaaa caaggggcg    300 aggcaaaaac caccccgggg ggaaggcaaa cccagtgcga gggttcaggt cttctgcttc    360
tctgcagtca gggctcgctc atttccaggt aagttcaccc caggccgtgt cccccctgca    420
cccctccctg cctcctgccc cagcaccagt ggggcgcatt ttgaaagcta ggccctcacc    480 tcaggggtg tatctggctg ccgacagggg tgaaacacgt ggaaggcctc caaggccacc    540
attgacttgt taatgcggct gatggtaggg taggggtga ggtccacctt gaacctgtca    600
gcatttgcca cctgcggcgc ta                                             622

<210> SEQ ID NO 165
```

<211> LENGTH: 763
<212> TYPE: DNA
<213> ORGANISM: Bos taurus

<400> SEQUENCE: 165

```
tttttgactt tcaaattgtc tttattacta ttttttttcaa ttaaaaaaca ttttcccact      60
tagaaaacag aagaaagatc tctggacttg ggcaagggtg cggcttgcct gtggagcttg     120
ttcctcgatc ctgagagtca gcagttcatg aagcattggg atgccccagg aactgtcatc     180
ttgagtcact ccgtaatgac aaagggatga gagtctgatg ctcaagcctc tgaagatctt     240
ttctaaattg gggccgttag gatcctctgg agccttcgtc ttatgctcgc actgtattgc     300
tccagcttgt cccagggctg aagggcctt gactggttgt ccacaaactg ttcccagcag     360
tcttcaaact ctgtgtgggt catgacagcc actgagatcc cagcgttctg cagatcctgc     420
agccccatct taaatgactt gatccagtgg aagtacaggc gggaggcaaa gatctccagt     480
ttcaggtggt tattcctggt gatgaaattg accagctcat tggcacagtt cgggcaaggg     540
ctccatgtga tatagcagat gattttgtag ctctggctcg gttcagatc cagtgagttg     600
atcttgtcaa taaagcgaat ttctgcatgc cgctgcttct tgttgcggaa gcagcctctg     660
tcaagcgtca agtcattacg ctgcttcagc tggtagcaca ggtaggtctt cctccggtag     720
taaggtgctg ggacccgggg ctggttgcca aactgctgct tga                       763
```

<210> SEQ ID NO 166
<211> LENGTH: 701
<212> TYPE: DNA
<213> ORGANISM: Bos taurus

<400> SEQUENCE: 166

```
tttttgaaga aaacttgccg gaatttattt ttaagataca ctataacaag agttcatcag      60
ttctgtgtcc cagcctggac actgaccatg gtgaaataga tgcctttctg tgccagcagc     120
tgctggtgtg tgccgtgctc cctgactctg ccattctcaa tcaccactat caagtctgcg     180
ttctggatgg tggacagccg gtgagcgatc acgatgcagg tgcggccttc tcgggctttg     240
tccagggctt cttggacaat cttctcactt tcagtatcca gtgctgacgt ggcttcatcc     300
agcagtagga tgcgggggtg tcggatgagg gctcgggcaa tagcaatcct ctgtttctgt     360
ccccggaaa gctgagtccc cttatctccc actcttgttt catatttctg caagttagcc     420
attaatagag ttagtaaagt tctagtttag aaaaatccta atagtatatt gaataaactt     480
ttacttctta acacttgaca gttctaatta taggaaaaaa taataggaaa taataataaa     540
gtttctataa caaccacgac gttgtgcatt tactttttt taatgtgacg ttcattttca     600
aaatcaaact agaatgttaa tgatcttagt tttcatttca tttcatatcc tgcaacaaat     660
tgtccaaatc ctatcattat ctgaacatca gttcccttct c                         701
```

<210> SEQ ID NO 167
<211> LENGTH: 636
<212> TYPE: DNA
<213> ORGANISM: Bos taurus

<400> SEQUENCE: 167

```
cgccgctgct ggtcatcgcc aacaagcagg acctgcccaa gtcgctgcct gtggcggaga      60
tcgagaagca gctggcgctg cacgagctca tcccggccac cacctaccac gtccagccgg     120
cgtgcgccat catcggcgag ggcctccacc agggcatgga caagctctac gagatgatcc     180
tgaaacgcag gaagtccctc aagcagaaga agaagcggta atgctctggg cggcgacgtt     240
```

```
ccggagctag gcgcggggag cgagcgagtc cggaatgaat gaatgaaagg ctgtgtggcc      300
cgcgcgcccg cgaacaaaga cagcgaacca aagcgacgct tcgaattttt aaagcggagt      360
ctctgcaccc acatgcagga ctggtgactt aacctggtat gtaagcaagc tggccagcct      420
gcgctcgacc tgcccccacc cccagctcag gggtcctttt gtctgaacgc cggagctact      480 caggggtgg gggacccggc tggggagtgg acgtgcaggt cccaccgtcc gccctgctgg       540
cccaggttgg aaggctcaga tatcagagac aaaagcgatt tcctcctact ccagcggggc      600
cagaagttca agcttccccg ccctcacggg ggatcg                                636
```

<210> SEQ ID NO 168
<211> LENGTH: 835
<212> TYPE: DNA
<213> ORGANISM: Bos taurus

<400> SEQUENCE: 168

```
cggagaagtc ctcggagagg actccaggga aggccttctc ccgtttgtct ctgccttgat       60
caagggacgc cttcctctcc ttgtctttgc tgtgcacgtc tttatgcttt tccttggcat      120 ccttttctc tttaaaacac ttatcaaact ctctgtccct ctgacatttc tcaaggatga      180 gttttttcgct tttgtccttg tcgctagact tctccttgtg tttctccagc ttcagcttct     240
ccttcttctc cctccctggg tggtgcctct cccagggctc caggctcttc ccaaagtcac      300
agccgtactc cttcaggtcc tccctgtgcg cctcctcggg cttcacgcgc ccatctctcc      360
gctccttagc agcctgggg gcctccttcc ggtcccggct gccctctgtg gactcacgcc       420
gccgtttgtc cttctcgcag agaaagctgg ggacaaccct gtgcctgtca gccacatgct      480
ctcgccgccg ctccaggctg tccctgtcct tcttccgaga gaagatgtcc ctgtcaccgc      540
gcttctcccg ggccttgctc tcccgccttt tctccttgct gtcctccttc accgtctcca      600
ggatcagcct ggccacagag tcgctcttca tgtccctgta gtctgtcacc ggggagtccc      660
agctgtcttc ccctttgaaa tcgaaggagg aatctgacag gtctgagaac cagcgatcct      720
gctggtcgtc agagagactg aacttggtgt cttcgttctc cagaaactga cttttgttac      780
agtactcatc aaaagcagag tcctcccgat acccttttc ttttctgagt ttttc           835
```

<210> SEQ ID NO 169
<211> LENGTH: 500
<212> TYPE: DNA
<213> ORGANISM: Bos taurus

<400> SEQUENCE: 169

```
caatttcctt ttgctctgct cgttatcatc ttcagaggat tcatcactct gttctttctc       60
tgagaacttc tcagcaacat cacataagcc acccagtatt ttctgacaca ttctggttcg      120
ctggtgctta ctcttttcctt tagattcagc aaccttttta tcttctggag aattaaaact      180
ctcctctttc ccagaacaaa gcttatcagc actctctgag gaaacattgg gctgctgctt      240
cttagagagg cgatctctca attccatgat ggtcttgtct ttatcaactg tgccttctgc      300
tgaagagaaa ttctctctct cttgtttcct ttcaacatca tcagatgatc cttcctgtgc      360
agtcctcaaa cttttatgac cttgattatc cattccttgt ttgctgtgtt tttcatcttc      420
agaagaatca taatattctt tatttggaac tcttttttgg ttgttctggc agtcccaatt      480
ttactcattc tctttatctc                                                  500
```

<210> SEQ ID NO 170

```
<211> LENGTH: 470
<212> TYPE: DNA
<213> ORGANISM: Bos taurus

<400> SEQUENCE: 170
ctctcagcct cttactgcac agctcagagg gacctcagcc atgaagcttc tcatcctgac     60
ctgcctggtg atctgcagtc tcgctgcata tactgtggaa ggtgtgggga gtgaagttct    120
agaaaagagc atctgtgtga gtctgactac acaacgactg ccaattaaaa acatcaagac    180
ctacaccatc aaggagggct ctgtgaaagc agtgatattc attaccagaa gaggatttaa    240
aatctgtgct gatcctcaag ctgcctgggt gaaaaaagcc gtccaaaaga tagacaggaa    300
aaatataagc caggccaagc ctacaggagc ctagcaatcc accaatacaa ctgtgaccct    360
gactgggtag tgaccttcca gcactttgtc ccttccctag ccagccacct catttccctt    420
caaagcctat ggactgatta cattatattc acttttcata aaaaaaaaa                470

<210> SEQ ID NO 171
<211> LENGTH: 254
<212> TYPE: DNA
<213> ORGANISM: Bos taurus

<400> SEQUENCE: 171
gcccacgcgt ccgctgcctc acttctgggg gttctgaatc agcgttcttt aacactggtt     60
cctgggaact aaagggcctt cgagtctgcc ttgtctttct attcccaggg catttatttc    120
ctttgtcatt aacacttggc gtcccaagtg gtgagttagt tagatttttt ttttaataaa    180
atgttcattg tattttggat tttcttgtat ttcatgggat gacgtggcaa ggcctggtaa    240
acttctactt caag                                                      254

<210> SEQ ID NO 172
<211> LENGTH: 734
<212> TYPE: DNA
<213> ORGANISM: Bos taurus

<400> SEQUENCE: 172
tttttcgact ataaactcat tttattatgc ttttgaaata agaaatatta tcataaatat     60
gtgatctatt agtgaagtca caatctgaaa aaaaaaaaaa gtcaaatggt acagtgtatc    120
tgcagaagtt acatatttct tttgcttttt ttaactcaat ttcaaagtag aacttgcagt    180
gatataaaga aatatttaag atgtaaaatc atcccaccac aattttgttc ttgattccac    240
aaaacaaaca catcattctc atgaatctct ccattttaaa ataaacagta taggcacatg    300
gaacgtgaca gtaaaatttt gtatagatga caatggtaac ctctaaaatc tacattttcc    360
ttactggttt tctaaaaatg ctgctccaaa agaaaaata aaatacaaat gtatgcctgt    420
ataaaatcag aatatcccaa atattttata caaatttta aaagctctga tctctatgct    480 cattttcat gaatatttat aatactttag agaaattaca ttgcagaaca agataaacat    540
aatattattg tgaccatcat aggaaaaaac atgtataaga atatttataa ctcttcatat    600
ttcaaacaat ctttaggttt gaagatttaa gaaataacat ttaatataaa gtgttattcc    660
aaacacatac aacttcattt taactttgac tgtttacaga tattttccaa acattgcttt    720
taaatggcaa atga                                                      734

<210> SEQ ID NO 173
<211> LENGTH: 658
<212> TYPE: DNA
<213> ORGANISM: Bos taurus
```

<400> SEQUENCE: 173

```
tttttaacat ttaaattatt ttaatgatgc cagttaacat ggatgctaca ggttgattaa      60
atgtcacaca aaagataaag ttacagacct aggatcatat atatattaca gcaggaaact     120
tccagagatc atctctgtcc aaaacctgat aattttttac atataaaata agtcagtgag     180
aaagtcctaa gtatagacct agtccaaata tacagtatag agtaaacaaa atgatgcga      240
taacattgga cctgtcttag gcaagtagct gtttggtaaa aagacaagat ctccagaaaa     300
gatgaaaaat ataaagttcc tctaaggtag tttctcaaat tttggtccat gaaattcaag     360
acccaggaaa tggaccacag aaaaaaattc cataatcaga taagcatggg aaatgtttca     420
ctctatggct ctctctcgga gattccaaa gcaatatttc aatattaaag tctctgaaaa      480
atcctccaat aaagtatcta taaacttttt tgctatcaag taattccaaa acttacttgc     540
tctctgagtc tactttttg ctctcatcct ctgactcttg accctatttc tcagggataa      600
aaccctccat gttggcagtt acctcacaca ccctatagca ttgtagttac caaaattg       658
```

<210> SEQ ID NO 174
<211> LENGTH: 630
<212> TYPE: DNA
<213> ORGANISM: Bos taurus

<400> SEQUENCE: 174

```
ggttctcagc tttatttata gtccaactct cacatccata tctcacattt tacatcaaaa     60
caacattccc ctttgaatgt acacattggg atgtgttgac ttgagattag tcttaaaaat    120
tttttatagg taaagcagta tcttttggga tatatttcat tcagtttcct gattttctg     180
acctatagag ttcctgtaaa atgtaattat attatagtcc tcttttatca ttacttcagg    240
aaagcagtca cagacgtatt ttctaaaaat gttgaatggg tgtcctaggg ggggtccct     300
tgctggtcct tccaatgttt ttatcttagg ataaatctgc ttctgaaacg tagtttaatt    360
tgaatgtaaa atggtcctat ttatgcagtc ctttaaacct gatttagcaa caaagggtac    420
ttaaagtctt taaatataa tacagctgcc gcctgtcttt ggtcctgctt tgacgctgcg     480
gtaggactgg gacagtcagg caggtgctaa aggaggccct tggaactagg ggtggtcatc    540
gcgctcagtg caggcttcgt ggttcttgtg gcattcgtct cctttcctaa aaaccagagg    600
gggggaaagt agagtccatg aaagccttat                                      630
```

<210> SEQ ID NO 175
<211> LENGTH: 528
<212> TYPE: DNA
<213> ORGANISM: Bos taurus
<220> FEATURE:
<221> NAME/KEY: misc_feature
<222> LOCATION: 444
<223> OTHER INFORMATION: n = A,T,C or G

<400> SEQUENCE: 175

```
tttttagtga tgattaaatc ttttatttta taacattttt aaaagacata aacataaac      60
ctatttttat gttttatata aacataaaaa catttccttt tatacataaa ggaaaataag    120
aattctaaac aaagacttat catgacacta ccactcccca cttttacct ttaaaccttc     180
taccctttcc ttgggtagac attcaaaaat aaggaacagc aaatttgtta ctcagatttc    240
ttttgtcttg tatatttaag ctctttattt atcggataaa tgtgtcagca ttcatttgg     300
agcattacta cttatcagaa aaatttgatt tttttctca gtgattagtg aaccagttcc     360
```

| | |
|---|---|
| atttggaatt tctaaagcct aatcttagtc aatattttca agtatgata aagctcagaa | 420 |
| ataatttgtt acctcagata acanataagt cattaaaatg gaaccaagac aagactctaa | 480 |
| aatacttgtt agtagtcaat ccacatttgt gaacattagc tcatgata | 528 |

<210> SEQ ID NO 176
<211> LENGTH: 5058
<212> TYPE: DNA
<213> ORGANISM: Bos taurus

<400> SEQUENCE: 176

| | |
|---|---|
| aattcggcac gaggcgcact ggagacccag cccgcgctca gtccgccccg gcgccggccc | 60 |
| gctgggtctt gggaattgct ggttcgcttt ggctccctcg cttgtacaaa ctcctggatc | 120 |
| tcacatgcct ctgtaacccc cacttccact ccatgtcccc atgctcctgc gccagcaaca | 180 |
| ggacctgttc tctggatgtc agctgagtta ctaaggtgac tctgcatgtc aagagacaga | 240 |
| ccttggtagc cagaacctca aggccctgg agacccatc cctccttctt tttttgtgcg | 300 |
| tgtgggtcct cactgaacat tcaaacctgt ttctccaaag ggttttgcaa aaactgagac | 360 |
| tgtttcccaa gcagaagcg ctggcgtcca cagcagaagc gatgggcagc gtgcgcacca | 420 |
| accgctacag catcgtctct tcagaggagg acggcatgaa gctggccacc ctggcggtgg | 480 |
| ccaacggatt cgggaatggc aagagcaaag tccacacccg ccagcagtgc aggagccgct | 540 |
| tcgtgaagaa ggacggacac tgcaacgtgc agttcatcaa cgtgggcgag aagggccagc | 600 |
| ggtacctggc ggacatcttc accacgtgcg tggacatccg ctggcggtgg atgctggtca | 660 |
| tcttctgcct ggctttcgtg ctctcctggc tcttcttcgg ctgtgtgttt tggttgatcg | 720 |
| cgctgctcca cggggacctg gatgcgtcca aggagagcaa agcctgcgtg tccgaggtca | 780 |
| acagcttcac ggctgccttc ctttctcca tcgagacgca gaccaccatc ggctacggct | 840 |
| tccgctgcgt cacggacgag tgccctgtgg ccgtcttcat ggtggtcttc cagtccatcg | 900 |
| tgggctgcat catcgacgcc ttcatcatcg gtgcggtaat ggccaagatg gccaagccca | 960 |
| aaaagagaaa cgagacgctg gtcttcagcc acaacgccgt gatcgccatg agggacggca | 1020 |
| agctctgcct catgtggcgg gtgggcaacc tccggaagag ccacttggtg gaggcgcacg | 1080 |
| tgcgcgcgca gctcctcaag tccagaatca cctccgaggg ggagtacatc cccctggatc | 1140 |
| agatagacat caacgtgggc ttcgacagcg gcatcgaccg catatttctg gtgtctccca | 1200 |
| tcaccatcgt ccacgagatc gatgaggaca gtcctctgta cgatctgagc aagcaggaca | 1260 |
| tcgacaacgc agactttgag atcgtggtca tcctcgaggg tatggtggag gccacggcca | 1320 |
| tgaccacgca gtgccggagc tcgtacctgg ccaacgagat cctctggggt caccgctacg | 1380 |
| agccggtgct cttcgaggag aaacactact acaaagtaga ctactccagg ttccacaaga | 1440 |
| cgtacgaagt ccccaacacg cccctgtgca gcgctaggga cttagcggag aagaaataca | 1500 |
| tcctgtcgaa cgctaactcg ttttgctacg aaaatgaggt cgccctcacg agcaaagagg | 1560 |
| aagacgacag tgagaacggg gtccccgaga gcacaagcac ggacacgccc ccggacatag | 1620 |
| acctgcacaa ccaggccagt gtacctctag agcccaggcc gttacgacgg gagtcggaga | 1680 |
| tatgactgag tcctcctggg gagtgcttcc tctgaaacac ggtctgttgg tcaaaggccc | 1740 |
| aaaacagtta cgcacacgac ggtaccaggg gcaggtggtt cgaggcaagt gaccacaagg | 1800 |
| gactggggct agcgcggtgg ttttagaaa agactgtaag cgcgaagacg aacctaaagc | 1860 |
| actaaacagg cctccccgtg gcccaaaggc gcataacacg ttgtagaata agttatgggg | 1920 |
| tgtttgtgtt ttgtgttttg aaccaaactt gaacttgcag gcaagccttg gttggtgggg | 1980 |

```
tgtttgactt ctccagaacg cttctctttg gggaacaaga atgttttta atggcatcac    2040
attttcaat gttttaaagg caagactctg ccttaacttt tgaaaagctg ctaactacac    2100
caacacgtgt cgtattgttg cagtgtagtg ttttttttc cttgtgtgta atttaaaaag    2160
tcagtgttga actttgttga aagctcatga tatgcgcttc aaagtggcaa gtatttggct    2220
attagctgcc aaacgagagc ctgattttt gaggccagta atttgtttgc tagaattgat    2280
tctctctctc cctctcgtgc tgtctgtctc tctggttaca taagggcatt atgtaacact    2340
agccaaatgg tagcctccgg gctgttgtta atgttttgt ttttgtttt ttttcccctc    2400
caagatgtta atgggttatt tcaaatttt agttagacta cctaaaataa ataccaaaga    2460
taatgcacat ttttgcacag tggagcttac actaaagg aaagaaagcc ccacggctgc    2520
cttgaaatca agagacaaga actttgaacc tcagcaagac cttgaactac cctctccttt    2580
tgcaccttat tgagaaaata gaacatcaca cacagagtta agtgtggtgc ttttaatttt    2640
ttgctctttc atgtaacttt catgtcatag gaagaagaca gggaaagta aaattcacac    2700
atacacacac acgaaagata taagcaactt tcctttcctt cgaggtggtg ctggacaggt    2760
gaatacaact ttgagcgatg atgatgaccc cttagatttt ttttttctgg atttttccat    2820
gttttgcaca ttccaaaatt tatcccagaa gataagacct aggtcgacat gagttggcac    2880
cctccgtgct gagccatcca actcgaaaga tcagtaggtt taaaccttca ggctgagttc    2940
cttgccctgg tggtgggtgc atctctggct tgagtttatt ttctaaaaga tgccacgcct    3000
ggcccgtggg ctggttcttc ccatcagact gtttggaccg agtcctccaa tatctgagag    3060
ggttgtgaat gccccagtga aagttagca agatgtggaa gagccgtttt gatgtagctc    3120
atcaacttaa gtatttagga agaaggggaa cattgccttt tttttttt aaatgataga    3180
gagcaggaat gaaaatgtct cagtatttta gggtcaacaa gagccacaac aatcctaaca    3240
gcgtcacaag taaaggagat aatggtctaa aagtgtcctt tccctccggt ggatccacac    3300
tcgtctttga accaagtgga tccctttgc ctgtgcagac ctggagcctg ttacttgggg    3360
cacatcattt cccagaagct tctcctgcct ggctgcctga ctcgctagga acattttgtt    3420
tggtttggtt ttccgctcta gcttgatata acggaactct gttttggttt aaagttcctt    3480
atttgtgaat tctggggtca ctgatttttt tcttttcaa tgggagtctc aaaatcaact    3540
ctctttacgg tattcaccc ctgtatgcca ttaaaaaaca gcttgttcta gaatcctgta    3600
tttcatcagc ccgtgtctgg gatggcctct ggttcctgac cagccgtatc tgcatggggt    3660
gcctgcagtc agaggacagt ctctgctctt gtctgccttt cgagtcggtg ggtttgaacc    3720
ctgtgtggtt atttgcatgg aaaccagatt agagccatca agcgagggga tgatatgtga    3780
agtccagact tacaggccga tgggggaagt tgtttagaga cttagaggaa ttgggatgga    3840
gtggacatag aatgtacagc cttctgtaca tggcgaccat cctgccattg atagggagag    3900
ggtgttgagg gtttcagctg ctgctattcc gatactttta caaggaaaaa taatcaaacc    3960
aaagagtatt ccgtgatctg taagttacat gaagatacag tggaggatgg gggtgacaaa    4020
ggcaccttct tgtcgcacag tgctgccact taaacacttg acatatttgc agtggggcgg    4080
atggaggggg gcaagaacga gggagggaac tcttgcaact tctttctaaa aagagaaaaa    4140
aaaattaaaa tttctggtgc acaggtttgt ttttttttt ttttccaaga aattttgca     4200
gaagctatgt ttttaaagtg tacatttat aaagtttatc agatattttc atattaag     4260
ccaaatgtaa atagaagtct gtaaagggaa gaaaattgcc atagaaagta taatttcagt    4320
```

```
gcagcaattt ctgagagcta gtacctgtat gctaccggtt agcatggttt tagcaaatat    4380
ttaccagcct tataaggttt gtcttgctat gttctcctgt tatttatttc agcatggact    4440
gttcatttga aaactttttc taggtattag tattttaaca gttacaagct ttaaatggca    4500 attttttgtgt ttgttttttt ttttttgtcaa gagccaagac acagtaatgc acaatgtttt    4560
tttttttttt tttgctgcat tttaccttca gaaccttggt ctttattgac tgggtctcct    4620
tacttagtgc acacatgtcg tgggaaagca gactgaagac actcacactg agtatctggg    4680
gtctgttgcc agattcttgt tgcttctctg ttgcaagcaa acccccactg aatttattta    4740
ggagttatcc ccttgtgaag aatctgtgcc cgtaactgga tgggcattat attttttggga    4800 ggaggtttag attcctgggt atcctatttt taaataaaag gtagacaaag tgaattctat    4860
tttgattatt gagaaaggaa tattaatagt tttctatccc tctaggatta tacttgaatc    4920
agacatttta aggatgtcac cgtaactctg aagtcatttc caaattcctg atgacaattt    4980
gttcagtttg ttttacctat tttttttttt tttaattcta tcagtgcatt attcgtccct    5040
tcctgctcgt gccgaatt                                                   5058

<210> SEQ ID NO 177
<211> LENGTH: 381
<212> TYPE: DNA
<213> ORGANISM: Bos taurus

<400> SEQUENCE: 177
atggcatctg tttatgtgaa tgacttgctg gaaaagttta agttcccaat gatctgaaac     60
tagagaataa ataccacata attacttcct ttcccttggt ggccctttc cccacccta     120 ccctgatttt atgacttcca tttggcaatt cttgaattat aactccattt gaacaaacag    180
gttcatgagg ataaattttc tgagacacat atatcttcat gctgtatact ttggttcttt    240
tttttccatg tgataagtga acataaaaac atcttttcca ggcgaaaaaa aaaaaaaaa    300 aaaaaagggg ggggccttttt aaaatttttcc ttggggggggc caaatttaac cctcccccttt    360 tttttttgaa aaggggggcc c                                               381

<210> SEQ ID NO 178
<211> LENGTH: 828
<212> TYPE: DNA
<213> ORGANISM: Bos taurus

<400> SEQUENCE: 178
tcaaaaagaa aaagaaagtc gagagaaaga acttatggac ttcagcaaat cagtaaatga     60
agcacgttca aagatggatg tagctcaatc agaacttgat atctatctca ggcgtcataa    120
tactgcagtg tctcaattag gtaaagccaa agaagcttta atggcagctt ctgagactct    180
caaagaaagg aaagctgcaa ttggagatat agaggcaaaa ctccctcaaa ctgaacatga    240
gctaaaggag aaagaaaaag aacttcaaaa acctacacaa gaagaaataa atttcaaaag    300
tttggctcgt gatcttttcc aaaaagttga agaagcaaag agttccttag caatgaatcg    360
aagtagggga aagtccttg atgcaataat tcaagaaaaa aaatctggca gaattccagg    420
aatatatgga cgactggggg acttaggaac aattgatgaa aaatacgatg ttgctatttc    480
atcttgttgt catgcattag actacattgt tgttgattct gttgatacag cccaagaatg    540
tgcaaacttc cttaaaagac aaaatattgg agttgcaacc ttcataggtt tggataagat    600
ggcagtgtgg gcaaagaaaa tgaccaaaat tcaaactcct gagaatacgc ctcggttatt    660
tgattttagt aaaagtaaaa gatggggcaa ttcgccaagc ttttactttt gccttacgga    720
```
taccttagta gctgacagct tagatcaagc cacacgagta gcttaccaaa aagatagaag    780
atggagagtg gtaacattac aagggcaaat catagaacag tcaggtac                828

<210> SEQ ID NO 179
<211> LENGTH: 208
<212> TYPE: DNA
<213> ORGANISM: Bos taurus

<400> SEQUENCE: 179
aattaacatg ttataatat gtacaattct ttctcccctc cctaccacac accttttcgt     60
gtgtgtgata aaccaactt ggtttgcaat aaaaccttga aaagtaaaaa aaaaaaaaaa    120
aaaaaaaaaa aagggggggg ccgttttaaa attttccttg gggggccaa atttaacccg    180 acccaatttt ttttgaaaaa aggggccc                                     208

<210> SEQ ID NO 180
<211> LENGTH: 649
<212> TYPE: DNA
<213> ORGANISM: Bos taurus

<400> SEQUENCE: 180
tttttggcat gtaagtactt tatttatatc ctctagccga ggaatgagtc aaatttgttt     60 ccatttttt tccatgatat ttctcatcac ctacttaaat tttgtgtggt atcagcattc    120
ttattgcatt ggactacaaa gtataactgt atttgctaac agtgtctttg ctacttttaa    180
tataaagcag gggttttaat ggaaatacca tagtgtgata aattgaggca gtaatataaa    240
atgacacatg tgtaatgagc atgttattct aaaaacatat ttaaaaaag tgttatttcc    300 tcttaattaa ggttgtaagc cttcagtgaa gcttacttct tcacttcctt tcaaattgaa    360
acagtatttt ttatttatgg agcccccagc aaaggaccca gcaattctta gtagcaattt    420
ctgtgagtta atgctttctc ttcctggtcc ctcagaaaaa aaattaagta agctctgaca    480
tagacagatg gacacctctg aagcttgtag cagtatccaa gggcttctgg acatgttcct    540
tttcaatcta acacagaaga aggagcagga cgaatgcagc aggtggggcc gtcgaaagtt    600
ctgcagcatg gactggaaaa cgctgtgctg cctgcctttg agcttttta               649

<210> SEQ ID NO 181
<211> LENGTH: 276
<212> TYPE: DNA
<213> ORGANISM: Bos taurus

<400> SEQUENCE: 181
ggagtcactc aggaccccag attccaggtc gtgaggagag gacagagcac gacactgaca     60
tgtgctcagg atctgggtca taactacatg tactggtacc gacaagacct gggacacggg    120
ctgaggctga tccattactc agctggtgtg cggtctagcg agccaggaga cgtgcccgac    180
aggtacagtg tcttcagatc aaacacagag aactttcctc tcacactgaa gtctgccaac    240
cgttcccaga catctgtgta cttctgtgcc agcggg                              276

<210> SEQ ID NO 182
<211> LENGTH: 436
<212> TYPE: DNA
<213> ORGANISM: Bos taurus
<220> FEATURE:
<221> NAME/KEY: misc_feature
<222> LOCATION: 66, 250, 261
<223> OTHER INFORMATION: n = A,T,C or G

<400> SEQUENCE: 182

```
gacaacaact tcgtctttta tttggcatta tttgagtgct tagttatgtg aaaaattttg      60
gtgttntgtc tctgttacat cagtttactt ctcatattta gctgttctat actcatgaag    120
ggatttaaag caatgttctt atattttcaa caagcttgat ttttacaaga ctataagaag    180
gttgatccca gggtgatggt gtgacctccg tgtgacctac caaagcagta gagatgggag    240
cagcatcttn ccagcagctg ngatttctca attctaagga cagtcaattg tgacagaaca    300
ggcccatcaa ctggtatctc ttctctccta gaggagatac ttgtttctgc cgaattatga    360
aaaaacatcc caacacacat tctggaccaa atattcaata acattattta tcaaaataaa    420
tttattaaaa gtattc                                                    436
```

<210> SEQ ID NO 183
<211> LENGTH: 291
<212> TYPE: DNA
<213> ORGANISM: Bos taurus

<400> SEQUENCE: 183

```
gaattcactc tacagtgttc tcagaaaatg aatcattatg caatgtactg gtatcgccaa      60
gatccgggat ttggacttcg gctgatctat tattcaactg ccctgactc ctttaagaaa     120
ggagatgtcc ctgaggggta tcacgtctct cgagatgagt tggaacattt ccccctgacc    180
ctgaagtccg ccagccccaa ccagacatct gtgtacttct gtgccagcgc tgaggtgggg    240
gcgggcaccc agcccctgta ctttggagct ggttccaagc tgactgtgct g             291
```

<210> SEQ ID NO 184
<211> LENGTH: 857
<212> TYPE: DNA
<213> ORGANISM: Bos taurus

<400> SEQUENCE: 184

```
gaattcttgg ctttattgcc caagctgtag gatatgaaaa gagtcacttt atcagagcac      60
tgacatcaag gttgctgtgt gccttccctg agtccacaga ggttaaaaaa aaatggacct    120
gctggagtta cagactcaac tcagaaaggg tttattggcc agagctgcag ggaagccaaa    180
gggacaagtt caggtgggct tcctgcagga ggctgccagc acagcagcac agggcggctt    240
ctactgcctt ccatgagccc agaggcccct caaccagcta tgggtgtc caggagcctc     300
ttggggatcg ctggaaccca gccagccctc ccaagccagg agcccttaat cctggccgag    360
ctgggctttc agagcctgta gctctccact atcgatgctg ttgcctccgc acacgatgac    420
cacgactggg gctggggaag ggcacaggtg gccctcagcc tggagcttcc ccaggaggcc    480
tgagtagatg gcagctaagg ctgccccgca ggcaggctcc accagtgttc gctcatcatc    540
caggaatcgc tgcacagcac tcacggcttc agcatcctcc accacctcag agaagatcct    600
aaactctttt gtacactcca gggcccgtgc agccactgtc ctggccccca ggctcttggc    660
tagactagtg atgccgggaa gcgtcaccag cttgcctgcc ttgatggccg cattgaagca    720
gtgtgcccct tgggtctcca tggcgattat gggcacgtgt tgccagccca cctctgccag    780
accagctgac accccggcca ggagacctcc accccgact gccagcacca gggcacccgg    840
tggggtcccc agcgctg                                                   857
```

<210> SEQ ID NO 185
<211> LENGTH: 346
<212> TYPE: DNA
<213> ORGANISM: Bos taurus

<400> SEQUENCE: 185

```
tttttgttct taaatggttc ttttattcag agcggttgct ttttaatgat gttgtcttac      60
ttttctgcta aacctgtttc atatctagtc atccaacatt aatatttatt ttgttcattt    120
actttaaaaa tattcttaaa gctgttacat ttattctact gctgctgaat ataattcagc    180
ataggcgcta ccatgaaaat gtcatagaaa ccatgatcaa tgtgttatag ctgtaatctg    240
gcttaataaa cacaacacta taaacaattc tagtaaatta agaaatatcc atactacaat    300
gtgctataaa atcaactgct gaatacatcc ttttttttaac ctctgt                  346
```

<210> SEQ ID NO 186
<211> LENGTH: 637
<212> TYPE: DNA
<213> ORGANISM: Bos taurus

<400> SEQUENCE: 186

```
tttttgcatt tacttatatc tttatttttac tcaggtatca agttccaatt tttttttta      60
agttgtagat ggagggcacc atgggtcggg ggagaggggc atggacaggg tgttttggga    120
tgcaagaaga aggagtctca tcggcgggat tcagaaataa gaatgtaaag cagagtacat    180
agcaatgtaa taaccatctg tagccctcat ggggagcatt cgcgagggat gaggcttccc    240
atttcaaaga aaactaaaga ttcagcaaac ttccaagata ttgctctgga gggaaaataa    300
ggctcagttc agctcagttc agttcagttt gtcagtcgtg tctgactctg tgaccccatg    360
aatcgcagca cgccaggcct ccctgtccat caccatctcg cagagttcac ttagactcac    420
gaccatcaaa tcagtgatgc catccagcca tctcatcctc tgtcgtcccc ttctcctcct    480
gccccccaatc cctcccagca tcagagtctt ttccaatgag tcaactcttc gcatgaggtg    540
gccaaagtac tggagtttca gctttagcat cattccttcc aaagaaatcc cagggctgat    600
ctccttcaga atggactggt tggatctccg tgcagtc                             637
```

<210> SEQ ID NO 187
<211> LENGTH: 668
<212> TYPE: DNA
<213> ORGANISM: Bos taurus

<400> SEQUENCE: 187

```
aaaaaataaa agtcatgtgt tatttataaa tcaatcatac agtaaaacaa ttattttaaa      60
aggtcacaaa tacaacagtt gcataaagtc agcttggagt caagtacctc ttaaaataca    120
ttgcaaatca tctctatttt agtgttcttt tccaaacaga tgtggttcaa actcaagaga    180
cggctttatc atttcatgtt tgacaaaaag tcaacaaaac tggcaataaa tagtccaaca    240
ataatttta aaaatactaa gtggtaaact cttaattgtg aaaaaaatct actattcaga    300
caacctgaag atttcactga agtcagtaaa gacacaaaat tagcttttgc acatttaaca    360
tgctcgtatt ttccttgaag tgataatgat acatacaaaa gctcaaagca ttaataaaga    420
aatgactgga agtcccaata agtcaatgaa cagactttgt tctgaactgg atgggaaaga    480
gacacaaaat gttctgtttt gctttatttt tcaaaaattg ccatggctcc ttgtcaagtg    540
gaagcagtac ccaaaccaaa ggttcccaaa cactggagta taagaaagac ttgttaaaat    600
gcaggttcct gggccctgcc ccagactctg agctctgatt cctgagtaca ataagtctac    660
attttcaa                                                             668
```

<210> SEQ ID NO 188

<211> LENGTH: 210
<212> TYPE: DNA
<213> ORGANISM: Bos taurus

<400> SEQUENCE: 188

| | | | | | |
|---|---|---|---|---|---|
| gaataagtgt | accatatttt | ctccaaaact | attttaaag | ctctgtatgc | attatcattc | 60 |
| tagctactga | atgtgtatga | tcccgggtcc | ccgtgaccca | actaaagagc | ccgtgtgctt | 120 |
| cagccaaaga | tcccacatga | cagaaaacct | gacacagcca | gataaatgaa | aaaacatttt | 180 |
| aaaataaata | aataaaagat | gatcggactt | | | | 210 |

<210> SEQ ID NO 189
<211> LENGTH: 393
<212> TYPE: DNA
<213> ORGANISM: Bos taurus

<400> SEQUENCE: 189

| | | | | | |
|---|---|---|---|---|---|
| atgaagacac | aaagaagagt | cttgctgagt | ctcttgtgga | tacagatttg | ctgcctcaga | 60 |
| gtgcagatga | aggtggagca | gagtccgggg | gttctgactc | tccaagaggg | gagaaattcc | 120 |
| tctctgatat | gcaattattc | tatttccatg | accagtgtgc | agtggttcca | acaaaatcct | 180 |
| gatggacgcc | tcatctcctt | gttttatata | gcttcaggaa | tgcagcagaa | aggaagactg | 240 |
| aaatccacca | ttaatagtaa | ggagcgttac | agtcaactct | acatcagaga | ctcccagcct | 300 |
| ggggactcag | ccacttactt | ctgtgctgcg | atcaggactg | acaattccag | aatcttcttt | 360 |
| ggaactggaa | cccaggtggt | ggtaaagccc | aaa | | | 393 |

<210> SEQ ID NO 190
<211> LENGTH: 550
<212> TYPE: DNA
<213> ORGANISM: Bos taurus

<400> SEQUENCE: 190

| | | | | | |
|---|---|---|---|---|---|
| ccacgcgtcc | gggagaaacg | tcgactgaat | gacctggttt | tggagaacaa | actcattgca | 60 |
| ctgggagaag | aaaacgccac | tttaaaagct | gaactgcttt | ccctaaaatt | aaagtttggt | 120 |
| ttaattagct | caacagccta | tgcccaggag | attcagaaac | tcagtaattc | tacagctgtg | 180 |
| tactttcaag | actaccagac | ttccaaatcc | actgtgagcg | cctttgtgga | tgagcatgag | 240 |
| ccctccatgg | tggccagcag | ttgcatttct | gtcatcaagc | actctcctca | gagttctctg | 300 |
| tctgatgttt | cagaagtatc | ctcgctagaa | cattcacagg | agggccctgt | gcagaatggc | 360 |
| tgcagaagcc | cagaaagcaa | gttccaggtc | atcaagcaag | agccaatgga | actggagagc | 420 |
| tatgccaggg | aacccagaga | tgaccgaggt | gcctaccgag | gggccgtgta | tcagaactac | 480 |
| atggggaatt | cctttcccgg | atactcgcac | tctcccccct | ctgctgcagg | tcaaccgatc | 540 |
| ctccagtaac | | | | | | 550 |

<210> SEQ ID NO 191
<211> LENGTH: 349
<212> TYPE: DNA
<213> ORGANISM: Bos taurus

<400> SEQUENCE: 191

| | | | | | |
|---|---|---|---|---|---|
| cacatttcat | gttttattat | tttttttaaa | ctcaactctt | cccagaacac | tttataataa | 60 |
| gataacatgt | aatatactat | atacatctct | ttaaaatagt | caagtaccct | aatgcccttta | 120 |
| aaacagggtc | tggtaagcca | gtaaggtcaa | ttatagttga | caaaatccac | tcagcatggg | 180 |
| gcatgccatg | tcacagcacc | cagtacaacg | ttgggactgt | tcacaggtta | tccttcatta | 240 |

```
ggaaagaaaa attagaactt ttgtgttcta gttgttttta cttccaccta aataagtgct    300
tatgcatgtt gtcttgacag atattttggg aatttaaaaa ttggggatc                349

<210> SEQ ID NO 192
<211> LENGTH: 416
<212> TYPE: DNA
<213> ORGANISM: Bos taurus
<220> FEATURE:
<221> NAME/KEY: misc_feature
<222> LOCATION: 296
<223> OTHER INFORMATION: n = A,T,C or G

<400> SEQUENCE: 192
gaaatgtttc atttaagctt ttgtgtattt catgtaattg tcaattacat atctctgtat     60
tcttaaaact atagctcatt ctagcctggc ttatttagaa atacacagga ccatattgaa    120
agttggggat tgcggcttta aggattattg tgctctgtca aactggtatc ttactccatt    180
tatgaaaaag actagagttg cttagtatca tattcatatt tgttgtacct gagtggagtg    240
tctgtgtttt gtacggcttg agattttcat gaataaaatt ttttctcacg gtggtnaaaa    300
aaaaaaaaaa aaaaaaaaaa aaaaaaaaaa gggggggggc ccttttaaaa ttttcctggg    360
gggggccaaa ttttcccccc cccttttttt tttaaaaaag ggggccctt tgggggg        416

<210> SEQ ID NO 193
<211> LENGTH: 339
<212> TYPE: DNA
<213> ORGANISM: Bos taurus

<400> SEQUENCE: 193
atgggctcca ggctcctctg ctgtgtgact ctctgcctcc tgggagcagg tctggtggat     60
tctggggtca cccagacccc caaatatctg atcaaatcaa gaaagcagca agtgatactg    120
agatgttccc ctgagtctgg acacctctat gtatcctggt accaacaagc cctgggccag    180
ggcccccagt tccttattca gtattttaat gggaaagaga atgagaaagg aaacatgcca    240
gatcgattct taggtgaaca gttcagtgac tctagctctc agatgaacct gagctccttg    300
gagctgacag actcagccat gtatctctgt gccagcagc                           339

<210> SEQ ID NO 194
<211> LENGTH: 769
<212> TYPE: DNA
<213> ORGANISM: Bos taurus

<400> SEQUENCE: 194
catgtggtaa ttttattgat taaaatatta caaagttcta cttctcatgt cttcatatac     60
aatatatccg agtgaactaa attaatcatt tatgatatga aaagacatta ttacatattg    120
gaagggtgac gttaattcat catcatggat tatctctact cctaaggtat atgcccatat    180
tacagagtca gccatggcct gtgactctgg ggaggtatgg aagagcactg agtccacagg    240
ccaggagtgc ttatcaagtc acgttttctg ctctgagagg aagaaattag gaaacctgga    300
ggaacaagga atagtcagtt cccagaaaac ttgggagatt tctcaaaaga aggaactgac    360
ataatttttc agttattttt atgaggaaat cttaaaacat atttgaatgc tgataagaca    420
gaaaaaatca tttaggttgc cttttcaaac tagttattta agtcatcgta tgaaagatat    480
taaacaatga aaagttatgg caaatatgtt ggcagagaaa atttaatgac gtgttctttt    540
ggaggagatg ataaatgatg tgggagttag acttgaatga tatattagtt ttaaatgaat    600
```

```
atttacataa aaatacttca tgatttattt caggttgaat attctcttaa aaattagagg      660
ggcctgaaat aaatatttt taatgcagaa gcatcttcag taaaaagagt tggtgaagca       720 ccccactct catcaagcaa gcgtgtgggt gagagaattt ctgatgggt                    769

<210> SEQ ID NO 195
<211> LENGTH: 464
<212> TYPE: DNA
<213> ORGANISM: Bos taurus

<400> SEQUENCE: 195
gcacggggag agaaacacaa aggctcttct ctacctctgt ggcattctcc ttaactccat       60
ctaccagtgc cctgagcaca gccaactgac aactgaaggg agtggatggg aaagagttcc     120
cagagcccca cctgggccag tggtacttta tcgcaggggc agctcccacc aaggaggagt     180
tggcgacttt tgaccctgtg acaacattg tcttcaacat ggctgtgggc tctgccccca      240
tgcagctcca gcttcgagcg accatccgca cgaaaaacgg gctttgcgtg ccccggaaat     300
ggatctacca cctgtctgat gggagcacag atctcagaac cgaaggccgc cctgacatga     360
agaccaagct cttctccagt gcatgccag gtggaatcat gctgaaagag acggccaggg      420
ttaccagcgc ttcctcctct acaatcgctc accccaccct cctg                      464

<210> SEQ ID NO 196
<211> LENGTH: 513
<212> TYPE: DNA
<213> ORGANISM: Bos taurus

<400> SEQUENCE: 196
gctcaggact tgcagcaagc tagactaccc ggatcctaca tctgtggact agtggccctc      60
ttcccgtcct gaggttaggc tgttcagagc tcagaccgct gctcagagca ctaaccgttt     120
ctcagaatgc tcccaggctc actcccgtc cccggctcca cgtcctgccc ctgcccgggc      180
cttcggtctc ggcaggaggc tgactggttg cccactgtt ggcccattgc tgagtgatca      240
gtgttcgctc tgctcatctt ccaaggcctg gttggtgaag ctctggggga aagtgttttc     300
aggttgagga ggctgaaatg ggatctccta gggcttcgga gttcagccct ggacggtggg     360
gacaagtgag caagcctgtg gtccagccca ggctggttgg gataacctag actgtgtcct     420
ggagtggggt tttccttgtc aaagaagggg tgcacttttc cgatatgcag gaagatactg     480
tatggccaga gccttgcagc tctagtgtgg tct                                   513

<210> SEQ ID NO 197
<211> LENGTH: 766
<212> TYPE: DNA
<213> ORGANISM: Bos taurus

<400> SEQUENCE: 197
gaaaccaacg cattctttat tgcagcctga agcgaagggc tcactcacac agtgggcttt      60
gatgtggggc cttctctgac tgcccaagct ttcccagcag gcatgggcaa actctccaag     120
cagagtagaa aacagcttcc aaaagccacc ctgtctaagg gccttaggcg atgacctggg     180
gaagcagcaa aggttatcca ggaaggccaa gcaaagccgg ctctcctctc ctggtggctt     240
tggatcagtc ccttcactgg gagcaccacg cagcctctgg aaagatcaaa ggggcccagg     300
ggctctgagg gctggtttaa ggggacataa gcagactcag actccaccga tggtgcagag     360
ggagagccga aaaccttcac cctcgactct gagaatgtcc ccaagatcac cccaggcccc     420
tgtttgtggg aatcagctgg cgatcttctg aaatgcagtt tctggttcca gaagtctaga     480
```

```
atggggcctg ggattctgca tttctatcgc gctcccatgg atgccaactc tgcaggcatc    540
cccacagacc acactagagc tgcaaggctc tggccataca gtatcttcct gcatatcgga    600
aaagtgcacc ccttctttga caaggaaaac cccactccag acacagtct aggttatccc     660 aaccagcctg gctggacca caggcttgct cacttgtccc caccgtccag ggctgaactc     720
cgaagcccta ggagatccca tttcaacctc ctcaacctga aaacac                   766
```

```
<210> SEQ ID NO 198
<211> LENGTH: 728
<212> TYPE: DNA
<213> ORGANISM: Bos taurus

<400> SEQUENCE: 198
```

```
aagcattaac tttcaatgag gttttccttt ttacctccat gatacagttt tcaagatgaa     60
ttaagtaaaa tgtaaagtgt acatacacac accttcatta aatgaatggt gacacatata    120
tacagcattt tcctgagaaa gtacaaagat gcagaaatgt tcacgtaggg ctcaaacaac    180
ctaacaaaga caaagggtcc ccagtggaaa agtttgtctt catgcaaaaa aaacctggca    240
tgaaaatagg aatgcaactc ttggggttgg attggctccc tctgagctcc cttaaaaccc    300
tgaagtttat cagtctctga attaattctt ccagtgattc ttcccaaaaa tatgcaaact    360
gctccggagg gacatttgga gaagttttgt ttattctttt aagccacgag cagcatataa    420
aagagcccca gttctcgaga actgaccatg agctaagcaa gtaacctaaa caaccagct    480 tttccaaaac ttcaccatac cgggcagaca cgaaatcgct aaggtcacta aaaggacagc    540
tgatttgtat tgcgatgctc tcaaatgaaa tattttccat taagttagaa aagcttggct    600
cctacatttt agaaaccact tcccatagac acagtcttcc ttgtagttct gtatttctac    660
ctccatacac attggttttc tttgggcatg atttcccaag tttctcagcg ttcattcctg    720
ttctctat                                                             728
```

```
<210> SEQ ID NO 199
<211> LENGTH: 501
<212> TYPE: DNA
<213> ORGANISM: Bos taurus

<400> SEQUENCE: 199
```

```
aggtatttcc acgccgccgt gtctcggccc ggcctccggg agcccctctt tatcaccgtc     60
ggctacgtgg acgacacgca gttcgtgcgg ttcgacagcg acgcccggga tccgaggaaa    120
gaaccacggc agccgtggat ggagaaggag gggccggagt attgggatcg cgagactcaa    180
atctccaagg aaaacgcact gaagtaccga gaggccttga acatcctgcg cggctactac    240
aaccagagcg aggccgggtc tcacacctat cagcggatgt acggctgcga cgtggggccg    300
gacgggcgcc tcctcagcgg gttcacgcag ttcggctacg atggcagaga ttacatcgct    360
ctgaacgagg acctgcgctc ctggaccgcg cggacccgg cggctcaggt ctccaaacgc     420
aagattgagc agagtggtgc tgcgaagggc gagaggaact acctgaaccg cgagtgcgtg    480 gagggggctcc gcagataccg t                                              501
```

```
<210> SEQ ID NO 200
<211> LENGTH: 619
<212> TYPE: DNA
<213> ORGANISM: Bos taurus

<400> SEQUENCE: 200
```

```
tttttctttt tttttttttt tttttttttt tttttttttt tttttttttt tttttttttt    60
ttttgagctc tgctgaaaaa catttattga gctgggggca ccccaaccc tgcagtggga     120 ttctggatca accccaagga aagggtctg gttcctgcaa tcaaaggctt ttcatgggtt     180
tctttatcca gggcaggaaa cttgaaactt tggtgaaggc cgtggagtt gatccatttt    240 tttttccata aaaacaatg ccctgggcca cattgtcaca cacaaaaagg ccccccgagt    300 cccctgaaa ggaaactttt tttgttttg ggtccccac acacagctgg atggggcggt      360 tataaaatt gcgtaagtag gcctcacact tttgatcctc ctgcacgatc aactttacct    420
actgtaatgt gtcaacgtaa gtgtccgtgg aatcccttcc ccaaccggcc acgctgaacg   480
tttgtcctgg cttcacccgg gccttggccc tgggcaaact aaagggcttc acaactgatg   540
tctgcttggc ctttctctcc aactttaaaa catgatgtcg ttggaaaaat tcttaagatt   600
ataatcaggg gggctgatg                                                619

<210> SEQ ID NO 201
<211> LENGTH: 370
<212> TYPE: DNA
<213> ORGANISM: Bos taurus

<400> SEQUENCE: 201
atcctctgtg atacacgacc ttctcaggga aacttgtggc ctccgcataa cagtaggaag    60
gtgttcctac tgggtctcac acatgtttga atgtgtaaga attgttcaaa aagaaaaga   120 aaaaaaagg aattgttcag atttgggaat aaagacagat catacctaaa actgctcttc   180
tacttctctt aagggcagaa ggagctgtga acattctctg acaccagat gtttgaatca    240 tattatcatt aataaatttc tgtgatgctg acaaaaaaaa aaaaaaaaa aaaaggggg    300 ggccctttta aattttcctt ggggggggcca aattttaccc gtccccttttt ttttgaaaa  360 agggggccct                                                         370

<210> SEQ ID NO 202
<211> LENGTH: 498
<212> TYPE: DNA
<213> ORGANISM: Bos taurus
<220> FEATURE:
<221> NAME/KEY: misc_feature
<222> LOCATION: 225, 226, 227, 228, 440, 441
<223> OTHER INFORMATION: n = A,T,C or G

<400> SEQUENCE: 202
tttttttttt tttttttgag cagcgcttga tttattagca ttaaaaaaac ccagttcata    60
tatacaaaac aagctgattt tgttgtcaa gtgttaaaag cactccttta aaattaaata   120
caatttaaag catggattaa tgagttgatt tcctgggaag cacttcagtg aatgaatatt   180
tgccaatgga aacatcagat gcacaccacg cgggcaccag ggggnnnngg gatccacagg   240
gctgctcatc acagcgtctg accccagaca ctgtaggtgc cacacacgtc cccgtgggt    300 attcccgcta agacccaggg cggggcacg acctgtgaaa attcacttgc acgttagaat    360
aacgaccaac ttcagctgca acttaaacct cgccccaggc ccaccgcagc tgcaccgatg   420
agccgtgaca ctcggggcgn ncagtgaaag ttcgctggac aatgttgtgt gaacgtccat   480
gctcggctgt gggccccg                                                498

<210> SEQ ID NO 203
<211> LENGTH: 635
<212> TYPE: DNA
<213> ORGANISM: Bos taurus
```

<400> SEQUENCE: 203

```
caatctagac attttatta agttccatta aaaaatagt aaacatttg aaaaactcac      60
aaagtttata aaacacactc atactcataa ttttcttatt ctgtgacagc tagtgctaca    120
tgttgaaatg ttacattaac atcaacccac aagagtgcaa aagtttactt ccacagtatt   180
taacaaatgt gcatctgaag aaaatatata tatatacacc ttgtataaaa gattgcaagt   240
tatttaaaaa aaacaaaact ttcccccct taaattcaat aagggttgtt tagctaattt    300
agtcagggtc atgataactt tatgttcttt taggtggtac tgggtaaatg caaaatgcta   360
ggaaaacact tttcaaaatg tacagtataa aagggcaact ccgattcata gctggatagc   420
atctgcttat ctaaatttct tgaaataact gatctcagga ttttttttt aaagatccag    480
tgatgcttaa caactctatc tgaacaaaga acacttaggc ctcctaccag ttagccatct   540
cagtcaggcc acttgttcag ctcttgcca taagctgcta tcaacagagt gatccctaga   600
gtgattagga attccaaaac tgtcaaaagg ctctg                              635
```

<210> SEQ ID NO 204
<211> LENGTH: 500
<212> TYPE: DNA
<213> ORGANISM: Bos taurus

<400> SEQUENCE: 204

```
caatttcctt ttgctctgct cgttatcatc ttcagaggat tcatcactct gttctttctc    60
tgagaacttc tcagcaacat cacataagcc acccagtatt ttctgacaca ttctggttcg   120
ctggtgctta ctctttcctt tagattcagc aaccttttta tcttctggag aattaaaact   180
ctcctctttc ccagaacaaa gcttatcagc actctctgag gaaacattgg gctgctgctt   240
cttagagagg cgatctctca attccatgat ggtcttgtct ttatcaactg tgccttctgc   300
tgaagagaaa ttctctctct cttgtttcct ttcaacatca tcagatgatc cttcctgtgc   360
agtcctcaaa cttttatgac cttgattatc cattccttgt ttgctgtgtt tttcatcttc   420
agaagaatca taatattctt tatttggaac tctttttggg ttgttctggc agtcccaatt   480
ttactcattc tctttatctc                                               500
```

<210> SEQ ID NO 205
<211> LENGTH: 640
<212> TYPE: DNA
<213> ORGANISM: Bos taurus

<400> SEQUENCE: 205

```
ttttcgtta atcaaatgat atttatatt aacttatgac ttatgctttg gaattctcta     60
agtcatatgt ggataatttt atatttataa aaatatatac attttatgta tacatggaaa   120
gattggaaat ttccttcaat aactttattc tttataaaac ctataaataa ataaaacttt   180
tcaacttcta aaggattacc acgtttaaga agaaggtata ttgctatcac cattctagat   240
tatgggaatg catcccattc cttcatcttc caatcctagt ggcaaagtgg gaactgaact   300
gaagttggat tgagacagga ctgccaggga tagacacata agaaataaa cacagacact    360
tccaaacatg gaatgctggg cctccaggaa agtggcagag cggagtctac tgagtcttgc   420
actctggcac atctcttcct gatgacattt gccaaggacc tggctgggga tcctcggtct   480
ccacttcagc agtttgttct tctggacaaa ggcctaaacc tgagttatca aaatagcgaa   540
ctggaggagg tactggtaaa gactttgatc ggttatcaaa aaaccaagat tcggcgact    600
```

```
ccttcggcac aggatcttgg acattccgtt ctttgcattg                 640

<210> SEQ ID NO 206
<211> LENGTH: 747
<212> TYPE: DNA
<213> ORGANISM: Bos taurus

<400> SEQUENCE: 206
aaatttctta gtgcttttat ttcatttctt ttggcatatc taaatgtcag aaagtacata   60
catacaaaat tccaaacacc ttcctaaaat ggttttagta ttggcgagtc tgatatctca  120
ggttgaattg tccaatatgt ctaaagtgca ttctcgcagc taatcaatag cagcatttgt  180
tctgtttata aatccttaaa aaatattcag acagcaggtg gaaaatcaca ataaaaagca  240
aagcgtgatc taaatatatt tttccttaat tatccaagac aaacacatgc atgaattagt  300
ttatacaaga aatatacaaa aaatagcaat ataaaaaagt tcatacagca atgagaaaga  360
ggggtctttc tctgctacta atattaaata tggcaaggtg tataatataa aaagtttgta  420
gaatcctaga tatctttgga gccacagggg aatccctgat ggaggccagt gtgtgatgac  480
atgaggtctg tgattttcaa caaagctgga gttttataag atggttttca gaaggcactg  540
ctttggagaa atcaccaaca caaatgatga aaatgttctt ttgttattga aactgtcaat  600
tcatggcttc ttgcgcttgg gttgtgcatg gtgctggtac ccaggcccca gctgagagcc  660
cgctctcatc tccacagcca cagagcacct tgtttctaca tcagtccatt cagactctgt  720
tccatctggc tgggcaggtg ctactgt                                     747
```